(12) United States Patent
Han et al.

(10) Patent No.: US 7,169,795 B2
(45) Date of Patent: Jan. 30, 2007

(54) SULFONYLAMINOVALEROLACTAMS AND DERIVATIVES THEREOF AS FACTOR XA INHIBITORS

(75) Inventors: Wei Han, Yardley, PA (US); Zilun Hu, Jamison, PA (US); Timur Gungor, Pennington, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 190 days.

(21) Appl. No.: 10/952,396

(22) Filed: Sep. 28, 2004

(65) Prior Publication Data

US 2005/0096309 A1 May 5, 2005

Related U.S. Application Data

(60) Provisional application No. 60/507,177, filed on Sep. 30, 2003.

(51) Int. Cl.
C07D 487/12 (2006.01)
C07D 401/04 (2006.01)
C07D 403/14 (2006.01)
A61K 31/445 (2006.01)
A61P 7/02 (2006.01)

(52) U.S. Cl. ............. 514/316; 544/186; 544/187; 544/188

(58) Field of Classification Search ........ 546/186, 546/187, 188; 514/316
See application file for complete search history.

(56) References Cited

U.S. PATENT DOCUMENTS

2002/0183324 A1* 12/2002 Jacobson et al. .......... 514/247
2004/0006062 A1* 1/2004 Smallheer et al. ..... 514/212.08

FOREIGN PATENT DOCUMENTS

WO WO 03/049735 6/2003
WO WO 03/050109 6/2003
WO WO03/053925 7/2003

OTHER PUBLICATIONS

U.S. Appl. No. 10/952,397, filed Sep. 28, 2004, Han et al.
U.S. Appl. No. 10/952,204, filed Sep. 28, 2004, Shi et al.
Elodi et al., "Optimization of conditions for the catalytic effect of the factor IXa-factor VIII Complex: Probable role of the complex in the amplification of blood coagulation", *Thromb. Res.*, vol. 15, pp. 617-629, 1979.

* cited by examiner

*Primary Examiner*—Bruck Kifle
(74) *Attorney, Agent, or Firm*—Jing G. Sun; David H. Vance

(57) ABSTRACT

The present application describes sulfonylaminovalerolactams and derivatives thereof of Formula Ia–If:

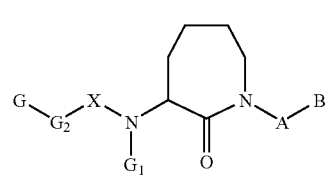

Ia

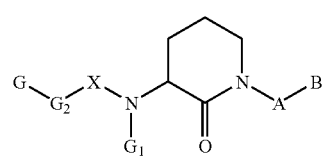

Ib

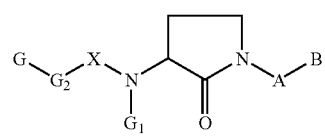

Ic

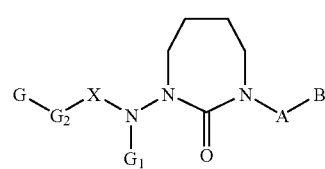

Id

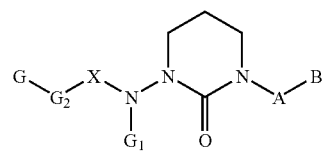

Ie

If or pharmaceutically acceptable salt forms thereof, wherein ring G is a mono- or bicyclic carbocycle or heterocycle. Compounds of the present invention are useful as inhibitors of trypsin-like serine proteases, specifically factor Xa.

23 Claims, No Drawings

SULFONYLAMINOVALEROLACTAMS AND DERIVATIVES THEREOF AS FACTOR XA INHIBITORS

CROSS-REFERENCE TO RELATED APPLICATIONS

The present application claims the priority benefit of U.S. Provisional Application No. 60/507,177, filed Sep. 30, 2003, which is expressly incorporated fully herein by reference.

FIELD OF THE INVENTION

This invention relates generally to sulfonylaminovalerolactams and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

The present invention provides novel sulfonylaminovalerolactams and derivatives thereof that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a host in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt thereof in an amount effective to treat a thromboembolic disorder.

The present invention provides a novel method, comprising: administering a compound of the present invention or a pharmaceutically acceptable salt thereof in an amount effective to treat a thromboembolic disorder.

The present invention provides novel lactam-containing compounds and derivatives thereof for use in therapy.

The present invention provides the use of novel lactam-containing compounds for the manufacture of a medicament for the treatment of a thromboembolic disorder.

These and other objects, which will become apparent during the following detailed description, have been achieved by the inventors' discovery that sulfonylaminovalerolactams of Formula Ia–If:

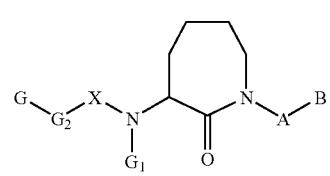

Ia

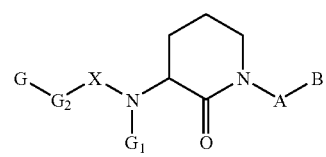

Ib

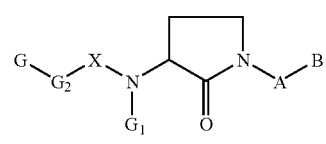

Ic

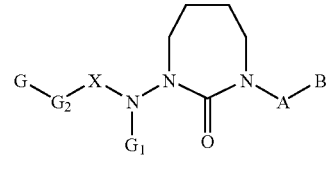

Id

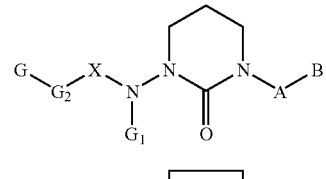

Ie

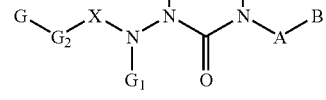

If wherein G, $G_1$, $G_2$, A, B, and X are defined below, or pharmaceutically acceptable salt or prodrug forms thereof, are effective factor Xa inhibitors.

DETAILED DESCRIPTION OF PREFERRED EMBODIMENTS

Thus, in a first embodiment, the present invention provides a novel compound of formula Ia–If:

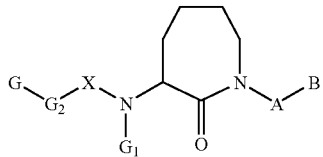
Ia

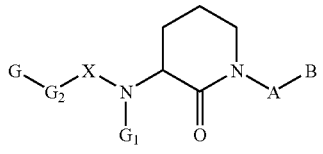
Ib

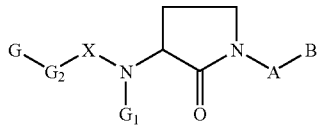
Ic

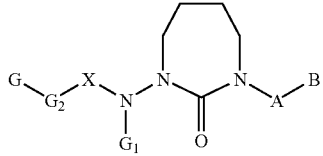
Id

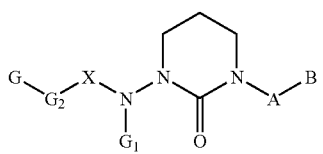
Ie

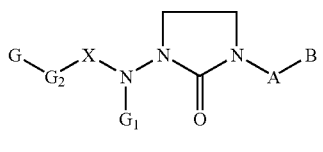
If or a stereoisomer or pharmaceutically acceptable salt thereof, wherein;

the central lactam ring is substituted with 0–2 $R^{1a}$ and 0–1 additional carbonyl groups;

X is selected from $SO_2$ and $NR^3C(O)$;

G is a group of formula IIa or IIb:

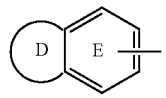
IIa

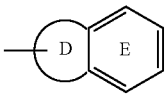
IIb ring D, including the two atoms of ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent, and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent, ring E is selected from phenyl, phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered ring consisting of: carbon atoms and 0–4 heteroatoms selected from the group consisting of N, O, and $S(O)_p$, wherein the 5–6 membered ring is substituted with 0–2 carbonyls and 1–2 R and has 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$;

alternatively, when 2 R groups are attached to adjacent atoms, they combine to form methylenedioxy or ethylenedioxy;

$G_1$ is selected from H, —CN, $(CR^3R^{3a})_{1-2}C(O)R^2$, $NR^2R^{2a}$, $(CR^3R^{3a})_{2-5}NR^2R^{2a}$, $OR^2$, $(CR^3R^{3a})_{2-5}OR^2$, $(CR^3R^{3a})_{1-2}S(O)_pR^2$, $NR^2C(O)R^2$, $(CR^3R^{3a})_{2-5}NR^2C(O)R^2$, $NR^2C(O)NR^2R^{2a}$, $(CR^3R^{3a})_{2-5}NR^2C(O)NR^2R^{2a}$, $NR^2C(O)OR^2$, $(CR^3R^{3a})_{2-5}NR^2C(O)OR^2$, $(CR^3R^{3a})_{1-2}S(O)_2NR^2R^{2a}$, $NR^2S(O)_2NR^2R^{2a}$, $(CR^3R^{3a})_{2-5}NR^2S(O)_2NR^2R^{2a}$, $OC(O)R^2$, $(CR^3R^{3a})_{2-5}OC(O)R^2$, $(CR^3R^{3a})_{1-2}C(O)OR^2$, $(CR^3R^{3a})_{1-2}C(O)NR^2R^{2a}$, $(CR^3R^{3a})_{1-2}C(O)NR^2(CR^3R^{3a})(CR^3R^{3a})_{1-2}OR^2$, $(CR^3R^{3a})_{1-2}C(O)NR^2(CR^3R^{3a})(CR^3R^{3a})_{1-2}NR^2R^{2a}$, $(CR^3R^{3a})C(O)NR^2(CR^3R^{3a})_{1-2}C(O)NR^2R^{2a}$, $(CR^3R^{3a})C(O)NR^2(CR^3R^{3a})_{1-2}C(O)OR^2$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $(CR^3R^{3a})_{0-4}$—$C_{3-10}$ carbocycle substituted with 0–3 $R^{1a}$, and $(CR^3R^{3a})_{0-4}$-5–12 membered heterocycle consisting of: carbon atoms and 1–4 heteroatoms selected from the group consisting of N, O, and $S(O)_p$ and substituted with 0–3 $R^{1a}$;

$G_2$ is absent or is selected from $CR^3R^{3a}CR^3R^{3a}$ and $CR^3=CR^3$;

A is selected from: $C_{3-10}$ cycloalkyl substituted with 0–2 $R^{4c}$, $C_{3-10}$ cycloalkenyl substituted with 0–2 $R^{4c}$, and 4–12 membered heterocycle consisting of: carbon atoms and 1–4 heteroatoms selected from the group consisting of N, O, and $S(O)_p$ and substituted with 0–2 $R^{4c}$, wherein the heterocycle has 0–1 ring double bonds;

B is selected from —CN, $C_{1-6}$ alkyl substituted with 0–2 $R^{4a}$, $C_{2-6}$ alkenyl substituted with 0–2 $R^{4a}$, $C_{2-6}$ alkynyl substituted with 0–2 $R^{4a}$, O—$C_{1-6}$ alkyl substituted with 0–2 $R^{4a}$, $S(O)_p$—$C_{1-6}$ alkyl substituted with 0–2 $R^{4a}$, $NR^{2d}$—$C_{1-6}$ alkyl substituted with 0–2 $R^{4a}$, $C_{3-6}$ cycloalkyl substituted with 0–2 $R^{2d}$, and a 3–7 membered saturated heterocycle substituted with 0–2 $R^{2d}$ and consisting of carbon atoms and 1–3 heteroatoms selected from the group consisting of N, O, and $S(O)_p$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})$—$R^{1b}$, —$C_{2-6}$ alkenylene-$R^{1b}$, —$C_{2-6}$ alkynylene-$R^{1b}$, —$(CR^3R^{3a})_r$—C(=$NR^{1b}$)$NR^3R^{1b}$, $NR^3(CR^3R^{3a})_rR^{1c}$, $O(CR^3R^{3a})_rR^{1c}$, $(CR^3R^{3a})_rSCR^3R^{3a}R^{1c}$, $(CR^3R^{3a})_rNR^3(CR^3R^{3a})_rR^{1b}$, $(CR^3R^{3a})_rC(O)NR^2(CR^3R^{3a})_rR^{1b}$, $CO_2(CR^3R^{3a})_rR^{1b}$, $O(CR^3R^{3a})_rR^{1b}$, $(CR^3R^{3a})_rS(CR^3R^{3a})_rR^{1b}$, $S(O)_p(CR^3R^{3a})_rR^{1d}$, $O(CR^3R^{3a})_rR^{1d}$, $NR^3(CR^3R^{3a})_rR^{1d}$, $OC(O)NR^3(CR^3R^{3a})_rR^{1d}$, $NR^3C(O)NR^3(CR^3R^{3a})_rR^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–10 membered carbocyclic or heterocyclic ring consisting of: carbon atoms and 0–4 heteroatoms selected from the group consisting of N, O, and $S(O)_p$, this ring being substituted with 0–2 $R^4$ and 0–3 ring double bonds;

alternatively, when two $R^{1a}$ groups are attached to adjacent atoms, together with the atoms to which they are attached, they form a 5–7 membered carbocyclic or heterocyclic ring consisting of: carbon atoms and 0–4 heteroatoms selected from the group consisting of N, O, and $S(O)_p$, this ring being substituted with 0–2 $R^{4b}$ and 0–3 ring double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2NR^2R^{2a}$, $NR^2SO_2R^2$, $C(O)NR^2SO_2R^2$, $SO_2R^2C(O)NR^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^{1d}$ is selected from $C_{3-6}$ carbocycle substituted with 0–2 $R^{4b}$ and 5–10 membered heterocycle consisting of carbon atoms and from 1–4 heteroatoms selected from the group consisting of N, O, and $S(O)_p$ and substituted with 0–2 $R^{4b}$, provided that $R^{1d}$ forms other than an N—S bond;

$R^2$, at each occurrence, is selected from H, $CF_3$, $C_{1-6}$ alkyl substituted with 0–2 $R^{4b}$, benzyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $C_{1-6}$ alkyl substituted with 0–2 $R^{4b}$, benzyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_r$-5–10 membered heterocycle containing from 1–4 heteroatoms selected from the group consisting of N, O, and $S(O)_p$ and substituted with 0–2 $R^{4b}$;

$R^{2d}$, at each occurrence, is selected from H and $C_{1-6}$ alkyl;

$R^{2e}$, at each occurrence, is selected from H and $C_{1-6}$ alkyl;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $NR^3R^{3a}$ forms a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^4$, at each occurrence, is selected from H, =O, $(CR^3R^{3a})_rOR^2$, $(CR^3R^{3a})_rF$, $(CR^3R^{3a})_rCl$, $(CR^3R^{3a})_rBr$, $(CR^3R^{3a})_rI$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rC(=NS(O)_2R^5)NR^2R^{2a}$, $(CR^3R^{3a})_rNR^2C(=NR^2)NR^2R^{2a}$, $(CR^3R^{3a})_rC(O)NR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2$—$C_{1-4}$ alkyl, $(CR^3R^{3a})_rNR^2SO_2R^5$, $(CR^3R^{3a})_rS(O)_pR^{5a}$, $(CR^3R^{3a})_r(CF_2)_rCF_3$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4a}$ is selected from H, =O, Cl, F, Br, I, $C_{1-4}$ alkyl, $C_{1-4}$ haloalkyl, $NR^{2d}R^{2d}$, $N(\rightarrow O)R^{2d}R^{2d}$, $OR^{2d}$, —$NR^{2d}C(O)R^{2d}$, —$C(O)R^{2d}$, —$OC(O)R^{2d}$, —$C(O)NR^{2d}R^{2d}$, —$(CR^{2e}R^{2e})_rC(O)OR^{2d}$, —$NR^{2d}C(O)NR^{2d}R^{2d}$, —$OC(O)NR^{2d}R^{2d}$, —$NR^{2d}C(O)OR^{2d}$, —$SO_2NR^{2d}R^{2d}$, —$NR^{2d}SO_2NR^{2d}R^{2d}$, —$C(O)NR^{2d}SO_2R^{2d}$, —$SO_2NR^{2d}C(O)R^{2d}$, —$NR^{2d}SO_2R^{2d}$, and —$S(O)_pR^{2d}$, provided that $S(O)^pR^{2d}$ forms other than $S(O)_2H$ or $S(O)H$ and further provided that $R^{4a}$ is other than a hydroxamic acid;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_rC(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_r NR^3SO_2CF_3$, $(CH_2)_r NR^3SO_2$-phenyl, $(CH_2)_r S(O)_p$ $CF_3$, $(CH_2)_r S(O)_p$—$C_{1-4}$ alkyl, $(CH_2)_r S(O)_p$-phenyl, and $(CH_2)_r(CF_2)_t CF_3$;

$R^{4c}$, at each occurrence, is selected from H, =O, $(CR^{2e}R^{2e})_r OR^{2e}$, $(CR^{2e}R^{2e})_r F$, $(CR^{2e}R^{2e})_r Cl$, $(CR^{2e}R^{2e})_r Br$, $(CR^{2e}R^{2e})_r I$, $C_{1-4}$ alkyl, $(CR^{2e}R^{2e})_r CN$, $(CR^{2e}R^{2e})_r NO_2$, $(CR^{2e}R^{2e})_r NR^{2e}R^{2e}$, $(CR^{2e}R^{2e})_r C(O)R^{2e}$, $(CR^{2e}R^{2e})_r NR^{2e}(O)R^{2e}$, $(CR^{2e}R^{2e})_r C(O)NR^{2e}R^{2e}$, $(CR^{2e}R^{2e})_r NR^{2e}(O)NR^{2e}R^{2e}$, $(CR^{2e}R^{2e})_r C(=NR^{2e})NR^{2e}R^{2e}$, $(CR^{2e}R^{2e})_r C(=NS(O)_2R^{2e})NR^{2e}R^{2e}$, $(CR^{2e}R^{2e})_r NR^{2e}(=NR^{2e})NR^{2e}R^{2e}$, $(CR^{2e}R^{2e})_r C(O)NR^{2e}(=NR^{2e})NR^{2e}R^{2e}$, $(CR^{2e}R^{2e})_r SO_2NR^{2e}R^{2e}$, $(CR^{2e}R^{2e})_r NR^{2e}SO_2NR^{2e}R^{2e}$, $(CR^{2e}R^{2e})_r NR^{2e}SO_2$—$C_{1-4}$ alkyl, $(CR^{2e}R^{2e})_r NR^{2e}SO_2R^{2e}$, $(CR^{2e}R^{2e})_r S(O)_p R^{2e}$, $(CR^{2e}R^{2e})_r (CF_2)_t CF_3$;

$R^5$, at each occurrence, is selected from H, $C_{1-6}$ alkyl, =O, $(CH_2)_r OR^3$, F, Cl, Br, I, —CN, $NO_2$, $(CH_2)_r NR^3R^{3a}$, $(CH_2)_r C(O)R^3$, $(CH_2)_r C(O)OR^{3c}$, $(CH_2)_r NR^3C(O)R^{3a}$, $(CH_2)_r C(O)NR^3R^{3a}$, $(CH_2)_r NR^3C(O)NR^3R^{3a}$, $(CH_2)_r CH(=NOR^{3d})$, $(CH_2)_r C(=NR^3)NR^3R^{3a}$, $(CH_2)_r NR^3C(=NR^3)NR^3R^{3a}$, $(CH_2)_r SO_2NR^3R^{3a}$, $(CH_2)_r NR^3SO_2NR^3R^{3a}$, $(CH_2)_r NR^3SO_2$—$C_{1-4}$ alkyl, $(CH_2)_r NR^3SO_2CF_3$, $(CH_2)_r NR^3SO_2$-phenyl, $(CH_2)_r S(O)_p CF_3$, $(CH_2)_r S(O)_p$—$C_{1-4}$ alkyl, $(CH_2)_r S(O)_p$-phenyl, $(CF_2)_t CF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_r OR^3$, $(CH_2)_r NR^3R^{3a}$, $(CH_2)_r C(O)R^3$, $(CH_2)_r C(O)OR^{3c}$, $(CH_2)_r NR^3C(O)R^{3a}$, $(CH_2)_r C(O)NR^3R^{3a}$, $(CF_2)_t CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

$R^6$, at each occurrence, is selected from H, OH, $(CH_2)_r OR^2$, halo, $C_{1-4}$ alkyl, CN, $NO_2$, $(CH_2)_r NR^2R^{2a}$, $(CH_2)_r C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-6}$ alkyl-OC(O)—, $C_{6-10}$ aryl-O—, $C_{6-10}$ aryl-OC(O)—, $C_{6-10}$ aryl-CH$_2$—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-NH$_2$—C(O)—, phenyl-NH$_2$—C(O)—, and phenyl $C_{0-4}$ alkyl-C(O)—;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6;

r1, at each occurrence, is selected from 1, 2, 3, 4, 5, and 6; and t, at each occurrence, is selected from 0, 1, 2, and 3.

In a second embodiment, the present invention provides a novel compound of formula Ib, Ic, Ie, or If, wherein:

G is a group of formula IIa or IIb:

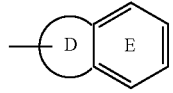

IIa

-continued

IIb ring D, including the two atoms of ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with a 5 membered heterocycle consisting of: carbon atoms and 1–4 heteroatoms selected from the group consisting of N, O, and $S(O)_p$, wherein the 5 membered heterocycle is substituted with 0–1 carbonyls and 1–2 R and has 0–3 ring double bonds;

R is selected from H, $C_{1-4}$ alkyl, F, Cl, OH, $OCH_3$, $OCH_2CH_3$, $OCH(CH_3)_2$, CN, $C(=NH)NH_2$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $(CR^8R^9)_r NR^7R^8$, $C(O)NR^7R^8$, $CH_2C(O)NR^7R^8$, $S(O)_p NR^7R^8$, $CH_2S(O)_p NR^7R^8$, and $OCF_3$;

alternatively, when 2 R groups are attached to adjacent atoms, they combine to form methylenedioxy or ethylenedioxy;

$G_1$ is selected from H, $(CR^3R^{3a})C(O)R^2$, $NR^2R^{2a}$, $(CR^3R^{3a})(CR^3R^{3a})NR^2R^{2a}$, $OR^2$, $(CR^3R^{3a})(CR^3R^{3a})OR^2$, $(CR^3R^{3a})S(O)_p R^2$, $NR^2C(O)R^2$, $(CR^3R^{3a})(CR^3R^{3a})NR^2C(O)R^2$, $NR^2C(O)NR^2R^{2a}$, $(CR^3R^{3a})(CR^3R^{3a})NR^2C(O)NR^2R^{2a}$, $NR^2C(O)OR^2$, $(CR^3R^{3a})(CR^3R^{3a})NR^2C(O)OR^2$, $(CR^3R^{3a})S(O)_2NR^2R^{2a}$, $NR^2S(O)_2NR^2R^{2a}$, $(CR^3R^{3a})NR^2S(O)_2NR^2R^{2a}$, $OC(O)R^2$, $(CR^3R^{3a})(CR^3R^{3a})OC(O)R^2$, $(CR^3R^{3a})C(O)OR^2$, $(CR^3R^{3a})C(O)NR^2R^{2a}$, $(CR^3R^{3a})C(O)NR^2(CR^3R^{3a})(CR^3R^{3a})OR^2$, $(CR^3R^{3a})C(O)NR^2(CR^3R^{3a})(CR^3R^{3a})(CR^3R^{3a})OR^2$, $(CR^3R^{3a})C(O)NR^2(CR^3R^{3a})(CR^3R^{3a})NR^2R^{2a}$, $(CR^3R^{3a})C(O)NR^2(CR^3R^{3a})(CR^3R^{3a})NR^2R^{2a}$, $(CR^3R^{3a})C(O)NR^2(CR^3R^{3a})(CR^3R^{3a})NR^2R^{2a}$, $(CR^3R^{3a})C(O)NR^2(CR^3R^{3a})C(O)NR^2R^{2a}$, $(CR^3R^{3a})C(O)NR^2(CR^3R^{3a})(CR^3R^{3a})C(O)NR^2R^{2a}$, $(CR^3R^{3a})C(O)NR^2(CR^3R^{3a})C(O)OR^2$, $(CR^3R^{3a})C(O)NR^2(CR^3R^{3a})C(O)OR^2$, $C_{1-6}$ alkyl substituted with 0–1 $R^{1a}$, $C_{2-6}$ alkenyl substituted with 0–1 $R^{1a}$, $C_{2-6}$ alkynyl substituted with 0–1 $R^{1a}$, $(CR^3R^{3a})_{0-4}$—$C_{3-10}$ carbocycle substituted with 0–1 $R^{1a}$, and $(CR^3R^{3a})_{0-4}$-5–12 membered heterocycle consisting of: carbon atoms and 1–4 heteroatoms selected from the group consisting of N, O, and $S(O)_p$ and substituted with 0–1 $R^{1a}$;

A is selected from: $C_{4-10}$ cycloalkyl substituted with 0–2 $R^{4c}$, $C_{4-10}$ cycloalkenyl substituted with 0–2 $R^{4c}$, and 5–10 membered heterocycle consisting of: carbon atoms and 1–4 heteroatoms selected from the group consisting of N, O, and $S(O)_p$ and substituted with 0–2 $R^{4c}$, wherein the heterocycle has 0–1 ring double bonds;

$R^{1a}$, at each occurrence, is selected from H, —$(CR^3R^{3a})_r$—$R^{1b}$, —$(CR^3R^{3a})_r$—O—$(CR^3R^{3a})_r$—$R^{1b}$, —$C_{2-6}$ alkenylene-$R^{1b}$, —$C_{2-6}$ alkynylene-$R^{1b}$, —$(CR^3R^{3a})_r$—C(=$NR^{1b}$)$NR^3R^{1b}$, $NR^3(CR^3R^{3a})_r R^{1c}$, $O(CR^3R^{3a})_r R^{1c}$, $(CR^3R^{3a})_r SCR^3R^{3a}R^{1c}$, $(CR^3R^{3a})_r NR^3(CR^3R^{3a})_r R^{1b}$, $(CR^3R^{3a})_rC(O)NR^2(CR^3R^{3a})_rR^{1b}$, $CO_2(CR^3R^{3a})_rR^{1b}$, $O(CR^3R^{3a})_rR^{1b}$, $S(O)_p(CR^3R^{3a})_rR^{1d}$, $O(CR^3R^{3a})_rR^{1d}$, $NR^3(CR^3R^{3a})_rR^{1d}$, $OC(O)NR^3(CR^3R^{3a})_rR^{1d}$, $NR^3C(O)NR^3(CR^3R^{3a})_rR^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–10 membered carbocyclic or heterocyclic ring consisting of: carbon atoms and 0–4 heteroatoms selected from the group consisting of N, O, and $S(O)_p$, this ring being substituted with 0–2 $R^4$ and 0–3 ring double bonds;

alternatively, when two $R^{1a}$ groups are attached to adjacent atoms, together with the atoms to which they are attached, they form a 5–7 membered carbocyclic or heterocyclic ring consisting of: carbon atoms and 0–4 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $(CR^3R^{3a})_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2a}$, $NR^2C(O)_2R^{2a}$, $OC(O)NR^{2a}$, $C(O)NR^2R^{2a}$, $C(O)NR^2(CH_2)_rOR^2$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2CH_2OH$, $CH_2CH_2CH_2OH$, $CH_2CH_2NMe_2$, $CH_2CH_2CH_2NMe_2$, benzyl, $C_{5-6}$ carbocycle substituted with 0–2 $R^{4b}$, a $C_{5-6}$ carbocyclic-$CH_2$ group substituted with 0–2 $R^{4b}$, a 5–6 membered heterocycle consisting of: carbon atoms and 1–4 heteroatoms selected from the group consisting of N, O, and $S(O)_p$ and substituted with 0–2 $R^{4b}$, and a 5–6 membered heterocycle-$CH_2$ group consisting of: carbon atoms and 1–4 heteroatoms selected from the group consisting of N, O, and $S(O)_p$ and substituted with 0–2 $R^{4b}$ $R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2CH_2OH$, $CH_2CH_2CH_2OH$, $CH_2CH_2NMe_2$, $CH_2CH_2CH_2NMe_2$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^{2e}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $NR^3R^{3a}$ forms a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, $=O$, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^5$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^{4a}$ is selected from H, $=O$, $C_{1-4}$ alkyl, $NR^{2d}R^{2d}$, $N(\rightarrow O)R^{2d}R^{2d}$, $OR^{2d}$, $—NR^{2d}C(O)R^{2d}$, $—C(O)R^{2d}$, $—OC(O)R^{2d}$, $—C(O)NR^{2d}R^{2d}$, $—C(O)OR^{2d}$, $—SO_2NR^{2d}R^{2d}$, $—NR^{2d}SO_2R^{2d}$, and $—S(O)_pR^{2d}$, provided that $S(O)_pR^{2d}$ forms other than $S(O)_2H$ or $S(O)H$ and further provided that $R^{4a}$ is other than a hydroxamic acid;

$R^{4b}$, at each occurrence, is selected from H, $=O$, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)R^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2$—$CF_3$;

$R^{4c}$, at each occurrence, is selected from H, $=O$, $OR^{2e}$, $CH_2OR^{2e}$, $(CH_2)_2OR^{2e}$, F, Cl, Br, I, $C_{1-4}$ alkyl, —CN, $NO_2$, $NR^{2e}R^{2e}$, $CH_2NR^{2e}R^{2e}$, $(CH_2)_2NR^{2e}R^{2e}$, $C(O)R^{2e}$, $NR^{2e}C(O)R^{2e}$, $C(O)NR^{2e}R^{2e}$, $SO_2NR^{2e}R^{2e}$, $S(O)_pR^{2e}$, $CF_3$, and $CF_2CF_3$;

$R^5$, at each occurrence, is selected from H, $=O$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, CF₃, phenyl substituted with 0–2 R⁶, naphthyl substituted with 0–2 R⁶, and benzyl substituted with 0–2 R⁶;

R⁵ᵃ, at each occurrence, is selected from CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, OR³, CH₂OR³, NR³R³ᵃ, CH₂NR³R³ᵃ, C(O)R³, CH₂C(O)R³, C(O)OR³ᶜ, CH₂C(O)OR³ᶜ, NR³C(O)R³ᵃ, CH₂NR³C(O)R³ᵃ, C(O)NR³R³ᵃ, CH₂C(O)NR³R³ᵃ, CF₃, CF₂CF₃, phenyl substituted with 0–2 R⁶, naphthyl substituted with 0–2 R⁶, and benzyl substituted with 0–2 R⁶, provided that R⁵ᵃ does not form a S—N or S(O)ₚ—C(O) bond; and R⁶, at each occurrence, is selected from H, OH, OR², F, Cl, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, —CN, NO₂, NR²R²ᵃ, CH₂NR²R²ᵃ, C(O)R²ᵇ, CH₂C(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂C₁₋₄ alkyl.

In a third embodiment, the present invention provides a novel compound, of formula Ib, Ic, Ie, or If, wherein:

X is SO₂;

G-G₂- is selected from the group:

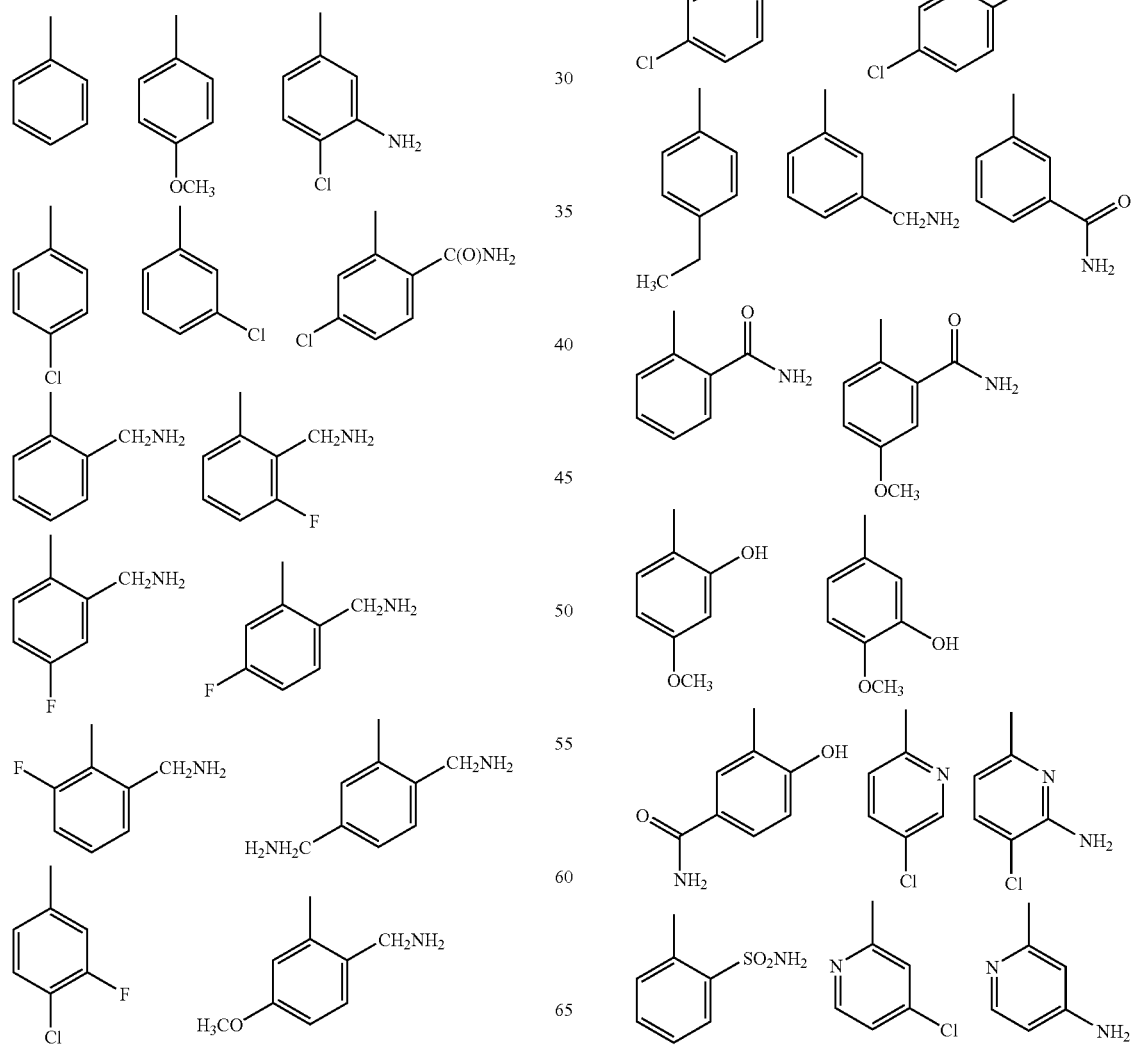

-continued
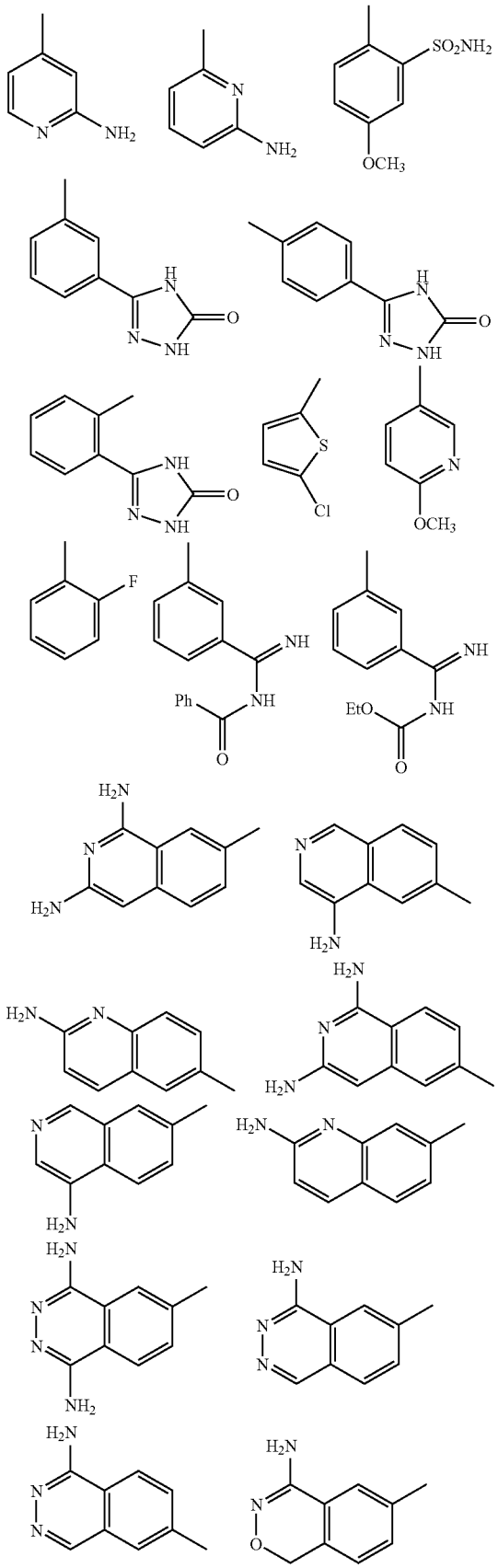
-continued
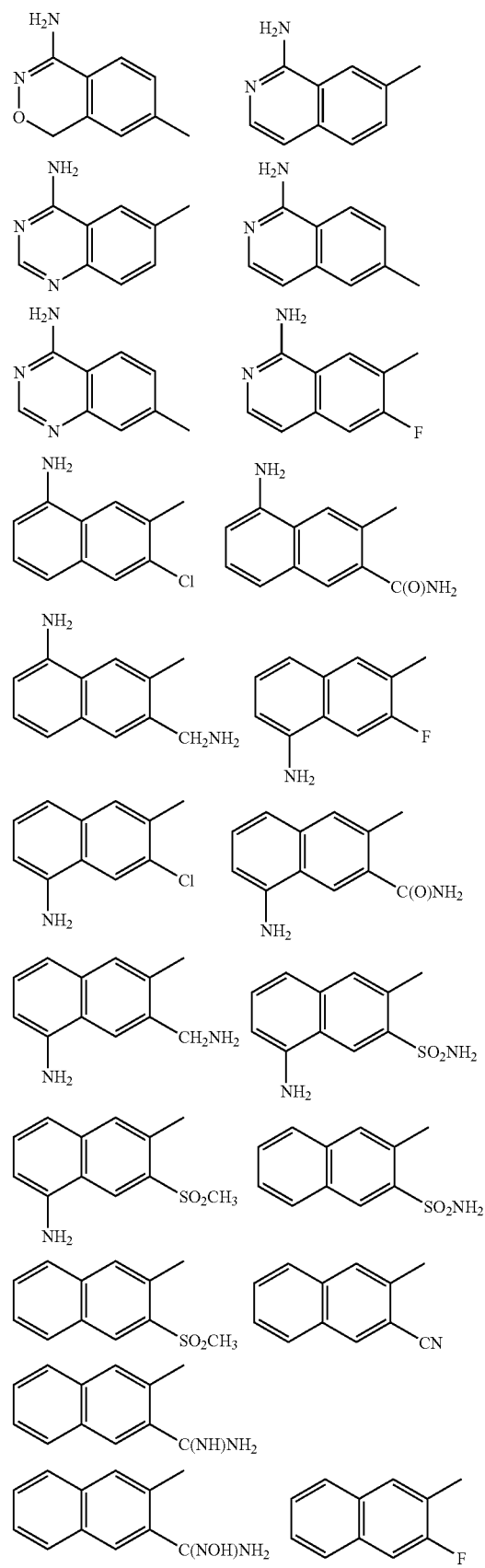

-continued
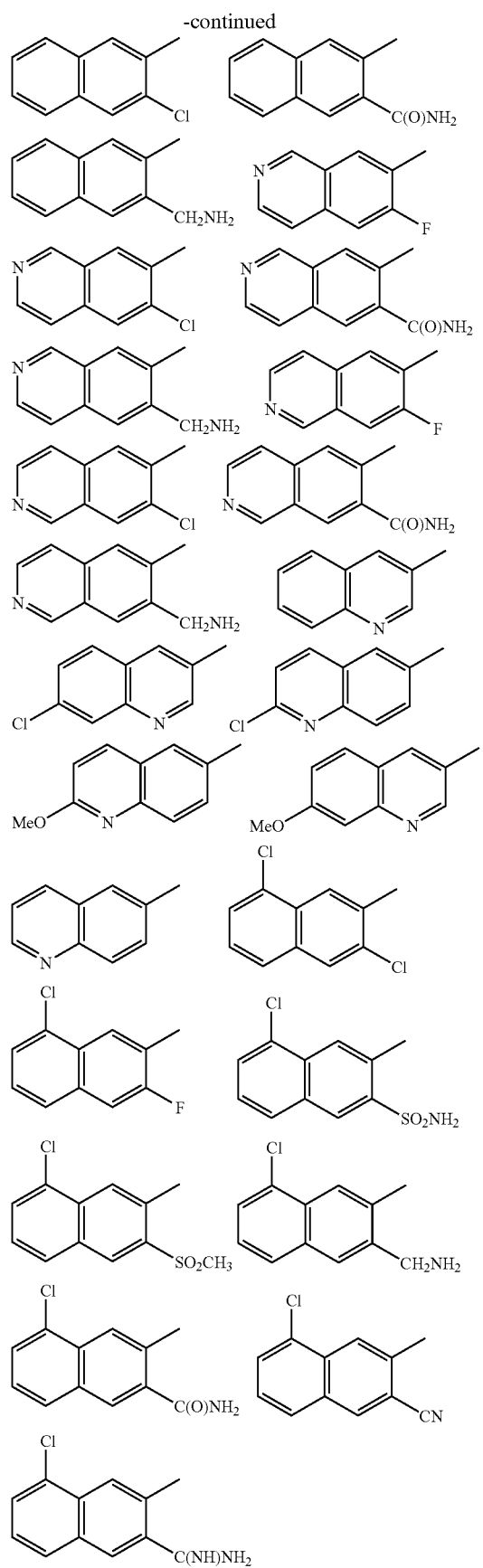
-continued
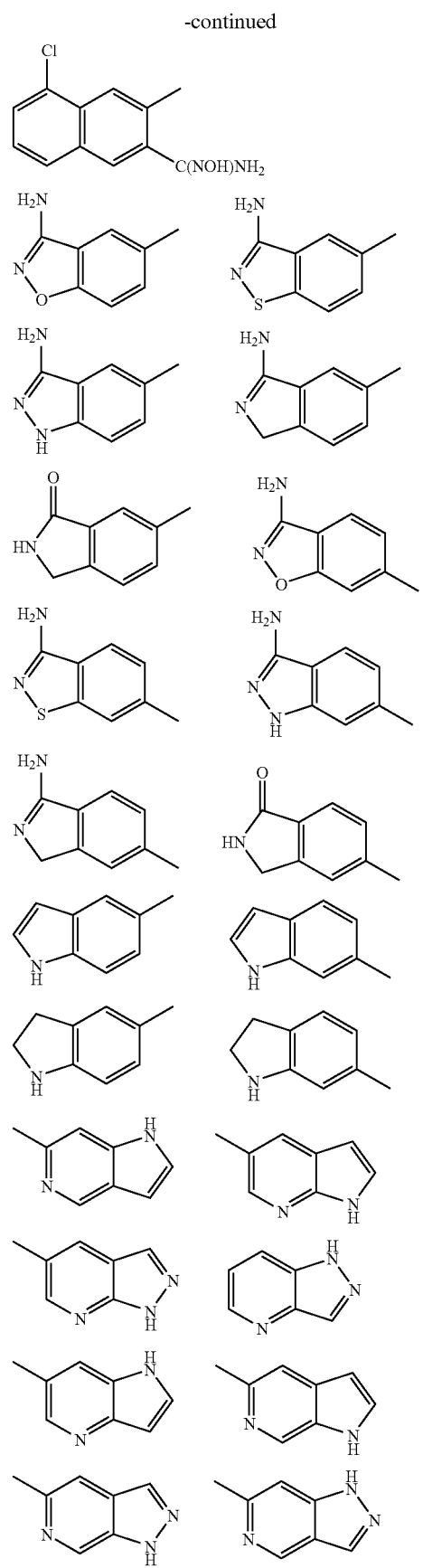

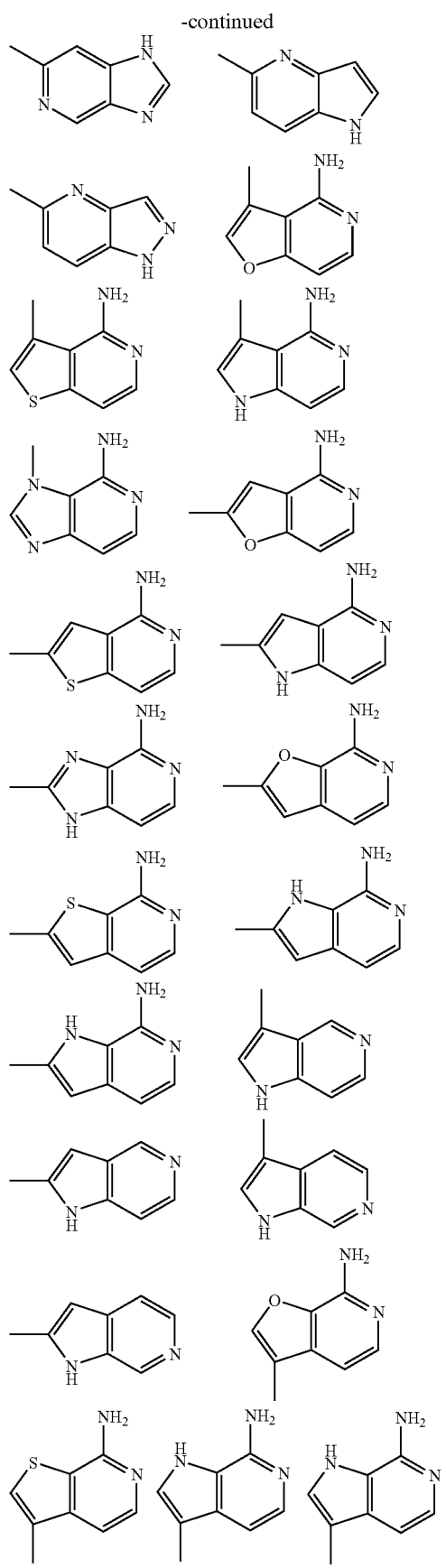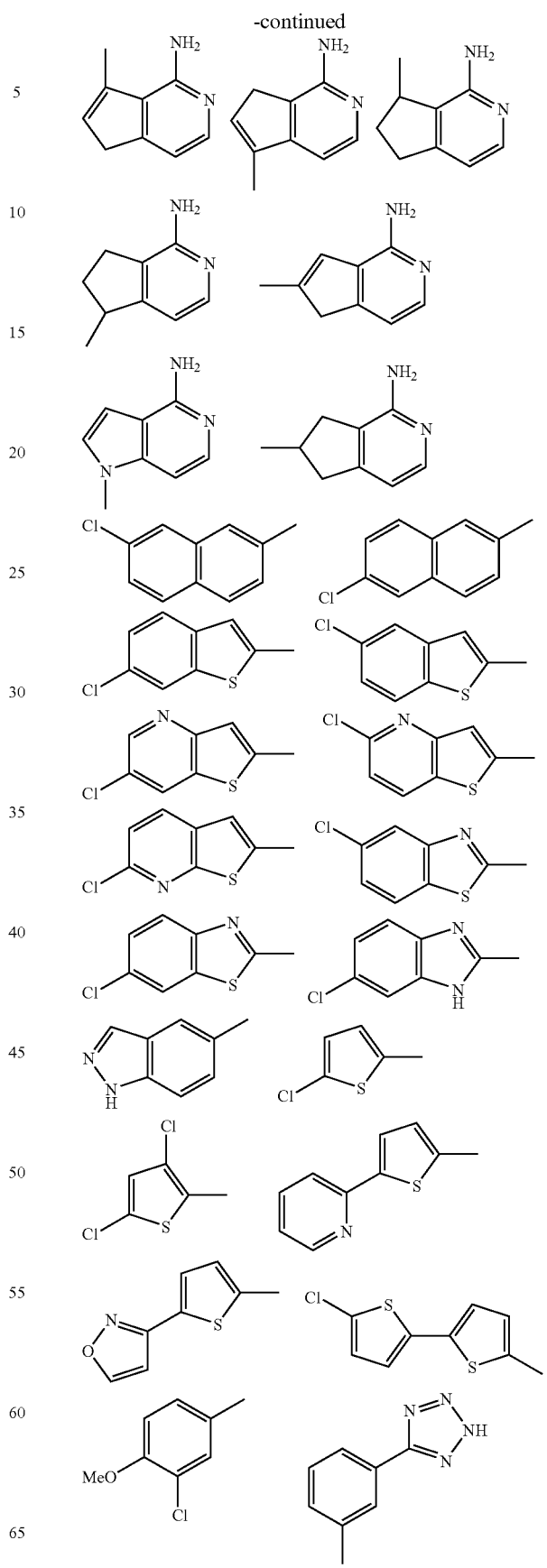

-continued
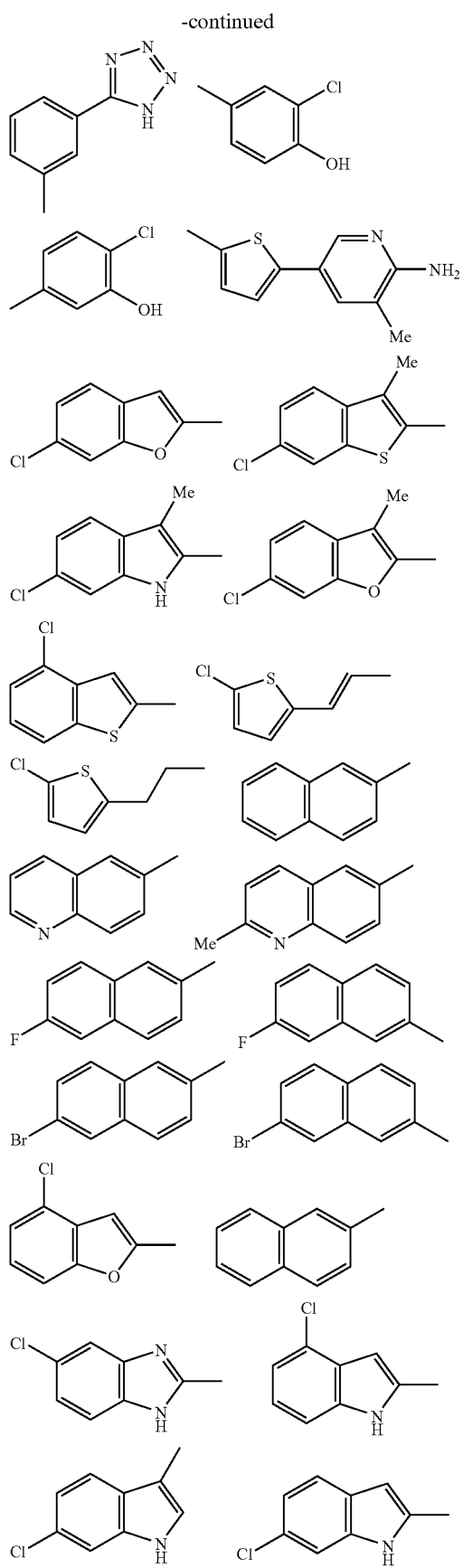
-continued
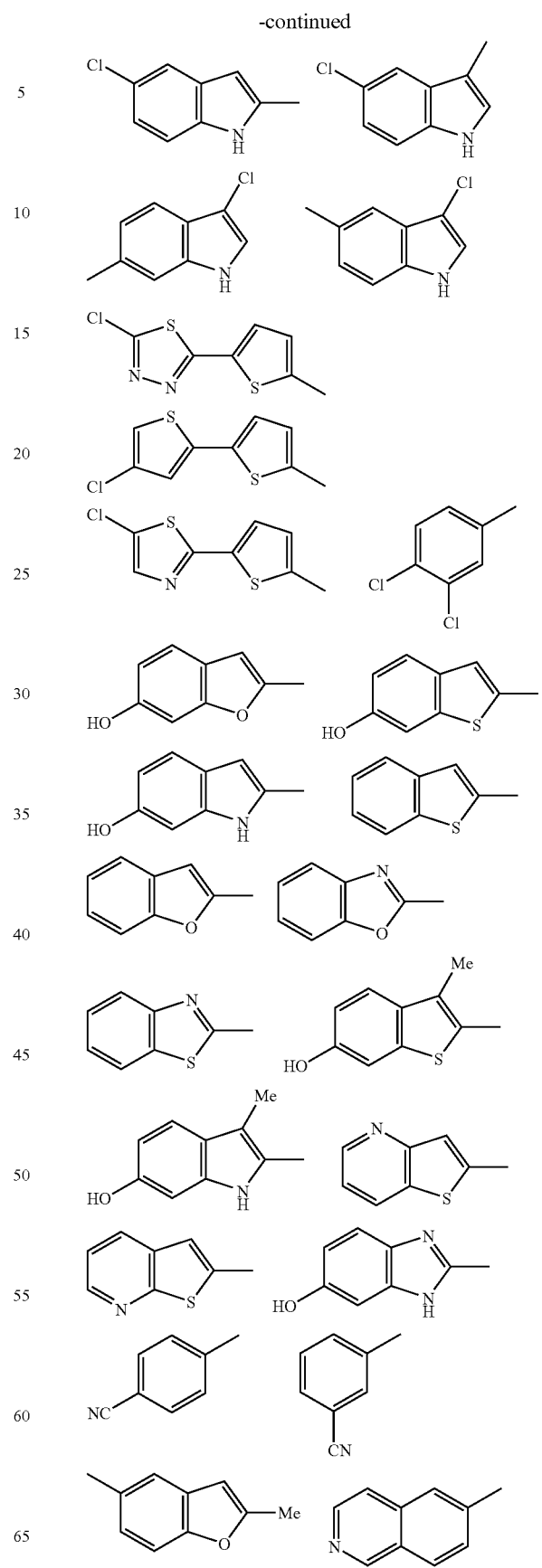

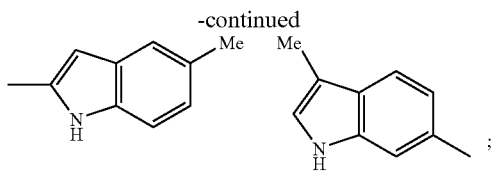

G₁ is selected from H, $C_{1-6}$ alkyl substituted with 0–1 $R^{1a}$, $CH_2C(O)OR^2$, $CH_2C(O)NR^2R^{2a}$, $CH_2C(O)NR^2CH_2CH_2OR^2$, $CH_2C(O)NR^2CH_2CH_2NR^2R^{2a}$, $CH_2C(O)NR^2CH_2C(O)NR^2R^{2a}$, $CH_2C(O)NR^2CH_2C(O)OR^2$, $CH_2C(O)NR^2CH_2CH_2C(O)OR^2$, $CH_2CH_2OR^2$, $CH_2(CH_3)_2OR^2$, $CH_2CN$, and $CH_2CH_2CN$;

alternatively, G₁ is selected from:

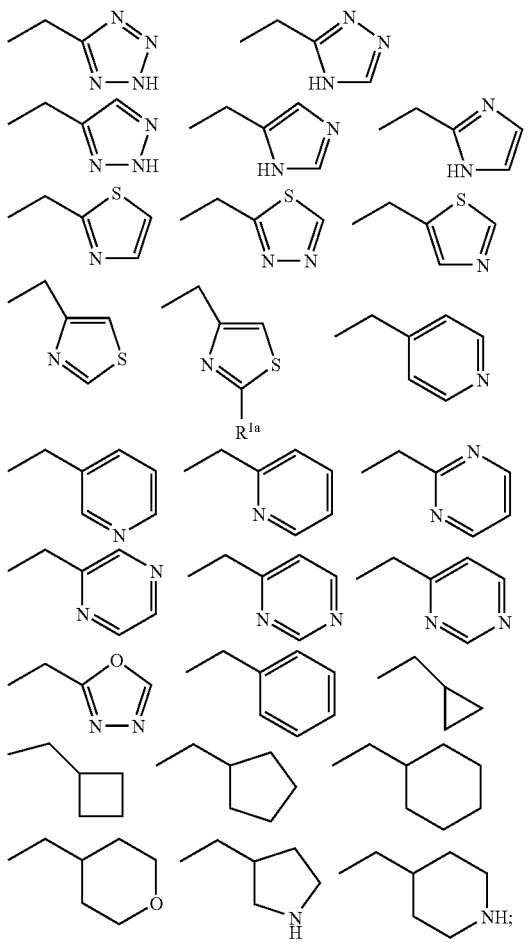

A is selected from one of the following carbocyclic and heterocyclic groups which are substituted with 0–2 $R^{4c}$;

cyclohexyl, cyclopentyl, azetidinyl, oxazolinyl, isoxazolinyl, thiazolinyl, isothiazolinyl, piperidinyl, piperazinyl, hexahydropyrimidyl, morpholinyl, and pyrrolidinyl;

B is selected methyl, ethyl, 2-propyl, 1-butyl, 2-methyl-1-propyl, 1,1-dimethyl-1-ethyl, 1-pentyl, 2-pentyl, 3-pentyl, 3-hexyl, cyclopropyl, cyclobutyl, cyclopentyl, cyclohexyl, $CH(CF_3)_2$, $CH(CHF_2)CH_3$, $CH_2CF_3$, $CH(CF_2CF_3)_2$, $CH(Cl)CF_3$, $C(O)CH_2CH_3$, $C(O)CH(CH_3)_2$, $C(O)CH_2CH_2CH_3$, $C(O)NHCH_2CH_3$, $C(O)N(CH_3)_2$, $C(O)N(CH_3)(CH_2CH_3)$, $C(O)OCH_2CH_3$, $C(O)C(CH_3)_3$, $SO_2CH_3$, $SO_2CH_2CH_3$, $SO_2CH_2CH_2CH_3$, $SO_2CH(CH_3)_2$, $SO_2CH(CH_3)CH_2CH_3$, $SO_2N(CH_3)_2$, $SO_2N(CH_3)CH_2CH_3$, $OCH_3$, $OCH_2CH_3$, $OCH(CH_3)_2$, $OCH(CH_3)CH_2CH_3$, $SCH_3$, $SCH_2CH_3$, $SCH(CH_3)_2$, $SCH(CH_3)CH_2CH_3$, $SCH(CH_2CH_3)_2$, $N(CH_3)_2$, $N(CH_2CH_3)_2$, $N(CH_3)CH_2CH_3$, $N(CH_2CH_3)CH_2CH_2CH_3$, $NHC(O)CH_3$, $NHC(O)CH_2CH_3$, $NHC(O)CH(CH_3)_2$, and $NHC(O)CH(CH_3)CH_2CH_3$;

$R^{1a}$, at each occurrence, is selected from H, $-(CH_2)_r-R^{1b}$, $-(CH_2)_r-O-(CH_2)_r-R^{1b}$, $-(CH_2)_r-C(=NR^{1b})NR^3R^{1b}$, $NR^3(CR^3R^{3a})_rR^{1c}$, $O(CR^3R^{3a})_rR^{1c}$, $(CH_2)_rNR^3(CH_2)_rR^{1b}$, $(CH_2)_rC(O)NR^2(CH_2)_rR^{1b}$, $CO_2(CH_2)_rR^{1b}$, $O(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–6 membered carbocyclic or heterocyclic ring consisting of: carbon atoms and 0–4 heteroatoms selected from the group consisting of N, O, and $S(O)_p$, this ring being substituted with 0–2 $R^4$ and 0–3 ring double bonds;

alternatively, when two $R^{1a}$ groups are attached to adjacent atoms, together with the atoms to which they are attached, they form a 5–6 membered carbocyclic or heterocyclic ring consisting of: carbon atoms and 0–4 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $(CH_2)_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2a}$, $C(O)NR^2R^{2a}$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, phenyl substituted with 0–2 $R^{4b}$, a benzyl substituted with 0–2 $R^{4b}$, a 5–6 membered heterocycle-$CH_2$ group wherein said heterocycle consists of: carbon atoms and 1–4 heteroatoms selected from the group consisting of N, O, and $S(O)_p$ and substituted with 0–2 $R^{4b}$, and a 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, benzyl, phenyl substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and S(O)$_p$ and substituted with 0–2 R$^{4b}$;

R$^{2c}$, at each occurrence, is selected from CF$_3$, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl, phenyl substituted with 0–2 R$^{4b}$, and 5–6 membered aromatic heterocycle containing from 1–4 heteroatoms selected from the group consisting of N, O, and S(O)$_p$ and substituted with 0–2 R$^{4b}$;

R$^4$, at each occurrence, is selected from H, =O, CH$_2$OR$^2$, (CH$_2$)$_2$OR$^2$, OR$^2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, SO$_2$NR$^2$R$^{2a}$, CF$_3$, and CF$_2$CF$_3$;

R$^{4a}$ is selected from H, =O, CH$_3$, NR$^{2d}$R$^{2d}$, OR$^{2d}$, —NR$^{2d}$C(O)R$^{2d}$, —C(O)R$^{2d}$, —OC(O)R$^{2d}$, —C(O)NR$^{2d}$R$^{2d}$, and —C(O)OR$^{2d}$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, CH$_2$—C(O)R$^3$, C(O)OR$^{3c}$, CH$_2$—C(O)OR$^{3c}$, NR$^3$C(O)R$^{3a}$, CH$_2$NR$^3$C(O)R$^{3a}$, C(O)NR$^3$R$^{3a}$, CH$_2$—C(O)NR$^3$R$^{3a}$, SO$_2$NR$^3$R$^{3a}$, CH$_2$SO$_2$NR$^3$R$^{3a}$, NR$^3$SO$_2$—C$_{1-4}$ alkyl, CH$_2$NR$^3$SO$_2$—C$_{1-4}$ alkyl, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, and CF$_3$;

R$^{4c}$, at each occurrence, is selected from H, =O, CH$_2$OR$^{2e}$, (CH$_2$)$_2$OR$^{2e}$, OR$^{2e}$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^{2e}$R$^{2e}$, CH$_2$NR$^{2e}$R$^{2e}$, (CH$_2$)$_2$NR$^{2e}$R$^{2e}$, C(O)R$^{2e}$, NR$^{2e}$C(O)R$^{2e}$, C(O)NR$^{2e}$R$^{2e}$, NR$^{2e}$C(O)NR$^{2e}$R$^{2e}$, SO$_2$NR$^{2e}$R$^{2e}$, CF$_3$, and CF$_2$CF$_3$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, SO$_2$NR$^2$R$^{2a}$, and NR$^2$SO$_2$C$_{1-4}$ alkyl.

In a fourth embodiment, the present invention provides a novel compound, wherein:

G-G$_2$- is selected from the group:

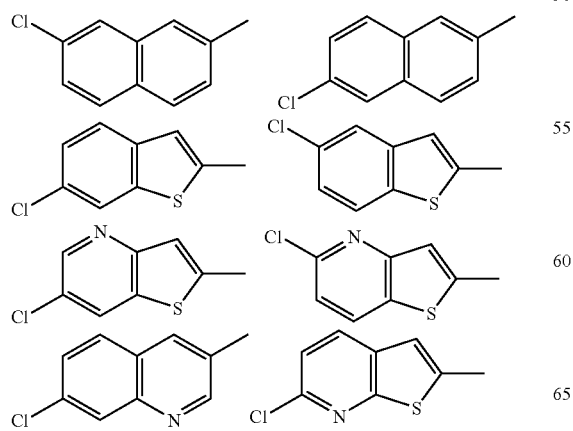

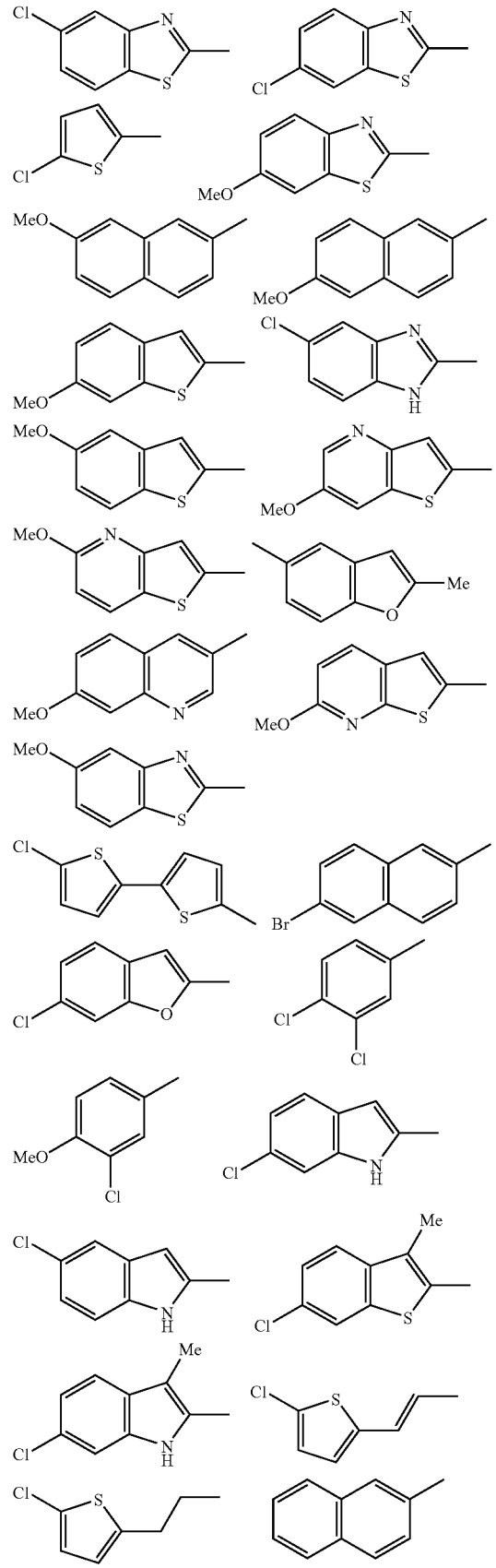

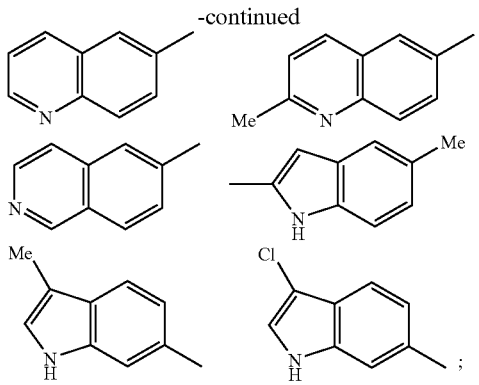

$G_1$ is selected from H, $C_{1-4}$ alkyl substituted with 0–1 $R^{1a}$, $CH_2C(O)OR^2$, $CH_2C(O)NR^2R^{2a}$, $CH_2C(O)NHCH_2CH_2OR^2$, $CH_2C(O)NHCH_2CH_2NR^2R^{2a}$, $CH_2C(O)N(CH_3)CH_2CH_2OR^2$, $CH_2C(O)N(CH_3)CH_2CH_2NR^2R^{2a}$, $CH_2C(O)NHCH_2C(O)NR^2R^{2a}$, $CH_2C(O)NHCH_2C(O)NR^2R^{2a}$, $CH_2C(O)NHCH_2C(O)OR^2$, $CH_2C(O)NHCH_2C(O)OR^2$, $CH_2CH_2OR^2$, $CH_2(CH_3)_2OR^2$, $CH_2CN$, and $CH_2CH_2CN$;

alternatively, $G_1$ is selected from:

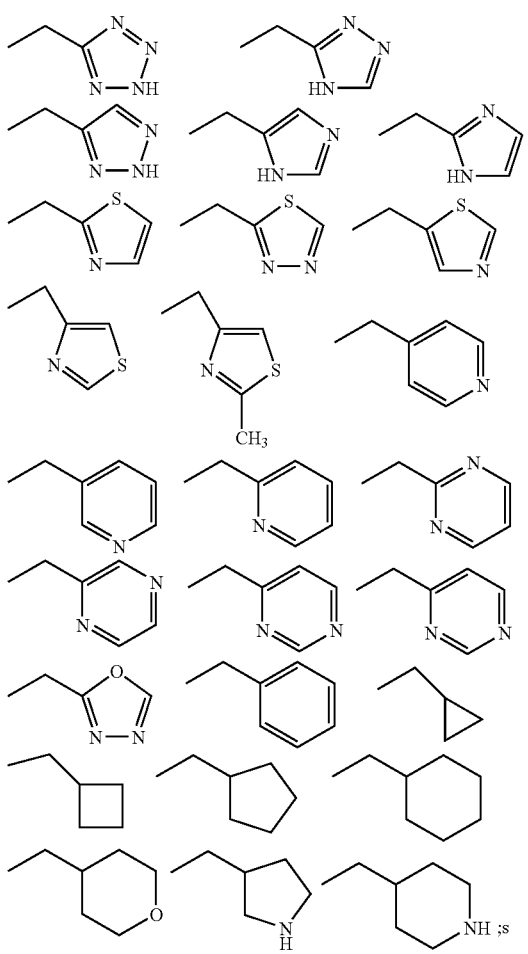

A is selected from one of the following carbocyclic and heterocyclic groups which are substituted with 0–2 $R^{4c}$;

cyclopentyl, cyclohexyl, piperidinyl, hexahydropyrimidyl, pyrrolidinyl, and piperazinyl;

$R^{1a}$ is selected from H, $R^{1b}$, $C(CH_3)_2R^{1b}$, $CH(CH_3)R^{1b}$, $CH_2R^{1b}$, $CH_2CH_2R^{1b}$, $CH_2OCH_2CH_2R^{1b}$, $OCH_2CH_2R^{1b}$, $(CH_2)_rNR^3CH_2CH_2R^{1b}$, $NR^3(CR^3R^{3a})_rR^{1c}$, $O(CR^3R^{3a})_rR^{1c}$, $(CH_2)_rC(O)NR^2(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—S, O—O, or N—CN bond;

alternatively, when two $R^{1a}$ groups are attached to the same carbon atom, together with the carbon atom to which they are attached they form a 3–6 membered carbocyclic or heterocyclic ring consisting of: carbon atoms and 0–4 heteroatoms selected from the group consisting of N, O, and $S(O)_p$, this ring being substituted with 0–2 $R^4$ and 0–2 ring double bonds;

alternatively, when two $R^{1a}$ groups are attached to adjacent atoms, together with the atoms to which they are attached, they form a 5–7 membered carbocyclic or heterocyclic ring consisting of: carbon atoms and 0–4 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $(CH_2)_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2a}$, $C(O)NR^2R^{2a}$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-6}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{2a}$, at each occurrence, is selected from H, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, and benzyl;

alternatively, $NR^2R^{2a}$ forms a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle containing from 1–4 heteroatoms selected from the group consisting of N, O, and $S(O)_p$ and substituted with 0–1 $R^{4b}$;

$R^4$, at each occurrence, is selected from H, =O, OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from H, =O, $CH_3$, $NR^{2d}R^{2d}$, and $OR^{2d}$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from H, =O, OH, $OR^{2e}$, $CH_2OR^{2e}$, $(CH_2)_2OR^{2e}$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2e}R^{2e}$, $CH_2NR^{2e}R^{2e}$, $(CH_2)_2NR^{2e}R^{2e}$, $C(O)R^{2e}$, $NR^{2e}C(O)R^{2e}$, $C(O)NR^{2e}R^{2e}$, $SO_2NR^{2e}R^{2e}$, $CF_3$, and $CF_2CF_3$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

In a fifth embodiment, the present invention provides a novel, wherein:

G-$G_2$- is selected from:

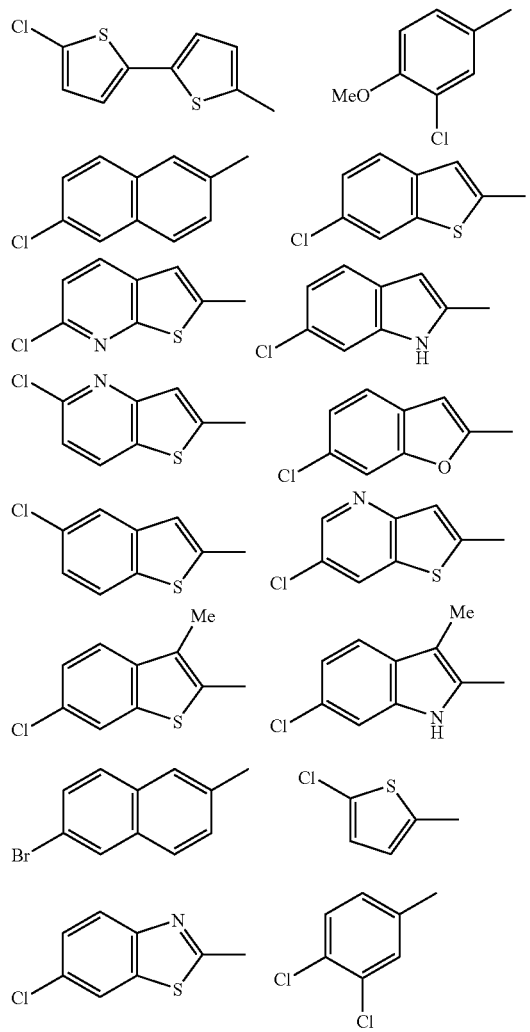

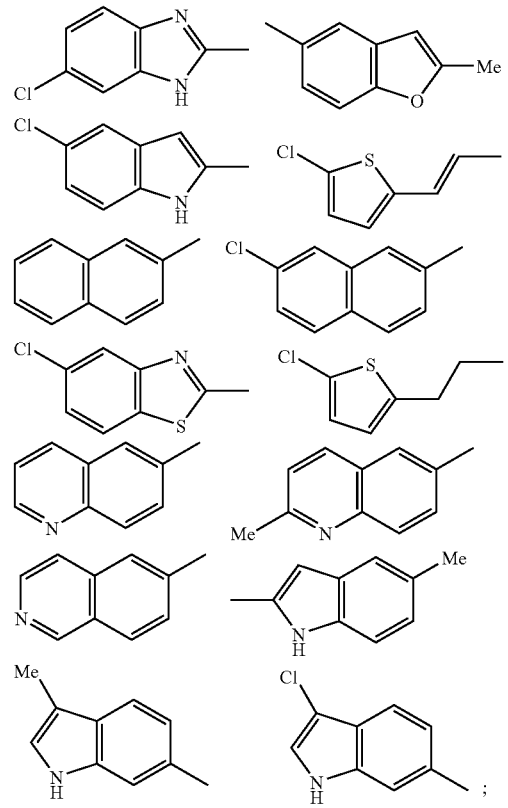

B is selected from methyl, ethyl, 2-propyl, 1-butyl, 2-methyl-1-propyl, 1-pentyl, cyclopropyl, cyclobutyl, cyclopentyl, cyclohexyl, $CH(CF_3)_2$, $CH(CHF_2)CH_3$, $CH_2CF_3$, $CH(CF_2CF_3)_2$, $C(O)NHCH_2CH_3$, $C(O)N(CH_3)_2$, $C(O)CH_2CH_2CH_3$, $C(O)C(CH_3)_3$, $N(CH_3)_2$, $N(CH_2CH_3)_2$, $NHC(O)CH_2CH_3$, $NHC(O)CH(CH_3)_2$, and $SO_2CH_3$;

$R^{1a}$ is selected from H, $CH_3$, $CH_2CH_3$, $CH_2CH_2CH_3$, $CH_2(CH_3)_2$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $NHCOCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, $NHSO_2NHCH_3$, $NHSO_2N(CH_3)_2$, $NHCO_2R^{2a}$, $NHC(O)NHR^{2a}$, $CH_2OCH_2CH_2NR^2R^{2a}$, $C(O)NR^2R^{2a}$, $CH_2CH_2OR^2$, $CH_2C(O)NR^2CH_2CH_2OR^2$, $C(O)NHCH_2CH_2NR^2R^{2a}$, $CH_2C(O)NHCH_2CH_2NR^2R^{2a}$, $C(O)NCH_3CH_2CH_2NR^2R^{2a}$, $CH_2C(O)NCH_3CH_2CH_2NR^2R^{2a}$, $CH_2NHCH_2CH_2NR^2R^{2a}$, $CH_2N(CH_3)CH_2CH_2NR^2R^{2a}$, phenyl substituted with 0–2 $R^{4b}$, —$CH_2$-phenyl substituted with 0–2 $R^{4b}$, 5–10 membered aromatic heterocycle consisting of carbon atoms and from 1–4 heteroatoms selected from the group consisting of N, O, and $S(O)_p$ and substituted with 0–2 $R^{4b}$, and —$CH_2$-5–10 membered aromatic heterocycle consisting of carbon atoms and from 1–4 heteroatoms selected from the group consisting of N, O, and $S(O)_p$ and substituted with 0–2 $R^{4b}$, provided that $R^{1a}$ forms other than an N-halo, N—S, O—O, or N—CN bond;

alternatively, when two $R^{1a}$ groups are attached to adjacent atoms, together with the atoms to which they are attached, they form a 5–6 membered carbocyclic or heterocyclic ring consisting of: carbon atoms and 0–1 heteroatoms selected from the group consisting of N, O, and S(O)$_p$, this ring being substituted with 0–2 R$^{4b}$ and 0–3 ring double bonds;

R$^2$, at each occurrence, is selected from H, CH$_3$, CH$_2$CH$_3$, CH$_2$CH$_2$CH$_3$, CH(CH$_3$)$_2$, CH$_2$CH$_2$OH, CH$_2$CH$_2$CH$_2$OH, CH$_2$CH$_2$NMe$_2$, CH$_2$CH$_2$CH$_2$NMe$_2$, phenyl substituted with 0–1 R$^{4b}$, benzyl substituted with 0–1 R$^{4b}$, 5 membered aromatic heterocycle-CH$_2$ group wherein the heterocycle consists of: carbon atoms and 1–4 heteroatoms selected from the group consisting of N, O, and S(O)$_p$ and substituted with 0–1 R$^{4b}$ and 5 membered aromatic heterocycle consisting of: carbon atoms and 1–4 heteroatoms selected from the group consisting of N, O, and S(O)$_p$ and substituted with 0–1 R$^{4b}$;

R$^{2a}$, at each occurrence, is selected from H, CH$_3$, and CH$_2$CH$_3$, CH$_2$CH$_2$OH, CH$_2$CH$_2$CH$_2$OH, CH$_2$CH$_2$NMe$_2$, and CH$_2$CH$_2$CH$_2$NMe$_2$, alternatively, NR$^2$R$^{2a}$ forms a 5 or 6 membered saturated, partially saturated or unsaturated ring substituted with 0–1 R$^{4b}$ and consisting of: 0–1 additional heteroatoms selected from the group consisting of N, O, and S(O)$_p$;

R$^{2b}$, at each occurrence, is selected from OCH$_3$, OCH$_2$CH$_3$, CH$_3$, and CH$_2$CH$_3$;

R$^{2c}$, at each occurrence, is selected from OH, OCH$_3$, OCH$_2$CH$_3$, CH$_3$, and CH$_2$CH$_3$;

R$^{4a}$ is selected from H, =O, CH$_3$, N(CH$_3$)$_2$, OH, and O-t-butyl; and

R$^{4b}$, at each occurrence, is selected from H, =O, OR$^3$, CH$_2$OR$^3$, F, Cl, CH$_3$, CH$_2$CH$_3$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$-phenyl, S(O)$_2$CH$_3$, S(O)$_2$-phenyl, and CF$_3$.

In a sixth embodiment, the present invention provides a novel compound, wherein the compound is selected from:

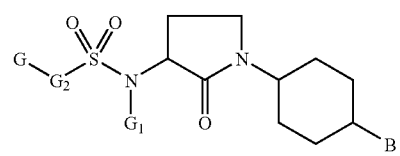

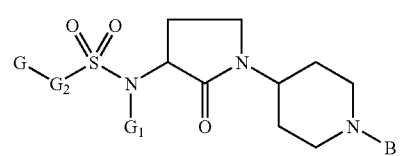

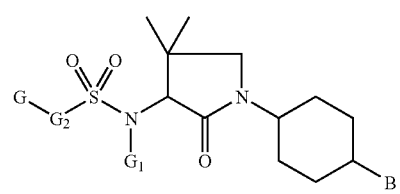

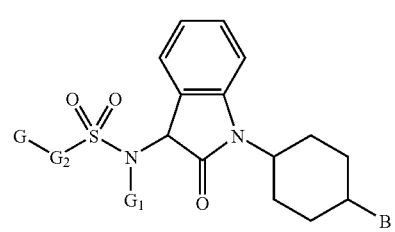

-continued

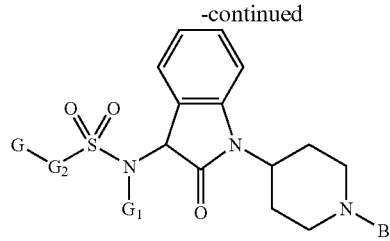

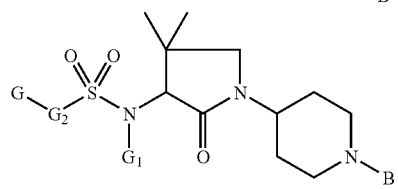

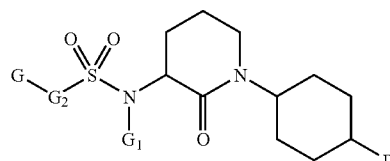

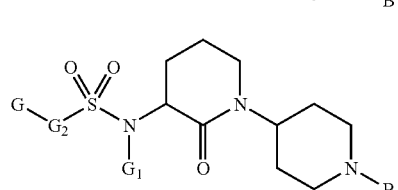

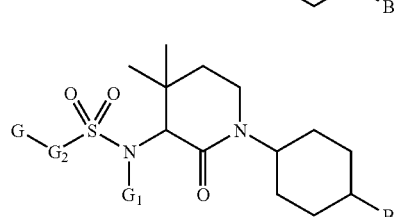

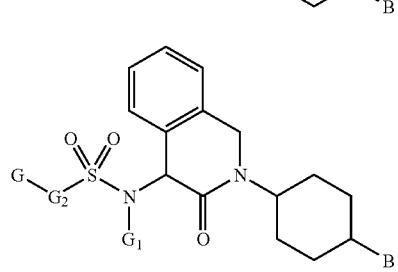

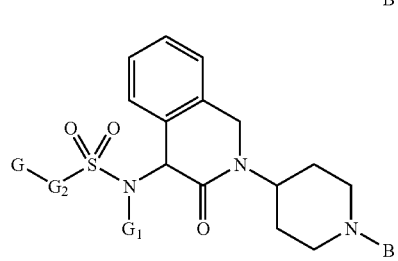

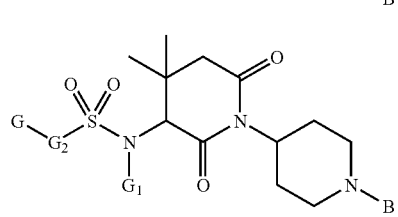

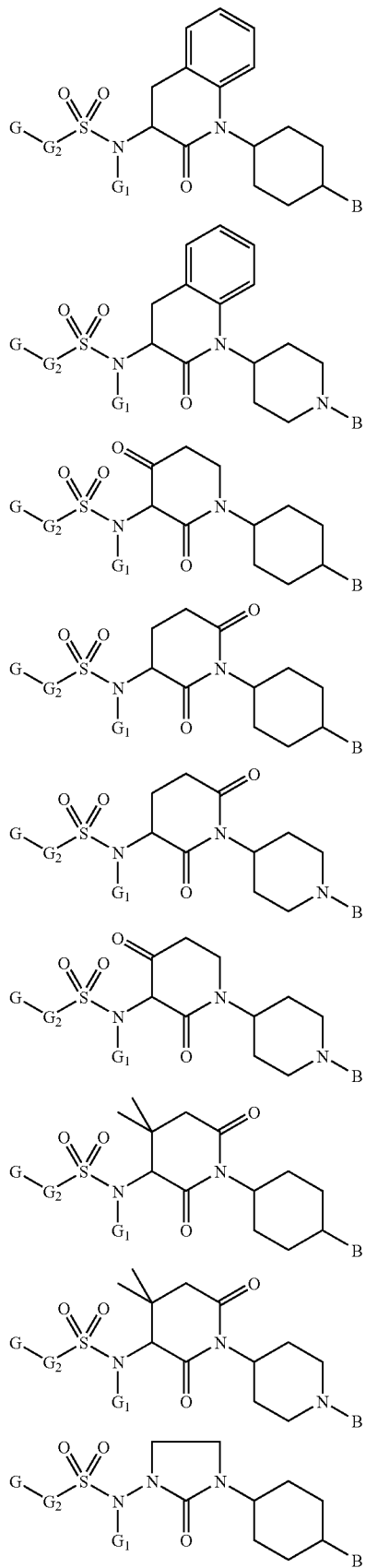
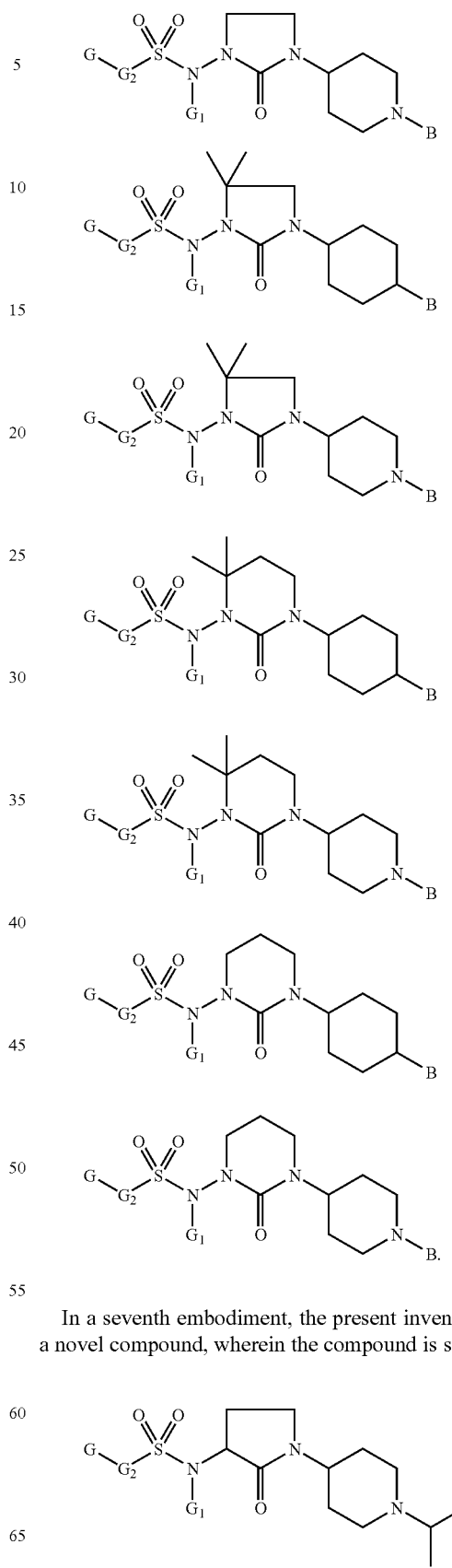
In a seventh embodiment, the present invention provides a novel compound, wherein the compound is selected from:
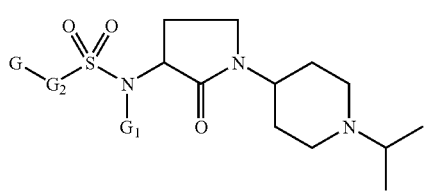

-continued
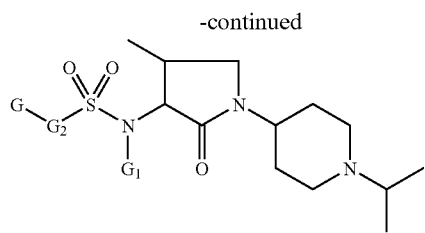
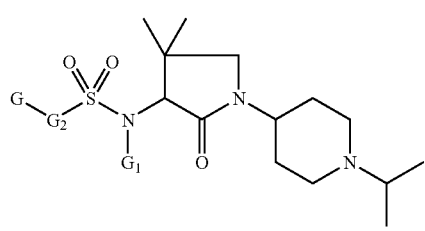
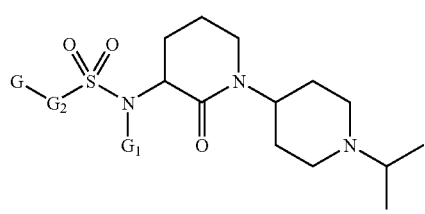
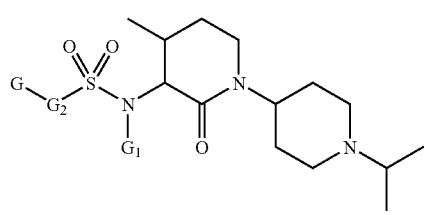
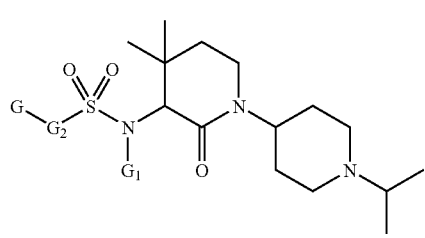
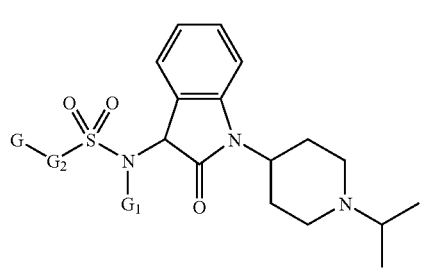
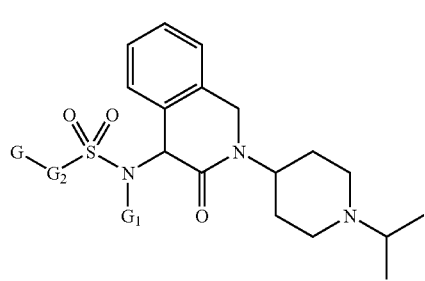
-continued
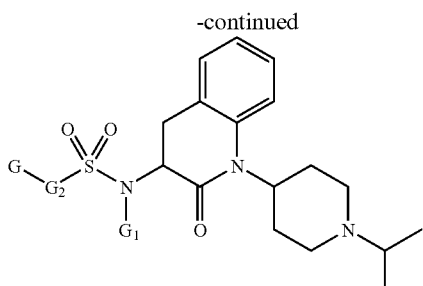
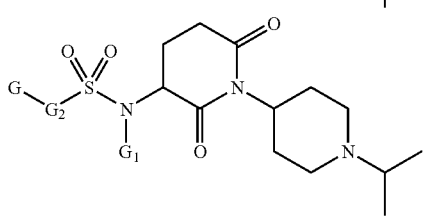
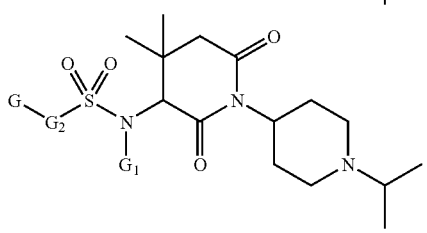
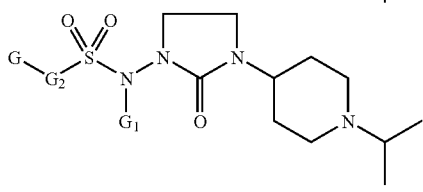
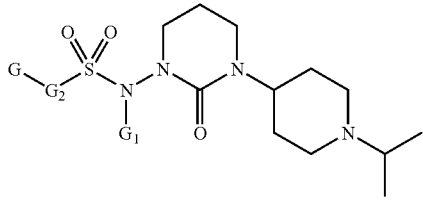
In an eighth embodiment, the present invention provides a novel compound, wherein the compound is selected from Examples 1–93, 96–100, and 102–107, or a pharmaceutically acceptable salt form thereof.
In a ninth embodiment, the present invention provides a novel compound of formula Ig–Ii:
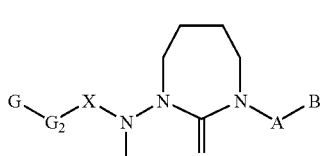
Ig
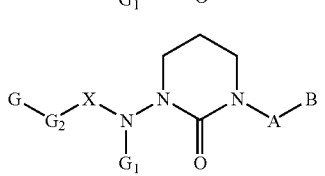
Ih

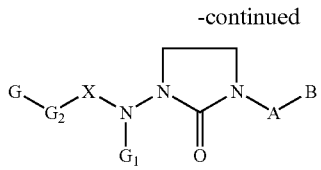

or a pharmaceutically acceptable salt thereof, wherein:

X is selected from $SO_2$, $CR^3R^3$, $C(O)$, $C(O)CR^3R^3$, and $NR^3C(O)$;

G is a group of formula Ia or IIb:

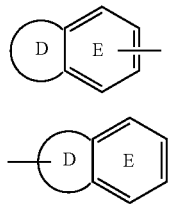

ring D, including the two atoms of Ring E to which it is attached, is a 5–6 membered ring consisting of carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–3 R and there are 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $C(=NR^8)NR^7R^9$, $NHC(=NR^8)NR^7R^9$, $ONHC(=NR^8)NR^7R^9$, $NR^8CH(=NR^7)$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rNR^7C(O)R^7$, $(CR^8R^9)_rOR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$, provided that $S(O)_pR^7$ and $S(O)_2R^3$ form other than $S(O)_2H$ or $S(O)H$;

alternatively, when 2 R groups are attached to adjacent atoms, they combine to form methylenedioxy or ethylenedioxy;

$G_1$ is selected from H, —CN, $(CR^3R^{3a})_{1-2}C(O)R^2$, $NR^2R^{2a}$, $(CR^3R^{3a})_{2-5}NR^2R^{2a}$, $OR^2$, $(CR^3R^{3a})_{2-5}OR^2$, $S(O)_pR^2$, $S(O)_pCR^3=CR^3R^2$, $(CR^3R^{3a})_{1-2}S(O)_pR^2$, $NR^2C(O)R^2$, $(CR^3R^{3a})_{2-5}NR^2C(O)R^2$, $NR^2C(O)NR^2R^{2a}$, $(CR^3R^{3a})_{2-5}NR^2C(O)NR^2R^{2a}$, $NR^2C(O)OR^2$, $(CR^3R^{3a})_{2-5}NR^2C(O)OR^2$, $(CR^3R^{3a})_{1-2}S(O)_2NR^2R^{2a}$, $NR^2S(O)_2NR^2R^{2a}$, $(CR^3R^{3a})_{2-5}NR^2S(O)_2NR^2R^{2a}$, $OC(O)R^2$, $(CR^3R^{3a})_{2-5}OC(O)R^2$, $(CR^3R^{3a})_{1-2}C(O)OR^2$, $(CR^3R^{3a})_{1-2}C(O)NR^2R^{2a}$, $(CR^3R^{3a})_{1-2}C(O)NR^2(CR^3R^{3a})(CR^3R^{3a})_{1-2}OR^2$, $(CR^3R^{3a})_{1-2}C(O)NR^2(CR^3R^{3a})(CR^3R^{3a})_{1-2}NR^2R^{2a}$, $(CR^3R^{3a})C(O)NR^2(CR^3R^{3a})_{1-2}C(O)NR^2R^{2a}$, $(CR^3R^{3a})C(O)NR^2(CR^3R^{3a})_{1-2}C(O)OR^2$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $(CR^3R^{3a})_{0-4}$–$C_{3-10}$ carbocycle substituted with 0–3 $R^{1a}$, and $(CR^3R^{3a})_{0-4}$-5–12 membered heterocycle consisting of: carbon atoms and 1–4 heteroatoms selected from the group consisting of N, O, and $S(O)_p$ and substituted with 0–3 $R^{1a}$;

$G_2$ is absent or is selected from $CR^3R^{3a}CR^3R^{3a}$ and $CR^3=CR^3$;

alternatively, $G_2$-X—N($G_1$) form a —CH=G group;

A is selected from: $C_{3-10}$ carbocycle substituted with 0–2 $R^4$, and 5–12 membered heterocycle consisting of: carbon atoms and 1–4 heteroatoms selected from the group consisting of N, O, and $S(O)_p$ and substituted with 0–2 $R^4$;

B is selected from Y, Z-Y, $N(B^1)C(O)C(R^3R^{3g})_{1-4}NB^2B^3$, $C(B^5)=NB^4$, and

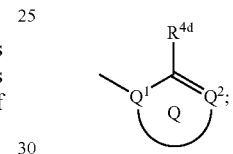

provided that lactam nitrogen and B are attached to different atoms on A and that the $R^{4d}$ shown is other than OH;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-2}$—$C_{3-7}$ carbocycle substituted with 0–2 $R^{4b}$, and —$(CH_2)_{0-2}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $C_{1-6}$ alkyl substituted with 0–2 $R^{4c}$, $C(O)R^{2e}$, $C(O)OR^{2d}$, $C(O)NR^{2d}R^{2d}$, $C(O)NH(CH_2)_2NR^{2d}R^{2d}$, $SO_2NR^{2d}R^{2d}$, $C(O)NHSO_2$—$C_{1-4}$ alkyl, and $S(O)_pR^{5a}$;

$B^3$ is selected from H, $C_{1-6}$ alkyl substituted with 0–2 $R^{4c}$, —$(CH_2)_{0-2}$-3–6 membered carbocycle substituted with 0–2 $R^5$, and a —$(CH_2)_{0-2}$-4–6 membered heterocycle consisting of: carbon atoms and 1–4 heteroatoms selected from the group consisting of N, O, and $S(O)_p$ and substituted with 0–2 $R^5$;

$B^4$ is selected from H, $SO_2R^{3b}$, $C(O)R^{3b}$, $SO_2NR^3R^{3b}$, $C(O)NR^3R^{3b}$, $OR^2$, $SR^2$, —CN, and $NO_2$;

$B^5$ is $NR^2R^{2f}$ or $CR^3R^2R^{2f}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

ring Q is a 5–8 membered ring consisting of, in addition to the $Q^1$-$CR^{4d}$=$Q^2$ group shown, carbon atoms and 0–2 heteroatoms selected from N, O, and $S(O)_p$, and the ring is substituted with an additional 0–2 $R^{4d}$;

Z is absent or is selected from —(CR$^2$R$^{2a}$)$_{1-4}$—, —CR$^2$(CR$^2$R$^{2b}$)(CH$_2$)$_r$—, —C(O)—, —C(=NR$^{1b}$)—, —CR$^2$(NR$^{1b}$R$^2$)—, —CR$^2$(OR$^2$)—, —CR$^2$(SR$^2$)—, —C(O)CR$^2$R$^{2a}$—, —CR$^{2a}$C(O), —S(O)—, —S(O)$_2$—, —SCR$^2$R$^{2a}$—, —S(O)CR$^2$R$^{2a}$, S(O)$_2$CR$^2$R$^{2a}$—, —CR$^{2a}$S(O)—, —CR$^2$R$^{2a}$S(O)$_2$—, —S(O)$_2$NR$^2$CR$^2$R$^{2a}$—, —NR$^2$S(O)$_2$—, —CR$^2$R$^{2a}$NR$^2$S(O)$_2$—, —NR$^2$S(O)$_2$CR$^2$R$^{2a}$—, —NR$^2$C(O)—, —C(O)NR$^2$CR$^2$R$^{2a}$—, —NR$^2$C(O)CR$^2$R$^{2a}$—, —CR$^2$R$^{2a}$NR$^2$C(O)—, —NR$^2$CR$^2$R$^{2a}$—, and —OCR$^2$R$^{2a}$;

Y is selected from: CY$^1$Y$^2$R$^{4a}$, NR$^3$R$^{3a}$, C(O)NR$^3$R$^{3a}$, SO$_2$R$^3$, SO$_2$NR$^3$R$^{3a}$, C$_{3-10}$ carbocycle substituted 0–2 R$^4$ and 0–1 R$^{4a}$, and, 3–10 membered heterocycle consisting of: carbon atoms and 1–4 heteroatoms selected from the group consisting of N, O, and S(O)$_p$ and substituted with 0–2 R$^4$ and 0–1 R$^{4a}$;

when ring A has 0–1 ring double bonds, then Y is additionally selected from C$_{1-6}$ alkyl, C$_{1-4}$ haloalkyl, —CN, C(O)R$^3$, C(O)OR$^3$, S(O)$_p$R$^3$, S(O)$_2$NR$^3$R$^3$, OR$^3$, NR$^3$C(O)R$^3$, C(O)NR$^3$SO$_2$R$^3$, NR$^3$C(O)NR$^3$R$^3$, NR$^3$R$^3$, C(S)R$^3$, NR$^3$C(S)NR$^3$R$^3$, C(S)OR$^3$, and NR$^3$C(O)R$^3$;

Y$^1$ and Y$^2$ are independently C$_{1-4}$ alkyl substituted with 0–2 R$^4$;

R$^{1a}$, at each occurrence, is selected from H, —(CR$^3$R$^{3a}$)$_r$—R$^{1b}$, —(CR$^3$R$^{3a}$)$_r$—CR$^3$R$^{1b}$R$^{1b}$, —(CR$^3$R$^{3a}$)$_r$—O—(CR$^3$R$^{3a}$)$_r$—R$^{1b}$, —(CR$^3$R$^{3a}$)$_r$—NR$^2$—(CR$^3$R$^{3a}$)$_r$R$^{1b}$, —(CR$^3$R$^{3a}$)$_r$—S(O)$_p$—(CR$^3$R$^{3a}$)$_r$—R$^{1b}$, —(CR$^3$R$^{3a}$)$_r$—CO$_2$—(CR$^3$R$^{3a}$)$_r$—R$^{1b}$, —(CR$^3$R$^{3a}$)$_r$—C(O)NR$^2$—(CR$^3$R$^{3a}$)$_r$—R$^{1b}$, —(CR$^3$R$^{3a}$)$_r$—C(O)—(CR$^3$R$^{3a}$)$_r$—R$^{1b}$, —C$_{2-6}$ alkenylene-R$^{1b}$, —C$_{2-6}$ alkynylene-R$^{1b}$, and —(CR$^3$R$^{3a}$)$_r$—C(=NR$^{1b}$)NR$^3$R$^{1b}$, provided that R$^{1a}$ forms other than an N-halo, N—S, O—O, or N—CN bond;

alternatively, when two R$^{1a}$ groups are attached to adjacent atoms, together with the atoms to which they are attached they form a 5–7 membered ring consisting of: carbon atoms and 0–2 heteroatoms selected from the group consisting of N, O, and S(O)$_p$, this ring being substituted with 0–2 R$^{4b}$ and 0–3 ring double bonds;

R$^{1b}$ is selected from H, C$_{1-3}$ alkyl, F, Cl, Br, I, —CN, —NO$_2$, —CHO, (CF$_2$)$_r$CF$_3$, (CR$^3$R$^{3a}$)$_r$OR$^2$, NR$^2$R$^{2a}$, C(O)R$^{2b}$, CO$_2$R$^{2b}$, OC(O)R$^2$, CH(CH$_2$OR$^2$)$_2$, (CF$_2$)$_r$CO$_2$R$^{2a}$, S(O)$_p$R$^{2b}$, NR$^2$(CH$_2$)$_r$OR$^2$, C(=NR$^{2c}$)NR$^2$R$^{2a}$, NR$^2$C(O)R$^{2b}$, NR$^2$C(O)NR$^2$R$^{2a}$, NR$^2$C(O)$_2$R$^{2a}$, OC(O)NR$^2$R$^{2a}$, C(O)NR$^2$R$^{2a}$, C(O)NR$^2$(CH$_2$)$_r$OR$^2$, SO$_2$NR$^2$R$^{2a}$, NR$^2$SO$_2$R$^2$, C(O)NR$^2$SO$_2$R$^2$, C$_{3-6}$ carbocycle substituted with 0–2 R$^{4b}$, and 5–10 membered heterocycle substituted with 0–2 R$^{4b}$ and consisting of carbon atoms and from 1–4 heteroatoms selected from the group consisting of N, O, and S(O)$_p$, provided that R$^{1b}$ forms other than an O—O, N-halo, N—S, or N—CN bond and provided that S(O)$_p$R$^2$ forms other than S(O)$_2$H or S(O)H;

R$^2$, at each occurrence, is selected from H, CF$_3$, C$_{1-6}$ alkyl, —(CH$_2$)$_r$—C$_{3-10}$ carbocycle substituted with 0–2 R$^{4b}$, and —(CH$_2$)$_r$-5–10 membered heterocycle consisting of: carbon atoms and 1–4 heteroatoms selected from the group consisting of N, O, and S(O)$_p$, and substituted with 0–2 R$^{4b}$;

R$^{2a}$, at each occurrence, is selected from H, CF$_3$, C$_{1-6}$ alkyl, —(CH$_2$)$_r$—C$_{3-10}$ carbocycle substituted with 0–2 R$^{4b}$, and —(CH$_2$)$_r$-5–10 membered heterocycle consisting of: carbon atoms and 1–4 heteroatoms selected from the group consisting of N, O, and S(O)$_p$, and substituted with 0–2 R$^{4b}$;

alternatively, NR$^2$R$^{2a}$ forms a 5 or 6 membered saturated, partially saturated or unsaturated ring substituted with 0–2 R$^{4b}$ and consisting of: 0–1 additional heteroatoms selected from the group consisting of N, O, and S(O)$_p$;

R$^{2b}$, at each occurrence, is selected from CF$_3$, C$_{1-4}$ alkoxy substituted with 0–2 R$^{4b}$, C$_{1-6}$ alkyl substituted with 0–2 R$^{4b}$, —(CH$_2$)$_r$—C$_{3-10}$ carbocycle substituted with 0–2 R$^{4b}$, and —(CH$_2$)$_r$-5–10 membered heterocycle consisting of: carbon atoms and 1–4 heteroatoms selected from the group consisting of N, O, and S(O)$_p$, and substituted with 0–2 R$^{4b}$;

R$^{2c}$, at each occurrence, is selected from CF$_3$, OH, C$_{1-4}$ alkoxy, C$_{1-6}$ alkyl, —(CH$_2$)$_r$—C$_{3-10}$ carbocycle substituted with 0–2 R$^{4b}$, and —(CH$_2$)$_r$-5–10 membered heterocycle containing from 1–4 heteroatoms selected from the group consisting of N, O, and S(O)$_p$, and substituted with 0–2 R$^{4b}$;

R$^{2d}$, at each occurrence, is selected from H, R$^{4c}$, C$_{1-6}$ alkyl substituted with 0–2 R$^{4c}$, —(CR$^3$R$^{3a}$)$_r$—C$_{3-10}$ carbocycle substituted with 0–2 R$^{4c}$, and —(CR$^3$R$^{3a}$)$_r$-5–10 membered heterocycle substituted with 0–2 R$^{4c}$ and consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

alternatively, NR$^{2d}$R$^{2d}$ forms a 5–10 membered saturated, partially saturated or unsaturated ring substituted with 0–2 R$^{4b}$ and consisting of: 0–1 additional heteroatoms selected from the group consisting of N, O, and S(O)$_p$;

R$^{2e}$, at each occurrence, is selected from H, R$^{4c}$, C$_{1-6}$ alkyl substituted with 0–2 R$^{4c}$, —(CR$^3$R$^{3a}$)$_r$—C$_{3-10}$ carbocycle substituted with 0–2 R$^{4c}$, and —(CR$^3$R$^{3a}$)$_r$-5–10 membered heterocycle substituted with 0–2 R$^{4c}$ and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^{2f}$, at each occurrence, is selected from H, CF$_3$, C$_{1-4}$ alkoxy substituted with 0–2 R$^{4b}$, C$_{1-6}$ alkyl substituted with 0–2 R$^{4b}$, —(CH$_2$)$_r$—C$_{3-10}$ carbocycle substituted with 0–2 R$^{4b}$, and —(CH$_2$)$_r$-5–10 membered heterocycle consisting of: carbon atoms and 1–4 heteroatoms selected from the group consisting of N, O, and S(O)$_p$ and substituted with 0–2 R$^{4b}$;

alternatively, CR$^2$R$^{2f}$ forms a 5–8 membered ring consisting of: carbon atoms and 0–2 heteroatoms selected from N, O, and S(O)$_p$, and this ring is substituted with 0–2 R$^{4b}$;

alternatively, NR$^2$R$^{2f}$ forms a 5–8 membered ring consisting of: carbon atoms and 0–2 additional heteroatoms selected from N, O, and S(O)$_p$, and this ring is substituted with 0–2 R$^{4b}$;

alternatively, when B$^4$ is SO$_2$R$^{3b}$ and B$^5$ is NR$^2$R$^{2f}$, R$^{3b}$ and R$^{2f}$ combine to form a 5–8 membered ring consisting of: carbon atoms and 0–2 additional heteroatoms selected from N, O, and S(O)$_p$, and this ring is substituted with 0–2 R$^{4b}$;

alternatively, when B$^4$ is C(O)R$^{3b}$ and B$^5$ is NR$^2$R$^{2f}$, R$^{3b}$ and R$^{2f}$ combine to form a 5–8 membered ring consisting of: carbon atoms and 0–2 additional heteroatoms selected from N, O, and S(O)$_p$, and this ring is substituted with 0–2 R$^{4b}$;

alternatively, when B$^5$ is NR$^2$R$^{2f}$, B$^4$ and R$^{2f}$ combine to form a 5–8 membered ring consisting of: carbon atoms and 0–2 additional heteroatoms selected from N, O, and S(O)$_p$, and this ring is substituted with 0–2 R$^{4b}$ and the R$^2$ group of NR$^2$R$^{2f}$, in addition to the groups recited below, is selected from SO$_2$R$^{3b}$, C(O)R$^{3b}$, and —CN;

R$^3$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

alternatively, R$^3$ and R$^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —($C_{0-4}$ alkyl)-5–10 membered carbocycle substituted with 0–3 $R^{1a}$, and —($C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —($C_{0-4}$ alkyl)-5–10 membered carbocycle substituted with 0–3 $R^{1a}$, and —($C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —($C_{0-4}$ alkyl)-5–10 membered carbocycle substituted with 0–3 $R^{1a}$, and —($C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_r$-3–6 membered carbocycle, and —$(CH_2)_r$-5–6 membered heterocycle consisting of: carbon atoms and 1–4 heteroatoms selected from the group consisting of N, O, and $S(O)_p$;

alternatively, $CR^3R^{3g}$ forms a cyclopropyl group;

$R^4$, at each occurrence, is selected from =O, CHO, $(CR^3R^{3a})_rOR^2$, $(CR^3R^{3a})_rF$, $(CR^3R^{3a})_rCl$, $(CR^3R^{3a})_rBr$, $(CR^3R^{3a})_rI$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rC(=NS(O)_2R^5)NR^2R^{2a}$, $(CR^3R^{3a})_rNR^2C(=NR^2)NR^2R^{2a}$, $(CR^3R^{3a})_rC(O)NR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2$—$C_{1-4}$ alkyl, $(CR^3R^{3a})_rNR^2SO_2R^5$, $(CR^3R^{3a})_rS(O)_pR^5$, $(CR^3R^{3a})_r(CF_2)_rCF_3$, $NHCH_2R^{1b}$, $OCH_2R^{1b}$, $SCH_2R^{1b}$, $NH(CH_2)_2(CH_2)_rR^{1b}$, $O(CH_2)_2(CH_2)_rR^{1b}$, $S(CH_2)_2(CH_2)_rR^{1b}$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4a}$ is selected from $C_{1-6}$ alkyl substituted with 0–2 $R^{4c}$, $C_{2-6}$ alkenyl substituted with 0–2 $R^{4c}$, $C_{2-6}$ alkynyl substituted with 0–2 $R^{4c}$, —$(CR^3R^{3g})_r$—$C_{5-10}$ membered carbocycle substituted with 0–3 $R^{4c}$, —$(CR^3R^{3g})_r$-5–10 membered heterocycle substituted with 0–3 $R^{4c}$ and consisting of: carbon atoms and 1–4 heteroatoms selected from the group consisting of N, O, and $S(O)_p$, $(CR^3R^{3g})_rCN$, $(CR^3R^{3g})_rC(NR^{2d})NR^{2d}R^{2d}$, $(CR^3R^{3g})_rNR^{2d}C(=NR^{2d})NR^{2d}R^{2d}$, $(CR^3R^{3g})_rNR^{2d}C(R^{2e})(=NR^{2d})$, $(CR^3R^{3g})_rNR^{2d}R^{2d}$, $(CR^3R^{3g})_rN(\to O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$OC(O)$ $R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$OC(O)NR^{2d}R^{2d}$, $(CR^3R^{3g})_r$—$NR^{2d}C(O)OR^{2d}$, $(CR^3R^{3g})_r$—$SO_2NR^{2d}R^{2d}$, $(CR^3R^{3g})_r$—$NR^{2d}SO_2NR^{2d}R^{2d}$, $(CR^3R^{3g})_r$—$C(O)NR^{2d}SO_2R^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$ and further provided that $R^{4a}$ is other than a hydroxamic acid;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_r$—$C(O)NR^3R^{3a}$, $(CH_2)_rNR^3C(O)NR^3R^{3a}$, $(CH_2)_r$—$C(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, and $(CH_2)_r(CF_2)_rCF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $C_{2-6}$ alkenyl, $C_{2-6}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\to O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NR^2(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rC(O)NR^2SO_2$—$C_{1-4}$ alkyl, $(CR^3R^{3a})_rNR^2SO_2R^{5a}$, $(CR^3R^{3a})_rC(O)NR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$4–10 membered heterocycle substituted with 0–2 $R^{4b}$ and consisting of carbon atoms and from 1–4 heteroatoms selected from the group consisting of N, O, and $S(O)_p$;

$R^{4d}$, at each occurrence, is selected from H, $(CR^3R^{3a})_rOR^2$, $(CR^3R^{3a})_rF$, $(CR^3R^{3a})_rBr$, $(CR^3R^{3a})_rCl$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NH(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNHC(=NR^2)NR^2R^{2a}$, $(CR^3R^{3a})_rSO_2NR^2R^{2a}$, $(CR^3R^{3a})_rNR^2SO_2NR^2R^{2a}$, $(CR_3R^{3a})_rNR^2SO_2$—$C_{1-4}$ alkyl, $(CR_3R^{3a})_rC(O)NHSO_2$—$C_{1-4}$ alkyl, $(CR^3R^{3a})_rNR^2SO_2R^5$, $(CR^3R^{3a})_rS(O)_pR^{5a}$, $(CR^3R^{3a})_r(CF_2)_rCF_3$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_rCH(=NOR^{3d})$, $(CH_2)_rC(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_rOR^3$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

R⁶, at each occurrence, is selected from H, OH, (CH₂)ᵣ-OR², halo, $C_{1-4}$ alkyl, CN, NO₂, (CH₂)ᵣNR²R²ᵃ, (CH₂)ᵣC(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂$C_{1-4}$ alkyl;

R⁷, at each occurrence, is selected from H, OH, $C_{1-6}$ alkyl, $C_{1-6}$ alkyl-C(O)—, $C_{1-6}$ alkyl-O—, (CH₂)ₙ-phenyl, $C_{1-4}$ alkyl-OC(O)—, $C_{6-10}$ aryl-O—, $C_{6-10}$ aryl-OC(O)—, $C_{6-10}$ aryl-CH₂—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-NH₂—C(O)—, phenyl-NH₂—C(O)—, and phenyl-$C_{1-4}$ alkyl-C(O)—;

R⁸, at each occurrence, is selected from H, $C_{1-6}$ alkyl, and (CH₂)ₙ-phenyl;

alternatively, R⁷ and R⁸, when attached to the same nitrogen, combine to form a 5–10 membered heterocyclic ring consisting of carbon atoms and 0–2 additional heteroatoms selected from the group consisting of N, O, and S(O)ₚ;

R⁹, at each occurrence, is selected from H, $C_{1-6}$ alkyl, and (CH₂)ₙ-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and t, at each occurrence, is selected from 0, 1, 2, and 3.

In a tenth embodiment, the present invention provides a novel compound of formula Ih–Ii, wherein:

X is selected from SO₂, CH₂, C(O), C(O)CH₂, and NHC(O);

G-G₂- is selected from the group:

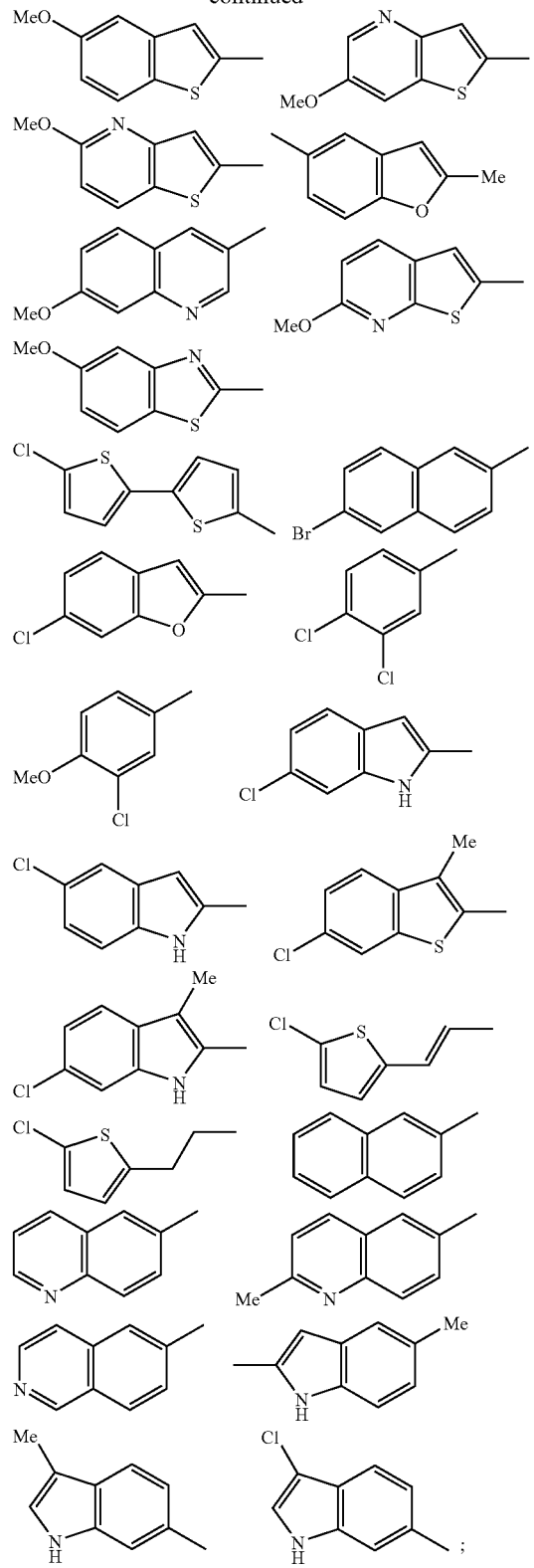

G₁ is selected from H, $C_{1-4}$ alkyl substituted with 0–1 R¹ᵃ, S(O)₂R², S(O)ₚCH=CHR², CH₂C(O)OR², CH₂C(O)NR²R²ᵃ, CH₂C(O)NHCH₂CH₂OR², CH₂C(O)NHCH₂CH₂NR²R²ᵃ, CH₂C(O)N(CH₃)CH₂CH₂OR², CH₂C (O)N(CH$_3$)CH$_2$CH$_2$NR$^2$R$^{2a}$, CH$_2$C(O)NHCH$_2$C(O)NR$^2$R$^{2a}$, CH$_2$C(O)NHCH$_2$C(O)NR$^2$R$^{2a}$, CH$_2$C(O)NHCH$_2$C(O)OR$^2$, CH$_2$C(O)NHCH$_2$C(O)OR$^2$, CH$_2$CH$_2$OR$^2$, CH$_2$(CH$_3$)$_2$OR$^2$, CH$_2$CN, and CH$_2$CH$_2$CN;

alternatively, G$_1$ is selected from:

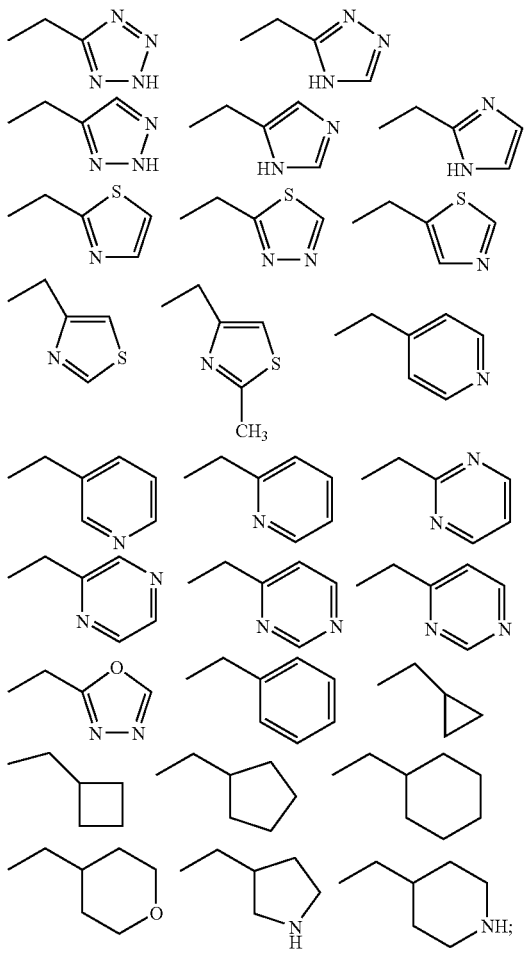

alternatively, G$_2$-X—N(G$_1$) form a —CH=G group;

A is selected from cyclohexyl, piperidinyl, piperazinyl, phenyl, pyridyl, and pyrimidyl, and is substituted with 0–2 R$^4$;

B is selected from Y, N(B$^1$)C(O)C(R$^3$R$^{3g}$)NB$^2$B$^3$,

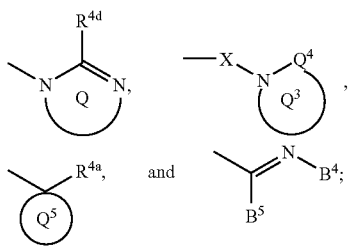

provided that the lactam nitrogen and B are attached to different atoms on A, the R$^{4d}$ shown is other than OH, and that the A-X—N moiety forms other than a N—N—N group;

B$^1$ is selected from H, CH$_3$, CH$_2$CH$_3$, CH$_2$CH$_2$CH$_3$, and CH(CH$_3$)$_2$;

B$^2$ is selected from H, CH$_3$, CH$_2$CH$_3$, CH$_2$CH$_2$CH$_3$, and CH(CH$_3$)$_2$;

B$^3$ is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, C$_{2-5}$ alkyl substituted with 1 R$^{4c}$, —(CH$_2$)$_{0-1}$-3–6 membered carbocycle substituted with 0–1 R$^5$, and a —(CH$_2$)$_{0-1}$-5–6 membered heterocycle consisting of: carbon atoms and 1–4 heteroatoms selected from the group consisting of N, O, and S(O)$_p$ and substituted with 0–1 R$^5$;

B$^4$ is selected from H, SO$_2$R$^{3b}$, and OR$^2$;

B$^5$ is NR$^2$R$^{2f}$, ring Q is a 5–6 membered ring consisting of, in addition to the N—CR$^{4d}$=N group shown, carbon atoms and 0–1 heteroatoms selected from N, O, and S(O)$_p$, and the ring is substituted with an additional 0–2 R$^{4d}$;

Q$^4$ is selected from C=O and SO$_2$;

ring Q$^3$ is a 6–7 membered ring consisting of, in addition to the N-Q$^4$ group shown, carbon atoms and 0–1 heteroatoms selected from NR$^{4c}$, O, S, S(O), and S(O)$_2$, wherein: 0–2 double bonds are present within the ring and the ring is substituted with 0–2 R$^4$;

alternatively, ring Q$^3$ is a 5–7 membered ring to which another ring is fused, wherein: the 5–7 membered ring consists of, in addition to the shown amide group, carbon atoms and 0–1 heteroatoms selected from NR$^{4c}$, O, S, S(O), and S(O)$_2$, and 0–1 double bonds are present within the ring; the fusion ring is phenyl;

ring Q$^3$, which includes the 5–7 membered ring and the fusion ring, is substituted with 0–2 R$^4$;

ring Q$^5$ is substituted with 0–1 R$^4$ and is selected from cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl;

Z is selected from CH$_2$, C(O), —S(O)$_2$—, —NHC(O)—, —N(CH$_3$)C(O)CH$_2$—, —C(O)NH—, —CH$_2$NH—, O, and —CH$_2$O—;

Y is selected from N(CH$_3$)$_2$, C(O)(CH$_3$)$_2$, C(CH$_3$)$_2$R$^{4a}$C(CH$_2$CH$_3$)$_2$R$^{4a}$, C(O)N(CH$_3$)$_2$, and SO$_2$N(CH$_3$)$_2$;

altneratively, Y is selected from phenyl, pyridyl, pyrrolidino, N-pyrrolidino-carbonyl, morpholino, tetrahydropyranyl, N-morpholino-carbonyl, 1,2,3-triazolyl, imidazolyl, and benzimidazolyl, and is substituted with 1 R$^{4a}$ and 0–1 R$^4$;

alternatively, when A is selected from cyclopentyl, cyclohexyl, piperidinyl, and piperazinyl, then Y is additionally selected from methyl, 1-propyl, 2-propyl, 2-methyl-1-propyl, 2-butyl, 1,1-dimethyl-1-ethyl, 3-pentyl, cyclopropyl, cyclobutyl, cyclopentyl, tetrahydropyranyl, —CN, CH(CF$_3$)$_2$, CH(CHF$_2$), CH(CH$_2$F), CH$_2$CF$_3$, CH(CF$_2$CF$_3$)$_2$, C(O)N(CH$_3$)$_2$, N(CH$_3$)$_2$, and SO$_2$CH$_3$, R$^{1a}$, at each occurrence, is selected from H, R$^{1b}$, CH(CH$_3$)R$^{1b}$, C(CH$_3$)$_2$R$^{1b}$, and CH$_2$R$^{1b}$, provided that R$^{1a}$ forms other than an N-halo, N—S, or N—CN bond;

R$^{1b}$ is selected from CH$_3$, CH$_2$CH$_3$, F, Cl, Br, —CN, CF$_3$, OR$^2$, NR$^2$R$^{2a}$, C(O)R$^{2b}$, CO$_2$R$^{2b}$, CO$_2$R$^{2a}$, S(O)$_p$R$^2$, C(O)NR$^2$R$^{2a}$, SO$_2$NR$^2$R$^{2a}$, NR$^2$SO$_2$R$^2$, and 5–6 membered aromatic heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0–1 R$^{4b}$, benzyl substituted with 0–1 R$^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

alternatively, $NR^2R^{2a}$ forms a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle containing from 1–4 heteroatoms selected from the group consisting of N, O, and $S(O)_p$, and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CH_3$, $CH_2CH_3$, $OCH_3$, and benzyl;

alternatively, $NR^2R^{2f}$ forms a 5–6 membered ring consisting of: carbon atoms and 0–1 additional heteroatoms selected from N, O, and $S(O)_p$, and this ring is substituted with 0–1 $R^{4b}$;

alternatively, $B^4$ and $R^{2f}$ combine to form a 5 membered ring consisting of: carbon atoms and 0–1 additional heteroatoms selected from N, O, and $S(O)_p$, and this ring is substituted with 0–2 $R^{4b}$ and the $R^2$ group of $NR^2R^{2f}$, in addition to the groups recited below, can be $SO_2R^{3b}$;

$R^{3b}$, at each occurrence, is selected from H and $CH_3$;

$R^4$, at each occurrence, is selected from H, =O, OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(→O)R^{2d}R^{2d}$, $(CR^3R^{3g})_rOR^{2d}$, $(CR^3R^{3g})_r$—C(O)$NR^{2d}R^{2d}$, $(CR^3R^{3g})_r$—$NR^{2d}C(O)R^{2e}$, $(CR^3R^{3g})_rC(O)R^{2e}$, $(CR^3R^{3g})_r$—$NR^{2d}C(O)NR^{2d}R^{2d}$, $(CR^3R^{3g})_r$—$NR^{2d}C(O)OR^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, $C_{2-3}$ alkenyl, $C_{2-3}$ alkynyl, —CN, $NO_2$, $NR^2R^{2a}$, $CH_2NR^2R^{2a}$, $N(→O)R^2R^{2a}$, $CH_2N(→O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, $(CH_2)C_{3-6}$ carbocycle substituted with 0–2 $R^{4b}$, 5–6 membered heterocycle consisting of carbon atoms and from 1–4 heteroatoms selected from the group consisting of N, O, and $S(O)_p$ and substituted with 0–2 $R^{4b}$, and $(CH_2)$-5–6 membered heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $CH_2OR^2$, $OR^2$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2NR^2R^{2a}$, $NR^2R^{2a}$, $C(O)R^{2c}$, $NR^2C(O)R^{2b}$, $C(O)NR^2R^{2a}$, $SO_2NR^2R^{2a}$, $NR^2SO_2R^5$, phenyl substituted with 0–1 $R^5$, and a 5–6 membered heterocycle consisting of: carbon atoms and 1 heteroatom selected from the group consisting of N, O, and $S(O)_p$ and substituted with 0–1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

In an eleventh embodiment, the present invention provides a novel compound, wherein:

X is selected from $SO_2$;

G-$G_2$- is selected from:

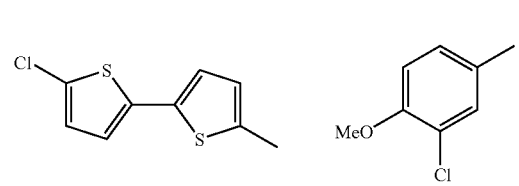

-continued

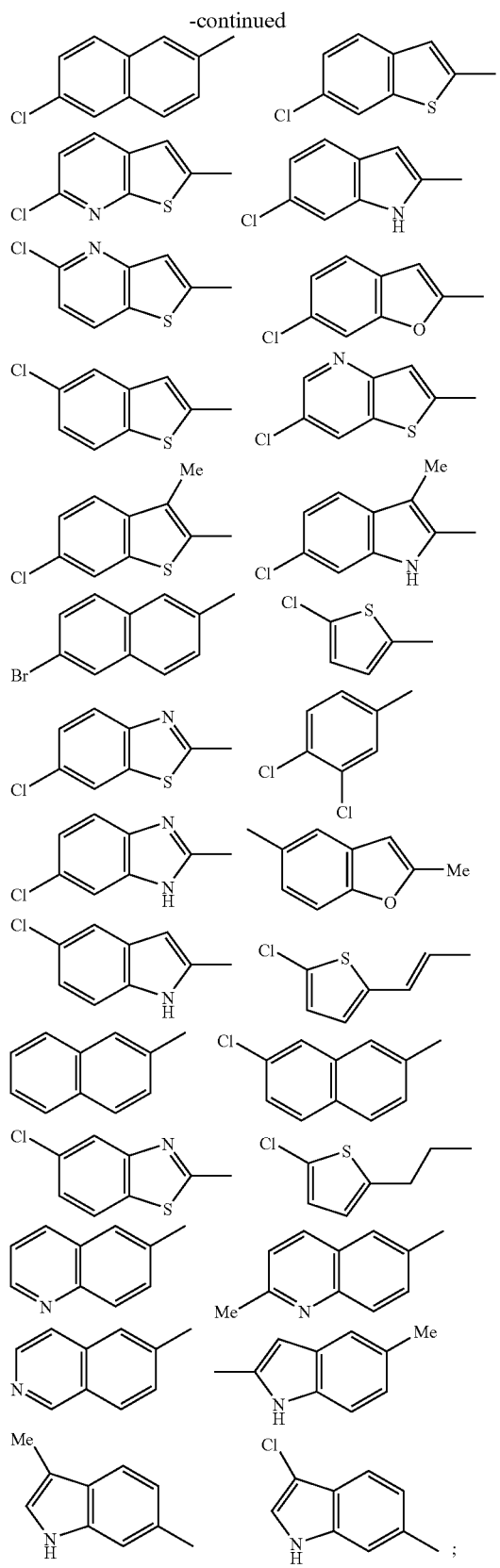

alternatively, $G_2$-X—N($G_1$) form a —CH=G group;
A is selected from the group: cyclohexyl, piperidinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from Y, $N(B^1)C(O)C(R^3R^{3g})NB^2B^3$,

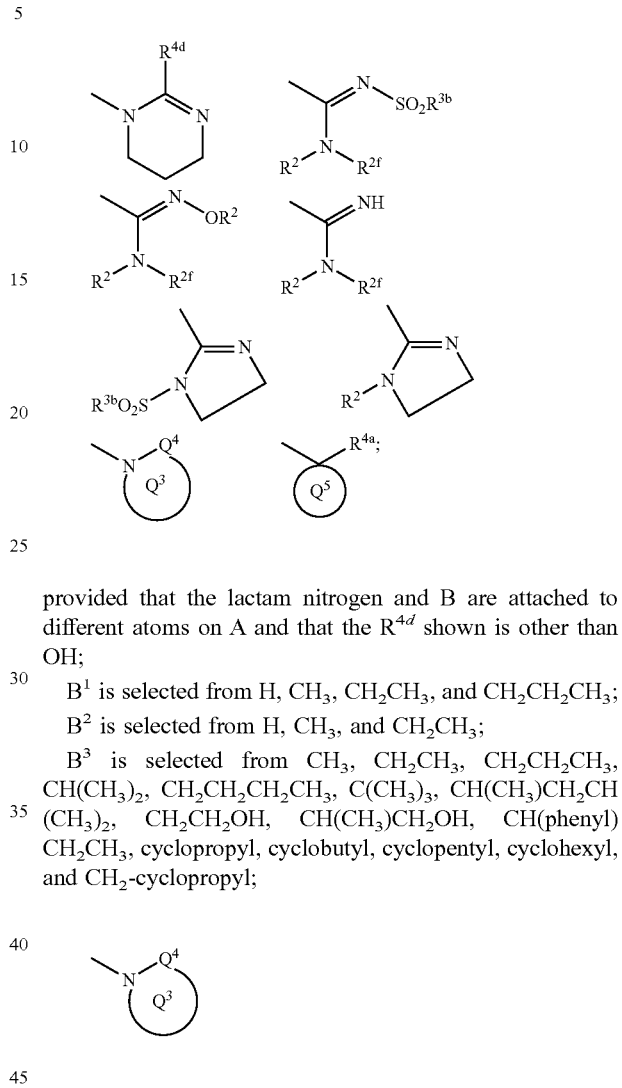

provided that the lactam nitrogen and B are attached to different atoms on A and that the $R^{4d}$ shown is other than OH;

$B^1$ is selected from H, $CH_3$, $CH_2CH_3$, and $CH_2CH_2CH_3$;

$B^2$ is selected from H, $CH_3$, and $CH_2CH_3$;

$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, cyclohexyl, and $CH_2$-cyclopropyl;

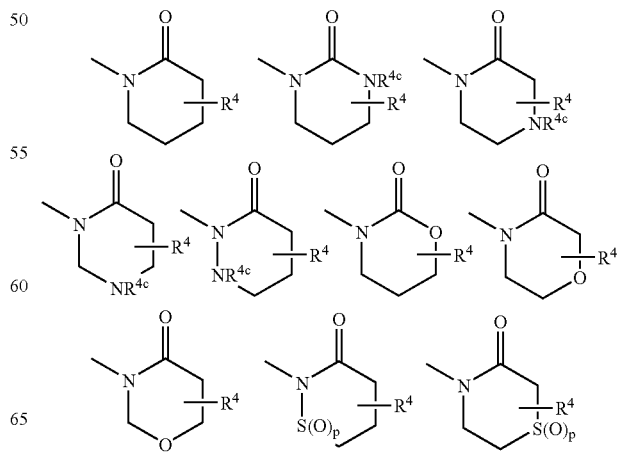

is attached to a different atom on A than M and is selected from the group:

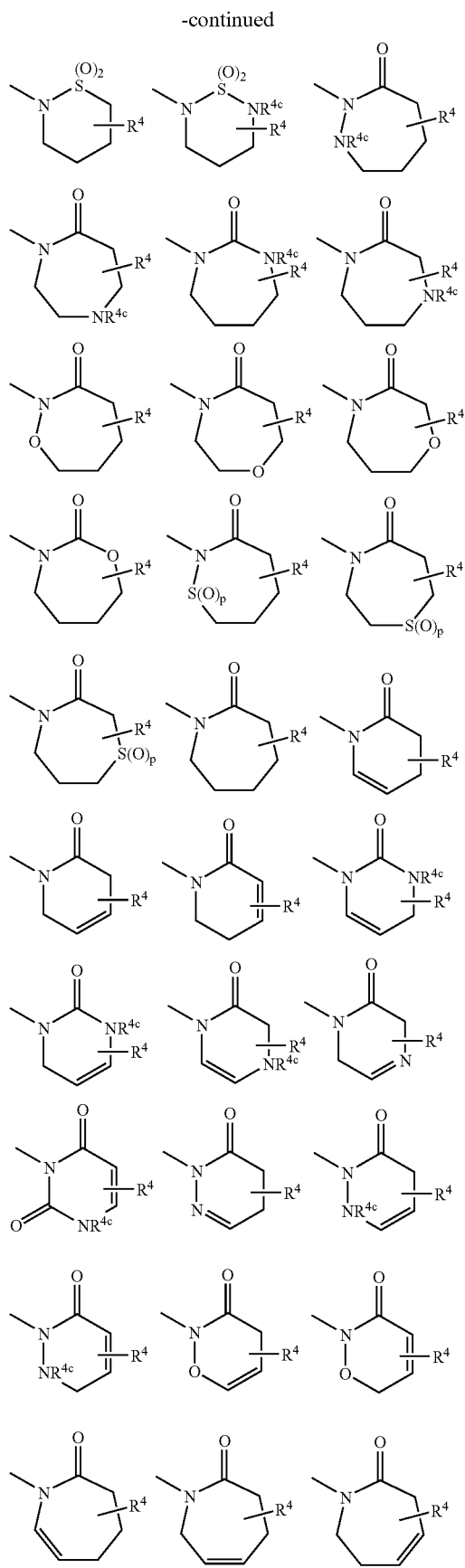

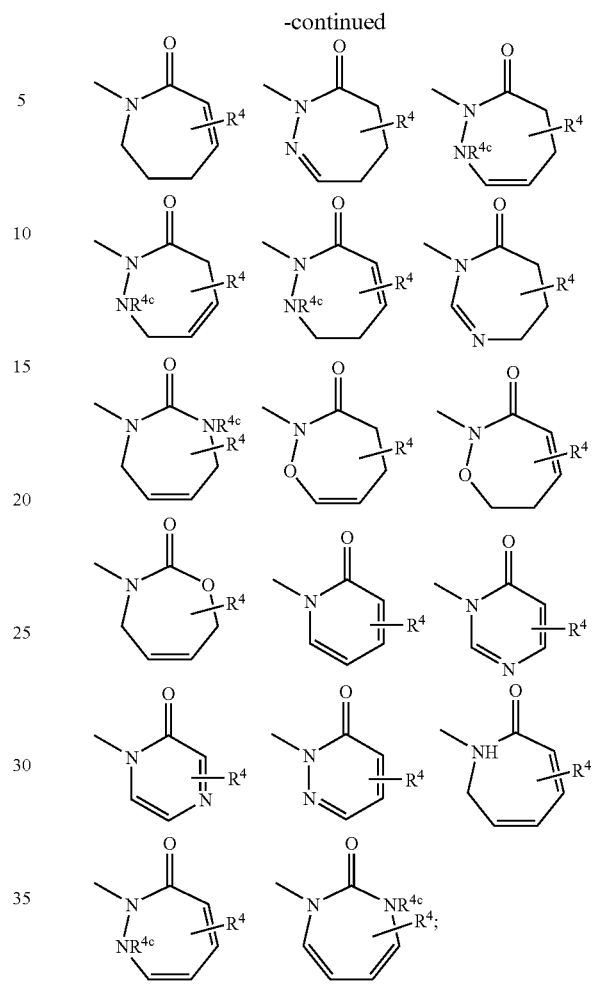

ring $Q^5$ is selected from cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$ at the 3-position), piperidinyl (attached to A and $R^{4a}$ at the 4-position), 4-piperdinonyl (attached to A and $R^{4a}$ at the 3-position), tetrahydrofuranyl, and tetrahydropyranyl (attached to A and $R^{4a}$ at the 4-position);

Y is selected from $N(CH_3)_2$, $C(O)(CH_3)_2$, $C(CH_3)_2R^{4a}$, $C(CH_2CH_3)_2R^{4a}$, $C(O)N(CH_3)_2$, and $SO_2N(CH_3)_2$;

alternatively, Y is selected from phenyl, pyridyl, 1,2,3-triazolyl, imidazolyl, morpholino, and benzimidazolyl, and is substituted with 1 $R^{4a}$;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5- yl, CH$_2$-1,2,3,4-tetrazol-1-yl, and CH$_2$-1,2,3,4-tetrazol-5-yl, provided that R$^{1a}$ forms other than an N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0–1 R$^{4b}$, benzyl substituted with 0–1 R$^{4b}$, and 5 membered aromatic heterocycle consisting of: carbon atoms and 1–4 heteroatoms selected from the group consisting of N, O, and S(O)$_p$, and substituted with 0–1 R$^{4b}$;

R$^{2a}$, at each occurrence, is selected from H, CH$_3$, and CH$_2$CH$_3$;

alternatively, NR$^2$R$^{2a}$ forms a 5 or 6 membered saturated, partially saturated or unsaturated ring substituted with 0–1 R$^{4b}$ and consisting of: 0–1 additional heteroatoms selected from the group consisting of N, O, and S(O)$_p$;

R$^{2b}$, at each occurrence, is selected from OCH$_3$, OCH$_2$CH$_3$, CH$_3$, and CH$_2$CH$_3$;

R$^{2c}$, at each occurrence, is selected from OH, OCH$_3$, OCH$_2$CH$_3$, CH$_3$, and CH$_2$CH$_3$;

R$^{2d}$, at each occurrence, is selected from H, R$^{4c}$, C$_{1-4}$ alkyl substituted with 0–2 R$^{4c}$, C$_{3-6}$ cycloalkyl substituted with 0–2 R$^{4c}$, phenyl substituted with 0–2 R$^{4c}$, and 5–6 membered aromatic heterocycle substituted with 0–2 R$^{4c}$ and consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-4}$ alkyl substituted with 0–2 R$^{4c}$, C$_{3-6}$ cycloalkyl substituted with 0–2 R$^{4c}$, phenyl substituted with 0–2 R$^{4c}$, and 5–6 membered aromatic heterocycle substituted with 0–2 R$^{4c}$ and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^{2f}$, at each occurrence, is selected from H, CH$_3$, CH$_2$CH$_3$, and OCH$_3$;

alternatively, NR$^2$R$^{2f}$ forms a ring selected from morpholine, piperazine, piperidine, and pyrrolidine;

R$^4$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, and C(CH$_3$)$_3$;

R$^{4a}$ is selected from —(CH$_2$)$_r$-5–6 membered carbocycle substituted with 0–3 R$^{4c}$, —(CH$_2$)$_r$-5–6 membered heterocycle substituted with 0–3 R$^{4c}$ and consisting of: carbon atoms and 1–4 heteroatoms selected from the group consisting of N, O, and S(O)$_p$, (CH$_2$)$_r$NR$^{2d}$R$^{2d}$, (CH$_2$)$_r$N(→O)R$^{2d}$R$^{2d}$, (CH$_2$)$_r$OR$^{2d}$, (CH$_2$)$_r$—C(O)NR$^{2d}$R$^{2d}$, (CH$_2$)$_r$—NR$^{2d}$C(O)R$^{2e}$, (CH$_2$)$_r$—C(O)R$^{2e}$, (CH$_2$)$_r$—NR$^{2d}$C(O) NR$^{2d}$R$^{2d}$, (CH$_2$)$_r$—NR$^{2d}$C(O)OR$^{2d}$, (CH$_2$)$_r$—NR$^{2d}$SO$_2$R$^{2d}$, and (CH$_2$)$_r$—S(O)$_p$R$^{2d}$, provided that S(O)$_p$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$N$^3$R$^{3a}$, NR$^3$SO$_2$-phenyl, S(O)$_2$CH$_3$, S(O)$_2$-phenyl, and CF$_3$;

R$^{4c}$, at each occurrence, is selected from =O, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, C$_{2-3}$ alkenyl, C$_{2-3}$ alkynyl, CH$_2$OH, CH$_2$OCH$_3$, CH$_2$OCH$_2$CH$_3$, CH$_2$OCH$_2$CH$_2$CH$_3$, CH$_2$OCH(CH$_3$)$_2$, F, Br, Cl, CF$_3$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, cyclopropyl substituted with 0–1 R$^{4b}$, cyclobutyl substituted with 0–1 R$^{4b}$, cyclopentyl substituted with 0–1 R$^{4b}$, phenyl substituted with 0–1 R$^{4b}$, —CH$_2$-cyclopropyl substituted with 0–1 R$^{4b}$, —CH$_2$-cyclobutyl substituted with 0–1 R$^{4b}$, —CH$_2$-cyclopentyl substituted with 0–1 R$^{4b}$, benzyl substituted with 0–2 R$^{4b}$, 5–6 membered aromatic heterocycle consisting of carbon atoms and from 1–4 heteroatoms selected from the group consisting of N, O, and S(O)$_p$ and substituted with 0–2 R$^{4b}$, and (CH$_2$)-5–6 membered aromatic heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, OCH$_3$, CH$_3$, CH$_2$CH$_3$, CH$_2$CH$_2$CH$_3$, CH(CH$_3$)$_2$, NR$^2$R$^{2a}$, NR$^2$C(O)R$^{2b}$, NR$^2$SO$_2$R$^5$, phenyl, 2-oxo-pyrrolidinyl, and 2-oxo-piperidinyl;

R$^5$, at each occurrence, is selected from H, =O, CH$_3$, CH$_2$CH$_3$, OR$^3$, CH$_2$OR$^3$, F, Cl, NR$^3$R$^{3a}$, CH$_2$NR$^3$R$^{3a}$, C(O) R$^3$, C(O)OR$^{3c}$, NR$^3$C(O)R$^{3a}$, C(O)NR$^3$R$^{3a}$, SO$_2$NR$^3$R$^{3a}$, NR$_3$SO$_2$—C$_{1-4}$ alkyl, NR$^3$SO$_2$-phenyl, S(O)$_2$—CH$_3$, S(O)$_2$-phenyl, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, NR$^2$R$^{2a}$, CH$_2$NR$^2$R$^{2a}$, C(O)R$^{2b}$, CH$_2$C(O)R$^{2b}$, NR$^2$C(O)R$^{2b}$, and SO$_2$NR$^2$R$^{2a}$.

In a twelfth embodiment, the present invention provides a novel compound selected from:

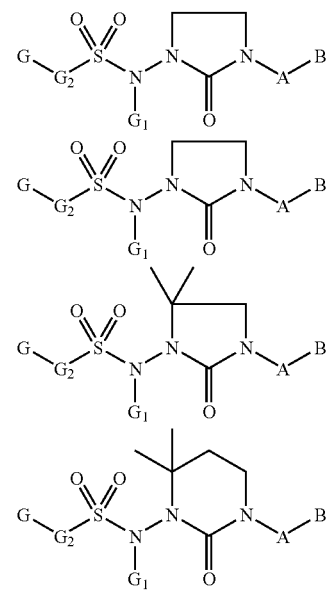

A is selected from the group: piperidinyl, phenyl, 2-pyridyl, 2-pyrimidyl, and 2-F-phenyl, wherein B is substituted at the 4-position of A;

B is selected from:

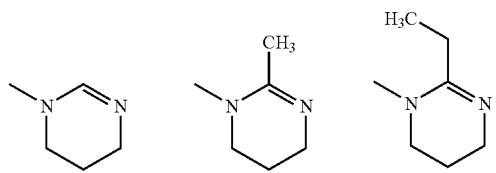

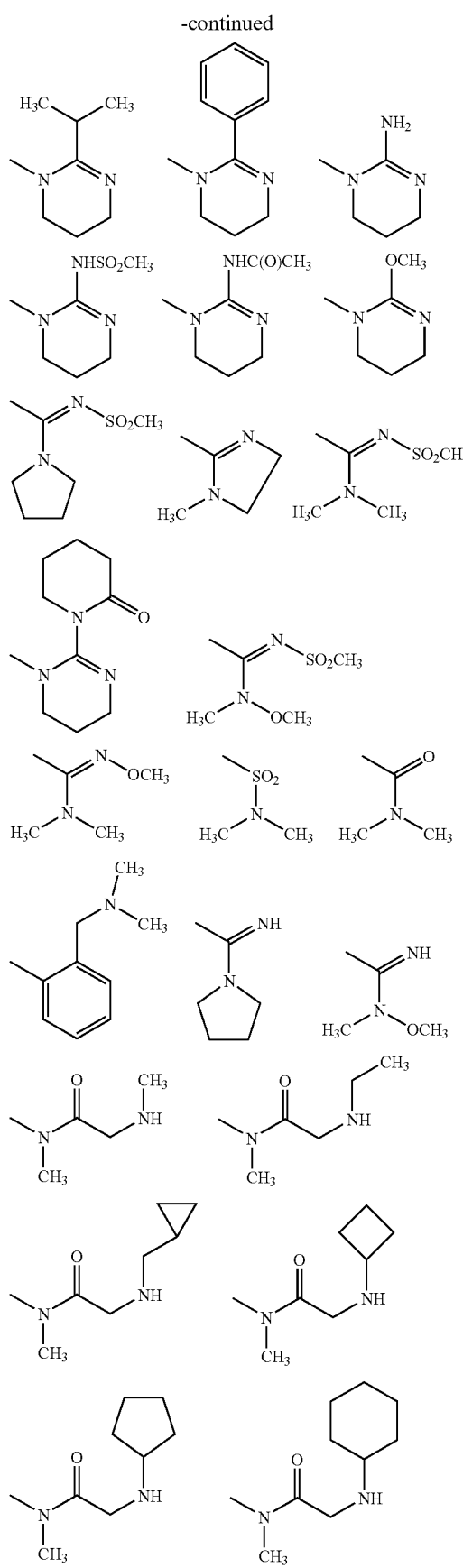
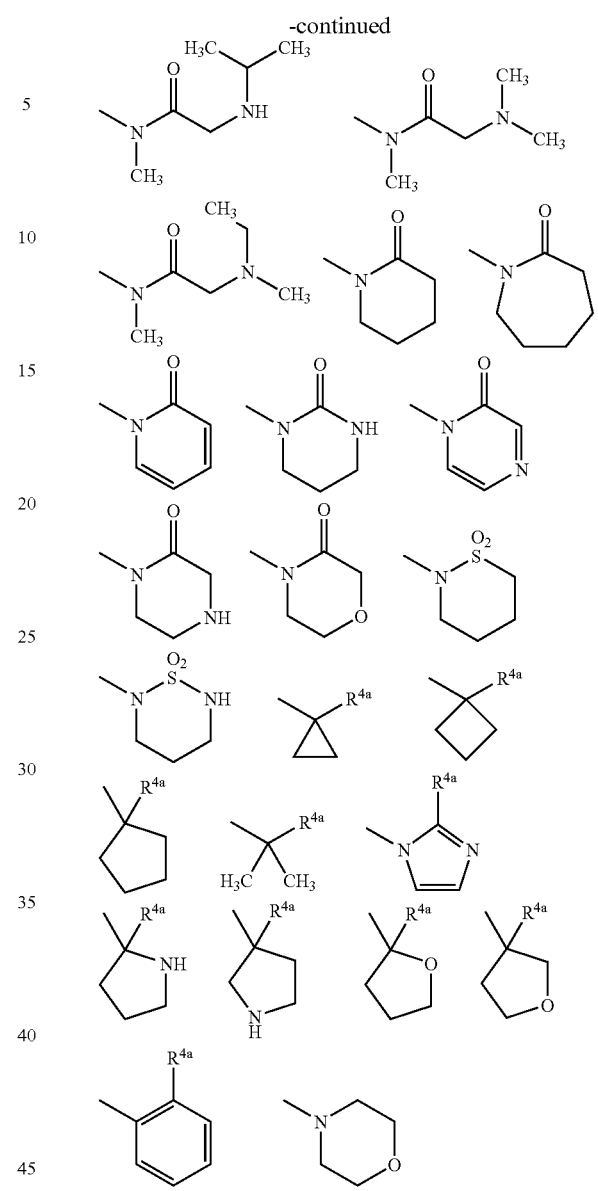

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—S$(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)$ $OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —$(CH_2)$-5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$ provided that $S(O)_pR^{2d}$ forms other than $S(O)_2H$ or $S(O)H$; and $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

In a thirteenth embodiment, the present invention provides a novel compound, wherein:

A-B is selected from:

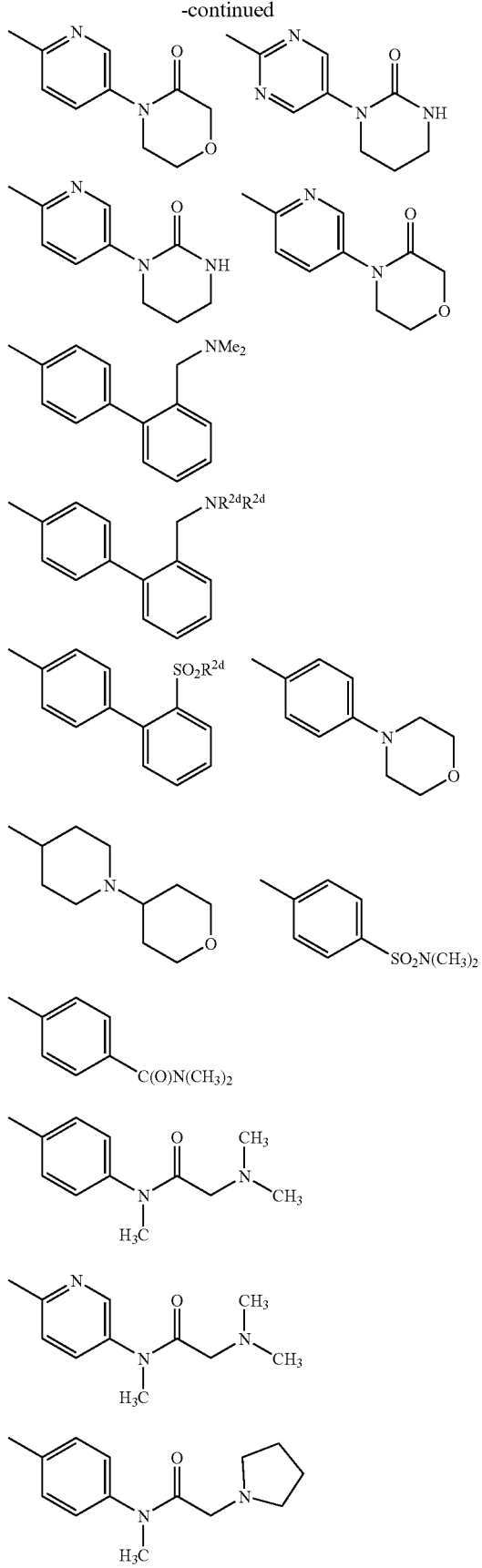

-continued
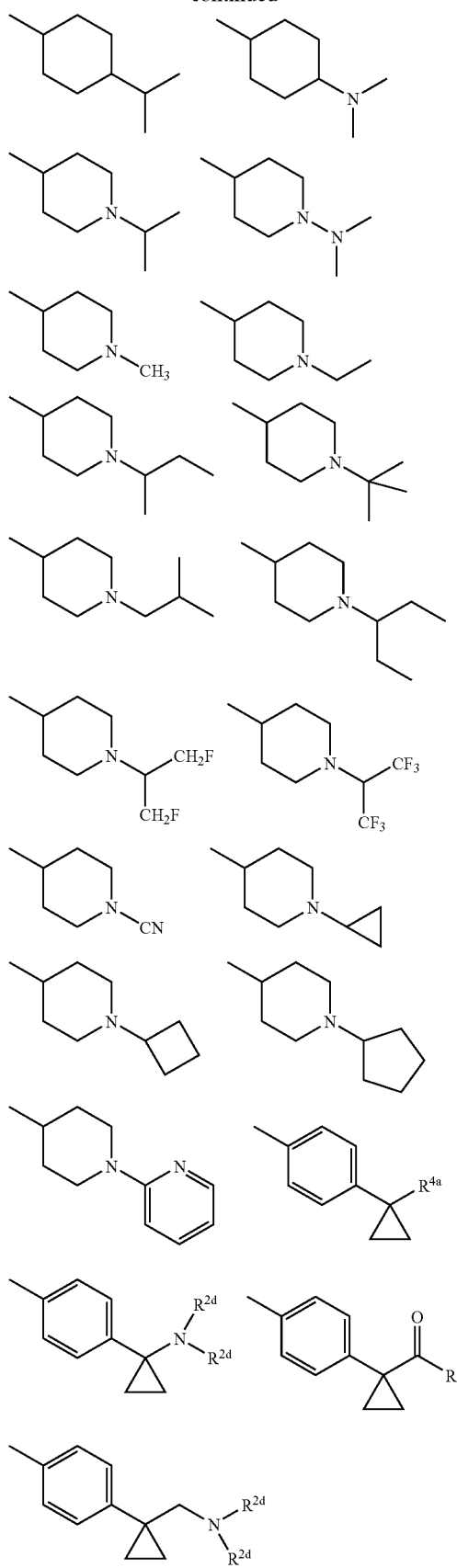
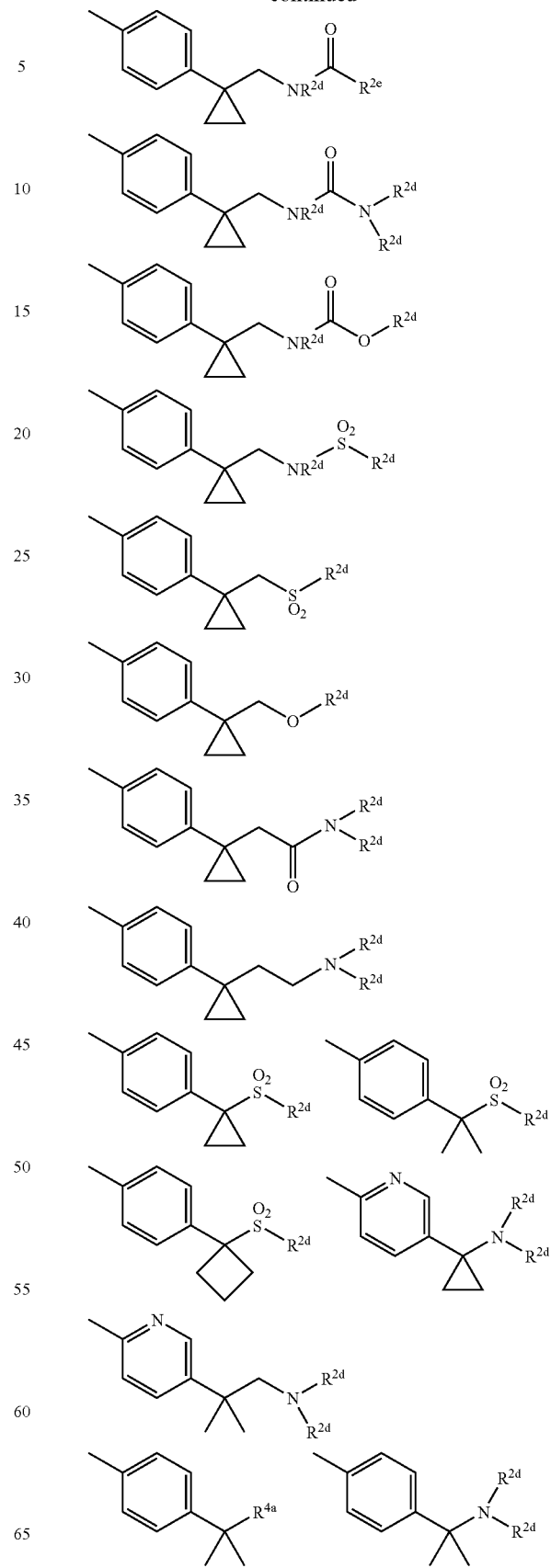

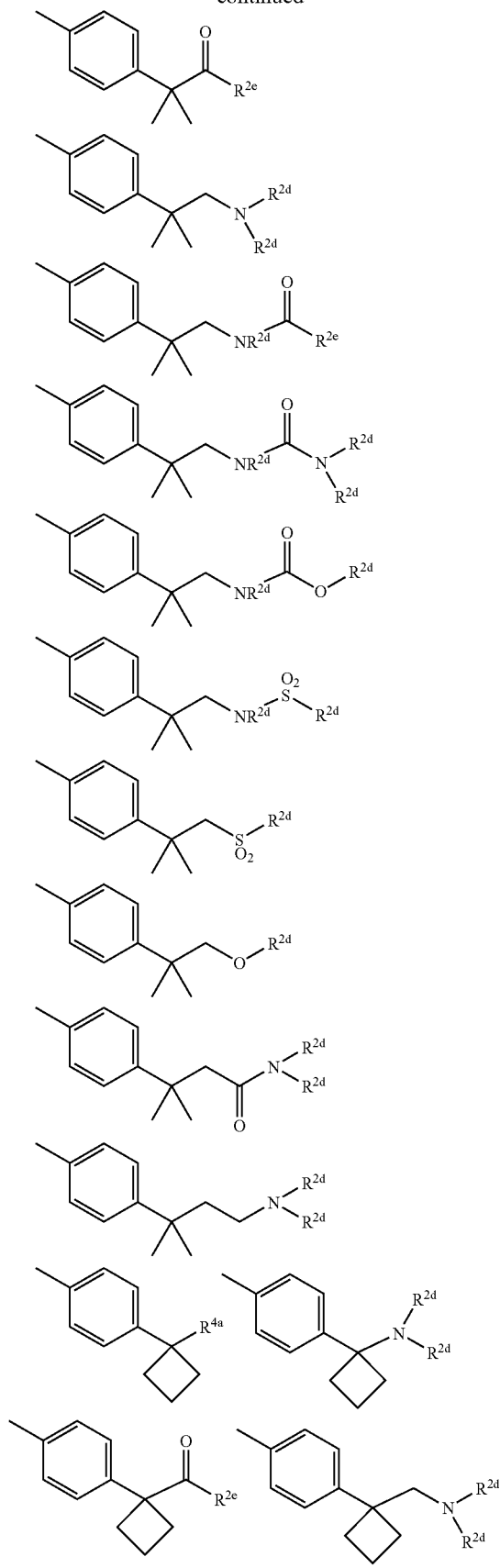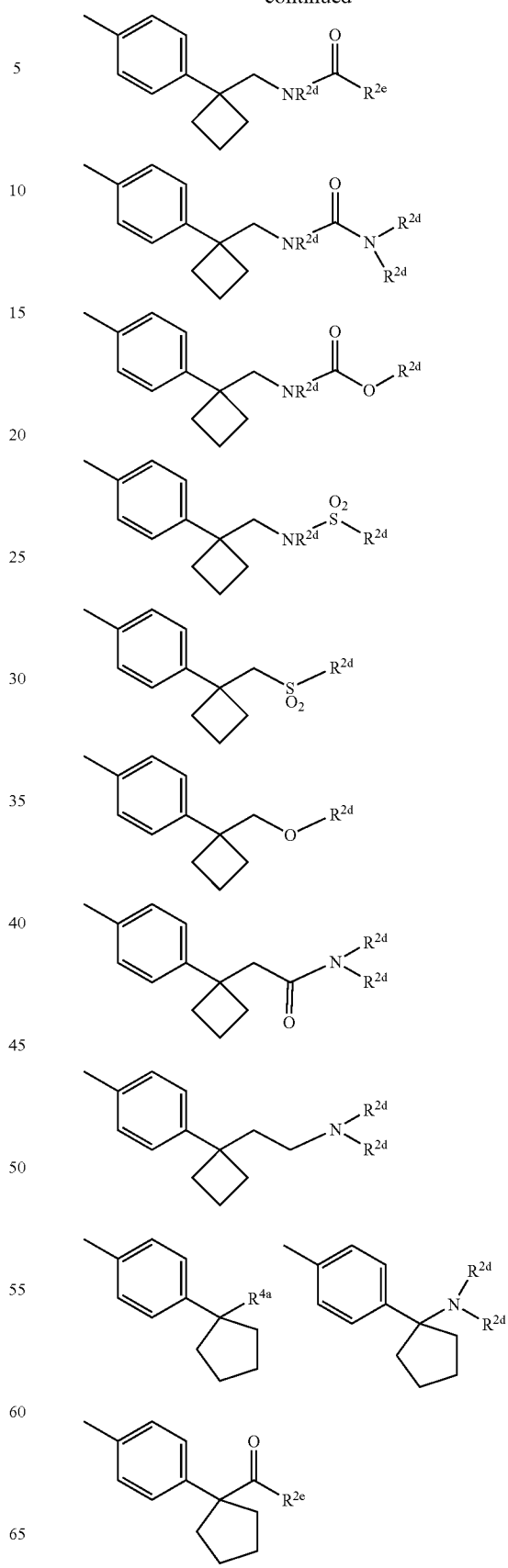

-continued
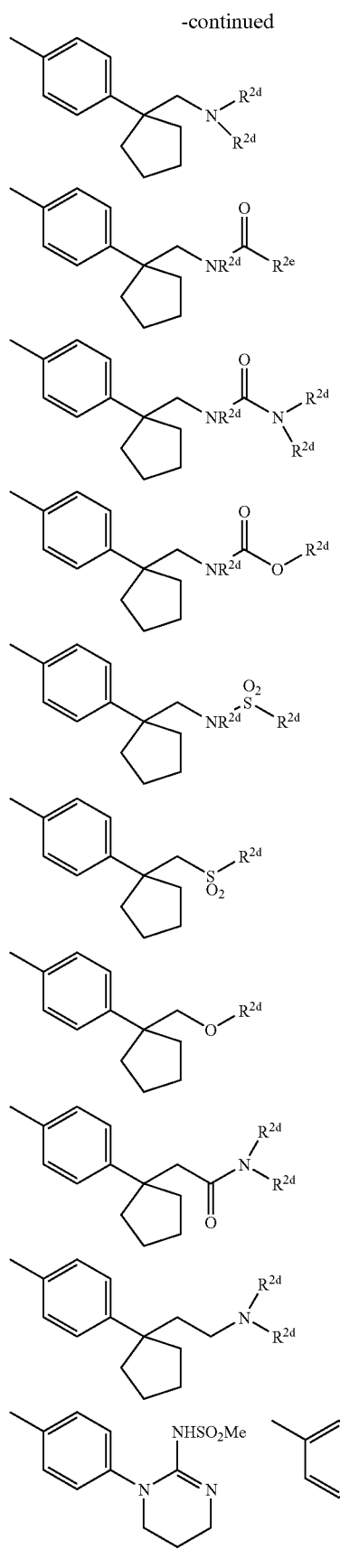
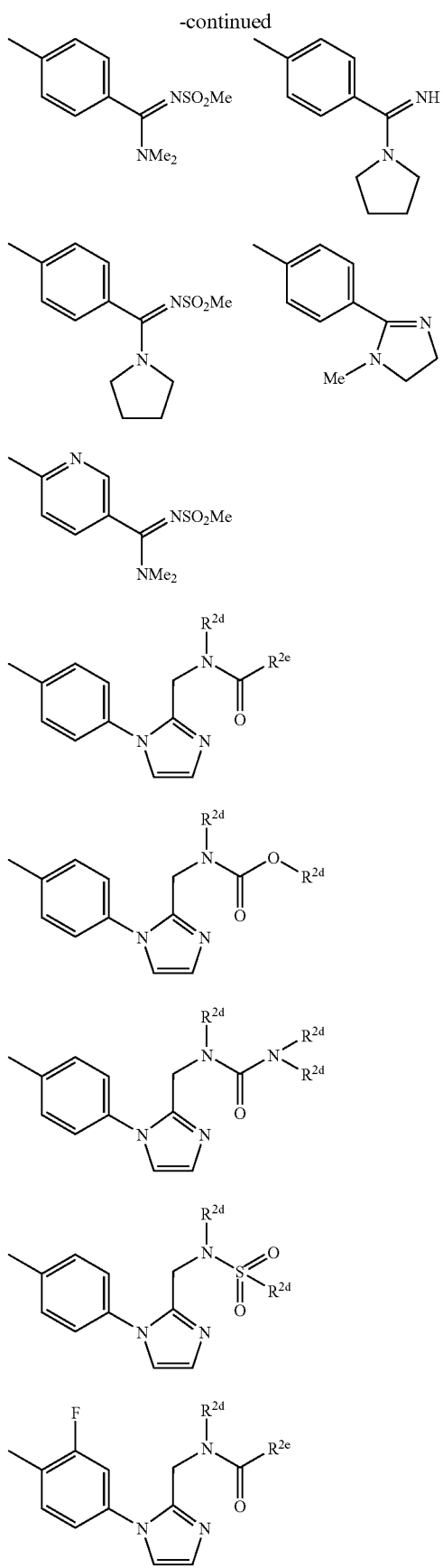

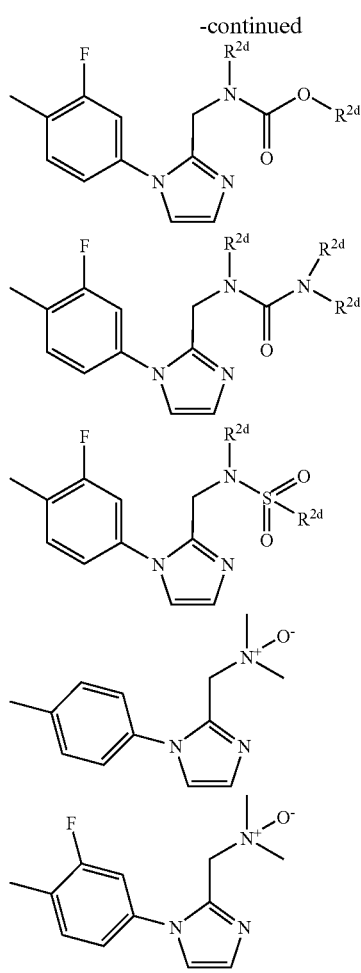

$R^{2d}$, at each occurrence, is selected from H, $CH_3$, $CH_2CH_3$, $CH_2CH_2CH_3$, $CH(CH_3)_2$, $CH_2CH(CH_3)_2$, $CH_2CH_2CH(CH_3)_2$, $CH_2CCH$, $CH_2CH_2OH$, $CH_2C(O)NH_2$, cyclopropyl, $CH_2$-cyclopropyl, cyclobutyl, cyclopentyl, and thiazolyl;

$R^{2e}$, at each occurrence, is selected from $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl;

$R^{4a}$ is substituted with 0–2 $R^{4c}$ and selected from morpholine, 1,1-dioxo-thiomorpholine, dihydropyridine, piperidine, piperazine, pyrrolidine, imidazole, imidazoline, imidazolidine, oxazoline, and thiazoline; and $R^{4c}$ is selected from =O, OH, $OCH_3$, and $CH_3$.

In a fourteenth another embodiment, the present invention provides a novel compound selected from Examples 108–126, or a pharmaceutically acceptable salt form thereof.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another embodiment, the present invention provides novel compounds as described above for use in therapy.

In another embodiment, the present invention provides the use of novel compounds as described above for the manufacture of a medicament for the treatment of a thromboembolic disorder.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising:
(d) a second container;
wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:
(d) a second container;
wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

Preferably, the molecular weight of compounds of the present invention is less than about 500, 550, 600, 650, 700, 750, 800, 850, 900, 950, or 1000 grams per mole. More preferably, the molecular weight is less than about 950 grams per mole. Even more preferably, the molecular weight is less than about 850 grams per mole. Still more preferably, the molecular weight is less than about 750 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is also intended to include all stable oxides of thiol and amino groups, even when not specifically written. When an amino group is listed as a substituent, the N-oxide derivative of the amino group is also included as a substituent. When a thiol group is present, the S-oxide and S,S-dioxide derivatives are also included.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-10}$ alkenyl is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-10}$ Alkynyl is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic group" is intended to mean a stable 3, 4, 5, 6, or 7-membered monocyclic or 7, 8, 9, 10, 11, or 12-membered bicyclic or tricyclic heterocyclic ring which is saturated, partially unsaturated or unsaturated (aromatic), and which consists of carbon atoms and 1, 2, 3, 4, or 5 ring heteroatoms independently selected from the group consisting of N, O and S. Heterocycle includes any bicyclic group in which one heterocyclic ring is fused to a second ring, which may be carbocyclic (e.g. benzo fusion) or heterocyclic. When a heterocycle is referred to as an "aromatic heterocycle" or "heteroaryl," this means that a fully unsaturated, i.e., aromatic, ring is present in the heterocycle. An aromatic heterocycle only requires one ring to be aromatic, if more than one ring is present. The aromatic portion of the aromatic heterocycle can be a carbocycle or heterocycle. The nitrogen and sulfur heteroatoms in the heterocycle may optionally be oxidized (i.e., N→O and S(O)p). The nitrogen atom may be unsubstituted (i.e., N or NH) or substituted (i.e., NR wherein R is a substituent) and may optionally be quaternized. The heterocyclic ring may be attached to its pendant group at any heteroatom or carbon atom that results in a stable structure. The heterocyclic rings described herein may be substituted on a carbon or on a nitrogen atom, if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. It is to be noted that total number of S and O atoms in the aromatic heterocycle is not more than 1. Bridged and spiro rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge. Spiro rings are formed when to or more atoms (i.e., C, O, N, or S) of a chain are attached to the same carbon atom of a heterocycle (or carbocycle if fused to a heterocycle). When a spiro ring is present, the substituents recited for the ring may also be present on the spiro.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two;

generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Compounds of this invention can be prepared as shown in Scheme 1, wherein an appropriately protected amino acid 1a is converted to compound 1c under reductive amination conditions with a appropriately substituted ketone 1b. The formation of lactam 1d is completed under coupling conditions. Deprotection of 1d followed by sulfonation with a appropriately substituted sulfonyl chloride provides compound 1e. Deprotection and reductive amination with a appropriately substituted ketone or aldehyde provides the target compound 1f. (See *Org Prep Proc Int,* 1979, 11; *Synthesis,* 1974, 549.)

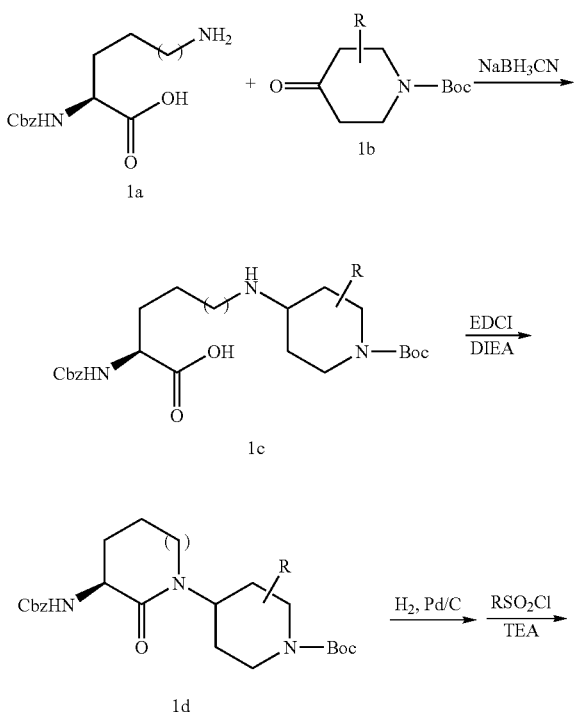

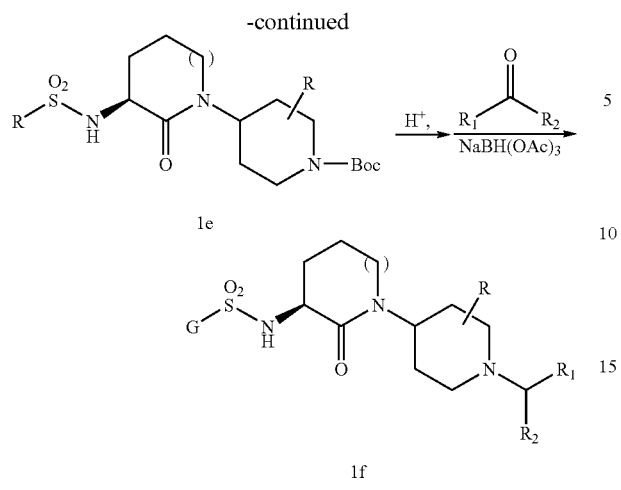

1e

1f

Compounds of this invention can also be prepared as outlined in Scheme 2. Treatment of amino acid 2a with appropriately substituted amine 2b under coupling conditions yields sulfide 2c. Compound 2c is converted to its corresponding sulfonium salt by treatment with methyl iodide and then to lactam 1d under basic conditions, such as $K_2CO_3$ or KHMDS. Following the procedures known to those skilled in the art, compounds 2d can be obtained.

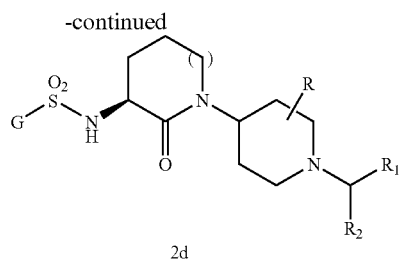

2d

Compounds of this invention can also be prepared as outlined in Scheme 3. Amino acid 3a is coupled with appropriately substituted amine 3b to give compound 3c. Under Mitsunobu conditions (Mitsunobu, *Synthesis*, 1981, 1), 3c is converted to 1d, which is then converted to compound 1f via procedures known to those skilled in the art.

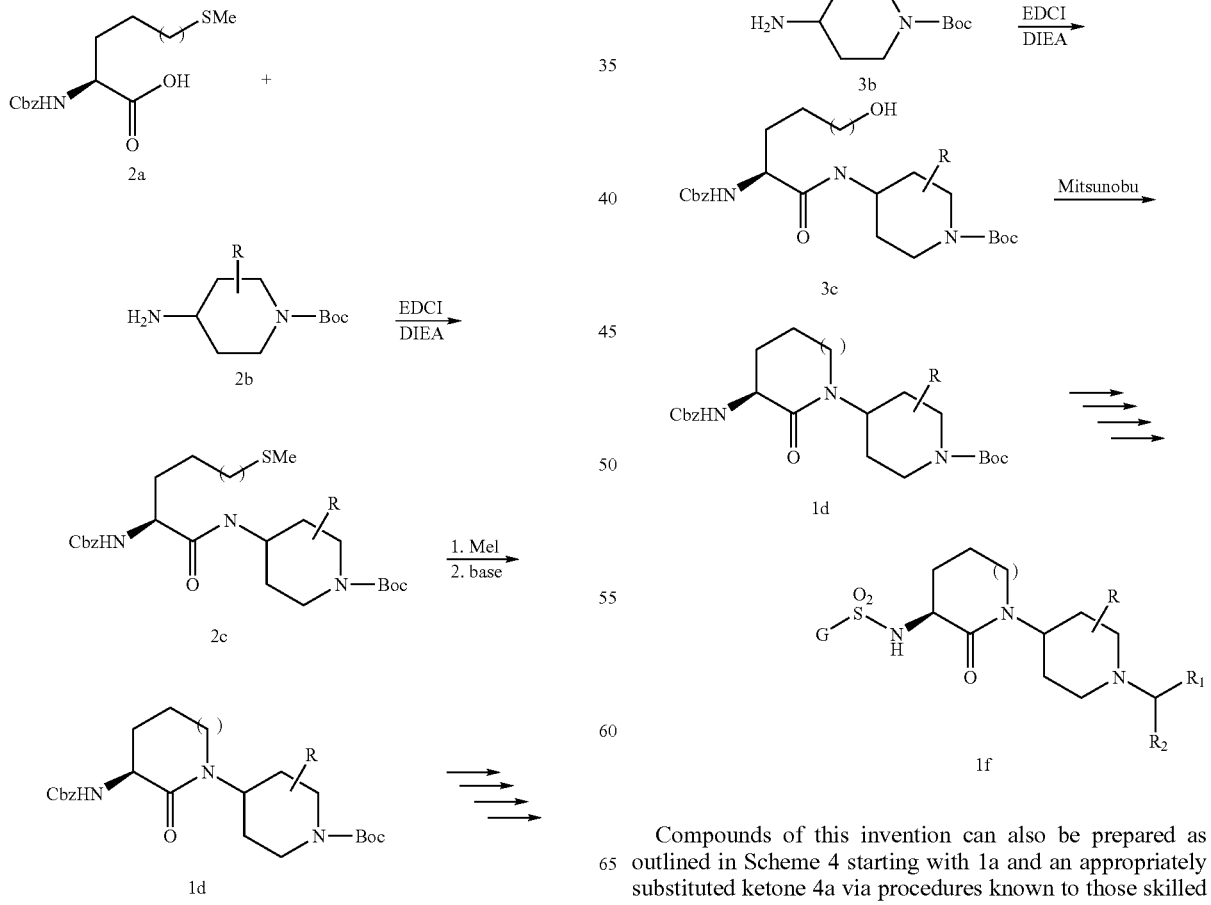

Compounds of this invention can also be prepared as outlined in Scheme 4 starting with 1a and an appropriately substituted ketone 4a via procedures known to those skilled in the art.

Scheme 4

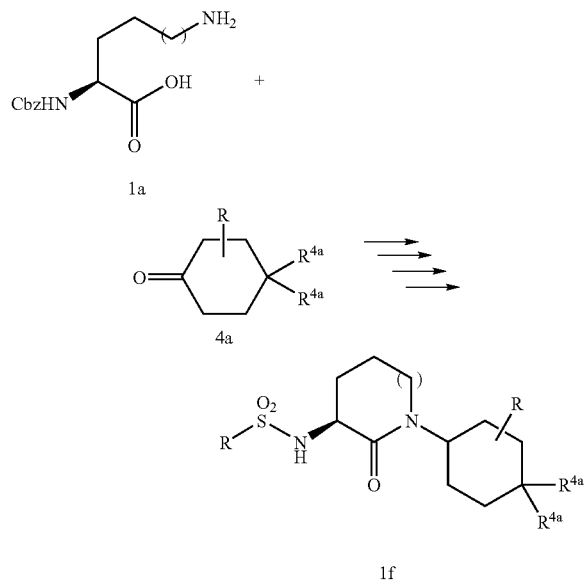

Alternatively, compounds of this invention can also be prepared as outlined in Scheme 5 starting with 2a or 3a and an appropriately substituted amine 5a via procedures known to those skilled in the art.

Scheme 5

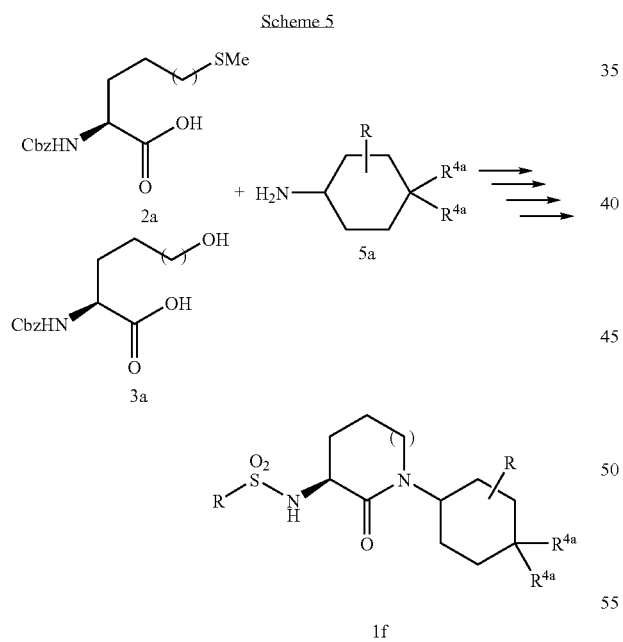

Alternatively, compounds of this invention can also be prepared as outlined in Scheme 6. Methylation of the appropriately protected amino acid 6a followed by cyclization under basic condition provides lactam 6b. Ullman, Goldberg, or Buchwald coupling of 6c with an appropriate -A-B moiety gives intermediate 6d, which then is converted to compounds of this invention via procedures known to those skilled in the art. (See *Tetrahedron* 1984, 40, 1433; *Organic Lett.* 2000, 2, 1101; Klapers et al. *JACS*, 2001, 123, 7727; *Tet. Lett.*, 1999, 40, 2657.)

Scheme 6

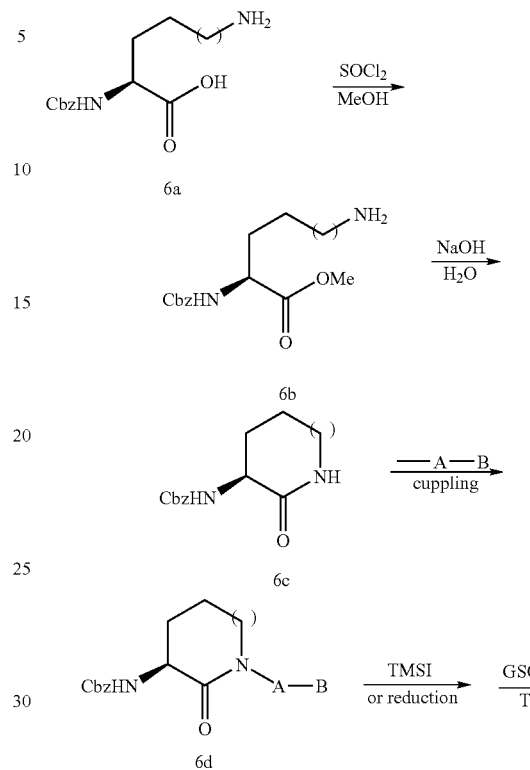

Compounds of this invention with $G_1$ substitutions, 7a, are prepared as outlined in Scheme 7 starting with 6e and halogen-$G_1$, under basic conditions.

Scheme 7

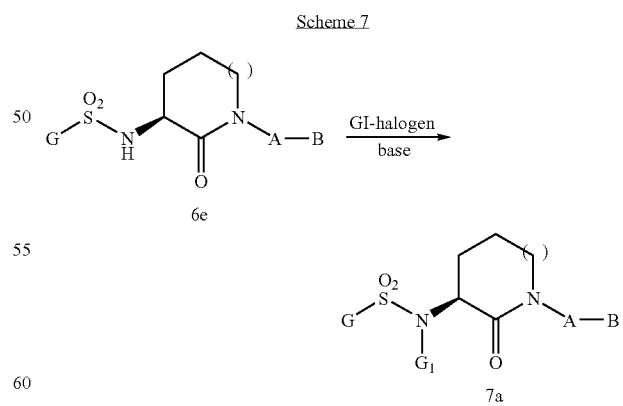

Alternatively, compounds of this invention containing a $G_1$ substitution group can also be prepared as outlined in Scheme 8. Alkylation of 7a occurs under basic conditions, and the G1 group can be further manipulated to give compounds of this invention such as 8b and 8c.

Scheme 8

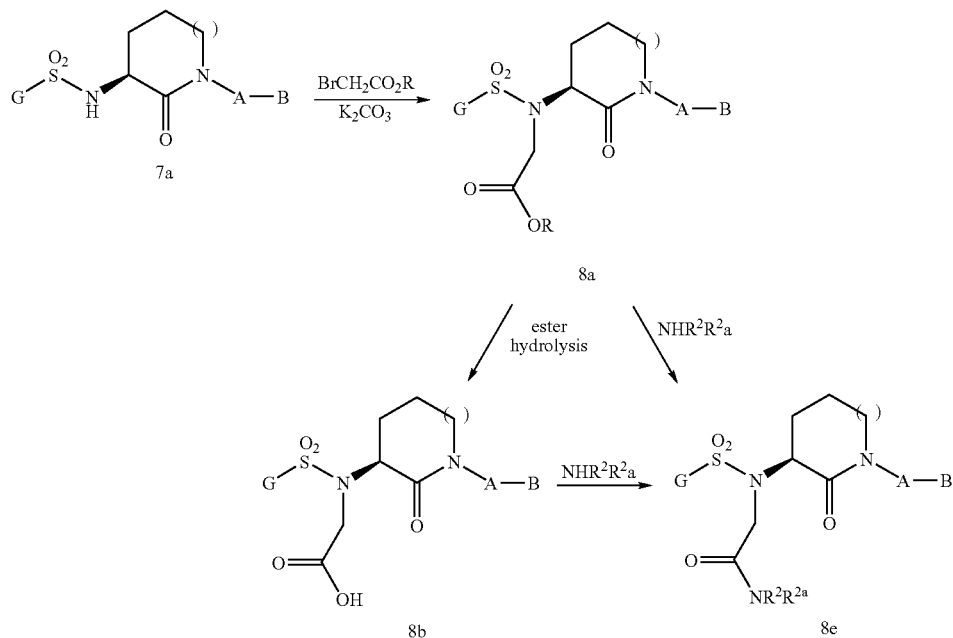

Alternatively, a fully elaborated A-B moiety can be prepared as the heterocyclic amine derivative shown in Scheme 9. Cyclization of 9a gives heterocycle 9b, which then can be converted to compounds of this invention via procedures known to those skilled in the art.

Scheme 9

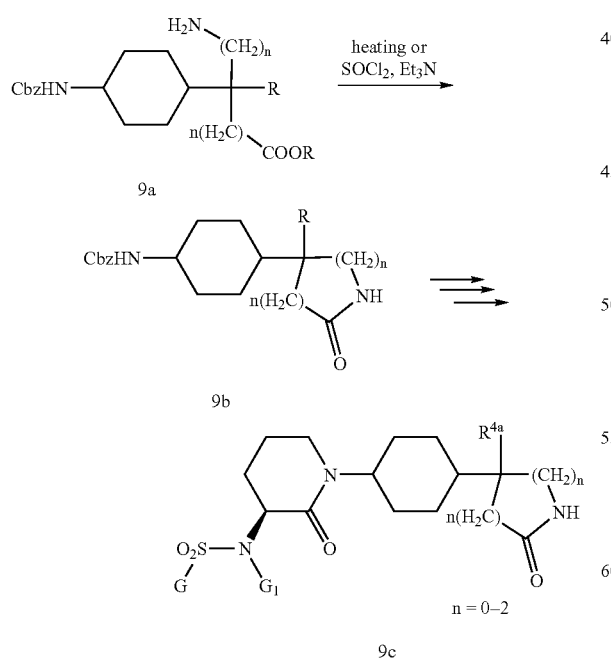

Alternatively, a fully elaborated A-B moiety such as 10b can be prepared as shown in Scheme 10, which then converted to compounds of this invention 10c via procedures known to those skilled in the art.

Scheme 10

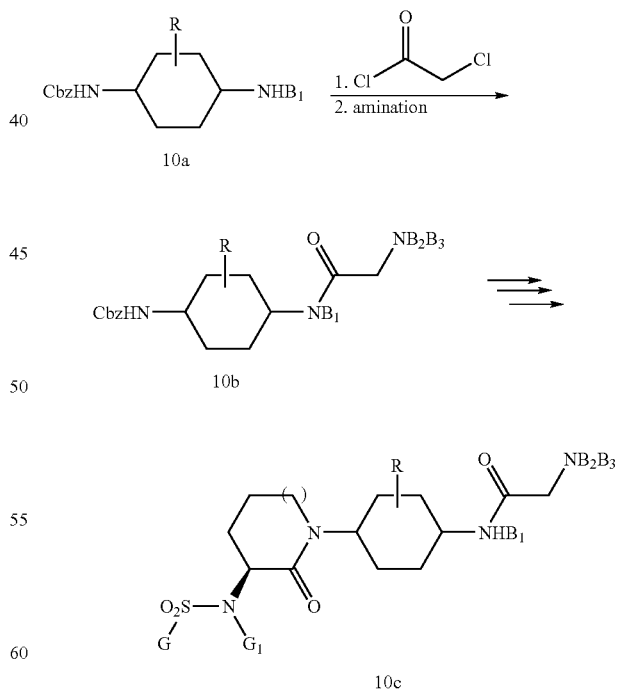

Alternatively, a fully elaborated A-B moiety such as 11b and 11c can be prepared as shown in Scheme 11, which then can be converted to compounds of this invention 11d and 11e via procedures known to those skilled in the art.

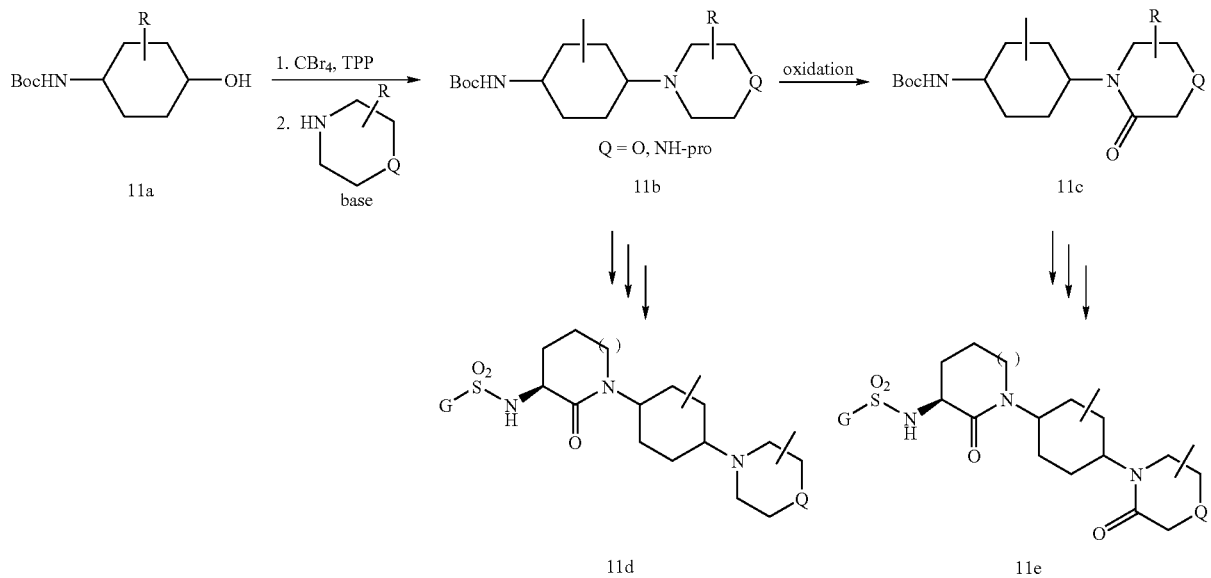

Semicarbazides can be prepared as shown in Scheme 12. The aniline jcan be reacted with an isocyanate to yield a urea. This compound can be cyclized under tBuOK/THF conditions. The cyclic urea can be N-aminated in a one pot reaction involving N—NO formation followed by the NO reduction to the corresponding amine. The N-amino ureas can then be reacted with an appropriate reagent to yield a desired compound, which can be further functionalized on the remaining free position to give the disubstituted derivatives.

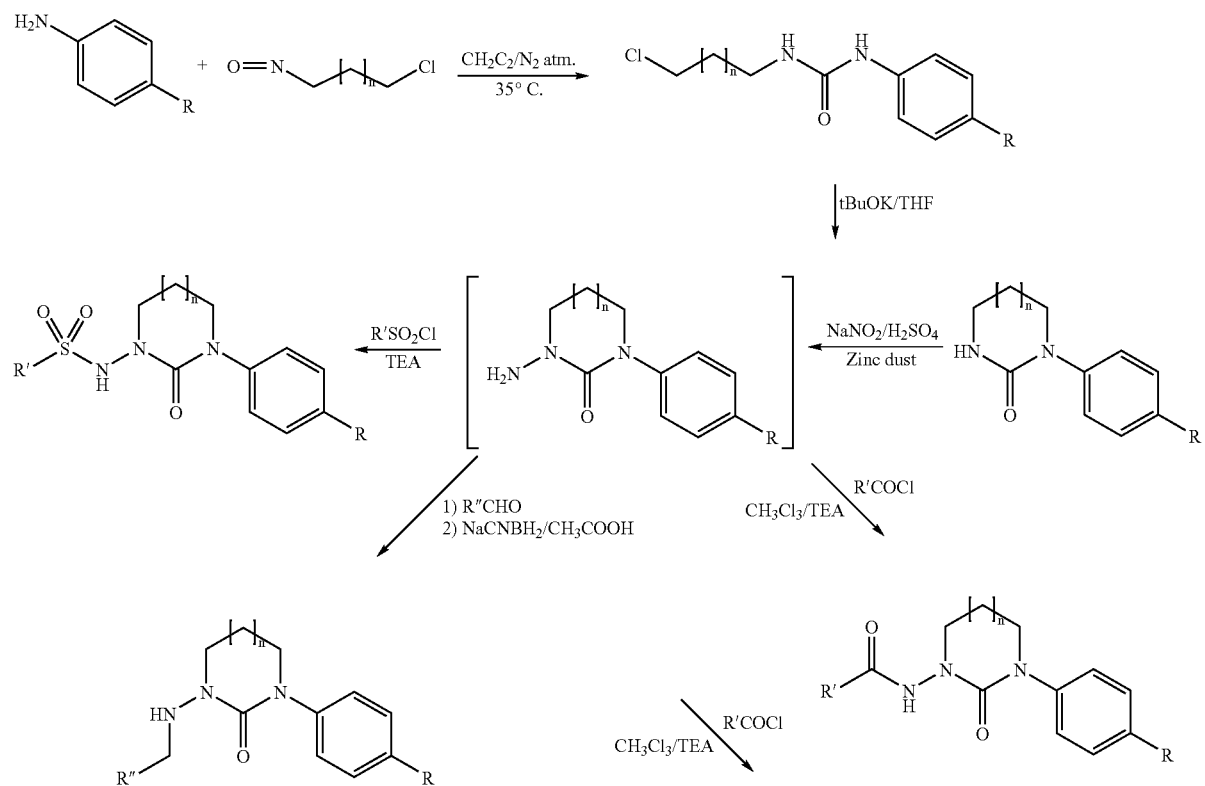

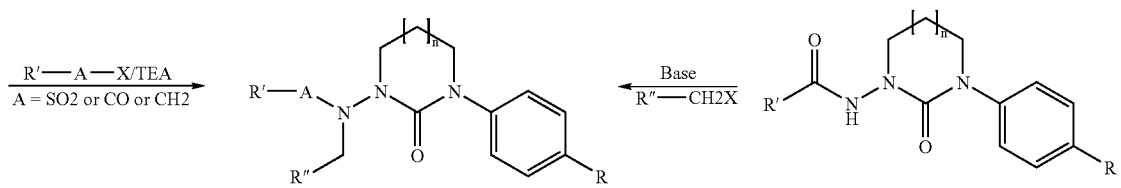
An alternative method was also developed and is outlined in Scheme 13. A p-halogeno aniline can be reacted with an isocyanate to yield a urea. This urea can be cyclized, N-aminated, and the intermediate N-amino derivative trapped as a Schiff base. Coupling with a 6-hydroxypyridine should yield to an intermediate, which can be functionalized as in Scheme 1.
Scheme 13
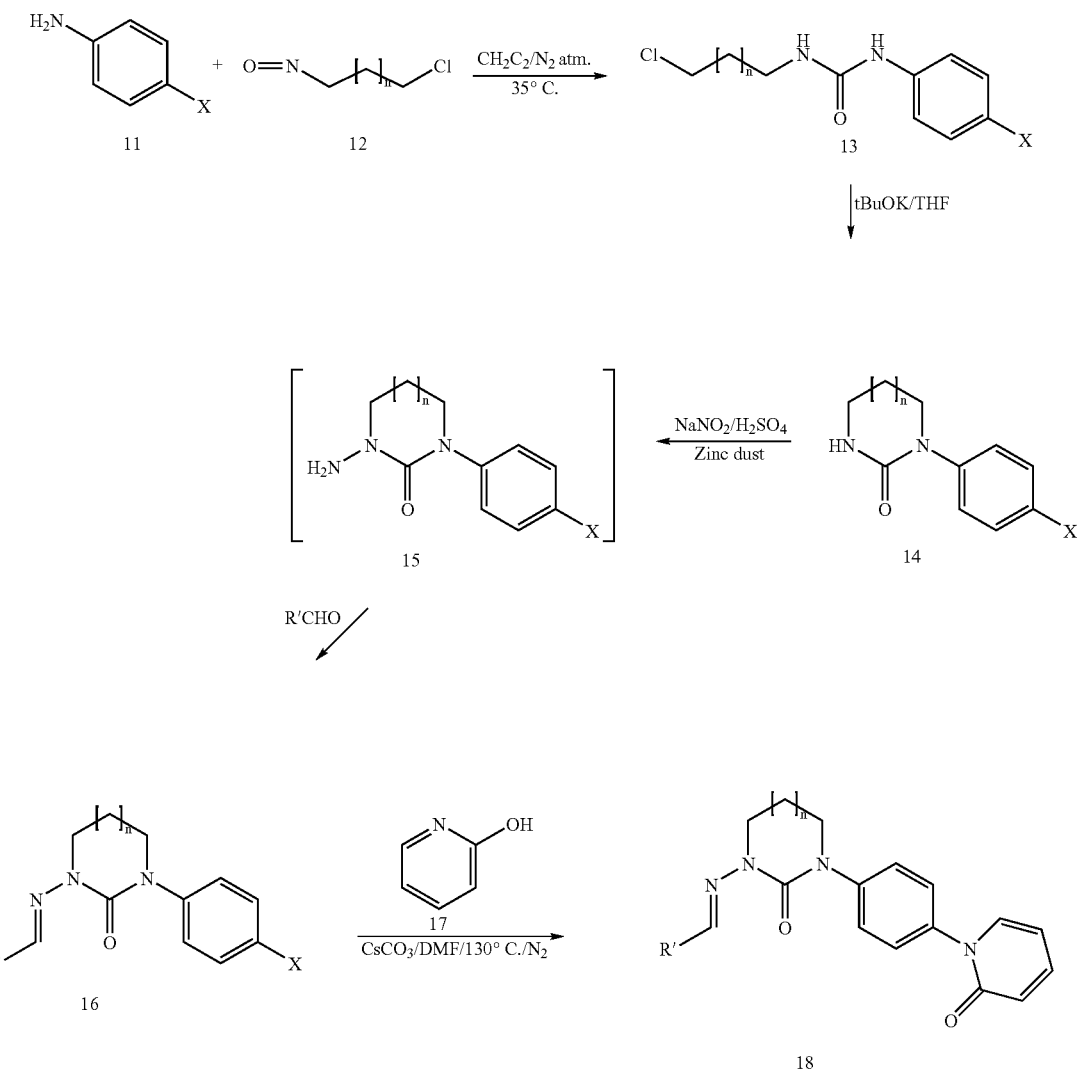

One stereoisomer of a compound of Formula I may display superior activity compared with the other. Thus, the following stereochemistries are considered to be a part of the present invention.

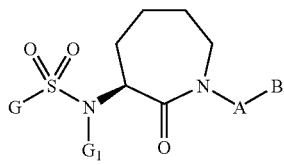
IIIa

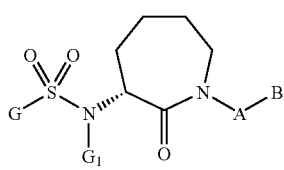
IIIb

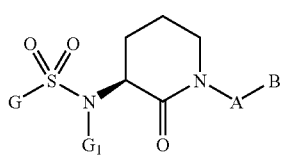
IIIc

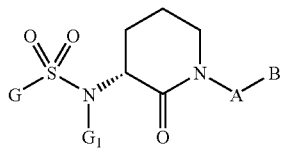
IIId

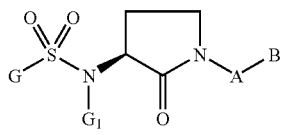
IIIe

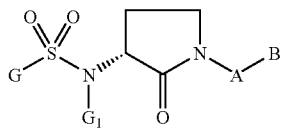
IIIf

When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421–431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

Example 1

(S)-6-Chloro-naphthalene-2-sulfonic acid (1'-cyclopentyl-2-oxo-[1,4']bipiperidinyl-3-yl)-amide Step a: To a suspension of L-CBZ-Ornithine (5.05 g, 18.9 mmol) in 100 mL THF was added 15 mL water (to make the mixture clear) followed by addition of 1-BOC-4-oxo-1-piperindine (3.78 g, 18.9 mmol). After being cooled to 0° C., sodium cyanoborohydride (1.19 g, 18.9 mmol) was added and the mixture was allowed to stir at room temperature over night. Solvent was removed under reduced pressure to leave the desired product as a solid. LC-MS found: $(M+1)^+$ =450.31.

Step b: To the solution of the product obtained from step a (18.9 mmol) in DMF (100 mL) at 0° C. were added EDCI (3.60 g, 18.9 mmol) and DIEA (3.31 mL, 18.9 mmol). The reaction was stirred from 0° C. to room temperature over night. The reaction mixture was diluted with ethyl acetate and washed with 1.0 N HCl(aq.), saturated $NaHCO_3$, and brine. The organic layer was dried over magnesium sulfate and concentrated. Column chromatography purification (silica gel, 50:50=ethyl acetate:hexane) gave the desired product as a white solid. LC-MS found: $(M+1)^+$=432.31.

Step c: The mixture of the product obtained from step b (283 mg, 0.66 mmol) in methanol was hydrogenated in the presence of a catalytic amount of 10% Pd/C at 1 atm for 3 hr at room temperature. The catalyst was filtered and removal of solvent provided the desired product as a white solid. LC-MS found: $(M+1)^+$=298.34.

Step d: To the mixture of the product obtained from step c (172 mg, 0.58 mmol) in dichloromethane (10 mL) were added 6-chloro-naphthalene-2-sulfonyl chloride (151 mg, 0.58 mmol) and DIEA (0.4 mL). After stirring at room temperature for 2 hr, the solvent was removed. Chromatography purification (silica gel, 0% to 50% gradient ethyl acetate/hexane or HPLC 50% to 100% acetonitrile/water gradient) provided the desired product as a white solid. LC-MS found: $(M+1)^+$=522.23.

Step e: To the mixture of the product obtained from step d (153 mg, 0.29 mmol) in dichloromethane (10 mL) was added 3.0 mL of TFA. After stirring at room temperature for 3 hr, the solvent was removed and the residue was dried under vacuum. The desired product was obtained as a white solid. LC-MS found: $(M+1)^+$=422.20.

Step f: To the mixture of the product obtained from step e (50 mg, 0.093 mmol) in anhydrous peroxide-free THF (5.0 mL), were added cyclopentanone (0.1 mL) and sodium cyanoborohydride (8.8 mg, 0.14 mmol) or sodium triacetoxyborohydride. The resulting mixture was stirred at room temperature for 5 hr. The solvent was removed. HPLC separation (30% to 100% acetonitrile/water gradient) gave (S)-6-Chloro-naphthalene-2-sulfonic acid (1'-cyclopentyl-2-oxo-[1,4']bipiperidinyl-3-yl)-amide as a white solid. LC-MS found: (M+1)+=490.75.

Example 2

(S)-6-Chloro-naphthalene-2-sulfonic acid (1''-methyl-2-oxo-[1,4';1',4'']terpiperidin-3-yl)-amide

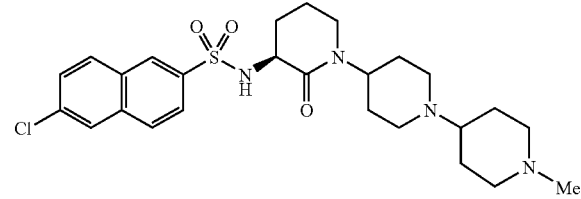

Following a procedure analogous to that described in Example 1, the title compound was obtained as a white solid. LC-MS found: (M+1)+=519.31.

Example 3

(S)-6-Chloro-naphthalene-2-sulfonic acid [1-(1-cyclopentyl-piperidin-4-yl)-2-oxo-pyrrolidin-3-yl]-amide

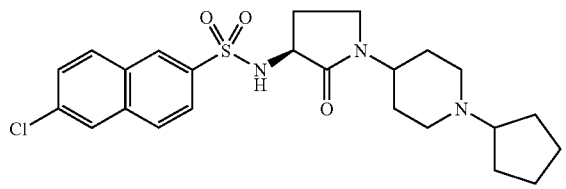

Following a procedure analogous to that described in Example 1, the title compound was provided as white solid. LC-MS found: (M+1)+=476.37.

Example 4

(S)-6-Chloro-naphthalene-2-sulfonic acid (1'-isopropyl-2-oxo-[1,4']bipiperidinyl-3-yl)-amide

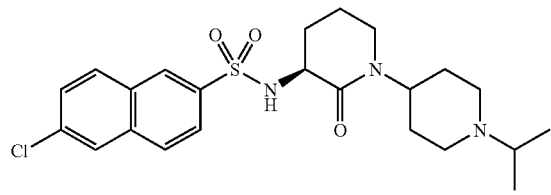

Following a procedure analogous to that described in Example 1, the title compound was obtained as a white solid. LC-MS found: (M+1)+=464.31.

Example 5

(S)-6-Chloro-naphthalene-2-sulfonic acid (1'-cyclohexyl-2-oxo-[1,4']bipiperidinyl-3-yl)-amide

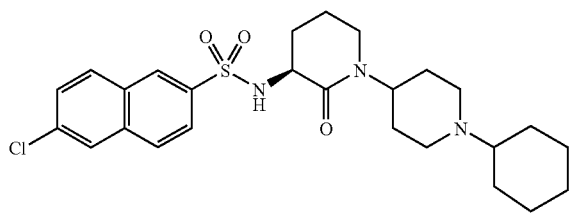

Following a procedure analogous to that described in Example 1, the title compound was obtained as a white solid. LC-MS found: (M+1)+=504.31.

Example 6

(S)-6-Chloro-naphthalene-2-sulfonic acid (1'-acetyl-2-oxo-[1,4']bipiperidinyl-3-yl)-amide

To 6-chloro-naphthalene-2-sulfonic acid (2-oxo-[1,4']bipiperidinyl-3-yl)-amide (20 mg, 0.047 mmol), obtained as described in Example 3, in THF (2.5 mL) were added 0.1 mL DIEA and 2 drops of acetic anhydride at 0° C. After stirring for 2 hr, the mixture was diluted with methanol. The solvent was removed. HPLC purification (30 to 100% acetonitrile/water) gave the title compound as a white solid. LC-MS found: (M+1)+=464.17.

Example 7

(S)-6-Chloro-naphthalene-2-sulfonic acid [1'-(2-dimethylamino-acetyl)-2-oxo-[1,4']bipiperidinyl-3-yl]-amide

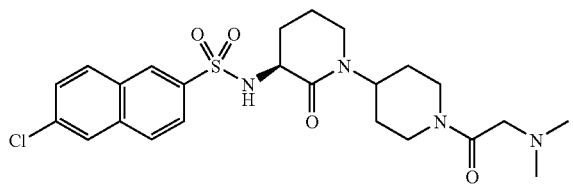

To a mixture of the product obtained from Example 3 (20 mg, 0.047 mmol) in THF/DMF (2.5/1.0 mL) were added DIEA (0.1 mL), N,N-dimethylglycine (50 mg), and BOP reagent (100 mg). The resulting mixture was stirred at 0° C. for 1.5 hr. The solvent was evaporated. HPLC separation (30% to 100% acetonitrile/water) gave the title compound as a white solid. LC-MS found: (M+1)+=507.26.

Example 8

(S)-[(6-Chloro-naphthalene-2-sulfonyl)-(1'-isopropyl-2-oxo-[1,4']bipiperidinyl-3-yl)-amino]-acetic acid methyl ester

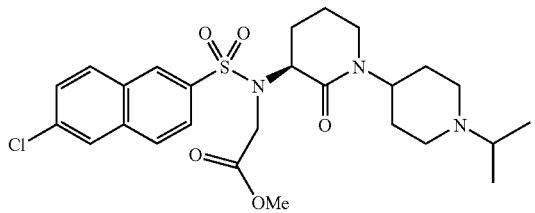

Step a: To a mixture of the product obtained from Example 1, step d (69 mg, 0.13 mmol) in DMF (2.0 mL) at 0° C. were added methyl bromoacetate (0.05 mL) and potassium carbonate (50 mg). After stirring at 0° C. for 2 hr, the solid was filtered out, and the solvent was removed. HPLC purification (50% to 100% acetonitrile/water) gave the desired product as a solid. LC-MS found: $(M+1)^+=$ 594.30.

Step b: To the mixture of the product obtained from above (25 mg, 0.043 mmol) in dichloromethane (1.0 mL) was added TFA (0.2 mL). The mixture was stirred at room temperature for 1.5 hr. The solvent was removed. The desired product was obtained as a solid. LC-MS found: $(M+1)^+=494.20$.

Step c: To the mixture of the product obtained from above in THF (3.0 mL) were added acetone (0.1 mL) and NaBH(OAc)$_3$. After stirring at room temperature for 5 hr, 2 drops of TFA was added. The solvent was removed. HPLC purification (30% to 100% acetonitrile/water) provided (S)-[(6-chloro-naphthalene-2-sulfonyl)-(1'-isopropyl-2-oxo-[1,4']bipiperidinyl-3-yl)-amino]-acetic acid methyl ester as a white solid. LC-MS found: $(M+1)^+=536.30$.

Example 9

(S)-2-[(6-Chloro-naphthalene-2-sulfonyl)-(1'-isopropyl-2-oxo-[1,4']bipiperidinyl-3-yl)-amino]-acetamide

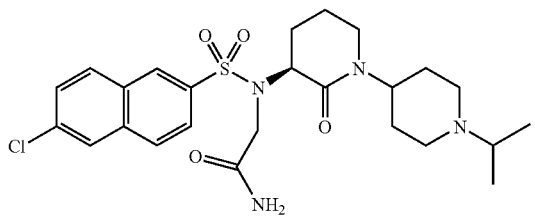

(S)-[(6-Chloro-naphthalene-2-sulfonyl)-(1'-isopropyl-2-oxo-[1,4']bipiperidinyl-3-yl)-amino]-acetic acid methyl ester (the product obtained in Example 8) was dissolved in 2.0M NH$_3$ in methanol (5.0 mL), and the mixture was stirred at room temperature for 48 hr. The solvent was removed. HPLC purification (10% to 100% acetonitrile/water) provided the title compound as a white solid. LC-MS found: $(M+1)^+=521.31$.

Example 10

(S)-6-Chloro-naphthalene-2-sulfonic acid (1'-cyclobutyl-2-oxo-[1,4']bipiperidinyl-3-yl)-amide

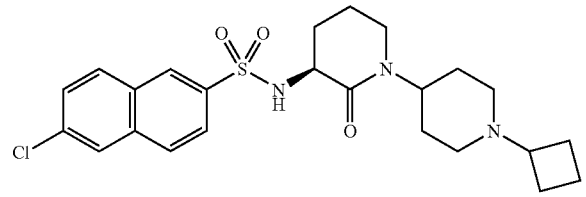

Following a procedure analogous to that described in Example 1, the title compound was obtained as a white solid. LC-MS found: $(M+1)^+=476.30$.

Example 11

(S)-6-Chloro-naphthalene-2-sulfonic acid [1'-(4-hydroxy-butyl)-2-oxo-[1,4']bipiperidinyl-3-yl]-amide

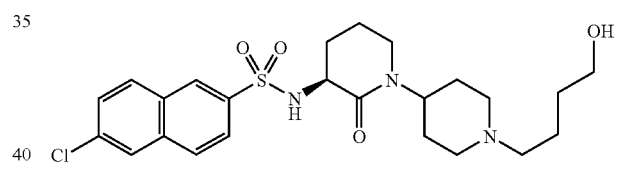

Following a procedure analogous to that described in Example 1, where peroxide present THF was used in Step F, the title compound was obtained as a white solid. LC-MS found: $(M+1)^+=494.34$.

Example 12

(S)-6-Chloro-naphthalene-2-sulfonic acid (1'-sec-butyl-2-oxo-[1,4']bipiperidinyl-3-yl)-amide

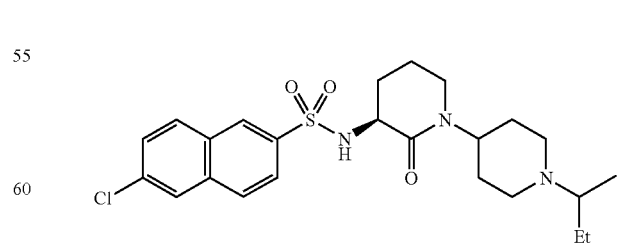

Following a procedure analogous to that described in Example 1, the title compound was obtained as a white solid. LC-MS found: $(M+1)^+=478.29$.

Example 13

(S)-6-Chloro-naphthalene-2-sulfonic acid [2-oxo-1'-(tetrahydro-pyran-4-yl)-[1,4']bipiperidinyl-3-yl]-amide

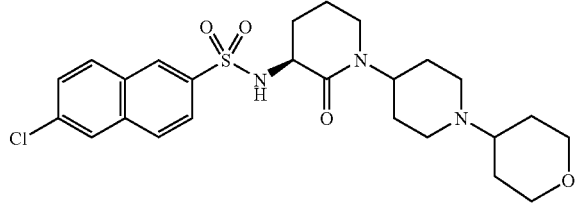

Following a procedure analogous to that described in Example 1, the title compound was obtained as a white solid. LC-MS found: (M+1)$^+$=506.29.

Example 14

(S)-6-Chloro-naphthalene-2-sulfonic acid (1'-methyl-2-oxo-[1,4']bipiperidinyl-3-yl)-amide

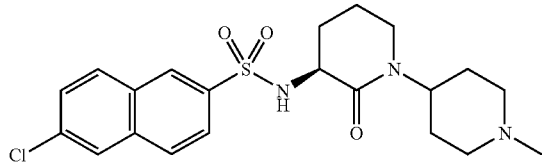

Following a procedure analogous to that described in Example 1, the title compound was obtained as a white solid. LC-MS found: (M+1)$^+$=436.24.

Example 15

(R)-6-Chloro-naphthalene-2-sulfonic acid (1'-isopropyl-2-oxo-[1,4']bipiperidinyl-3-yl)-amide

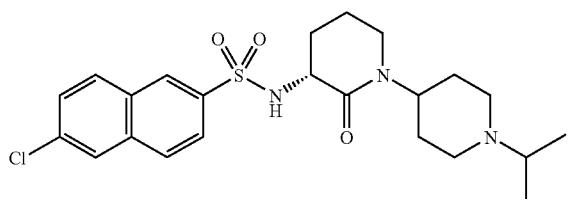

Following a procedure analogous to that described in Example 1, when D-CBZ-ornithine was used, the title compound was obtained as a white solid. LC-MS found: (M+1)$^+$=464.23.

Example 16

(S)-6-Chloro-naphthalene-2-sulfonic acid [1'-(1-ethyl-propyl)-2-oxo-[1,4']bipiperidinyl-3-yl]-amide

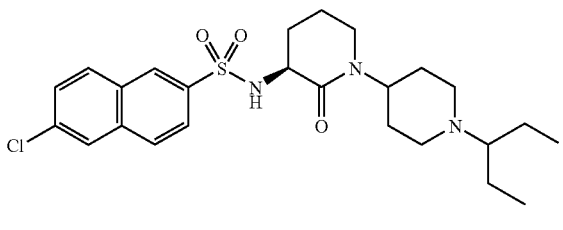

Following a procedure analogous to that described in Example 1, the title compound was obtained as a white solid. LC-MS found: (M+1)$^+$=492.36.

Example 17

(S)-6-Chloro-naphthalene-2-sulfonic acid (1'-ethyl-2-oxo-[1,4']bipiperidinyl-3-yl)-amide

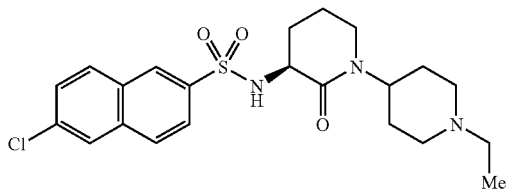

Following a procedure analogous to that described in Example 1, the title compound was obtained as a white solid. LC-MS found: (M+1)$^+$=450.32.

Example 18

(S)-6-Chloro-naphthalene-2-sulfonic acid [1-(1-isopropyl-piperidin-4-yl)-2-oxo-pyrrolidin-3-yl]-amide

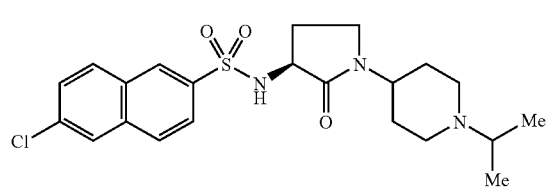

Step a: To a suspension of L-4-amino-2-benzyloxycarbonylamino-butyric acid (3.12 g, 12.4 mmol) in THF (100 mL) were added water (20 mL or till the mixture turned clear) and 4-oxo-1-BOC-piperidine (2.47 g, 12.4 mmol), followed by addition of NaBH$_3$CN (0.93 g, 14.9 mmol). The mixture was stirred at room temperature for 3 hr. The solvent was removed, and the desired product was obtained as a solid. LC-MS found: (M+1)$^+$=436.32.

Step b: To the mixture of the product obtained from above (12.4 mmol) in DMF (80 mL) at 0° C. were added EDCI (2.38 g, 12.4 mmol) and DIEA (2.16 mL, 12.4 mmol). The resulting mixture was stirred from 0° C. to room temperature for 7 hr. The reaction mixture was diluted with ethyl acetate (300 mL) and washed with water, saturated NaHCO₃, and brine. The organic layer was dried over magnesium sulfate and concentrated. HPLC purification (30% to 100% acetonitrile/water gradient) gave the desired product as a white solid. LC-MS found: $(M+1)^+=418.36$.

Step c: The mixture of the product obtained from above (274 mg, 0.66 mmol) in methanol was hydrogenated in the presence of a catalytic amount of 10% Pd/C at 1 atm over night. The catalyst was filtered out and removal of solvent provided the desired product as a white solid. LC-MS found: $(M+1)^+=284.27$.

Step d: To the mixture of the product obtained from above (184 mg, 0.65 mmol) in dichloromethane (6 mL) were added 6-chloro-naphthalene-2-sulfonyl chloride (170 mg, 0.65 mmol) and DIEA (0.4 mL). The resulting mixture was stirred at room temperature for 2 hr. The solvent was removed. Chromatography purification (0% to 50% gradient ethyl acetate/hexane or 50% to 100% acetonitrile/water HPLC) provided the desired product as a white solid. LC-MS found: $(M+1)^+=508.30$.

Step e: TFA (2 mL) was added to the solution of the product obtained from above (260 mg, 0.51 mmol) in dichloromethane (10 mL). After stirring at room temperature for 1.5 hr, the solvent was removed, and the residue was dried under vacuum to leave the desired product as a solid. LC-MS found: $(M+1)^+=408.20$.

Step f: To the mixture of the product obtained from above (20 mg, 0.049 mmol) in anhydrous peroxide free THF (5.0 mL) were added acetone (0.2 mL) and sodium cyanoborohydride (10 mg) or sodium triacetoxyborohydride. The mixture was stirred at room temperature for 8 hr. The solvent was removed. HPLC purification (30% to 100% acetonitrile/water gradient) gave (S)-6-chloro-naphthalene-2-sulfonic acid [1-(1-isopropyl-piperidin-4-yl)-2-oxo-pyrrolidin-3-yl]-amide as a white solid. LC-MS found: $(M+1)^+=450.28$.

Example 19

(S)-4-[3-(6-Chloro-naphthalene-2-sulfonylamino)-2-oxo-pyrrolidin-1-yl]-piperidine-1-carboxylic acid tert-butyl ester

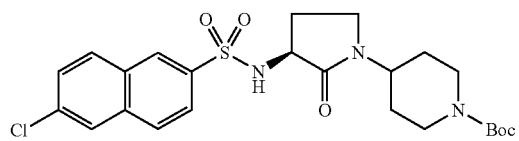

Following a procedure analogous to that described in Example 18, the title compound was obtained as a white solid. LC-MS found: $(M+1)^+=508.30$.

Example 20

(S)-6-Chloro-naphthalene-2-sulfonic acid {1-[1-(4-hydroxy-butyl)-piperidin-4-yl]-2-oxo-pyrrolidin-3-yl}-amide

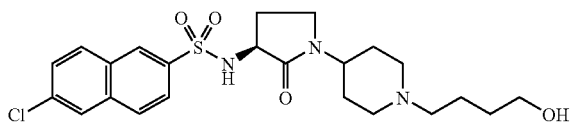

Following a procedure described in Example 18, when peroxide containing THF was used as solvent, the title compound was obtained as a white solid. LC-MS found: $(M+1)^+=480.26$.

Example 21

(S)-6-Chloro-naphthalene-2-sulfonic acid [1-(1-cyclohexyl-piperidin-4-yl)-2-oxo-pyrrolidin-3-yl]-amide

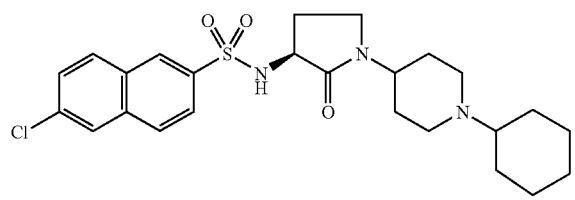

Following a procedure analogous to that described in Example 18, the title compound was obtained as a white solid. LC-MS found: $(M+1)^+=490.27$.

Example 22

(S)-6-Chloro-naphthalene-2-sulfonic acid [1-(4-isopropyl-cyclohexyl)-2-oxo-pyrrolidin-3-yl]-amide

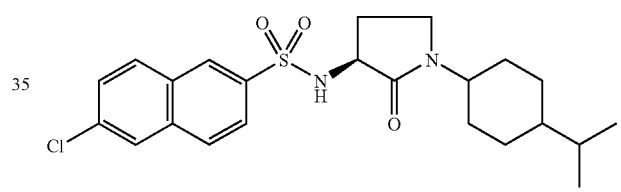

Step a: To the suspension of L-4-amino-2-benzyloxycarbonylamino-butyric acid (2.16 g, 8.57 mmol) in THF (60 m) were added water (20 mL, till the mixture turned clear) and 4-isopropylcyclohexanone (1.50 g, 10.7 mmol), followed by addition of NaBH₃CN (0.65 g, 10.3 mmol). The mixture was stirred at room temperature for 3.5 hr. The solvent was removed, and the desired product was obtained as a solid. LC-MS found: $(M+1)^+=377.33$.

Step b: To the mixture of the product obtained from above (8.57 mmol) in DMF (40 mL) at 0° C. were added EDCI (2.46 g, 12.8 mmol) and DIEA (1.49 mL, 8.57 mmol). The mixture was stirred from 0° C. to room temperature for 20 hr. The reaction mixture was diluted with ethyl acetate (300 mL) and washed with water, 1.0N HCl, saturated NaHCO₃, and brine. The organic layer was dried over magnesium sulfate and concentrated. Silica gel flash chromatography (0% to 100% ethyl acetate/hexane gradient) purification gave the desired product as a white solid. LC-MS found: $(M+1)^+=359.36$.

Step c: The mixture of the product obtained from above (372 mg, 1.0 mmol) in methanol was hydrogenated in the present of catalytic amount of 10% Pd/C at 1 atm over night. The catalyst was filtered out, and removal of solvent provided the desired product as a white solid. LC-MS found: $(M+1)^+=225.31$.

Step d: To the mixture of the product obtained from above (34 mg, 0.15 mmol) in dichloromethane (5 mL) were added 6-chloro-naphthalene-2-sulfonyl chloride (34 mg, 0.13 mmol) and DIEA (0.2 mL). After stirring at room temperature for 2 hr, the solvent was removed. HPLC purification (50% to 100% acetonitrile/water gradient) provided (S)-6-chloro-naphthalene-2-sulfonic acid [1-(4-isopropyl-cyclohexyl)-2-oxo-pyrrolidin-3-yl]-amide as a white solid. LC-MS found: $(M+1)^+=449.30$.

Example 23

(S)-Naphthalene-2-sulfonic acid (1'-isopropyl-2-oxo-[1,4']bipiperidinyl-3-yl)-amide

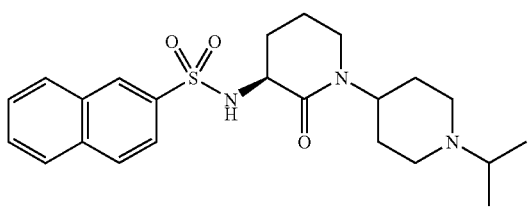

Following a procedure analogous to that described in Example 1, the title compound was obtained as a white solid. LC-MS found: $(M+1)^+=430.35$.

Example 24

(S)-6-Chloro-benzo[b]thiophene-2-sulfonic acid (1'-isopropyl-2-oxo-[1,4']bipiperidinyl-3-yl)-amide

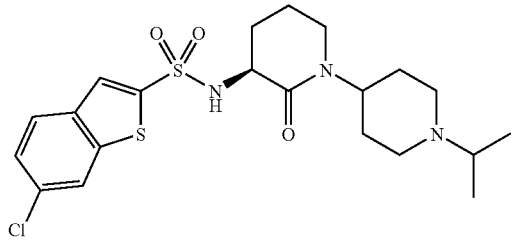

Following a procedure analogous to that described in Example 1, the title compound was obtained as a white solid. LC-MS found: $(M+1)^+=470.23$.

Example 25

(S)-5-Chloro-benzo[b]thiophene-2-sulfonic acid (1'-isopropyl-2-oxo-[1,4']bipiperidinyl-3-yl)-amide

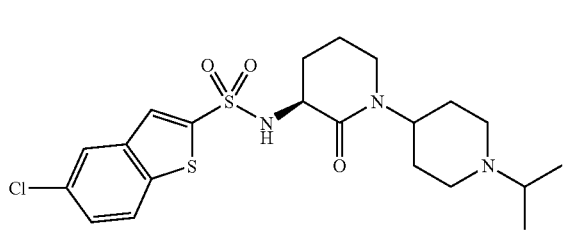

Following a procedure analogous to that described in Example 1, the title compound was obtained as a white solid. LC-MS found: $(M+1)^+=470.28$.

Example 26

(S)-5-Chloro-thiophene-2-sulfonic acid (1'-isopropyl-2-oxo-[1,4']bipiperidinyl-3-yl)-amide

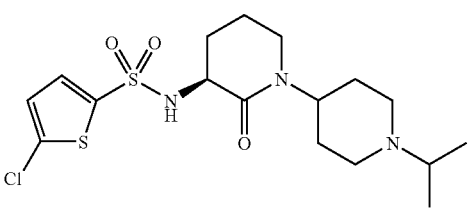

Following a procedure analogous to that described in Example 1, the title compound was obtained as a white solid. LC-MS found: $(M+1)^+=420.23$.

Example 27

(S)-7-Chloro-naphthalene-2-sulfonic acid (1'-isopropyl-2-oxo-[1,4']bipiperidinyl-3-yl)-amide

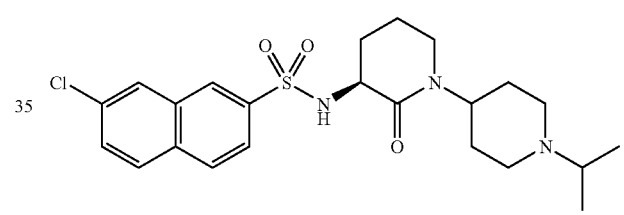

Following a procedure analogous to that described in Example 1, the title compound was obtained as a white solid. LC-MS found: $(M+1)^+=464.34$.

Example 28

(S)-6-Bromo-naphthalene-2-sulfonic acid (1'-isopropyl-2-oxo-[1,4']bipiperidinyl-3-yl)-amide

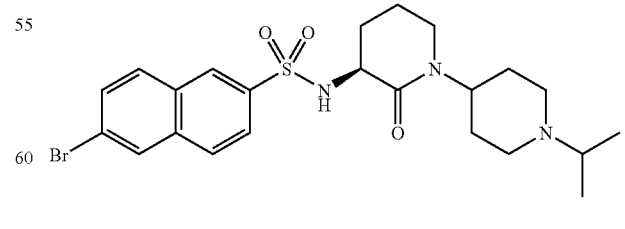

Following a procedure analogous to that described in Example 1, the title compound was provide as a white solid. LC-MS found: $(M+1)^+=508.3$.

Example 29

(S)-5-Chloro-1H-indole-2-sulfonic acid (1'-isopropyl-2-oxo-[1,4']bipiperidinyl-3-yl)-amide

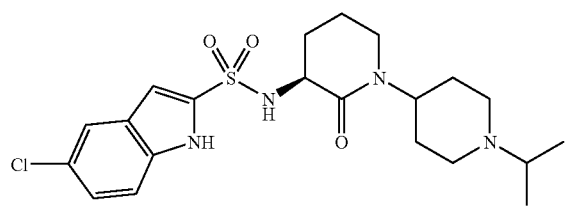

Following a procedure analogous to that described in Example 1, the title compound was obtained. LC-MS found: (M+1)⁺=553.3.

Example 30

(S)-Benzo[b]thiophene-2-sulfonic acid (1'-isopropyl-2-oxo-[1,4']bipiperidinyl-3-yl)-amide

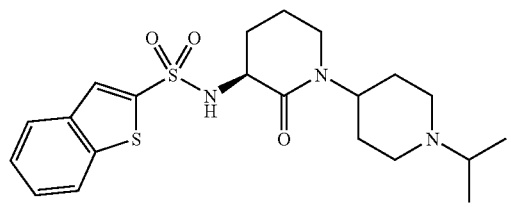

Following a procedure analogous to that described in Example 1, the title compound was obtained as a solid. LC-MS found: (M+1)⁺=436.37.

Example 31

(S)-2-(5-Chloro-thiophen-2-yl)-ethenesulfonic acid (1'-isopropyl-2-oxo-[1,4']bipiperidinyl-3-yl)-amide

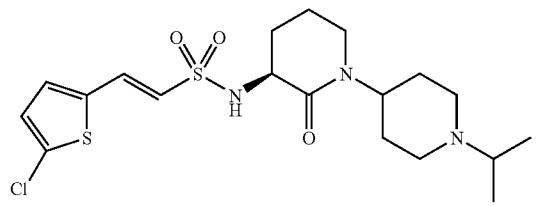

Following a procedure analogous to that described in Example 1, the title compound was obtained as a solid. LC-MS found: (M+1)⁺=446.34.

Example 32

(S)-2-Methyl-quinoline-6-sulfonic acid (1'-isopropyl-2-oxo-[1,4']bipiperidinyl-3-yl)-amide

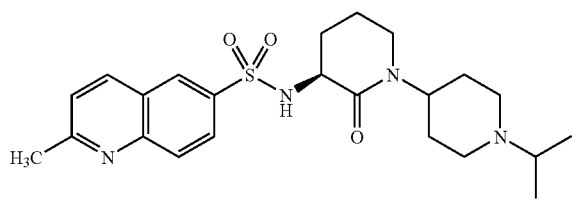

Following a procedure analogous to that described in Example 1, the title compound was obtained as a solid. LC-MS found: (M+1)⁺=445.5.

Example 33

(S)-5-Chloro-thieno[3,2-b]pyridine-2-sulfonic acid (1'-isopropyl-2-oxo-[1,4']bipiperidinyl-3-yl)-amide

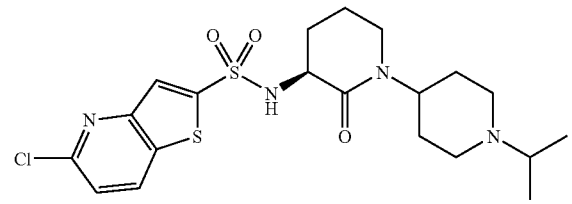

Following a procedure analogous to that described in Example 1, the title compound was obtained as a solid. LC-MS found: (M+1)⁺=471.35.

Example 34

(S)-2-(4-Chloro-phenyl)-ethenesulfonic acid (1'-isopropyl-2-oxo-[1,4']bipiperidinyl-3-yl)-amide

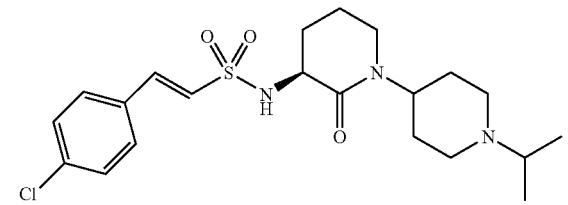

Following a procedure analogous to that described in Example 1, the title compound was obtained as a solid. LC-MS found: (M+1)⁺=440.38.

Example 35

(S)-2-Thiophen-2-yl-ethanesulfonic acid (1'-isopropyl-2-oxo-[1,4']bipiperidinyl-3-yl)-amide

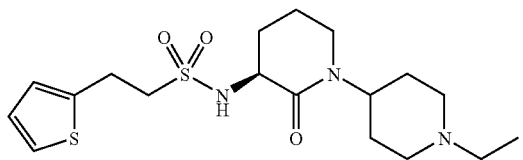

A mixture of (S)-2-(5-chloro-thiophen-2-yl)-ethenesulfonic acid (1'-isopropyl-2-oxo-[1,4']bipiperidinyl-3-yl)-amide (example 31, 10 mg) in MeOH (1.0 mL) was hydrogenated in the presence of catalytic amount of 5% Pd/C at 1 atm 1 hr. Filtration and HPLC purification (30% to 100% acetonitrile/water gradient) gave the desired product as a white solid. LC-MS found: $(M+1)^+=414.41$.

Example 36

(S)-{(6-Chloro-naphthalene-2-sulfonyl)-[1-(1-isopropyl-piperidin-4-yl)-2-oxo-pyrrolidin-3-yl]-amino}-acetic acid

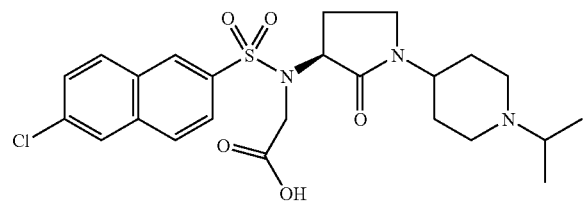

Step a: To a mixture of 4-[3-(6-chloro-naphthalene-2-sulfonylamino)-2-oxo-pyrrolidin-1-yl]-piperidine-1-carboxylic acid tert-butyl ester (example 19, 57 mg, 0.11 mmol) in DMF (3.0 mL) at 0° C. were added potassium carbonate (50 mg) and tert-butyl bromoacetate (0.1 mL). After stirring for 2 hr, the mixture was filtered. The filtrate was purified by HPLC (60% to 100% acetonitril/water gradient) and the desired product was obtained as a solid. LC-MS found: $(M+1)^+=622.54$.

Step b: TFA (1.0 mL was added to the mixture of the product (61 mg) obtained from above in dichloromethane (5.0 mL). The mixture was stirred at rt for 2 hr. The solvent and excessive TFA were removed under reduced pressure, and the desired product was obtained as a solid. LC-MS found: $(M+1)^+=466.29$.

Step c: To the mixture of the product obtained from above in THF (5.0 mL) was added acetone (0.2 mL). After stirring at rt for 10 min, NaBH(OAc)$_3$ (50 mg) was added, and the resulting mixture was stirred at rt for 7 hr. The solvent was removed, and the residue was purified by PHLC (30%–100% acetonitrile/water gradient) to provid (S)-{(6-chloro-naphthalene-2-sulfonyl)-[1-(1-isopropyl-piperidin-4-yl)-2-oxo-pyrrolidin-3-yl]-amino}-acetic acid as a white solid. LC-MS found: $(M+1)^+=508.36$.

Example 37

(S)-6-Chloro-benzo[b]thiophene-2-sulfonic acid [1-(1-isopropyl-piperidin-4-yl)-2-oxo-pyrrolidin-3-yl]-amide

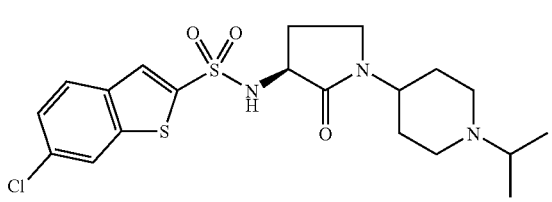

Following a procedure analogous to that described in Example 18, when L-4-amino-2-benzyloxycarbonylaminobutyric acid was used, the title compound was obtained as a white solid. LC-MS found: $(M+1)^+=456.30$.

Example 38

(S)-5-Chloro-thieno[3,2-b]pyridine-2-sulfonic acid [1-(1-isopropyl-piperidin-4-yl)-2-oxo-pyrrolidin-3-yl]-amide

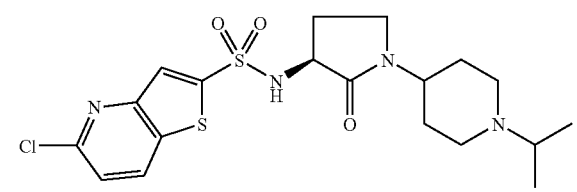

Following a procedure analogous to that described in Example 18, the title compound was obtained as a white solid. LC-MS found: $(M+1)^+=457.30$.

Example 39

(S)-2-(5-Chloro-thiophen-2-yl)-ethenesulfonic acid [1-(1-isopropyl-piperidin-4-yl)-2-oxo-pyrrolidin-3-yl]-amide

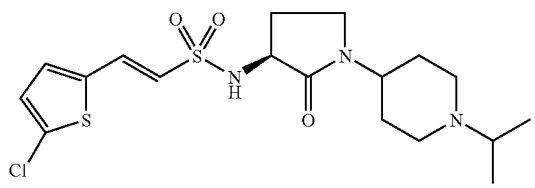

Following a procedure analogous to that described in Example 18, the title compound was obtained as a solid. LC-MS found: $(M+1)^+=432.43$.

Example 40

(S)-6-Amino-pyridine-3-sulfonic acid [1-(1-isopropyl-piperidin-4-yl)-2-oxo-pyrrolidin-3-yl]-amide

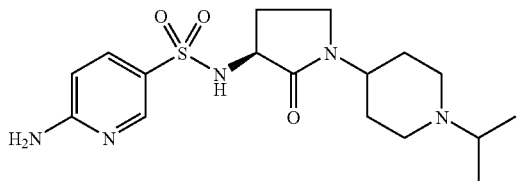

Following a procedure analogous to that described in Example 18, the title compound was obtained as a solid. LC-MS found: (M+1)$^+$=382.4.

Example 41

(S)-6-Bromo-naphthalene-2-sulfonic acid [1-(1-isopropyl-piperidin-4-yl)-2-oxo-pyrrolidin-3-yl]-amide

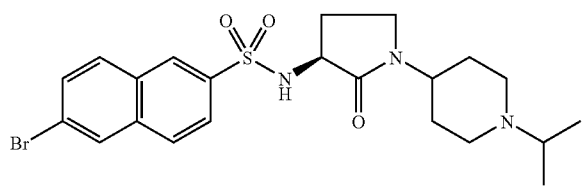

Following a procedure analogous to that described in Example 18, the title compound was obtained as a solid. LC-MS found: (M+1)$^+$=494/496.29.

Example 42

(S)-5-Chloro-thiophene-2-sulfonic acid [1-(1-isopropyl-piperidin-4-yl)-2-oxo-pyrrolidin-3-yl]-amide

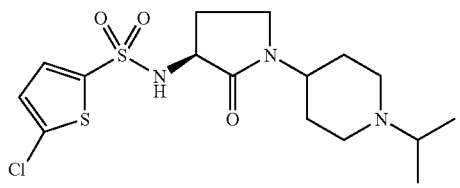

Following a procedure analogous to that described in Example 18, the title compound was obtained as a solid. LC-MS found: (M+1)$^+$=406.29.

Example 43

(S)-3-Methyl-isoquinoline-7-sulfonic acid [1-(1-isopropyl-piperidin-4-yl)-2-oxo-pyrrolidin-3-yl]-amide

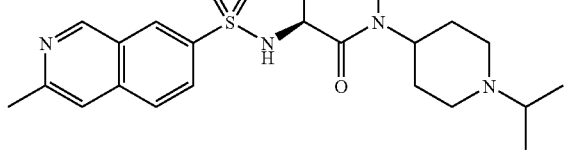

Following a procedure analogous to that described in Example 18, the title compound was obtained as a solid. LC-MS found: (M+1)$^+$=431.3.

Example 44

(S)-N-[1-(1-Isopropyl-piperidin-4-yl)-2-oxo-pyrrolidin-3-yl]-3-pyrazol-1-yl-benzenesulfonamide

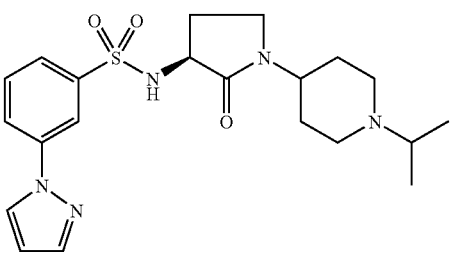

Following a procedure analogous to that described in Example 18, the title compound was obtained as a solid. LC-MS found: (M+1)$^+$=432.39.

Example 45

(S)-1H-Indazole-6-sulfonic acid [1-(1-isopropyl-piperidin-4-yl)-2-oxo-pyrrolidin-3-yl]-amide

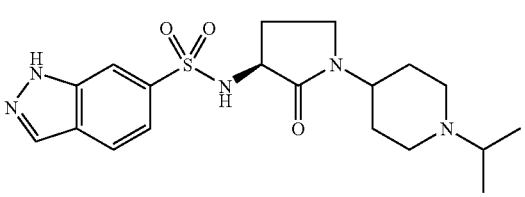

Following a procedure analogous to that described in Example 18, the title compound was obtained as a solid. LC-MS found: (M+1)$^+$=406.4.

Example 46

(S)-5'-Chloro-[2,2']bithiophenyl-5-sulfonic acid [1-(1-isopropyl-piperidin-4-yl)-2-oxo-pyrrolidin-3-yl]-amide

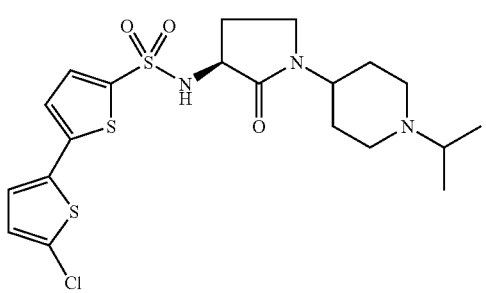

Following a procedure analogous to that described in Example 18, the title compound was obtained as a solid. LC-MS found: (M+1)$^+$=488.30.

Example 47

(S)-2-Methyl-benzothiazole-6-sulfonic acid [1-(1-isopropyl-piperidin-4-yl)-2-oxo-pyrrolidin-3-yl]-amide

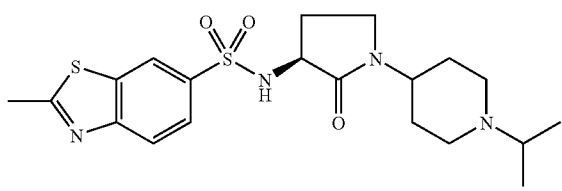

Following a procedure analogous to that described in Example 18, the title compound was obtained as a solid. LC-MS found: (M+1)$^+$=437.47.

Example 48

(S)-Naphthalene-2-sulfonic acid [1-(1-isopropyl-piperidin-4-yl)-2-oxo-pyrrolidin-3-yl]-amide

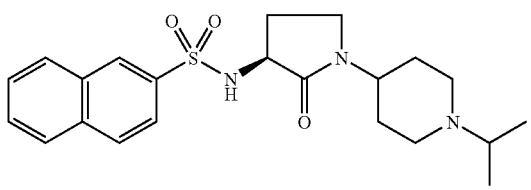

Following a procedure analogous to that described in Example 18, the title compound was obtained as a solid. LC-MS found: (M+1)$^+$=416.39.

Example 49

(S)-N-{2-Chloro-4-[1-(1-isopropyl-piperidin-4-yl)-2-oxo-pyrrolidin-3-ylsulfamoyl]-phenyl}-acetamide

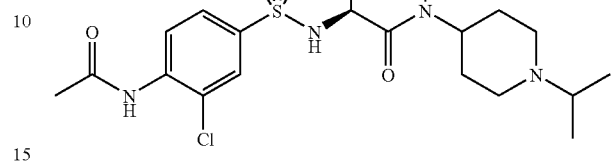

Following a procedure analogous to that described in Example 18, the title compound was obtained as a solid. LC-MS found: (M+1)$^+$=457.34.

Example 50

(S)-3-Cyano-N-[1-(1-isopropyl-piperidin-4-yl)-2-oxo-pyrrolidin-3-yl]-benzenesulfonamide

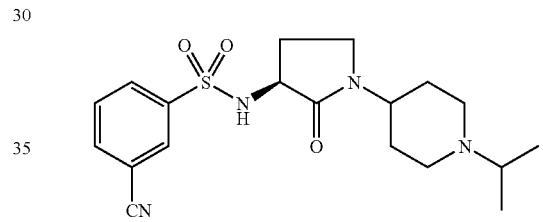

Following a procedure analogous to that described in Example 18, the title compound was obtained as a solid. LC-MS found: (M+1)$^+$=391.36.

Example 51

(S)-3-Chloro-N-[1-(1-isopropyl-piperidin-4-yl)-2-oxo-pyrrolidin-3-yl]-benzenesulfonamide

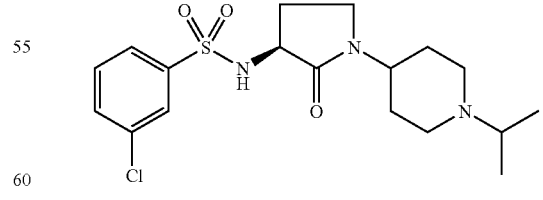

Following a procedure analogous to that described in Example 18, the title compound was obtained as a solid. LC-MS found: (M+1)$^+$=400.33.

Example 52

(S)-Quinoxaline-6-sulfonic acid [1-(1-isopropyl-piperidin-4-yl)-2-oxo-pyrrolidin-3-yl]-amide

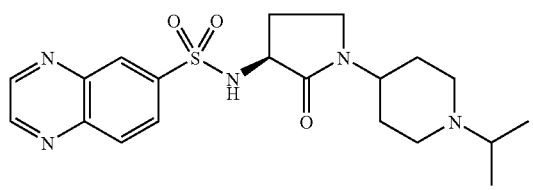

Following a procedure analogous to that described in Example 18, the title compound was obtained as a solid. LC-MS found: (M+1)$^+$=418.4.

Example 53

(S)-Quinoline-7-sulfonic acid [1-(1-isopropyl-piperidin-4-yl)-2-oxo-pyrrolidin-3-yl]-amide

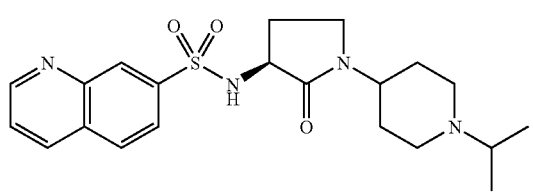

Following a procedure analogous to that described in Example 18, the title compound was obtained as a solid. LC-MS found: (M+1)$^+$=417.49.

Example 54

(S)-3-Chloro-1H-indole-6-carboxylic acid [1-(1-isopropyl-piperidin-4-yl)-2-oxo-pyrrolidin-3-yl]-amide

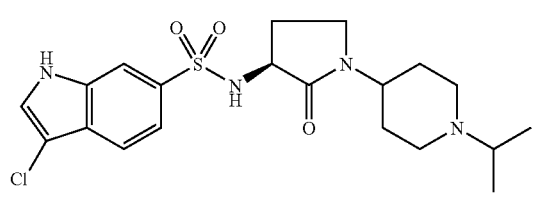

Following a procedure analogous to that described in Example 18, the title compound was obtained as a solid. LC-MS found: (M+1)$^+$=403.39.

Example 55

(S)-6-Chloro-naphthalene-2-sulfonic acid [1-(1-isopropyl-piperidin-4-yl)-2-oxo-pyrrolidin-3-yl]-methyl-amide

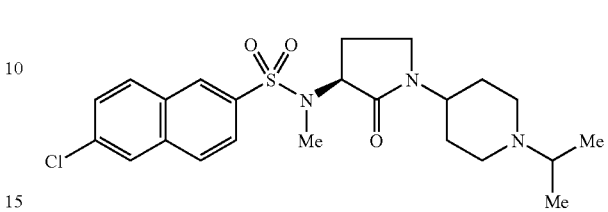

Following a similar procedure to that described in Example 36, the title compound was obtained as a white solid. LC-MS found: (M+1)$^+$=464.38.

Example 56

(S)-6-Chloro-naphthalene-2-sulfonic acid [1-(1-isobutyl-piperidin-4-yl)-2-oxo-pyrrolidin-3-yl]-amide

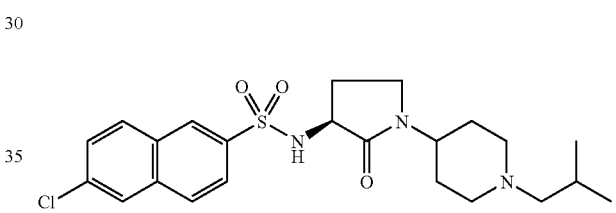

Following a similar procedure to that described in Example 18, the title compound was obtained as a white solid. LC-MS found: (M+1)$^+$=464.37.

Example 57

(S)-6-Chloro-naphthalene-2-sulfonic acid {2-oxo-1-[1-(propane-2-sulfonyl)-piperidin-4-yl]-pyrrolidin-3-yl}-amide

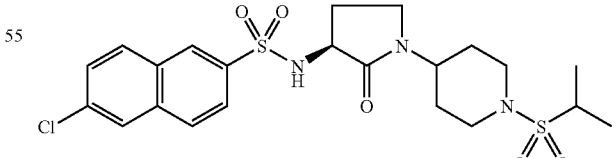

Following a procedure analogous to that described in Example 1, the title compound was obtained as white solid. LC-MS found: (M+1)$^+$=514.31.

Example 58

(S)-6-Chloro-naphthalene-2-sulfonic acid [1-(1-ethyl-piperidin-4-yl)-2-oxo-pyrrolidin-3-yl]-amide

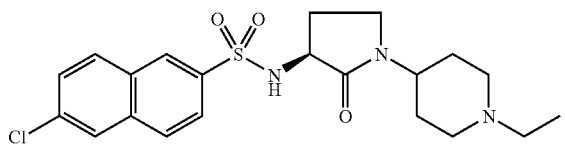

Following a procedure analogous to that described in Example 1, the title compound was obtained as white solid. LC-MS found: (M+1)$^+$=436.33.

Example 59

(S)-6-Chloro-naphthalene-2-sulfonic acid [1-(1-cyclopentyl-azetidin-3-yl)-2-oxo-pyrrolidin-3-yl]-amide

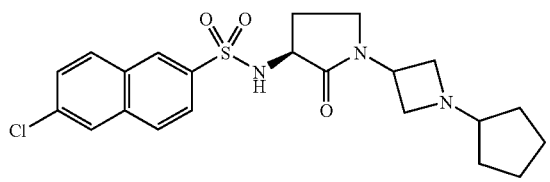

Following a procedure analogous to that described in Example 1, the title compound was provided as white solid. LC-MS found: (M+1)$^+$=448.38.

Example 60

(S)-{4-[3-(6-Chloro-naphthalene-2-sulfonylamino)-2-oxo-pyrrolidin-1-yl]-cyclohexyl}-carbamic acid tert-butyl ester

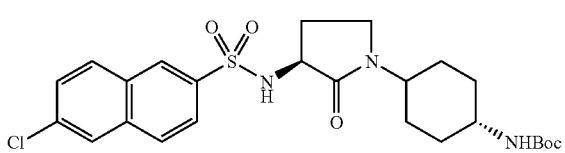

Following a procedure analogous to that described in Example 1, the title compound was provided as white solid. LC-MS found: (M+1)$^+$=522.45.

Example 61

(S)-6-Chloro-naphthalene-2-sulfonic acid [1-(4-diethylamino-cyclohexyl)-2-oxo-pyrrolidin-3-yl]-amide

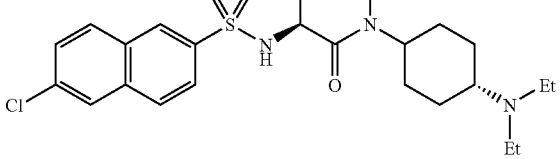

Following a procedure analogous to that described in Example 1, the title compound was provided as white solid. LC-MS found: (M+1)$^+$=478.42.

Example 62

(S)-6-Chloro-naphthalene-2-sulfonic acid [trans-1-(4-methylamino-cyclohexyl)-2-oxo-pyrrolidin-3-yl]-amide

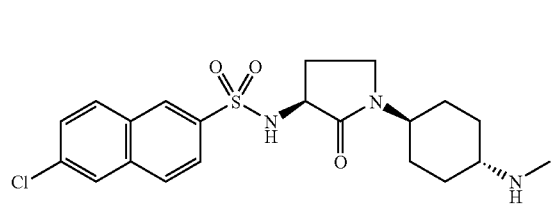

Following a procedure analogous to that described in Example 1, the title compound was provided as white solid. LC-MS found: (M+1)$^+$=436.34.

Example 63

(S)-[(6-Chloro-naphthalene-2-sulfonyl)-(1'-isopropyl-2-oxo-[1,4']bipiperidinyl-3-yl)-amino]-acetic acid

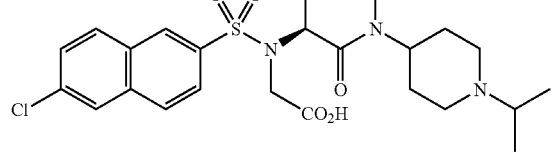

Following a procedure analogous to that described in Example 1, the title compound was provided as white solid. LC-MS found: (M+1)$^+$=522.47.

Example 64

(S)-6-Chloro-N-ethyl-N-(1-(1-isopropylpiperidin-4-yl)-2-oxopyrrolidin-3-yl)naphthalene-2-sulfonamide

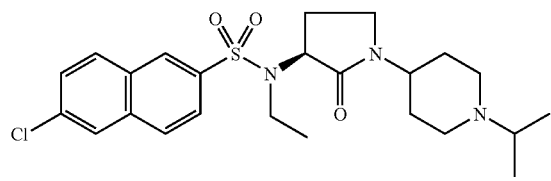

Following a procedure analogous to that described above, the title compound was obtained as a white solid. LC-MS found: (M+1)$^+$=478.39.

Example 65

(S)-6-Chloro-N-(cyanomethyl)-N-(1-(1-isopropylpiperidin-4-yl)-2-oxopyrrolidin-3-yl)naphthalene-2-sulfonamide

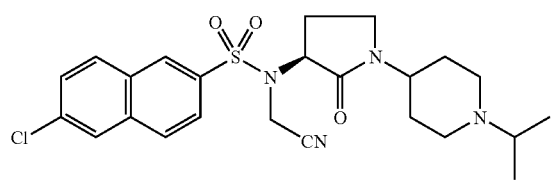

Following a procedure analogous to that described above, the title compound was obtained as a white solid. LC-MS found: (M+1)$^+$=489.42.

Example 66

(S)-6-Chloro-N-(1-(1-isopropylpiperidin-4-yl)-2-oxopyrrolidin-3-yl)-N-(pyridin-3-ylmethyl)naphthalene-2-sulfonamide

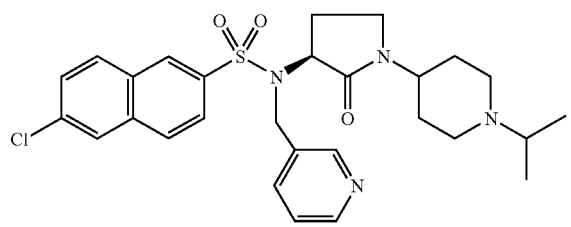

Following a procedure analogous to that described above, the title compound was obtained as a white solid. LC-MS found: (M+1)$^+$=541.48.

Example 67

(S)-6-Chloro-N-(1-(1-isopropylpiperidin-4-yl)-2-oxopyrrolidin-3-yl)-N-(pyridin-4-ylmethyl)naphthalene-2-sulfonamide

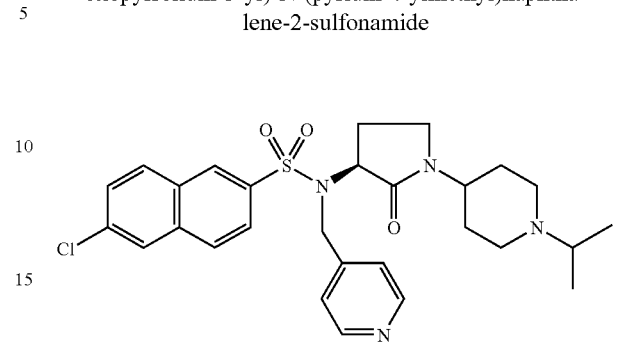

Following a procedure analogous to that described above, the title compound was obtained as a white solid. LC-MS found: (M+1)$^+$=541.48.

Example 68

(S)-N-Benzyl-6-chloro-N-(1-(1-isopropylpiperidin-4-yl)-2-oxopyrrolidin-3-yl)naphthalene-2-sulfonamide

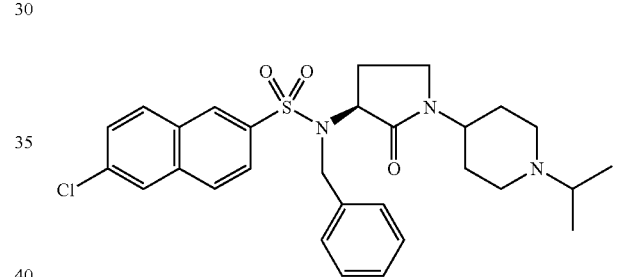

Following a procedure analogous to that described above, the title compound was obtained as a white solid. LC-MS found: (M+1)$^+$=540.49.

Example 69

(S)-6-Chloro-N-(1-(1-isopropylpiperidin-4-yl)-2-oxopyrrolidin-3-yl)-N-(pyridin-2-ylmethyl)naphthalene-2-sulfonamide

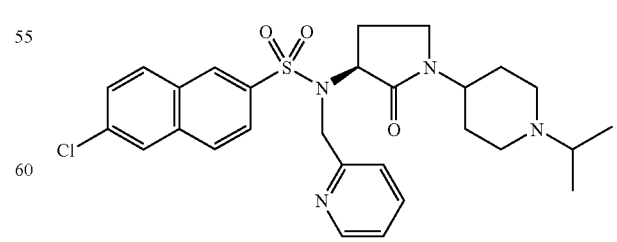

Following a procedure analogous to that described above, the title compound was obtained as a white solid. LC-MS found: (M+1)$^+$=541.5.

Example 70

(S)-6-Chloro-N-isobutyl-N-(1-(1-isopropylpiperidin-4-yl)-2-oxopyrrolidin-3-yl)naphthalene-2-sulfonamide

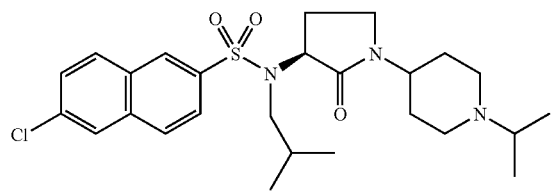

Following a procedure analogous to that described above, the title compound was obtained as a white solid. LC-MS found: $(M+1)^+=506.47$.

Example 71

(S)-6-Chloro-5-fluoro-N-(1-(1-isopropylpiperidin-4-yl)-2-oxopiperidin-3-yl)benzo[b]thiophene-2-sulfonamide

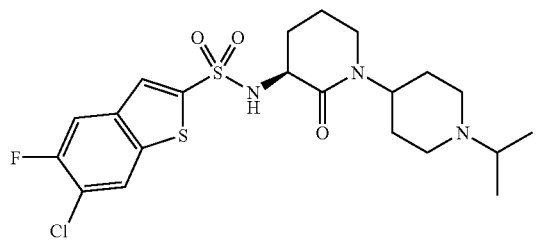

Following a procedure analogous to that described above, the title compound was obtained as a white solid. LC-MS found: $(M+1)^+=504.26$.

Example 72

(S)-6-Chloro-N-(1-(1-isopropylpiperidin-4-yl)-2-oxopyrrolidin-3-yl)-N-(thiazol-4-ylmethyl)naphthalene-2-sulfonamide

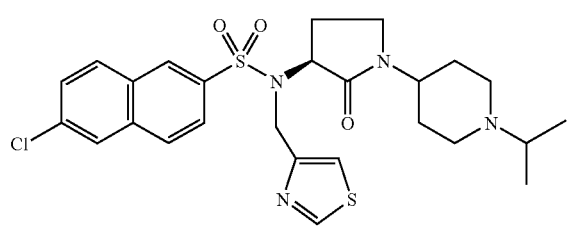

Following a procedure analogous to that described above, the title compound was obtained as a white solid. LC-MS found: $(M+1)^+=547.41$.

Example 73

(S)-6-Chloro-N-(1-(1-isopropylpiperidin-4-yl)-2-oxopyrrolidin-3-yl)-N-((2-methylthiazol-4-yl)methyl)naphthalene-2-sulfonamide

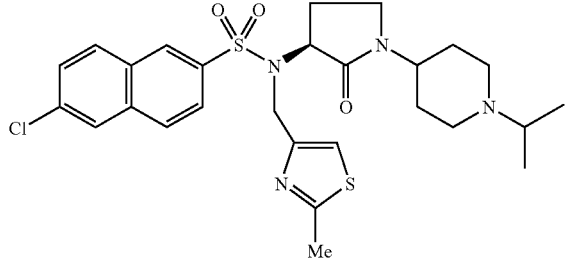

Following a procedure analogous to that described above, the title compound was obtained as a white solid. LC-MS found: $(M+1)^+=561.47$.

Example 74

(S)-6-Chloro-N-(cyclopropylmethyl)-N-(1-(1-isopropylpiperidin-4-yl)-2-oxopyrrolidin-3-yl)naphthalene-2-sulfonamide

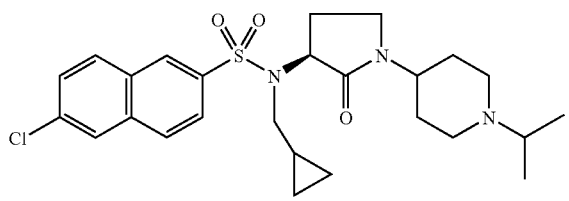

Following a procedure analogous to that described above, the title compound was obtained as a white solid. LC-MS found: $(M+1)^+=504.42$.

Example 75

(S)-Methyl 2-(2-chloro-N-(1-(1-isopropylpiperidin-4-yl)-2-oxopyrrolidin-3-yl)naphthalene-6-sulfonamido)acetate

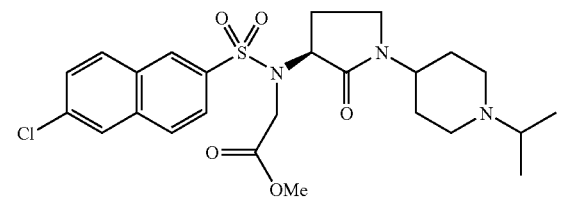

Following a procedure analogous to that described above, the title compound was obtained as a white solid. LC-MS found: $(M+1)^+=522.46$.

Example 76

(S)-2-(2-Chloro-N-(1-(1-isopropylpiperidin-4-yl)-2-oxopyrrolidin-3-yl)naphthalene-6-sulfonamido)acetamide

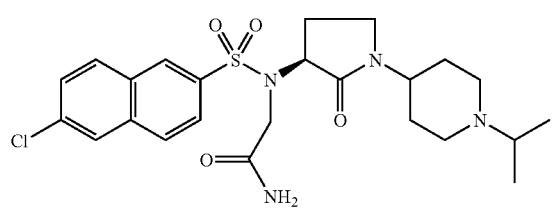

Following a procedure analogous to that described above, the title compound was obtained as a white solid. LC-MS found: $(M+1)^+=507.35$.

Example 77

(S)-6-Chloro-N-(1-(1-isopropylpiperidin-4-yl)-2-oxopiperidin-3-yl)-N-methylnaphthalene-2-sulfonamide

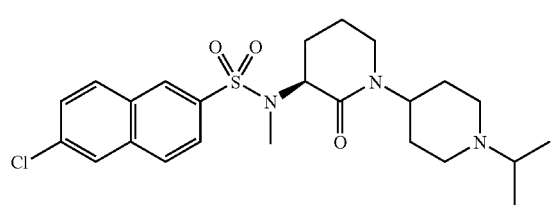

Following a procedure analogous to that described above, the title compound was obtained as a white solid. LC-MS found: $(M+1)^+=478.34$.

Example 78

(S)-6-Chloro-N-(cyanomethyl)-N-(1-(1-isopropylpiperidin-4-yl)-2-oxopiperidin-3-yl)naphthalene-2-sulfonamide

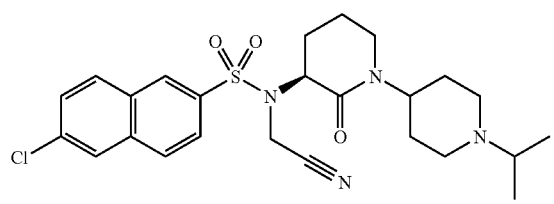

Following a procedure analogous to that described above, the title compound was obtained as a white solid. LC-MS found: $(M+1)^+=503.39$.

Example 79

(S)-6-Chloro-N-ethyl-N-(1-(1-isopropylpiperidin-4-yl)-2-oxopiperidin-3-yl)naphthalene-2-sulfonamide

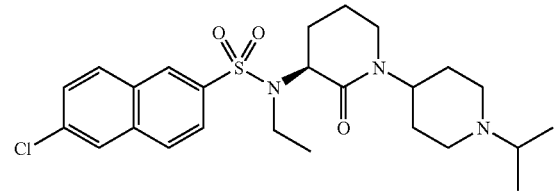

Following a procedure analogous to that described above, the title compound was obtained as a white solid. LC-MS found: $(M+1)^+=492.37$.

Example 80

(S)-5-Bromo-N-(1-(1-isopropylpiperidin-4-yl)-2-oxopiperidin-3-yl)-3-methylbenzo[b]thiophene-2-sulfonamide

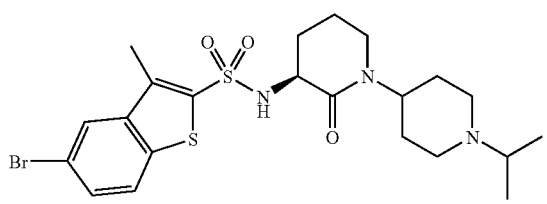

Following a procedure analogous to that described above, the title compound was obtained as a white solid. LC-MS found: $(M+1)^+=530.27$.

Example 81

(S)-5-Chloro-N-(1-(1-isopropylpiperidin-4-yl)-2-oxopiperidin-3-yl)-3-methylbenzo[b]thiophene-2-sulfonamide

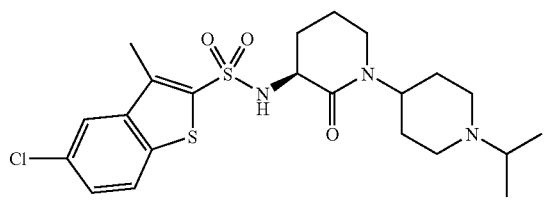

Following a procedure analogous to that described above, the title compound was obtained as a white solid. LC-MS found: $(M+1)^+=484.31$.

Example 82

(S)-6-Chloro-N-(1-(1-isopropylpiperidin-4-yl)-2-oxopiperidin-3-yl)-N-((2-methylthiazol-4-yl)methyl)naphthalene-2-sulfonamide

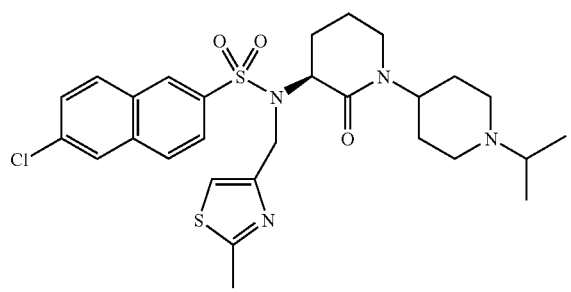

Following a procedure analogous to that described above, the title compound was obtained as a white solid. LC-MS found: $(M+1)^+ = 575.43$.

Example 83

(S)-6-Chloro-N-(1-(1-isopropylpiperidin-4-yl)-2-oxopiperidin-3-yl)-N-(thiazol-4-ylmethyl)naphthalene-2-sulfonamide

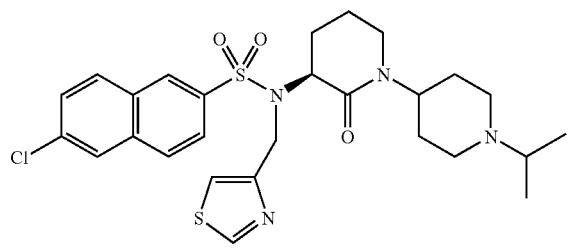

Following a procedure analogous to that described above, the title compound was obtained as a white solid. LC-MS found: $(M+1)^+ = 561.35$.

Example 84

(S)-6-Chloro-N-(1-(1-isopropylpiperidin-4-yl)-2-oxopiperidin-3-yl)-N-((5-methylisoxazol-3-yl)methyl)naphthalene-2-sulfonamide

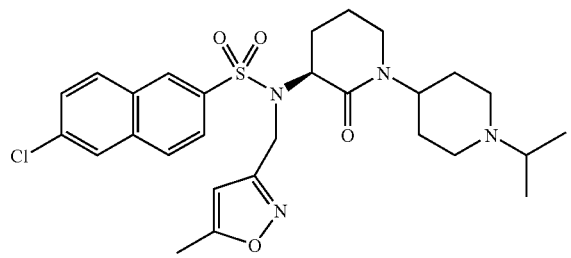

Following a procedure analogous to that described above, the title compound was obtained as a white solid. LC-MS found: $(M+1)^+ = 559.37$.

Example 85

(S)-6-Chloro-N-((3,5-dimethylisoxazol-4-yl)methyl)-N-(1-(1-isopropylpiperidin-4-yl)-2-oxopiperidin-3-yl)naphthalene-2-sulfonamide

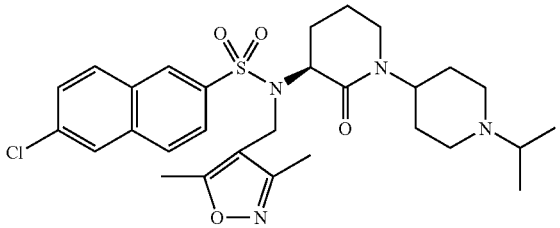

Following a procedure analogous to that described above, the title compound was obtained as a white solid. LC-MS found: $(M+1)^+ = 573.38$.

Example 86

(S)-6-Chloro-N-(1-(1-isopropylpiperidin-4-yl)-2-oxopiperidin-3-yl)-N-methylbenzo[b]thiophene-2-sulfonamide

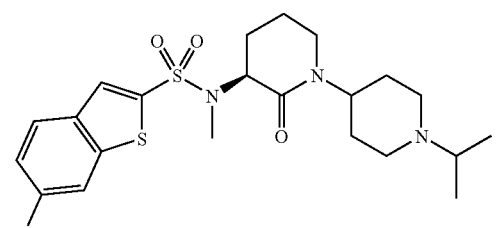

Following a procedure analogous to that described above, the title compound was obtained as a white solid. LC-MS found: $(M+1)^+ = 484.35$.

Example 87

(S)-6-Chloro-N-(cyanomethyl)-N-(1-(1-isopropylpiperidin-4-yl)-2-oxopiperidin-3-yl)benzo[b]thiophene-2-sulfonamide

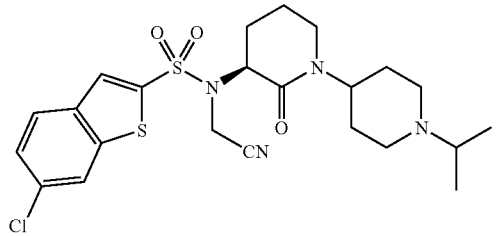

Following a procedure analogous to that described above, the title compound was obtained as a white solid. LC-MS found: $(M+1)^+ = 509.36$.

Example 88

(S)-Methyl 2-(6-chloro-N-(1-(1-isopropylpiperidin-4-yl)-2-oxopiperidin-3-yl)benzo[b]thiophene-2-sulfonamido)acetate

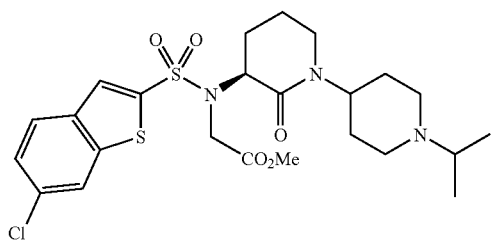

Following a procedure analogous to that described above, the title compound was obtained as a white solid. LC-MS found: (M+1)$^+$=542.38.

Example 89

(S)-2-(6-Chloro-N-(1-(1-isopropylpiperidin-4-yl)-2-oxopiperidin-3-yl)benzo[b]thiophene-2-sulfonamido)acetic acid

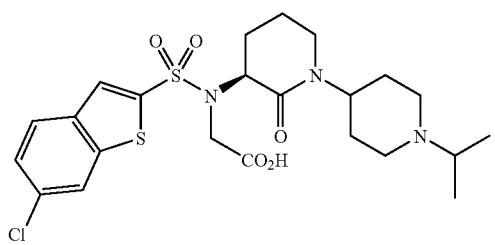

Following a procedure analogous to that described above, the title compound was obtained as a white solid. LC-MS found: (M+1)$^+$=528.35.

Example 90

(S)-2-(6-Chloro-N-(1-(1-isopropylpiperidin-4-yl)-2-oxopiperidin-3-yl)benzo[b]thiophene-2-sulfonamido)acetamide

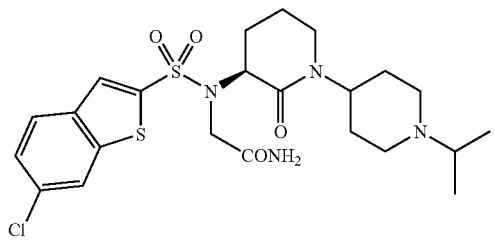

Following a procedure analogous to that described above, the title compound was obtained as a white solid. LC-MS found: (M+1)$^+$=527.24.

Example 91

(S)-tert-Butyl 2-(2-chloro-N-(1-(1-isopropylpiperidin-4-yl)-2-oxopiperidin-3-yl)naphthalene-6-sulfonamido)acetate

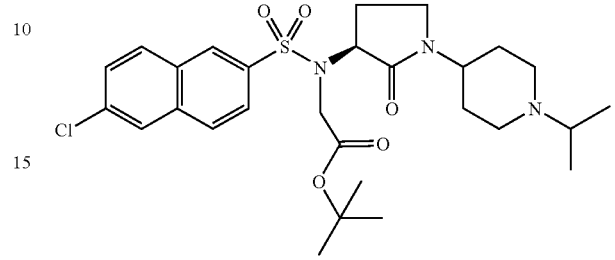

Following a procedure analogous to that described above, the title compound was obtained as a white solid. LC-MS found: (M+1)$^+$=578.22.

Example 92

(S)-6-Chloro-N-(1-(1-cyanopiperidin-4-yl)-2-oxopyrrolidin-3-yl)naphthalene-2-sulfonamide

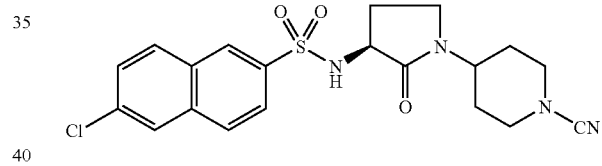

Following a procedure analogous to that described above, the title compound was obtained as a white solid. LC-MS found: (M+1)$^+$=432.24.

Example 93

(S)-6-Chloro-N-cyano-N-(1-(1-cyanopiperidin-4-yl)-2-oxopyrrolidin-3-yl)naphthalene-2-sulfonamide

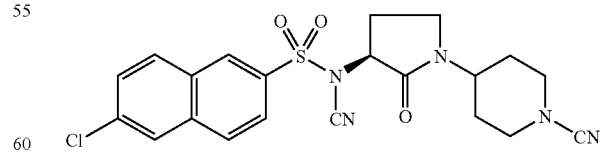

Following a procedure analogous to that described above, the title compound was obtained as a white solid. LC-MS found: (M+1)$^+$=458.30.

Example 94

(S)-N-(1-(1-(2-Nitrobenzylsulfonyl)piperidin-4-yl)-2-oxopiperidin-3-yl)-6-chloronaphthalene-2-sulfonamide

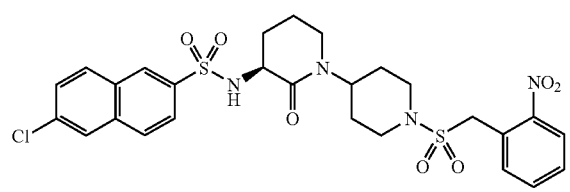

Following a procedure analogous to that described above, the title compound was obtained as a white solid. LC-MS found: (M+1)$^+$=621.20.

Example 95

(S)-N-(1-(1-(Benzylsulfonyl)piperidin-4-yl)-2-oxopiperidin-3-yl)-6-chloronaphthalene-2-sulfonamide

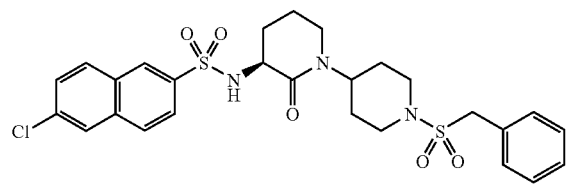

Following a procedure analogous to that described above, the title compound was obtained as a white solid. LC-MS found: (M+1)$^+$=576.20.

Example 96

(S)-5-Chloro-N-(1-(1-isopropylpiperidin-4-yl)-2-oxopiperidin-3-yl)-N-methylbenzo[b]thiophene-2-sulfonamide

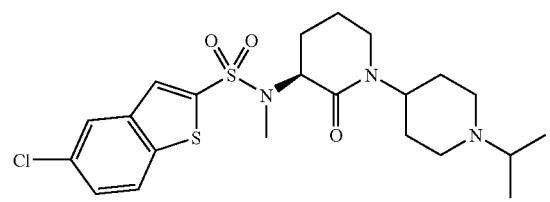

Following a procedure analogous to that described above, the title compound was obtained as a white solid. LC-MS found: (M+1)$^+$=484.30.

Example 97

(S)-5-Chloro-N-(cyanomethyl)-N-(1-(1-isopropylpiperidin-4-yl)-2-oxopiperidin-3-yl)benzo[b]thiophene-2-sulfonamide

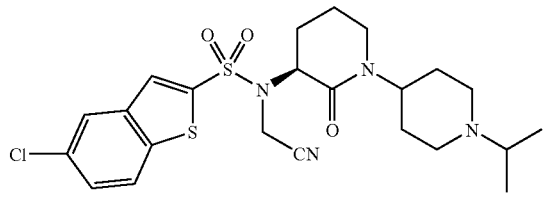

Following a procedure analogous to that described above, the title compound was obtained as a white solid. LC-MS found: (M+1)$^+$=509.29.

Example 98

(S)-2-(5-Chloro-N-(1-(1-isopropylpiperidin-4-yl)-2-oxopiperidin-3-yl)benzo[b]thiophene-2-sulfonamido)acetic acid

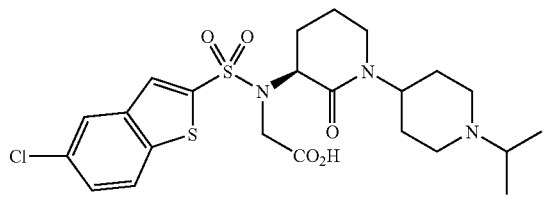

Following a procedure analogous to that described above, the title compound was obtained as a white solid. LC-MS found: (M+1)$^+$=528.26.

Example 99

(S)-6-Chloro-N-(1-(1-isopropylpiperidin-4-yl)-2-oxopiperidin-3-yl)thieno[2,3-b]pyridine-2-sulfonamide

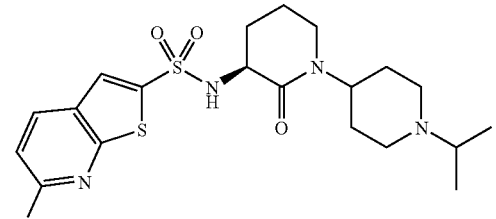

Following a procedure analogous to that described above, the title compound was obtained as a white solid. LC-MS found: (M+1)$^+$=471.26.

Example 100

(S)-4,6-Dichloro-N-(1-(1-isopropylpiperidin-4-yl)-2-oxopiperidin-3-yl)benzo[b]thiophene-2-sulfonamide

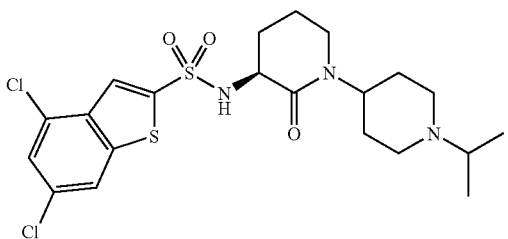

Following a procedure analogous to that described above, the title compound was obtained as a white solid. LC-MS found: $(M+1)^+=504.26$.

Example 101

(3S,4S)-1-(1-Isopropylpiperidin-4-yl)-4-methyl-3-(9-phenyl-9H-fluoren-9-ylamino)pyrrolidin-2-one

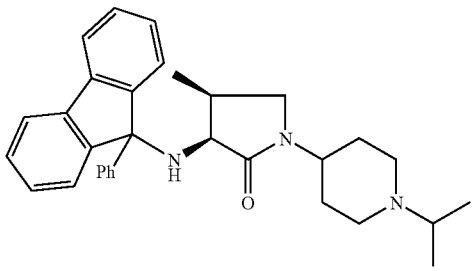

Step a: To a suspension of L-Asp-OH (1.33 g, 10 mmol) in methanol at 0° C. was added thionyl chloride (10 mL). After addition, the resulting mixture was stirred at room temperature for 3.5 hrs. Removal of solvent provided the desired (S)-dimethyl 2-aminosuccinate as white solid. LC-MS found: $(M+1)^+=162.25$.

Step b: To a mixture of the product obtained above (161 mg, 1.0 mmol) and 9-bromo-9-phenyl-9H-fluorene (385 mg, 1.2 mmol) in $CH_3NO_2$ at room temperature under $N_2$ was added $K_3PO_4$ (2.0 mmol). The resulting mixture was stirred for 3.5 days. The mixture was filtered through a pad of Celite®, and the residue was purified by silicon chromatography (20% ethyl acetate in hexane) to provide (S)-dimethyl 2-(9-phenyl-9H-fluoren-9-ylamino)succinate. LC-MS found: $(M+1)^+=402.22$.

Step c: To a solution of the product obtained above (200 mg, 0.5 mmol) in THF at −78° C. under $N_2$ was added KHMDS (1.5 mmol). The mixture was stirred for 40 min at this temperature and then MeI was added. The resulting mixture was stirred for 1.5 hrs. The mixture was quenched with sat. $NH_4Cl$ and most of the solvent was evaporated. The residue was diluted with ethyl acetate; washed with water, sat. $NaHCO_3$, and brine; and dried. Chromatography purification provided (3S)-dimethyl 2-methyl-3-(9-phenyl-9H-fluoren-9-ylamino)succinate. The two diastereomers were separated. LC-MS found: $(M+1)^+=416.25$.

Step d: To a solution of the product obtained above (163 mg, 0.39 mmol) in THF at −35° C. was added DIBAL (2.0 mmol). After addition, the mixture was stirred at this temperature for 2.5 hrs. The mixture was quenched with water; diluted with ethyl acetate; washed with 1N HCl, sat. $NaHCO_3$, and brine; and dried. Chromatography purification provided (2S,3R)-methyl 4-hydroxy-3-methyl-2-(9-phenyl-9H-fluoren-9-ylamino)butanoate. LC-MS found: $(M+1)^+=388.42$.

Step e: To a solution of the product obtained above (193 mg, 0.5 mmol) in dichloromethane in the presence of molecular sieves was added Dess-Martin reagent (1.2 mmol) at room temperature under $N_2$. The mixture was stirred for 3 hrs and then filtered. The residue was diluted with ethyl acetate; washed with water, 1N HCl, and sat. $NaHCO_3$; and dried. Flash chromatography purification provide aldehyde {(2S,3R)-methyl 3-methyl-4-oxo-2-(9-phenyl-9H-fluoren-9-ylamino)butanoate}. LC-MS found: $(M+1)^+=386.42$.

To the mixture of the product obtained above (108 mg, 0.28 mmol) and 1-isopropylpiperidin-4-amine (80 mg) in methanol at room temperature under $N_2$ was added $NaCNBH_3$. The mixture was stirred for 6 hrs and then was quenched with water. Methanol was evaporated. The residue was diluted with ethyl acetate, washed with water and brine, and dried. HPLC purification (30% acetonitrile in water) provided (2S,3S)-methyl 4-(1-isopropylpiperidin-4-ylamino)-3-methyl-2-(9-phenyl-9H-fluoren-9-ylamino)butanoate. LC-MS found: $(M+1)^+=512.12$.

Step f: A mixture of the product obtained above (170 mg, 0.33 mmol) in toluene was stirred at reflux under $N_2$ for 20 hrs. The reaction mixture was cooled to room temperature. Solvent was removed, and the residue was purified by HPLC (30% acetonitrile in water) to provide (3S,4S)-1-(1-isopropylpiperidin-4-yl)-4-methyl-3-(9-phenyl-9H-fluoren-9-ylamino)pyrrolidin-2-one. LC-MS found: $(M+1)^+=480.22$.

Example 102

6-Chloro-N-((3S,4S)-1-(1-isopropylpiperidin-4-yl)-4-methyl-2-oxopyrrolidin-3-yl)naphthalene-2-sulfonamide

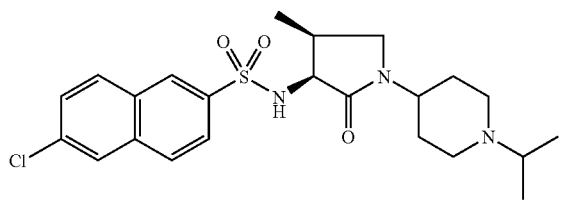

The mixture of the product obtained from Example 102 in methanol was hydrogenated under 1 atm for 8 hrs. The solid was filtered through a pad of Celite®. Removal of solvent provided (3S,4S)-3-amino-1-(1-isopropylpiperidin-4-yl)-4-methylpyrrolidin-2-one as the desired product. LC-MS found: $(M+1)^+=240.22$.

To a mixture of the product obtained above (24 mg, 0.1 mmol) and 6-chloronaphthalene-2-sulfonyl chloride (0.1 mmol) in dichloromethane at room temperature under $N_2$ was added TEA (0.5 mmol). The mixture was stirred for 2 hrs, diluted with ethyl acetate, washed with water and brine, and dried. HPLC purification (30% acetonitrile in water) provided 6-chloro-N-((3S,4S)-1-(1-isopropylpiperidin-4-

Example 103

6-Chloro-N-((3S,4R)-1-(1-isopropylpiperidin-4-yl)-4-methyl-2-oxopyrrolidin-3-yl)naphthalene-2-sulfonamide

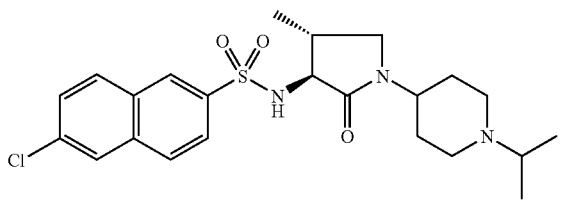

Following a procedure analogous to that described above, the title compound was obtained as a white solid. LC-MS found: (M+1)$^+$=464.22.

Example 104

6-Chloro-N-((3S)-1-(1-isopropylpiperidin-4-yl)-4-methyl-2-oxopyrrolidin-3-yl)benzo[b]thiophene-2-sulfonamide

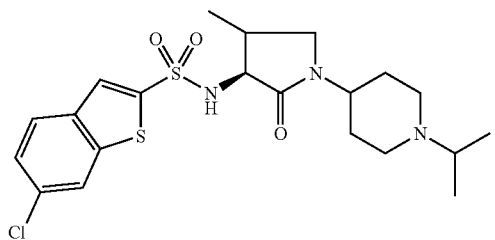

Following a procedure analogous to that described above, the title compound was obtained as a white solid. LC-MS found: (M+1)$^+$=470.42.

Example 105

6-Chloro-N-((3S,4R)-1-(1-isopropylpiperidin-4-yl)-4-methyl-2-oxopiperidin-3-yl)naphthalene-2-sulfonamide

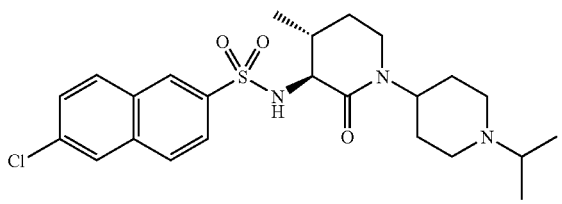

Step a: To CuI (3.36 g, 17.64 mmol) in THF (15 mL) was added at −78° C. MeLi.LiBr (1.5M in ether, 23.5 mL, 35.28 mmol), and the resulting mixture was stirred at −78° C. for 15 min. TMSCl (1.52 mL, 17.64 mmol) and Me$_2$CuLi (generated above) were added in sequence at −78° C. to (S,E)-tert-butyl 4-(3-ethoxy-3-oxoprop-1-enyl)-2,2-dimethyloxazolidine-3-carboxylate (0.88 g, 2.94 mmol), and the resulting mixture was slowly warmed up to rt. Ammonium chloride-ammonium hydroxide buffer (pH~8) was added to the reaction mixture. The mixture was extracted with ether, washed with brine, dried over sodium sulfate, and concentrated. Flash chromatography (silica gel, 2:8=ethyl acetate:hexanes) gave (S)-tert-butyl 4-((R)-4-ethoxy-4-oxobutan-2-yl)-2,2-dimethyloxazolidine-3-carboxylate as a clear oil.

Step b: LAH (1.M in THF, 1.34 mL, 1.34 mmol) was added to a solution of above obtained ester (0.42 g, 1.34 mmol) in THF (10 mL) and stirring was allowed at rt. for 2 hr. Saturated sodium tartrate solution was added slowly to quench the reaction. The mixture was extracted with ether. The organic phase was washed with brine and dried over magnesium sulfate. Removal of solvent left (S)-tert-butyl 4-((R)-4-hydroxybutan-2-yl)-2,2-dimethyloxazolidine-3-carboxylate as a clear oil.

Step c: To the above obtained alcohol (1.34 mmol) in dichloromethane (10 mL) were added Dess-Martin's reagent (1.14 g, 2.68 mmol) and sodium bicarbonate (100 mg). After stirring at rt. for 3 hr, it was filtered through a pad of Celite® and silica gel. The solvent was removed from the filtrate to leave (S)-tert-butyl 2,2-dimethyl-4-((R)-4-oxobutan-2-yl)oxazolidine-3-carboxylate.

Step d: To the product from Step c dissolved in THF (20 mL) was added 1-isopropylpiperidin-4-amine (0.5 mL, excess) followed by the addition of sodium triacetoxyborohydride (0.85 g, 4.02 mmol). The mixture was stirred at rt. over night. Into the same pot mixture were added water (6.0 mL), sodium carbonate (0.5 g), and CBZCl (0.5 mL). The mixture was stirred at rt. for 2 hr. The mixture was extracted with ethyl acetate. Organic phase was washed with sodium bicarbonate and brine and dried over sodium sulfate. The product, (S)-tert-butyl 4-((R)-4-(benzyloxycarbonyl)butan-2-yl)-2,2-dimethyloxazolidine-3-carboxylate, was obtained after reverse phase HPLC purification (acetonitrile/water 30% to 100% gradient). LC-MS found: (M+1)$^+$=532.47.

Step e: To the product from step d (130 mg) in acetone (7 mL) was added Jones' reagent (1.0 mL) at 0° C. The mixture, while stirring, was allowed warm from 0° C. to rt. for 1 hr. Sodium bicarbonate and methanol were added, and the solvent was evaporated. The crude product was purified by reverse phase HPLC purification (acetonitrile/water 30% to 100% gradient) to provide (2S,3R)-5-(benzyloxycarbonyl)-2-(tert-butoxycarbonyl)-3-methylpentanoic acid as a clear oil. LC-MS found: (M+1)$^+$=506.40.

Step f: The product obtained from step e (93 mg, 0.18 mmol) dissolved in MeOH (5.0 mL) was hydrogenated at atmosphere catalyzed with 10% Pd/C for 12 hr. Filtration of the catalyst and removal of the solvent provide the desired product. LC-MS found: (M+1)$^+$372.4.

Step g: The product from step f (71 mg, 0.19 mmol) in dicloromethane (5.0 mL) were added 0° C. HOBt (13.5 mg, 0.1 mmol), EDCI (55 mg, 0.28 mmol) and DIEA (0.1 mL). The mixture was warmed from 0° C. to rt. for 1.5 hr. The solvent was removed, and the resulting product was dried in vacuum. LC-MS found: (M+1)$^+$354.4.

Step h: The above crude product was dissolved in dichloromethane (5.0 mL), and TFA (2.0 mL) was added. After stirring at rt. for 1 hr, the solvent was removed under reduced pressure. LC-MS found: (M+1)$^+$=254.3.

Step i: To the product from step h (0.08 mmol) dissolved in dichloromethane (4.0 mL) were added 6-chloronaphthalene-2-sulfonyl chloride (30 mg) and DIEA (0.1 mL). After stirring at rt. for 3 hr, the solvent was removed. The crude product was purified by reverse phase HPLC purification (acetonitrile/water 30% to 100% gradient) to provide 6-chloro-N-((3S,4R)-1-(1-isopropylpiperidin-4-yl)-4-methyl-2-oxopiperidin-3-yl)naphthalene-2-sulfonamide as a white solid. LC-MS found: $(M+1)^+=478.28$.

Example 106

6-Chloro-N-((3S,4R)-1-(1-isopropylpiperidin-4-yl)-4-methyl-2-oxopiperidin-3-yl)benzo[b]thiophene-2-sulfonamide

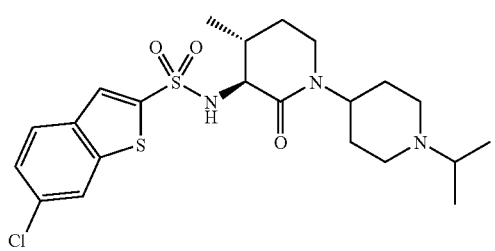

Following a procedure analogous to that described above, the title compound was obtained as a white solid. LC-MS found: $(M+1)^+=484.22$.

Example 107

(S)-N-(4-(3-(2-Chloronaphthalene-6-sulfonamido)-2-oxopyrrolidin-1-yl)phenyl)-2-(dimethylamino)-N-methylacetamide

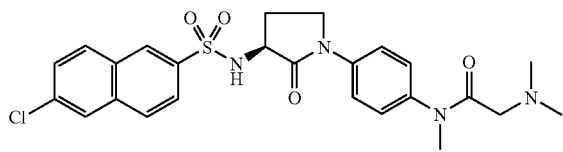

Following a procedure analogous to that described above, the title compound was obtained as a white solid. LC-MS found: $(M+1)^+=515.41$.

The following are intermediates are useful for preparing compounds of the present invention.

1-(3-Chloro-propyl)-3-[4-(2-dimethylaminomethyl-imidazol-1-yl)-2-fluoro-phenyl]-urea

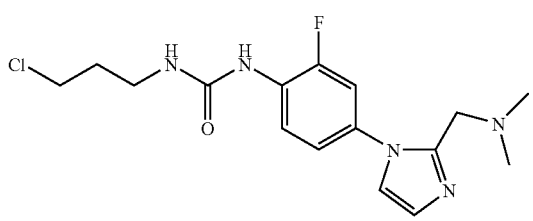

To a solution of 234.3 mg (1 mmol) of 4-(2-dimethylaminomethyl-imidazol-1-yl)-2-fluoro-phenylamine in 5 mL of anhydrous $CH_2Cl_2$ and under $N_2$ atmosphere were added 179 mg (1.5 mmol) of 3-chlorophenylisocyanate. The mixture was stirred for 3 days at room temperature. The volatiles were concentrated to yield quantitatively 1-(3-chloro-propyl)-3-[4-(2-dimethylaminomethyl-imidazol-1-yl)-2-fluoro-phenyl]-urea as a viscous oil. This compound can be was used without further purification. $^1$H NMR (400 MHz, $CDCl_3$) δ 8.25 (t, J=8.6 Hz, 1H), 7.44 (dd, J=9.7 Hz, and J=2.1 Hz, 1H), 7.25 (m, 1H), 7.13 (m, 1H), 7.065 (d, J=6.5 Hz, 1H), 5.65 (t, 1H), 3.65 (t, J=6.5 Hz, 2H), 3.47 (m, 2H), 3.38 (s, 2H), 2.24 (s, 6H), 2.05 (m, 2H), ppm. LC-MS (ESI) 354.0 $[M+H]^+$, $t_R$=2.51 min (Shimadzu Phenomenex S5 ODS 4.6×50 mm Luna flow rate 2.5 mL/mn; detection at 220 nM; Gradient elution 0% to 100% B over 8 min; (A=10% MeOH, 90% $H_2O$, 0.2% $H_3PO_4$ & B=90% MeOH, 10% $H_2O$, 0.2% $H_3PO_4$). HRMS (ESI) m/z calcd for $C_{16}H_{22}ClFN_5O$ $[M+H]^+$ 354.1497, found 354.1491.

According to the same procedure and using an appropriated aniline and isocyanate, the following intermediates were prepared:

1-(2-Chloro-ethyl)-3-[4-(2-dimethylaminomethyl-imidazol-1-yl)-2-fluoro-phenyl]-urea

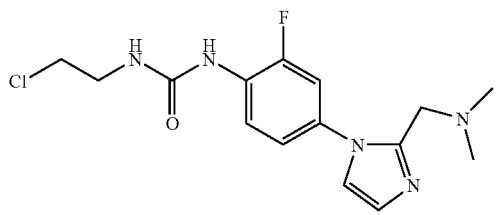

$^1$H NMR (500 MHz, $CDCl_3$) δ 8.26 (t, J=8.7 Hz, 1H), 8.08 (s, 1H), 7.33 (dd, J=11.8 Hz and J=2.4 Hz, 1H), 7.17 (d, J=9.4 Hz, 1H), 7.07 (s, 1H), 7.04 (s, 1H), 6.81 (t, 1H), 3.63 (m, 4H), 3.45 (s, 2H), 2.24 (s, 6H), ppm. $t_R$=2.219 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% $H_2O$, 0.2% $H_3PO_4$ & B=90% MeOH, 10% $H_2O$, 0.2% $H_3PO_4$).

1-(3-Chloro-propyl)-3-[4-(2-oxo-2H-pyridin-1-yl)-phenyl]-urea

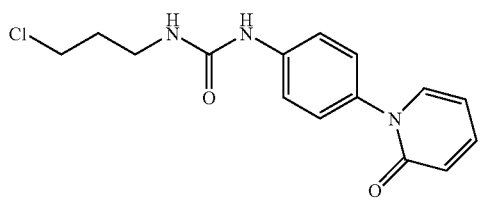

$^1$H NMR (400 MHz, $CDCl_3$) δ 7.85 (s, 1H), 7.54 (m, 1H), 7.34 (d, J=4.8 Hz, 1H), 7.13 (s, 4H), 6.71 (d, J=9.1 Hz, 1H), 6.39 (t, J=6.2 Hz, 1H), 6.3 (m, 0.1H), 3.61 (m, 2H), 3.37 (m, 2H), 1.98 (m, 2H), ppm. LC-MS (ESI) 306.0 $[M+H]^+$, $t_R$=4.133 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% $H_2O$, 0.2% $H_3PO_4$ & B=90% MeOH, 10% $H_2O$, 0.2% $H_3PO_4$). HRMS (ESI) m/z calcd for $C_{15}H_{17}N_3O_2Cl$ $[M+H]^+$ 306.1009, found 306.1015.

123

1-(3-Chloro-propyl)-3-[4-(2-oxo-piperidin-1-yl)-phenyl]-urea

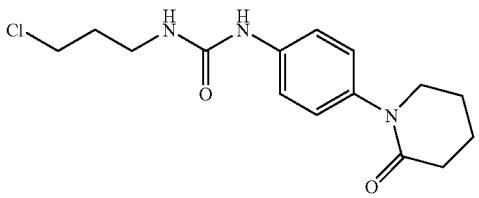

$^1$H NMR (400 MHz, CDCl$_3$) δ 7.38 (s, 1H), 6.98 (m, 4H), 6.03 (bs, 1H), 3.6 (m, 4H), 3.35 (bs, 2H), 2.57 (bs, 2H), 1.97 (bs, 6H) ppm. LC-MS (ESI) 310.0 [M+H]$^+$, $t_R$=4.353 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{15}$H$_{21}$N$_3$O$_2$Cl [M+H]$^+$ 310.1324, found 310.1316.

1-(3-Chloro-propyl)-3-(4-iodo-phenyl)-urea

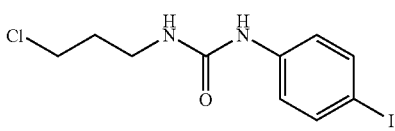

$^1$H NMR (500 MHz, CDCl$_3$) δ 8.63 (s, 1H), 7.52 (d, J=8.7 Hz, 2H), 7.24 (d, J=8.7 Hz, 2H), 6.33 (bs, 1H), 3.67 (t, J=6.7 Hz, 2H), 3.19 (m, 2H), 1.88 (m, 2H), ppm. $t_R$=3.227 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$ & B=90% MeOH, 10% H$_2$O, 0.2% H$_3$PO$_4$).

1-(2-Chloro-ethyl)-3-(4-iodo-phenyl)-urea

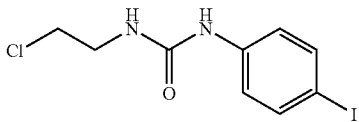

$^1$H NMR (400 MHz, DMSO d$_6$) δ 8.77 (s, 1H), 7.53 (d, J=8.8 Hz, 2H), 7.25 (d, J=8.8 Hz, 2H), 6.43 (t, 1H), 3.64 (t, J=6.2 Hz, 2H), 3.41 (m, 2H) ppm. $t_R$=3.109 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$ & B=90% MeOH, 10% H$_2$O, 0.2% H$_3$PO$_4$).

124

1-[4-(2-Dimethylaminomethyl-imidazol-1-yl)-2-fluoro-phenyl]-tetrahydro-pyrimidin-2-one

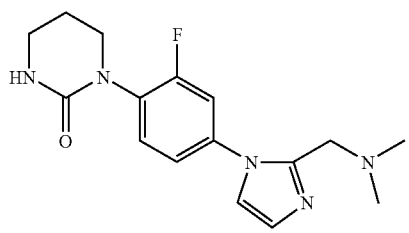

The crude open urea derivative 1-(2-chloro-ethyl)-3-[4-(2-dimethylaminomethyl-imidazol-1-yl)-2-fluoro-phenyl]-urea obtained as above (1 mmol) was dissolved in 5 mL of anhydrous THF. Under N$_2$ atmosphere were added 5 mL (5 mmol) of tBuOK/THF (1N) solution. After 1 h at room temperature, no starting material remained. 3 mL of water were added, and the solution's pH adjusted to 7–8 with 1N HCl. The mixture was extracted with CH$_2$Cl$_2$ (3×15 mL), and the organic phases were dried over MgSO$_4$ and concentrated. The obtained oil was triturated with petroleumether/ether to yield 219.3 mg of a yellow solid. Analytically pure sample was obtained after purification by preparative HPLC.

$^1$H NMR (400 MHz, CDCl$_3$) δ 7.50 (t, J=8.4 Hz, 1H), 7.3 (s, 1H), 7.15–7.21 (m, 31H), 6.12 (bs, 1H), 4.38 (s, 2H), 3.73 (m, 2H), 3.47 (m, 2H), 3.51 (m, 2H), 2.85 (s, 6H), 2.17 (m, 2H), ppm. LC-MS (ESI) 318.0 [M+H]$^+$, $t_R$=1.597 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{16}$H$_{21}$N$_5$OF [M+H]$^+$ 318.1730, found 318.1741.

According to the same procedure the following cyclic ureas were prepared:

1-[4-(2-Dimethylaminomethyl-imidazol-1-yl)-2-fluoro-phenyl]-imidazolidin-2-one

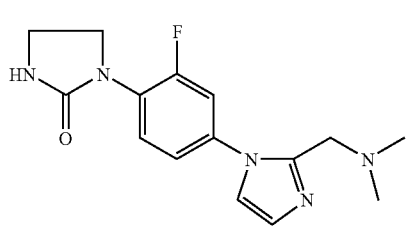

$^1$H NMR (400 MHz, CDCl$_3$) δ 7.63 (t, J=8.4 Hz, 1H), 7.58 (dd, J=12 Hz and 2.3 Hz, 1H), 7.31 (m, 1H), 7.05 (m, 31H), 6.0 (bs, 1H), 4.38 (s, 2H), 3.99 (m, 2H), 3.61 (m, 2H), 3.36 (s, 2H), 2.23 (s, 6H), ppm. LC-MS (ESI) 304.0 [M+H]$^+$, $t_R$=0.803 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$ & B=90% MeOH, 10% H$_2$O, 0.2% H$_3$PO$_4$).

1-[4-(2-Oxo-2H-pyridin-1-yl)-phenyl]-tetrahydro-pyrimidin-2-one

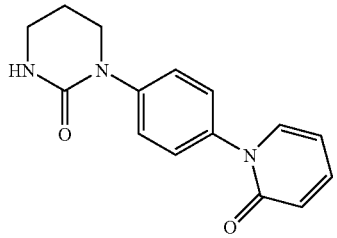

$^1$H NMR (400 MHz, CDCl$_3$) δ 7.33–7.45 (m, 6H), 6.45 (d, J=9.2 Hz, 1H), 5.65 (td, J=1.1 Hz, and 6.8 Hz, 1H), 3.75 (t, J=5.7 Hz, 2H), 3.46 (m, 2H), 2.13 (m, 2H), ppm. LC-MS (ESI) 269.9 [M+H]+, tR=2.803 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$& B=90% MeOH, 10% H$_2$O, 0.2% H$_3$PO$_4$). HRMS (ESI) m/z calcd for C$_{16}$H$_{16}$N$_3$O$_2$ [M+H]$^+$ 270.1243, found 270.1247.

1-(4-Iodo-phenyl)-tetrahydro-pyrimidin-2-one

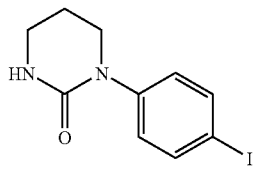

LC-MS (ESI) 303.19 [M+H]+, $t_R$=2.69 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$& B=90% MeOH, 10% H$_2$O, 0.2% H$_3$PO$_4$).

1-(4-Iodophenyl)imidazolidin-2-one

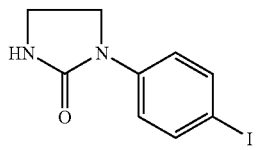

$^1$H NMR (400 MHz, CDCl$_3$) δ 7.55 (d, J=8.7 Hz, 2H), 7.28 (d, J=8.7 Hz, 2H), 3.84 (t, J=7.4 Hz, 2H), 3.52 (t, J=7.4 Hz, 2H), ppm. $t_R$=2.889 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$& B=90% MeOH, 10% H$_2$O, 0.2% H$_3$PO$_4$).

Example 108

1-(Benzylidene-amino)-3-[4-(2-dimethylaminomethyl-imidazol-1-yl)-2-fluoro-phenyl]-tetrahydro-pyrimidin-2-one

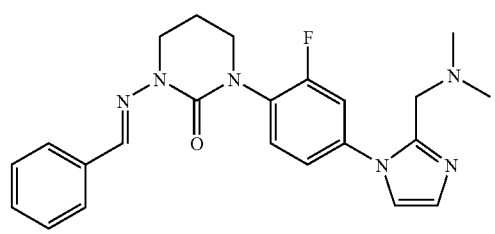

Previously prepared 1-[4-(2-dimethylaminomethyl-imidazol-1-yl)-2-fluoro-phenyl]-tetrahydro-pyrimidin-2-one, (475.5 mg; 1.5 mmol) was dissolved in 10 mL of 10% H$_2$SO$_4$ solution. The mixture was then cooled to 0° C. and 103.5 mg, (1.5 mmol) of NaNO$_2$ were added portionwise. After 3h at 0° C., 245.2 mg (3.75 mmol) of Zn dust were added in small portions. Bubbling occurred immediately. After the end of intense bubbling, the cooling bath was removed, and the mixture stirred 1 h at the room temperature. The mixture was filtered through Celite® 545 to remove suspensions. 143.3 mg (1.35 mmol) of benzaldehyde were then introduced, and the reaction mixture stirred for 2 h. The pH of the mixture was made neutral with NaOH prior to extractions with CH$_2$Cl$_2$. The organic phases were dried over MgSO$_4$ and concentrated to yield 364.3 mg of the target material as a viscous oil. An analytically pure sample was obtained after purification on an IST Isolute Flash Cartridge (loading with CH$_2$Cl$_2$ and eluting with 5% MeOH/CH$_2$Cl$_2$). $^1$H NMR (400 MHz, CDCl$_3$) δ 8.11 (s, 1H), 7.76 (m, 2H), 7.62 (dd, 1H), 7.49 (t, 1H), 7.3–7.4 (m, 4H), 7.11 (d, 2H), 3.89 (t, 2H), 3.73 (t, 2H), 3.42 (s, 2H), 2.41 (m, 2H), 2.3 (s, 6H), ppm. LC-MS (ESI) 421.1 [M+H]$^+$, $t_R$=3.207 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$& B=90% MeOH, 10% H$_2$O, 0.2% H$_3$PO$_4$). HRMS (ESI) m/z calcd for C$_{23}$H$_{26}$N$_6$OF [M+H]$^+$ 421.2152, found 421.2147.

According to the same procedure the following compounds were prepared:

Example 109

1-(4-Chlorobenzylideneamino)-3-(4-(2-((dimethylamino)methyl)-1H-imidazol-1-yl)-2-fluorophenyl)-tetrahydropyrimidin-2(1H)-one

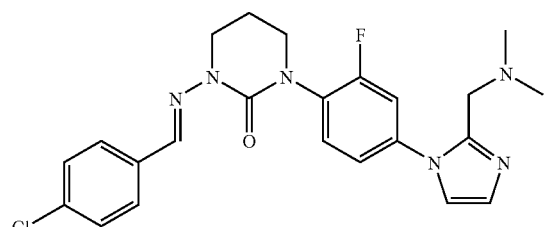

$^1$H NMR (400 MHz, CDCl$_3$) δ 8.07 (s, 1H), 7.6–7.7 (m, 3H), 7.46 (t, 1H), 7.3–7.4 (m, 3H), 7.08 (d, 2H), 3.87 (t, 2H), 3.72 (t, 2H), 3.40 (s, 2H), 2.38 (t, 2H), 2.28 (s, 6H), ppm. LC-MS (ESI) 455.0 [M+H]$^+$, $t_R$=3.863 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$& B=90% MeOH, 10% H$_2$O, 0.2% H$_3$PO$_4$). HRMS (ESI) m/z calcd for C$_{23}$H$_{25}$ClFN$_6$O [M+H]$^+$ 455.1762, found 455.1776.

Example 110

1-(3-Chlorobenzylideneamino)-3-(4-(2-((dimethylamino)methyl)-1H-imidazol-1-yl)-2-fluorophenyl)-tetrahydropyrimidin-2(1H)-one

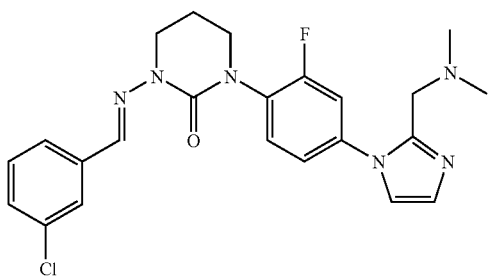

$^1$H NMR (400 MHz, CDCl$_3$) δ 8.0 (s, 1H), 7.69 (s, 1H), 7.59 (dd, 1H) 7.53 (m, 1H), 7.38 (t, 1H), 7.32 (dd, 1H), 7.23 (m, 2H), 7.04 (m, 2H), 3.82 (t, 2H), 3.68 (t, 2H), 3.34 (s, 2H), 2.34 (t, 2H), 2.22 (s, 6H), ppm. LC-MS (ESI) 455.0 [M+H]$^+$, $t_R$=3.883 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$& B=90% MeOH, 10% H$_2$O, 0.2% H$_3$PO$_4$). HRMS (ESI) m/z calcd for C$_{23}$H$_{25}$ClFN$_6$O [M+H]$^+$ 455.1762, found 455.1774.

Example 111

1-(4-Methoxybenzylideneamino)-3-(4-(2-((dimethylamino)methyl)-1H-imidazol-1-yl)-2-fluorophenyl)-tetrahydropyrimidin-2(1H)-one

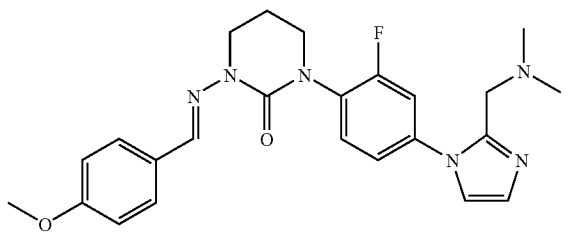

$^1$H NMR (400 MHz, CDCl$_3$) δ 8.02 (s, 1H), 7.62 (d, J=8, 8 Hz, 2H), 7.55 (dd, J=11.4 Hz and J=2.2 Hz, 1H), 7.4 (t, 1H), 7.31 (dd, 1H), 7.04 (d, J=1.3 Hz, 1H), 7.02 (d, J=1.3 Hz, 1H), 6.84 (d, J=8.8 Hz, 1H), 3.8 (t, 2H), 3.76 (s, 3H), 3.66 (t, 2H), 3.33 (s, 2H), 2.32 (t, 2H), 2.12 (s, 6H), ppm. LC-MS (ESI) 451.0 [M+H]$^+$, $t_R$=3.433 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$& B=90% MeOH, 10% H$_2$O, 0.2% H$_3$PO$_4$). HRMS (ESI) mn/z calcd for C$_{24}$H$_{28}$FN$_6$O$_2$ [M+H]$^+$ 455.2258, found 451.2272.

1-(Benzylidene-amino)-3-(4-iodo-phenyl)-tetrahydro-pyrimidin-2-one

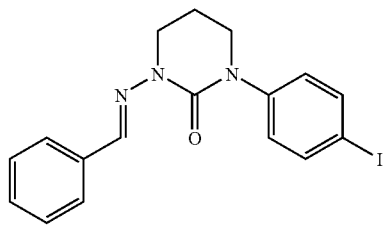

LC-MS (ESI) 406.19 [M+H]$^+$, $t_R$=3.270 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$& B=90% MeOH, 10% H$_2$O, 0.2% H$_3$PO$_4$).

Example 112

1-(Benzylidene-amino)-3-[4-(2-oxo-2H-pyridin-1-yl)-phenyl]-tetrahydro-pyrimidin-2-one

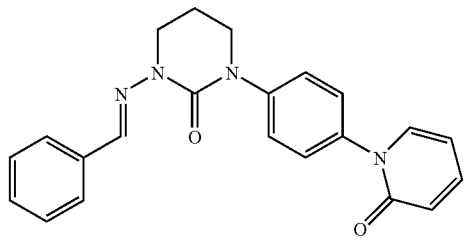

LC-MS (ESI) 373.18 [M+H]$^+$, $t_R$=2.487 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$& B=90% MeOH, 10% H$_2$O, 0.2% H$_3$PO$_4$).

Example 113

3-(Benzylamino)-1-(4-(2-oxopyridin-1-(2H)-yl)phenyl)-tetrahydropyrimidin-2(1H)-one

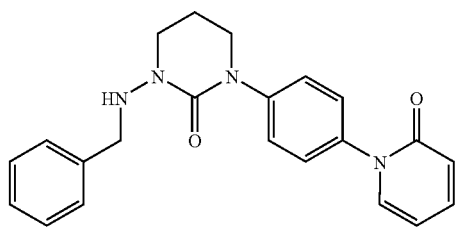

40.3 mg (0.108 mmol) of the Schiff base prepared as above were dissolved in 3 mL of MeOH. The solution was cooled to 0° C. and 8.8 mg (0.141 mmol, 1.3 eq) of NaCNBH$_3$ were added together with one drop of CH$_3$COOH. The reaction mixture was stirred at room temperature for two days. The solvent was evaporated to dryness, and 10 mL of CH$_2$Cl$_2$ were added. The organic phase was washed twice with 2 mL of water, dried over MgSO$_4$, and concentrated to yield 27.7 mg of the crude derivative, which was purified by preparative HPLC to give the title compound. $^1$H NMR (400 MHz, CDCl$_3$) δ 7.52 (m, 1H), 7.3–7.42 (m, 6H), 6.82 (d, J=8.8 Hz, 1H), 6.42 (t, J=6.6 and 1.3 Hz, 1H), 4.12 (s, 2H), 3.67 (t, 2H), 3.52 (t, 2H), 2.08 (m, 2H), ppm. LC-MS (ESI) 375.0 [M+H]$^+$, $t_R$=4.507 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{22}$H$_{23}$N$_4$O$_2$ [M+H]$^+$ 375.1821, found 375.1815.

According to the same procedure the following compounds were prepared:

Example 114

1-(4-Chlorobenzylamino)-3-(4-(2-((dimethylamino)methyl)-1H-imidazol-1-yl)-2-fluorophenyl)-tetrahydropyrimidin-2(1H)-one

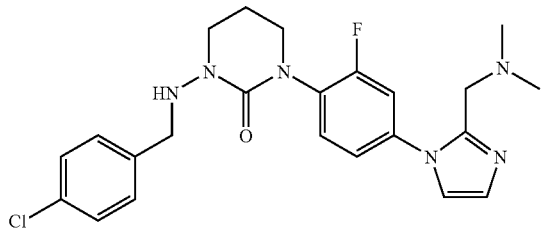

$^1$H NMR (500 MHz, CDCl$_3$) δ 7.42 (t, 1H), 7.20–7.34 (m, 6H), 7.11 (s, 1H), 7.07 (s, 1H), 3.95 (s, 2H) 3.77 (s, 2H), 3.57 (t, J=6.05 Hz, 2H), 3.40 (t, J=6.05 Hz, 2H), 2.51 (s, 6H), 2.02 (t, J=6.05 Hz, 2H), ppm. LC-MS (ESI) 457.0 [M+H]$^+$, $t_R$=4.192 min (Shimadzu Phenomenex S5 ODS 4.6×50 mm Luna flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{23}$H$_{27}$ClFN$_6$O [M+H]$^+$ 457.18407, found 457.1924.

Example 115

1-(3-Chlorobenzylamino)-3-(4-(2-((dimethylamino)methyl)-1H-imidazol-1-yl)-2-fluorophenyl)-tetrahydropyrimidin-2(1H)-one

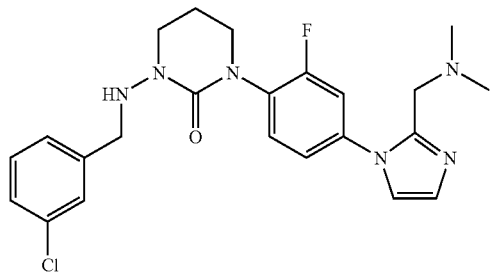

$^1$H NMR (500 MHz, CDCl$_3$) δ 7.52 (s, 1H), 7.49 (t, 1H), 7.40 (s, 1H), 7.37 (s, 1H), 7.24–7.30 (m, 5H), 4.87 (s, 2H) 4.09 (s, 2H), 3.62 (t, J=6.05 Hz, 2H), 3.50 (t, J=6.05 Hz, 2H), 2.9 (s, 6H), 2.11 (t, J=6.05 Hz, 2H), ppm. LC-MS (ESI) 456.9 [M+H]$^+$, $t_R$=4.172 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) in/z calcd for C$_{23}$H$_{27}$ClFN$_6$O [M+H]$^+$ 457.1919, found 457.1921.

Example 116

N-(4-Chlorobenzyl)-2-chloro-N-(3-(4-(2-((dimethylamino)methyl)-1H-imidazol-1-yl)-2-fluorophenyl)-2-oxo-tetrahydropyrimidin-1(2H)-yl)acetamide

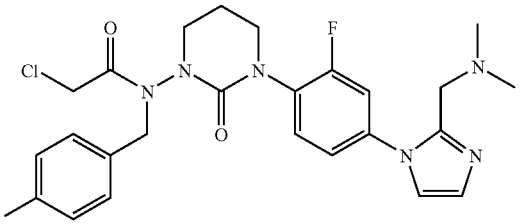

16 mg (0.035 mmol) of the 1-(4-chlorobenzylamino)-3-(4-(2-((dimethylamino)methyl)-1H-imidazol-1-yl)-2-fluorophenyl)-tetrahydropyrimidin-2(1H)-one prepared as above were dissolved in 1.5 mL of CH$_2$Cl$_2$. 5.3 mg (0.053 mmol, 1.5 equivalent) of TEA were introduced followed by 4.1 mg (0.0525 mmol, 1.5 eq) of 2-chloroacetyl chloride. The mixture was stirred overnight at 54° C. An additional 2 mL of CH$_2$Cl$_2$ were added, and the mixture washed twice with 1 mL of saturated NaHCO$_3$ solution. The organic phases were dried over MgSO$_4$ and concentrated to yield an oily residue, which was purified by preparative HPLC. $^1$H NMR (500 MHz, CDCl$_3$) δ 7.32 (m, 9H), 5.17 (d, J=14.1 Hz, 1H) 4.89 (s, 2H), 4.34 (d, J=14.8 Hz, 1H), 4.19 (d, J=13.4 Hz, 1H), 4.10 (d, J=13.4 Hz, 1H), 3.59 (m, 3H), 3.2 (m, 1H), 3.9 (s, 9H), 2.19 (m, 1H), 1.96 (m, 1H), ppm. LC-MS (ESI) 532.9 [M+H]$^+$, $t_R$=4.122 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{25}$H$_{28}$Cl$_2$FN$_6$O$_2$ [M+H]$^+$ 535.1635, found 535.1624.

According to the same procedure and by the reaction of the appropriated amine prepared as above with the corresponding chloride the following molecules were prepared:

Example 117

N-(4-Chlorobenzyl)-N-(3-(4-(2-((dimethylamino)methyl)-1H-imidazol-1-yl)-2-fluorophenyl)-2-oxo-tetrahydropyrimidin-1(2H)-yl)methanesulfonamide

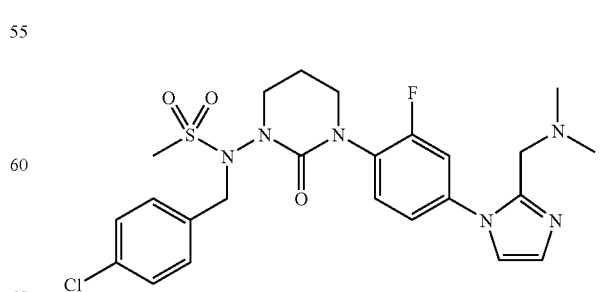

LC-MS (ESI) 534.9 [M+H]$^+$, $t_R$=4.405 min (Shimadzu Phenomenex S5 ODS 4.6×50 mm Luna flow rate 2.5 ml/mn;

detection at 220 nM; Gradient elution 0% to 100% B over 8 min; (A=10% MeOH, 90% H₂O, 0.2% H₃PO₄ & B=90% MeOH, 10% H₂O, 0.2% H₃PO₄). HRMS (ESI) m/z calcd for $C_{24}H_{29}ClFN_6O_3S[M+H]^+$ 535.1694, found 535.1669.

Example 118

N-(4-Chlorobenzyl)-3-chloro-N-(3-(4-(2-((dimethylamino)methyl)-1H-imidazol-1-yl)-2-fluorophenyl)-2-oxo-tetrahydropyrimidin-1(2H)-yl)benzenesulfonamide

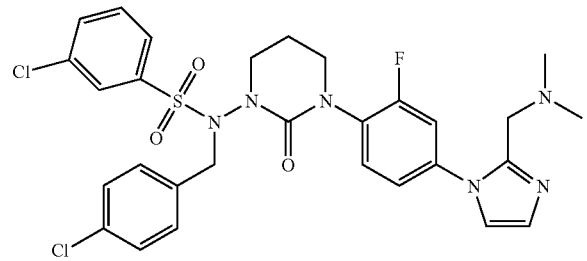

LC-MS (ESI) 630.9 [M+H]+, tR=5.745 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H₂O, 0.2% H₃PO₄ & B=90% MeOH, 10% H₂O, 0.2% H₃PO₄). HRMS (ESI) m/z calcd for $C_{29}H_{30}Cl_2FN_6O_3S$ [M+H]+ 631.1461, found 631.1459.

Example 119

N-Benzyl-N-(2-oxo-3-(4-(2-oxopyridin-1(2H)-yl)phenyl)-tetrahydropyrimidin-1(2H)-yl)methanesulfonamide

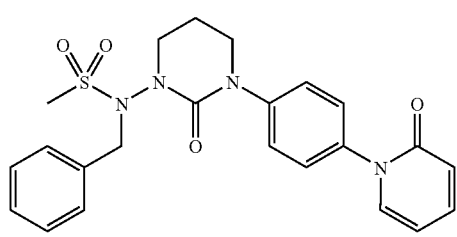

LC-MS (ESI) 470.2 [M+NH₄]+, $t_R$=5.078 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H₂O, 0.2% H₃PO₄ & B=90% MeOH, 10% H₂O, 0.2% H₃PO₄). HRMS (ESI) m/z calcd for $C_{23}H_{25}N_4O_4S$ [M+H]+ 453.15966, found 453.1612.

1-Amino-3-(4-(2-((dimethylamino)methyl)-1H-imidazol-1-yl)-2-fluorophenyl)-tetrahydropyrimidin-2(1H)-one

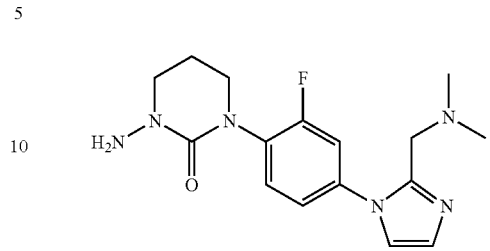

364.3 mg (0.866 mmol) of the Schiff base 1-(benzylideneamino)-3-(4-(2-((dimethylamino)methyl)-1H-imidazol-1-yl)-2-fluorophenyl)-tetrahydropyrimidin-2(1H)-one prepared as above were mixed with 3 mL of concentrated HCl and 5 mL of water. The mixture was distilled under vacuum to dryness. The residue was triturated with MeOH to yield 250 mg of the HCl salt of 1-amino-3-(4-(2-((dimethylamino)methyl)-1H-imidazol-1-yl)-2-fluorophenyl)-tetrahydropyrimidin-2(1H)-one as a yellow powder. This material could be used without any further purification. LC-MS (ESI) 333.21 [M+NH₄]+, $t_R$=0.863 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H₂O, 0.1% TFA & B=90% MeOH, 10% H₂O, 0.1% TFA).

Example 120

2-(5-Chlorothiophen-2-yl)-N-(3-(4-(2-((dimethylamino)methyl)-1H-imidazol-1-yl)-2-fluorophenyl)-2-oxo-tetrahydropyrimidin-1(2H)-yl)ethenesulfonamide

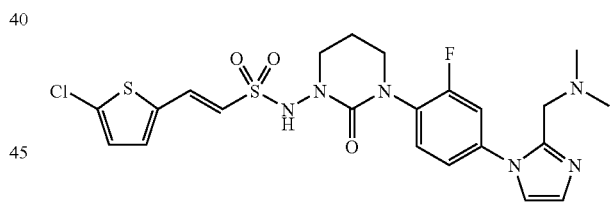

18.6 mg (0.046 mmol) of the diHCl salt of 1-amino-3-(4-(2-((dimethylamino)methyl)-1H-imidazol-1-yl)-2-fluorophenyl)-tetrahydropyrimidin-2(1H)-one prepared as above, were dissolved in 3 mL of anhydrous CH₂Cl₂. To this solution placed under N₂ atmosphere were added 50 µL of TEA followed by 11.2 mg (0.046 mmol) of 2-(5-chlorothiophen-2-yl)ethenesulfonyl chloride. The mixture was stirred at room temperature overnight. An additional 3 mL of CH₂Cl₂ were added, and the mixture was washed twice with 2 mL of saturated NaHCO₃ solution. The organic phase was dried and concentrated to yield 17.2 mg of a brown oil. A pur compound was obtained after purification by preparative HPLC. ¹H NMR (500 MHz, MeOD) δ 7.53 (t, 1H), 7.49 (s, 1H) 7.41 (d, J=10.4 Hz, 1H), 7.29 (s, 1H), 7.27 (d, J=8.2 Hz, 1H), 6.93 (d, J=3.8 Hz, 1H), 6.86 (d, J=3.8 Hz, 1H), 5.1 (m, 1H), 4.45 (q, 2H), 3.5 (m, 2H), 3.14 (m, 1H), 2.86 (s, 6H), 2.0 (m, 2H), ppm. LC-MS (ESI) 556.8 [M+NH4]+, tR=4.645 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{22}$H$_{25}$ClFN$_6$O$_3$S$_2$ [M+H]$^+$ 539.1102, found 539.1105.

According to the experimental procedure described above the following compounds were prepared:

Example 121

1-Bis N,N-(-2-(5-chlorothiophen-2-yl)vinylsulfonyl-amino-3-(4-(2-((dimethylamino)methyl)-1H-imidazol-1-yl)-2-fluorophenyl)-tetrahydropyrimidin-2(1H)-one

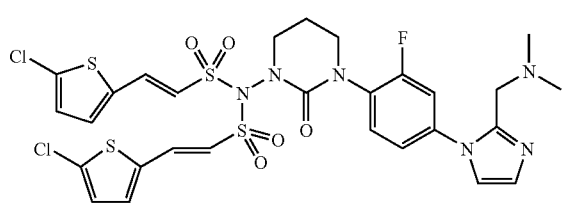

$^1$H NMR (500 MHz, MeOD) δ 7.63 (d, J=14.8 Hz, 1H), 7.49 (m, 1H) 7.45 (m, 2H), 7.8–7.32 (m, 3H), 7.01 (m, 2H), 6.77 (d, J=14.8 Hz, 1H), 6.68 (d, J=14.8 Hz, 1H), 4.45 (s, 2H), 4.01 (t, 1H), 3.74 (t, 1H) 3.63 (t, 1H), 3.3 (m, 1H), 2.88 (s, 6H), 2.33 (t, 1H), 1.97 (t, 1H), ppm. LC-MS (ESI) 744.7 [M+H]$^+$, t$_R$=6.371 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{28}$H$_{28}$Cl$_2$FN$_6$O$_5$S$_4$ [M+H]$^+$ 745.03652, found 745.0365.

Example 122

N-(3-(4-(2-((Dimethylamino)methyl)-1H-imidazol-1-yl)-2-fluorophenyl)-2-oxo-tetrahydropyrimidin-1(2H)-yl)-2-naphthamide

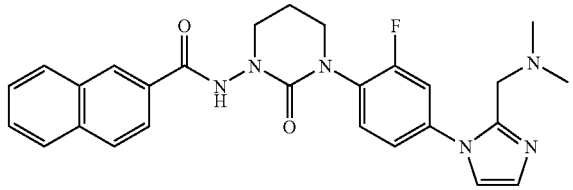

$^1$H NMR (500 MHz, MeOD) δ 8.46 (s, 1H), 7.91–8.0 (m, 4H) 7.68 (t, J=8.4 Hz, 1H), 7.57–7.63 (m, 2H) 7.51 (d, J=1.3 Hz, 1H), 7.47 (dd, J=2.3 Hz and J=10.4 Hz, 1H), 7.35 (m, 1H), 7.33 (d, J=1.3 Hz, 1H), 4.46 (s, 2H), 3.85 (m, 4H), 2.86 (s, 6H), 2.40 (m, 2H), ppm. LC-MS (ESI) 487.2 [M+H]+, tR=3.892 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{27}$H$_{27}$FN$_6$O$_2$ [M+H]$^+$ 487.22579, found 487.2244.

Example 123

6-Chloro-N-(3-(4-(2-((dimethylamino)methyl)-1H-imidazol-1-yl)-2-fluorophenyl)-2-oxo-tetrahydropyrimidin-1(2H)-yl)naphthalene-2-sulfonamide

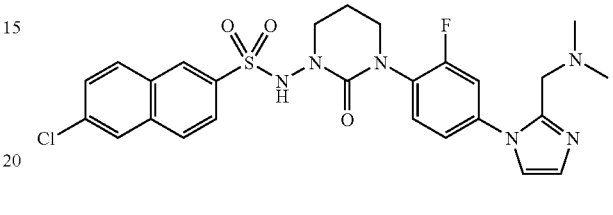

$^1$H NMR (500 MHz, MeOD) δ 8.53 (s, 1H), 8.08 (d, J=8.7 Hz, 1H) 7.99 (bs, 1H), 7.95 (m, 2H) 7.60 (dd, J=8.7 Hz and J=2 Hz, 1H), 7.36 (s, 1H), 7.23–7.32 (m, 2H), 7.09–7.14 (m, 2H), 4.3 (s, 2H), 3.92 (m, 2H), 3.63 (t, 2H), 2.79 (s, 6H), 2.27 (m, 2H), ppm. LC-MS (ESI) 557.2 [M+H]$^+$, t$_R$=4.722 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{26}$H$_{27}$ClFN$_6$O$_3$S [M+H]$^+$ 557.1538, found 557.1533.

Example 124

N-(3-(4-(2-((Dimethylamino)methyl)-1H-imidazol-1-yl)-2-fluorophenyl)-2-oxo-tetrahydropyrimidin-1(2H)-yl)naphthalene-2-sulfonamide

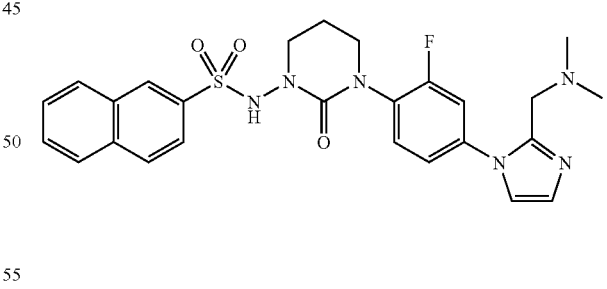

$^1$H NMR (500 MHz, CDCl$_3$) δ 8.52 (s, 1H), 8.07 (d, J=8.1 Hz, 1H) 8.0 (d, J=8.7 Hz, 1H), 7.94 (d, J=7.4 Hz, 1H), 7.92 (dd, J=8.7 Hz and J=1.3 Hz, 1H) 7.64 (m, 2H), 7.36 (s, 1H), 7.23–7.32 (m, 2H), 7.09–7.14 (m, 2H), 4.3 (s, 2H), 3.92 (m, 2H), 3.63 (t, J=5.7 Hz, 2H), 2.79 (s, 6H), 2.27 (m, 2H), ppm. LC-MS (ESI) 523.2 [M+H]$^+$, t$_R$=4.132 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{26}$H$_{28}$FN$_6$O$_3$S [M+H]$^+$ 523.19277, found 523.1918.

Example 125

2-(4-Chlorophenyl)-N-(3-(4-(2-((dimethylamino)methyl)-1H-imidazol-1-yl)-2-fluorophenyl)-2-oxo-tetrahydropyrimidin-1(2H)-yl)acetamide

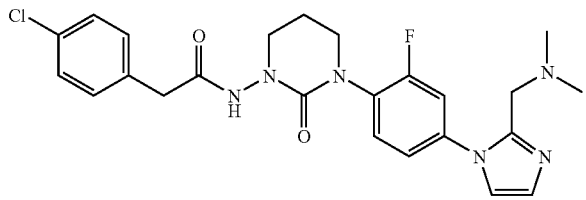

$^1$H NMR (500 MHz, MeOD) δ 7.61 (t, J=8.1 Hz, 1H), 7.50 (s, 1H), 7.45 (dd, J=2.3 Hz and J=10.4 Hz, 1H), 7.29–7.34 (m, 6H), 4.45 (s, 2H), 3.74 (t, J=5.7 Hz, 2H), 3.67 (t, J=6.05 Hz, 2H), 3.56 (s, 2H), 2.86 (s, 6H), 2.28 (m, 2H) ppm. LC-MS (ESI) 485.2 [M+H]$^+$, $t_R$=3.645 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$& B=90% MeOH, 10% H$_2$O, 0.2% H$_3$PO$_4$). HRMS (ESI) m/z calcd for C$_{23}$H$_{27}$ClFN$_6$O$_2$ [M+H]$^+$ 485.18682, found 485.1873.

Example 126

1-(4-Chlorophenyl)-3-(3-(4-(2-((dimethylamino)methyl)-H-imidazol-1-yl)-2-fluorophenyl)-2-oxo-tetrahydropyrimidin-1(2H)-yl)urea

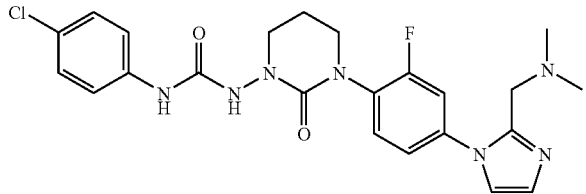

$^1$H NMR (500 MHz, CDCl$_3$) δ 7.64 (t, 1H), 7.51 (bs, 1H), 7.46 (dd, J=2 Hz and J=9.1 Hz, 1H), 7.42 (d, J=9.4 Hz, 2H), 7.34 (m, 2H), 7.25 (d, J=9.4 Hz 2H), 4.47 (s, 2H), 3.77 (m, 4H), 2.85 (s, 6H), 2.31 (m, 2H) ppm. LC-MS (ESI) 486.1 [M+H]$^+$, $t_R$=3.682 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$& B=90% MeOH, 10% H$_2$O, 0.2% H$_3$PO$_4$). HRMS (ESI) m/z calcd for C$_{23}$H$_{26}$ClFN$_7$O$_2$ [M+H]$^+$ 486.18206, found 486.1844.

UTILITY

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1 + S/K_m))$$

where:

$v_o$ is the velocity of the control in the absence of inhibitor;
$v_s$ is the velocity in the presence of inhibitor;
I is the concentration of inhibitor;
$K_i$ is the dissociation constant of the enzyme:inhibitor complex;
S is the concentration of substrate;
$K_m$ is the Michaelis constant.

Compounds tested in the above assay are considered to be active if they exhibit a $K_i$ of ≦10 μM. Preferred compounds of the present invention have $K_i$'s of ≦1 μM. More preferred compounds of the present invention have $K_i$'s of ≦0.1 μM. Even more preferred compounds of the present invention have $K_i$'s of ≦0.01 μM. Still more preferred compounds of the present invention have $K_i$'s of ≦0.001 μM. Using the methodology described above, a number of compounds of the present invention were found to exhibit $K_i$'s of ≦10 µM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 µm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as I$_{Ach}$ inhibitors, and I$_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

DOSAGE AND FORMULATION

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70–80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Numerous modifications and variations of the present invention are possible in light of the above teachings. It is therefore to be understood that within the scope of the appended claims, the invention may be practiced otherwise that as specifically described herein.

What is claimed is:

1. A compound of formula Ia–If:

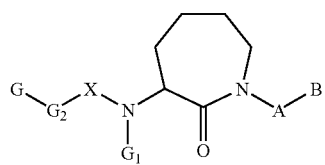
Ia

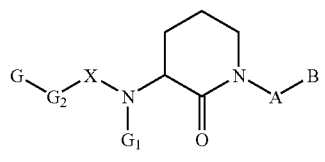
Ib

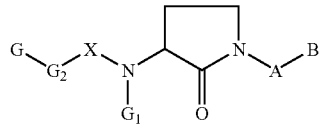
Ic

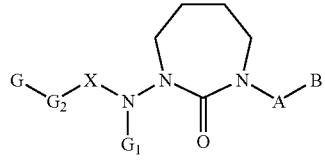
Id

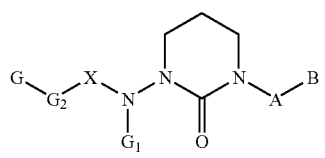
Ie

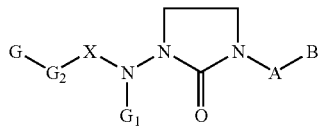
If or a stereoisomer or pharmaceutically acceptable salt thereof, wherein;

the central lactam ring is substituted with 0–2 $R^{1a}$ and 0–1 additional carbonyl groups;

G is a group of formula IIa or IIb:

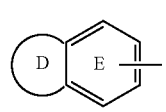
IIa

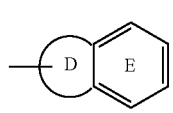
IIb ring D, including the two atoms of ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent, and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent, ring E is selected from phenyl, phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered ring consisting of: carbon atoms and 0–4 heteroatoms selected from the group consisting of N, O, and $S(O)_p$, wherein the 5–6 membered ring is substituted with 0–2 carbonyls and 1–2 R and has 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, $C(=NR^8)NR^7R^9$, $NHC(=NR^8)NR^7R^9$, $NR^8CH(=NR^7)$, $NH_2$, $NH(C_{1-3}\text{ alkyl})$, $N(C_{1-3}\text{ alkyl})_2$, $C(=NH)NH_2$, $CH_2NH_2$, $CH_2NH(C_{1-3}\text{ alkyl})$, $CH_2N(C_{1-3}\text{ alkyl})_2$, $CH_2CH_2NH_2$, $CH_2CH_2NH(C_{1-3}\text{ alkyl})$, $CH_2CH_2N(C_{1-3}\text{ alkyl})_2$, $(CR^8R^9)_tC(O)H$, $(CR^8R^9)_tC(O)R^2{}^c$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$;

alternatively, when 2 R groups are attached to adjacent atoms, they combine to form methylenedioxy or ethylenedioxy;

$G_1$ is selected from H, —CN, $(CR^3R^{3a})_{1-2}C(O)R^2$, $NR^2R^{2a}$, $(CR^3R^{3a})_{2-5}NR^2R^{2a}$, $OR^2$, $(CR^3R^{3a})_{2-5}OR^2$, $(CR^3R^{3a})_{1-2}S(O)_pR^2$, $NR^2C(O)R^2$, $(CR^3R^{3a})_{2-5}NR^2C(O)R^2$, $NR^2C(O)NR^2R^{2a}$, $(CR^3R^{3a})_{2-5}NR^2C(O)NR^2R^{2a}$, $NR^2C(O)OR^2$, $(CR^3R^{3a})_{2-5}NR^2C(O)OR^2$, $(CR^3R^{3a})_{1-2}S(O)_2NR^2R^{2a}$, $NR^2S(O)_2NR^2R^{2a}$, $(CR^3R^{3a})_{2-5}NR^2S(O)_2NR^2R^{2a}$, $OC(O)R^2$, $(CR^3R^{3a})_{2-5}OC(O)R^2$, $(CR^3R^{3a})_{1-2}C(O)OR^2$, $(CR^3R^{3a})_{1-2}C(O)NR^2R^{2a}$, $(CR^3R^{3a})_{1-2}C(O)NR^2(CR^3R^{3a})(CR^3R^{3a})_{1-2}OR^2$, $(CR^3R^{3a})_{1-2}C(O)NR^2(CR^3R^{3a})(CR^3R^{3a})_{1-2}NR^2R^{2a}$, $(CR^3R^{3a})C(O)NR^2(CR^3R^{3a})_{1-2}C(O)NR^2R^{2a}$, $(CR^3R^{3a})C(O)NR^2(CR^3R^{3a})_{1-2}C(O)OR^2$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $(CR^3R^{3a})_{0-4}C_{3-10}$ carbocycle substituted with 0–3 $R^{1a}$, and $(CR^3R^{3a})_{0-4}$-5–12 membered heterocycle consisting of: carbon atoms and 1–4 heteroatoms selected from the group consisting of N, O, and $S(O)_p$ and substituted with 0–3 $R^{1a}$;

$G_2$ is absent or is selected from $CR^3R^{3a}CR^3R^{3a}$ and $CR^3=CR^3$;

B is selected from —CN, $C_{1-6}$ alkyl substituted with 0–2 $R^{4a}$, $C_{2-6}$ alkenyl substituted with 0–2 $R^{4a}$, $C_{2-6}$ alkynyl substituted with 0–2 $R^{4a}$, O—$C_{1-6}$ alkyl substituted with 0–2 $R^{4a}$, $S(O)_p$—$C_{1-6}$ alkyl substituted with 0–2 $R^{4a}$, $NR^{2d}$—$C_{1-6}$ alkyl substituted with 0–2 $R^{4a}$, $C_{3-6}$ cycloalkyl substituted with 0–2 $R^{2d}$, and a 3–7 membered saturated heterocycle substituted with 0–2 $R^{2d}$ and consisting of carbon atoms and 1–3 heteroatoms selected from the group consisting of N, O, and $S(O)_p$;

$R^{1a}$, at each occurrence, is selected from H, —($CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$C_{2-6}$ alkenylene-$R^{1b}$, —$C_{2-6}$ alkynylene-$R^{1b}$, —$(CR^3R^{3a})_r$—C(=NR$^{1b}$)NR$^3R^{1b}$, NR$^3(CR^3R^{3a})_rR^{1c}$, O$(CR^3R^{3a})_rR^{1c}$, $(CR^3R^{3a})_rSCR^3R^{3a}R^{1c}$, $(CR^3R^{3a})_rNR^3(CR^3R^{3a})_rR^{1b}$, $(CR^3R^{3a})_rC(O)NR^2(CR^3R^{3a})_rR^{1b}$, $CO_2(CR^3R^{3a})_rR^{1b}$, $O(CR^3R^{3a})_rR^{1b}$, $(CR^3R^{3a})_rS(CR^3R^{3a})_rR^{1b}$, $S(O)_p(CR^3R^{3a})_rR^{1d}$, $O(CR^3R^{3a})_rR^{1d}$, $NR^3(CR^3R^{3a})_rR^{1d}$, $OC(O)NR^3(CR^3R^{3a})_rR^{1d}$, $NR^3C(O)NR^3(CR^3R^{3a})_rR^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;

$R^{1b}$ is selected from H, $C_{1-3}$ alkyl, F, Cl, Br, I, —CN, —NO$_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $(CF_2)_rCO_2R^{2a}$, $S(O)_pR^{2b}$, $NR^2(CH_2)_rOR^2$, C(=NR$^{2c}$)NR$^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2NR^2R^{2a}$, $NR^2SO_2R^2$, $C(O)NR^2SO_2R^2$, $SO_2R^2C(O)NR^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^{1c}$ is selected from H, CH(CH$_2$OR$^2$)$_2$, C(O)R$^{2c}$, C(O)NR$^2R^{2a}$, $S(O)R^2$, $S(O)_2R^2$, and $SO_2NR^2R^{2a}$;

$R^{1d}$ is selected from $C_{3-6}$ carbocycle substituted with 0–2 $R^{4b}$ and 5–10 membered heterocycle consisting of carbon atoms and from 1–4 heteroatoms selected from the group consisting of N, O, and $S(O)_p$ and substituted with 0–2 $R^{4b}$, provided that $R^{1d}$ forms other than an N—S bond;

$R^2$, at each occurrence, is selected from H, CF$_3$, $C_{1-6}$ alkyl substituted with 0–2 $R^{4b}$, benzyl, —(CH$_2$)$_r$—$C_{3-10}$ carbocycle substituted with 0–2 $R^{4b}$, and —(CH$_2$)$_r$-5–10 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, CF$_3$, $C_{1-6}$ alkyl substituted with 0–2 $R^{4b}$, benzyl, —(CH$_2$)$_r$—$C_{3-10}$ carbocycle substituted with 0–2 $R^{4b}$, and —(CH$_2$)$_r$-5–10 membered heterocycle consisting of: carbon atoms and 1–4 heteroatoms selected from the group consisting of N, O, and $S(O)_p$ and substituted with 0–2 $R^{4b}$;

alternatively, NR$^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^2b$, at each occurrence, is selected from CF$_3$, $C_{1-4}$ alkoxy substituted with 0–2 $R^{4b}$, $C_{1-6}$ alkyl substituted with 0–2 $R^{4b}$, —(CH$_2$)$_r$—$C_{3-10}$ carbocycle substituted with 0–2 $R^{4b}$, and —(CH$_2$)$_4$-5–10 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from CF$_3$, OH, $C_{1-4}$ alkoxy, $C_{1-6}$ alkyl, —(CH$_2$)$_r$—$C_{3-10}$ carbocycle substituted with 0–2 $R^{4b}$, and —(CH$_2$)$_4$-5–10 membered heterocycle containing from 1–4 heteroatoms selected from the group consisting of N, O, and $S(O)_p$ and substituted with 0–2 $R^{4b}$;

$R^{2d}$, at each occurrence, is selected from H and $C_{1-6}$ alkyl;

$R^{2e}$, at each occurrence, is selected from H and $C_{1-6}$ alkyl;

$R^3$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

$R^{3a}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)3, benzyl, and phenyl;

alternatively, NR$^3R^{3a}$ forms a 5 or 6 membered saturated, partially unsaturated, or unsaturated ring consisting of: carbon atoms, the nitrogen atom to which R$^3$ and R$^{3a}$ are attached, and 0–1 additional heteroatoms selected from the group consisting of N, O, and $S(O)_p$;

$R^{3c}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

$R^{3d}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, $C_{1-4}$ alkyl-phenyl, and C(=O)R$^{3c}$;

$R^4$, at each occurrence, is selected from H, =O, (CR$^3R^{3a}$)$_r$OR$^2$, $(CR^3R^{3a})_r$F, $(CR^3R^{3a})_r$Cl, $(CR^3R^{3a})_r$Br, $(CR^3R^{3a})_r$I, $C_{1-4}$ alkyl, $(CR^3R^{3a})_r$CN, $(CR^3R^{3a})_r$NO$_2$, $(CR^3R^{3a})_r$NR$^2R^{2a}$, $(CR^3R^{3a})_r$C(O)R$^{2c}$, $(CR^3R^{3a})_r$NR$^2$C(O)R$^{2b}$, $(CR^3R^{3a})_r$C(O)NR$^2R^{2a}$, $(CR^3R^{3a})_r$NR$^2$C(O)NR$^2R^{2a}$, $(CR^3R^{3a})_r$C(=NR$^2$)NR$^2R^{2a}$, $(CR^3R^{3a})_r$C(=NS(O)$_2$R$^5$)NR$^2R^{2a}$, $(CR^3R^{3a})_r$NR$^2$C(=NR$^2$)NR$^2R^{2a}$, $(CR^3R^{3a})_r$C(O)NR$^2$C(=NR$^2$)NR$^2R^{2a}$, $(CR^3R^{3a})_r$SO$_2$NR$^2R^{2a}$, $(CR^3R^{3a})_r$NR$^2$SO$_2$NR$^2R^{2a}$, $(CR^3R^{3a})_r$NR$^2$SO$_2$—$C_{1-4}$ alkyl, $(CR^3R^{3a})_r$NR$^2$SO$_2$R$^5$, $(CR^3R^{3a})_r$S(O)$_p$R$^{5a}$, $(CR^3R^{3a})_r$(CF$_2$)$_r$CF$_3$, $(CR^3R^{3a})_r$-5–6 membered carbocycle substituted with 0–1 R$^5$, and a $(CR^3R^{3a})_r$-5–6 membered heterocycle consisting of: carbon atoms and 1–4 heteroatoms selected from the group consisting of N, O, and $S(O)_p$ and substituted with 0–1 R$^5$;

$R^{4a}$ is selected from H, =O, Cl, F, Br, I, $C_{1-4}$ alkyl, $C_{1-4}$ haloalkyl, NR$^{2d}R^{2d}$, N(→O)R$^{2d}R^{2d}$, OR$^{2d}$, —NR$^{2d}$C(O)R$^{2d}$, —C(O)R$^{2d}$, —OC(O)R$^{2d}$, —C(O)NR$^{2d}R^{2d}$, —(CR$^{2e}R^{2e}$)$_r$C(O)OR$^{2d}$, —NR$^{2d}$C(O)NR$^{2d}R^{2d}$, —OC (O)NR$^{2d}$R$^{2d}$, —NR$^{2d}$C(O)OR$^{2d}$, —SO$_2$NR$^{2d}$R$^{2d}$, —NR$^{2d}$SO$_2$NR$^{2d}$R$^{2d}$, —C(O)NR$^{2d}$SO$_2$R$^{2d}$, —SO$_2$NR$^{2d}$C(O)R$^{2d}$, —NR$^{2d}$SO$_2$R$^{2d}$, and —S(O)$_p$R$^{2d}$, provided that S(O)$_p$R$^{2d}$ forms other than S(O)$_2$H or S(O)H and further provided that R$^{4a}$ is other than a hydroxamic acid;

R$^{4b}$, at each occurrence, is selected from H, =O, (CH$_2$)$_r$OR$^3$, (CH$_2$)$_r$F, (CH$_2$)$_r$Cl, (CH$_2$)$_r$Br, (CH$_2$)$_r$I, C$_{1-4}$ alkyl, (CH$_2$)$_r$CN, (CH$_2$)$_r$NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$—C(O)NR$^3$R$^{3a}$, (CH$_2$)$_r$NR$^3$C(O)NR$^3$R$^{3a}$, (CH$_2$)$_r$—C(=NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, and (CH$_2$)$_r$(CF$_2$)$_r$CF$_3$;

R$^5$, at each occurrence, is selected from H, C$_{1-6}$ alkyl, =O, (CH$_2$)$_r$OR$^3$, F, Cl, Br, I, —CN, NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CH$_2$)$_r$NR$^3$C(O)NR$^3$R$^{3a}$, (CH$_2$)$_r$CH(=NOR$^{3d}$), (CH$_2$)$_r$C(=NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, (CF$_2$)$_r$CF$_3$, phenyl substituted with 0–2 R$^6$, naphthyl substituted with 0–2 R$^6$, and benzyl substituted with 0–2 R$^6$;

R$^{5a}$, at each occurrence, is selected from C$_{1-6}$ alkyl, (CH$_2$)$_r$OR$^3$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CF$_2$)$_r$CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond;

R$^6$, at each occurrence, is selected from H, OH, (CH$_2$)$_r$OR$^2$, halo, C$_{1-4}$ alkyl, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkyl-C(O)—, C$_{1-6}$ alkyl-O—, (CH$_2$)$_n$-phenyl, C$_{1-6}$ alkyl-OC(O)—, C$_{6-10}$ aryl-O—, C$_{6-10}$ aryl-OC(O)—, C$_{6-10}$ aryl-CH$_2$—C(O)—, C$_{1-4}$ alkyl-C(O)O—C$_{1-4}$ alkyl-OC(O)—, C$_{6-10}$ aryl-C(O)O—C$_{1-4}$ alkyl-OC(O)—, C$_{1-6}$ alkyl-NH$_2$—C(O)—, phenyl-NH$_2$—C(O)—, and phenyl C$_{0-4}$ alkyl-C(O)—;

R$^8$, at each occurrence, is selected from H, C$_{1-6}$ alkyl, and (CH$_2$)$_n$-phenyl;

alternatively, R$^7$ and R$^8$, when attached to the same nitrogen, combine to form a 5–10 membered heterocyclic ring consisting of carbon atoms and 0–2 additional heteroatoms selected from the group consisting of N, O, and S(O)$_p$;

R$^9$, at each occurrence, is selected from H, C$_{1-6}$ alkyl, and (CH$_2$)$_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and t, at each occurrence, is selected from 0, 1, 2, and 3.

2. A compound according to claim 1, wherein:
G is a group of formula IIa or IIb:

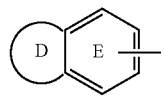

IIa

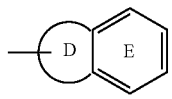

IIb ring D, including the two atoms of ring E to which it is attached, is a 5–6 membered ring consisting of: carbon atoms and 0–2 heteroatoms selected from the group consisting of N, O, and S(O)$_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with a 5 membered heterocycle consisting of: carbon atoms and 1–4 heteroatoms selected from the group consisting of N, O, and S(O)$_p$, wherein the 5 membered heterocycle is substituted with 0–1 carbonyls and 1–2 R and has 0–3 ring double bonds;

R is selected from H, C$_{1-4}$ alkyl, F, Cl, OH, OCH$_3$, OCH$_2$CH$_3$, OCH(CH$_3$)$_2$, CN, C(=NH)NH$_2$, NH$_2$, NH(C$_{1-3}$ alkyl), N(C$_{1-3}$ alkyl)$_2$, C(=NH)NH$_2$, CH$_2$NH$_2$, CH$_2$NH(C$_{1-3}$ alkyl), CH$_2$N(C$_{1-3}$ alkyl)$_2$, (CR$^8$R$^9$)$_r$NR$^7$R$^8$, C(O)NR$^7$R$^8$, CH$_2$C(O)NR$^7$R$^8$, S(O)$_p$NR$^7$R$^8$, CH$_2$S(O)$_p$NR$^7$R$^8$, and OCF$_3$;

alternatively, when 2 R groups are attached to adjacent atoms, they combine to form methylenedioxy or ethylenedioxy;

G$_1$ is selected from H, (CR$^3$R$^{3a}$)C(O)R$^2$, NR$^2$R$^{2a}$, (CR$^3$R$^{3a}$)(CR$^3$R$^{3a}$)NR$^2$R$^{2a}$, OR$^2$, (CR$^3$R$^{3a}$)(CR$^3$R$^{3a}$)OR$^2$, (CR$^3$R$^{3a}$)S(O)$_p$R$^2$, NR$^2$C(O)R$^2$, (CR$^3$R$^{3a}$)(CR$^3$R$^{3a}$)NR$^2$C(O)R$^2$, NR$^2$C(O)NR$^2$R$^{2a}$, (CR$^3$R$^{3a}$)(CR$^3$R$^{3a}$)NR$^2$C(O)NR$^2$R$^{2a}$, NR$^2$C(O)OR$^2$, (CR$^3$R$^{3a}$)(CR$^3$R$^{3a}$)NR$^2$C(O)OR$^2$, (CR$^3$R$^{3a}$)S(O)$_2$NR$^2$R$^{2a}$, NR$^2$S(O)$_2$NR$^2$R$^{2a}$, (CR$^3$R$^{3a}$)(CR$^3$R$^{3a}$)NR$^2$S(O)$_2$NR$^2$R$^{2a}$, OC(O)R$^2$, (CR$^3$R$^{3a}$)(CR$^3$R$^{3a}$)OC(O)R$^2$, (CR$^3$R$^{3a}$)C(O)OR$^2$, (CR$^3$R$^{3a}$)C(O)NR$^2$R$^{2a}$, (CR$^3$R$^{3a}$)C(O)NR$^2$(CR$^3$R$^{3a}$)(CR$^3$R$^{3a}$)OR$^2$, (CR$^3$R$^{3a}$)C(O)NR$^2$(CR$^3$R$^{3a}$)(CR$^3$R$^{3a}$)(CR$^3$R$^{3a}$)OR$^2$, (CR$^3$R$^{3a}$)C(O)NR$^2$(CR$^3$R$^{3a}$)(CR$^3$R$^{3a}$)NR$^2$R$^{2a}$, (CR$^3$R$^{3a}$)C(O)NR$^2$(CR$^3$R$^{3a}$)(CR$^3$R$^{3a}$)(CR$^3$R$^{3a}$)NR$^2$R$^{2a}$, (CR$^3$R$^{3a}$)C(O)NR$^2$(CR$^3$R$^{3a}$)C(O)NR$^2$R$^{2a}$, (CR$^3$R$^{3a}$)C(O)NR$^2$(CR$^3$R$^{3a}$)(CR$^3$R$^{3a}$)C(O)NR$^2$R$^{2a}$, (CR$^3$R$^{3a}$)C(O)NR$^2$(CR$^3$R$^{3a}$)C(O)OR$^2$, (CR$^3$R$^{3a}$)C(O)NR$^2$(CR$^3$R$^{3a}$)C(O)OR$^2$, C$_{1-6}$ alkyl substituted with 0–1 R$^{1a}$, C$_{2-6}$ alkenyl substituted with 0–1 R$^{1a}$, C$_{2-6}$ alkynyl substituted with 0–1 R$^{1a}$, (CR$^3$R$^{3a}$)$_{0-4}$—C$_{3-10}$ carbocycle substituted with 0–1 R$^{1a}$, and (CR$^3$R$^{3a}$)$_{0-4}$-5–12 membered heterocycle consisting of: carbon atoms and 1–4 heteroatoms selected from the group consisting of N, O, and S(O)$_p$ and substituted with 0–1 R$^{1a}$;

R$^{1a}$, at each occurrence, is selected from H, —(CR$^3$R$^{3a}$)$_r$—R$^{1b}$, —(CR$^3$R$^{3a}$)$_r$—O—(CR$^3$R$^{3a}$)$_r$—R$^{1b}$, —C$_{2-6}$ alkenylene-R$^{1b}$, —C$_{2-6}$ alkynylene-R$^{1b}$, —(CR$^3$R$^{3a}$)$_r$—C(=NR$^{1b}$)NR$^3$R$^{1b}$, NR$^3$(CR$^3$R$^{3a}$)$_r$R$^{1c}$, O(CR$^3$R$^{3a}$)$_r$R$^{1c}$, (CR$^3$R$^{3a}$)$_r$SCR$^3$R$^{3a}$R$^{1c}$, (CR$^3$R$^{3a}$)$_r$NR$^3$(CR$^3$R$^{3a}$)$_r$R$^{1b}$, (CR$^3$R$^{3a}$)$_r$C(O)NR$^2$(CR$^3$R$^{3a}$)$_r$R$^{1b}$, CO$_2$(CR$^3$R$^{3a}$)$_r$R$^{1b}$, O(CR$^3$R$^{3a}$)$_r$R$^{1b}$, S(O)$_p$(CR$^3$R$^{3a}$)$_r$R$^{1d}$, O(CR$^3$R$^{3a}$)$_r$R$^{1d}$, NR$^3$(CR$^3$R$^{3a}$)$_r$R$^{1d}$, OC(O)NR$^3$(CR$^3$R$^{3a}$)$_r$R$^{1d}$, NR$^3$C(O)NR$^3$(CR$^3$R$^{3a}$)$_r$R$^{1d}$, NR$^3$C(O)O(CR$^3$R$^{3a}$)$_r$R$^{1d}$, and NR$^3$C(O)(CR$^3$R$^{3a}$)$_r$R$^{1d}$, provided that R$^{1a}$ forms other than an N-halo, N—S, O—O, or N—CN bond;

R$^{1b}$ is selected from H, CH$_3$, CH$_2$CH$_3$, CH$_2$CH$_2$CH$_3$, CH(CH$_3$)$_2$, F, Cl, Br, I, —CN, —CHO, CF$_3$, (CR$^3$R$^{3a}$)$_r$OR$^2$, NR$^2$R$^{2a}$, C(O)R$^{2b}$, CO$_2$R$^{2b}$, OC(O)R$^2$, CO$_2$R$^{2a}$, S(O)$_p$R$^2$, NR$^2$(CH$_2$)$_r$OR$^2$, NR$^2$C(O)R$^{2b}$, NR$^2$C(O)NR$^2$R$^{2a}$, NR$^2$C(O)$_2$R$^{2a}$, OC(O)NR$^2$R$^{2a}$, C(O)NR$^2$R$^{2a}$, C(O)NR$^2$(CH$_2$)$_r$OR$^2$, SO$_2$NR$^2$R$^{2a}$, NR$^2$SO$_2$NR$^2$R$^{2a}$, NR$^2$SO$_2$R$^2$, C(O)NR$^2$SO$_2$R$^2$, SO$_2$NR$^2$C(O)R$^2$, C$_{3-10}$ carbocycle substituted with 0–2 R$^4$, and 4–10 membered heterocycle consisting of carbon atoms and from 1–4 heteroatoms selected from the group consisting of N, O, and S(O)$_p$ and substituted with 0–2 R$^4$, provided that R$^{1b}$ forms other than an O—O, N-halo, N—S, or N—CN bond;

R$^{1c}$ is selected from H, CH(CH$_2$OR$^2$)$_2$, C(O)R$^{2c}$, C(O)NR$^2$R$^{2a}$, S(O)R$^2$, S(O)$_2$R$^2$, and SO$_2$NR$^2$R$^{2a}$;

R$^2$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, CH$_2$CH$_2$OH, CH$_2$CH$_2$CH$_2$OH, CH$_2$CH$_2$NMe$_2$, CH$_2$CH$_2$CH$_2$NMe$_2$, benzyl, C$_{5-6}$ carbocycle substituted with 0–2 R$^{4b}$, a C$_{5-6}$ carbocyclic-CH$_2$ group substituted with 0–2 R$^{4b}$, a 5–6 membered heterocycle consisting of: carbon atoms and 1–4 heteroatoms selected from the group consisting of N, O, and S(O)$_p$ and substituted with 0–2 R$^{4b}$, and a 5–6 membered heterocycle-CH$_2$ group consisting of: carbon atoms and 1–4 heteroatoms selected from the group consisting of N, O, and S(O)$_p$ and substituted with 0–2 R$^{4b}$ R$^{2a}$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, CH$_2$CH$_2$OH, CH$_2$CH$_2$CH$_2$OH, CH$_2$CH$_2$NMe$_2$, CH$_2$CH$_2$CH$_2$NMe$_2$, benzyl, C$_{5-6}$ carbocycle substituted with 0–2 R$^{4b}$, and 5–6 membered heterocycle consisting of: carbon atoms and 1–4 heteroatoms selected from the group consisting of N, O, and S(O)$_p$ and substituted with 0–2 R$^{4b}$;

alternatively, NR$^2$R$^{2a}$ forms a 5 or 6 membered saturated, partially saturated or unsaturated ring substituted with 0–2 R$^{4b}$ and consisting of: 0–1 additional heteroatoms selected from the group consisting of N, O, and S(O)$_p$;

R$^{2b}$, at each occurrence, is selected from CF$_3$, C$_{1-4}$alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, C$_{5-6}$ carbocycle substituted with 0–2 R$^{4b}$, and 5–6 membered heterocycle consisting of: carbon atoms and 1–4 heteroatoms selected from the group consisting of N, O, and S(O)$_p$ and substituted with 0–2 R$^{4b}$;

R$^{2c}$, at each occurrence, is selected from CF$_3$, OH, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, C$_{5-6}$ carbocycle substituted with 0–2 R$^{4b}$, and 5–6 membered heterocycle containing from 1–4 heteroatoms selected from the group consisting of N, O, and S(O)$_p$ and substituted with 0–2 R$^{4b}$;

R$^{2d}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, and C(CH$_3$)$_3$;

R$^{2e}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, and C(CH$_3$)$_3$;

R$^3$, at each occurrence, is selected from H, CH$_3$, CH$_2$CH$_3$, CH$_2$CH$_2$CH$_3$, CH(CH$_3$)$_2$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, benzyl, and phenyl;

alternatively, NR$^3$R$^{3a}$ forms a 5 or 6 membered saturated, partially unsaturated, or unsaturated ring consisting of: carbon atoms and the nitrogen atom to which R$^3$ and R$^{3a}$ are attached;

R$^{3c}$, at each occurrence, is selected from CH$_3$, CH$_2$CH$_3$, CH$_2$CH$_2$CH$_3$, CH(CH$_3$)$_2$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$-phenyl, CH$_2$CH$_2$-phenyl, and C(=O)R$^{3c}$;

R$^4$, at each occurrence, is selected from H, =O, OR$^2$, CH$_2$OR$^2$, (CH$_2$)$_2$OR$^2$, F, Cl, Br, I, C$_{1-4}$ alkyl, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, S(O)$_p$R$^5$, CF$_3$, CF$_2$CF$_3$, 5–6 membered carbocycle substituted with 0–1 R$^5$, and a 5–6 membered heterocycle consisting of: carbon atoms and 1–4 heteroatoms selected from the group consisting of N, O, and S(O)$_p$ and substituted with 0–1 R$^5$;

R$^{4a}$ is selected from H, =O, C$_{1-4}$ alkyl, NR$^{2d}$R$^{2d}$, N(→O)R$^{2d}$R$^{2d}$, OR$^{2d}$, —NR$^{2d}$C(O)R$^{2d}$, —C(O)R$^{2d}$, —OC(O)R$^{2d}$, —C(O)NR$^{2d}$R$^{2d}$, —C(O)OR$^{2d}$, —SO$_2$NR$^{2d}$R$^{2d}$, —NR$^{2d}$SO$_2$R$^{2d}$, and —S(O)$_p$R$^{2d}$, provided that S(O)$_p$R$^{2d}$ forms other than S(O)$_2$H or S(O)H and further provided that R$^{4a}$ is other than a hydroxamic acid;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^3$R$^{3a}$, CH$_2$NR$^3$R$^{3a}$, C(O)R$^3$, CH$_2$—C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, NR$^3$C(O)NR$^3$R$^{3a}$, CH$_2$NR$^3$C(O)NR$^3$R$^{3a}$, C(=NR$^3$)NR$^3$R$^{3a}$, CH$_2$C(=NR$^3$)NR$^3$R$^{3a}$, NR$^3$C(=NR$^3$)NR$^3$R$^{3a}$, CH$_2$NR$^3$C(=NR$^3$)NR$^3$R$^{3a}$, SO$_2$NR$^3$R$^{3a}$, CH$_2$SO$_2$NR$^3$R$^{3a}$, NR$^3$SO$_2$NR$^3$R$^{3a}$, CH$_2$NR$^3$SO$_2$NR$^3$R$^{3a}$, NR$_3$SO$_2$—C$_{1-4}$ alkyl, CH$_2$NR$^3$SO$_2$—C$_{1-4}$ alkyl, NR$^3$SO$_2$CF$_3$, CH$_2$NR$^3$SO$_2$CF$_3$, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, CF$_3$, and CH$_2$—CF$_3$;

R$^5$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$_3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$;

R$^{5a}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, NR$^3$R$^{3a}$, CH$_2$NR$^3$R$^{3a}$, C(O)R$^3$, CH$_2$C(O)R$^3$, C(O)

OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, CF$_3$, CF$_2$CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl.

3. A compound according to claim 2, wherein:

G-G$_2$- is selected from the group:

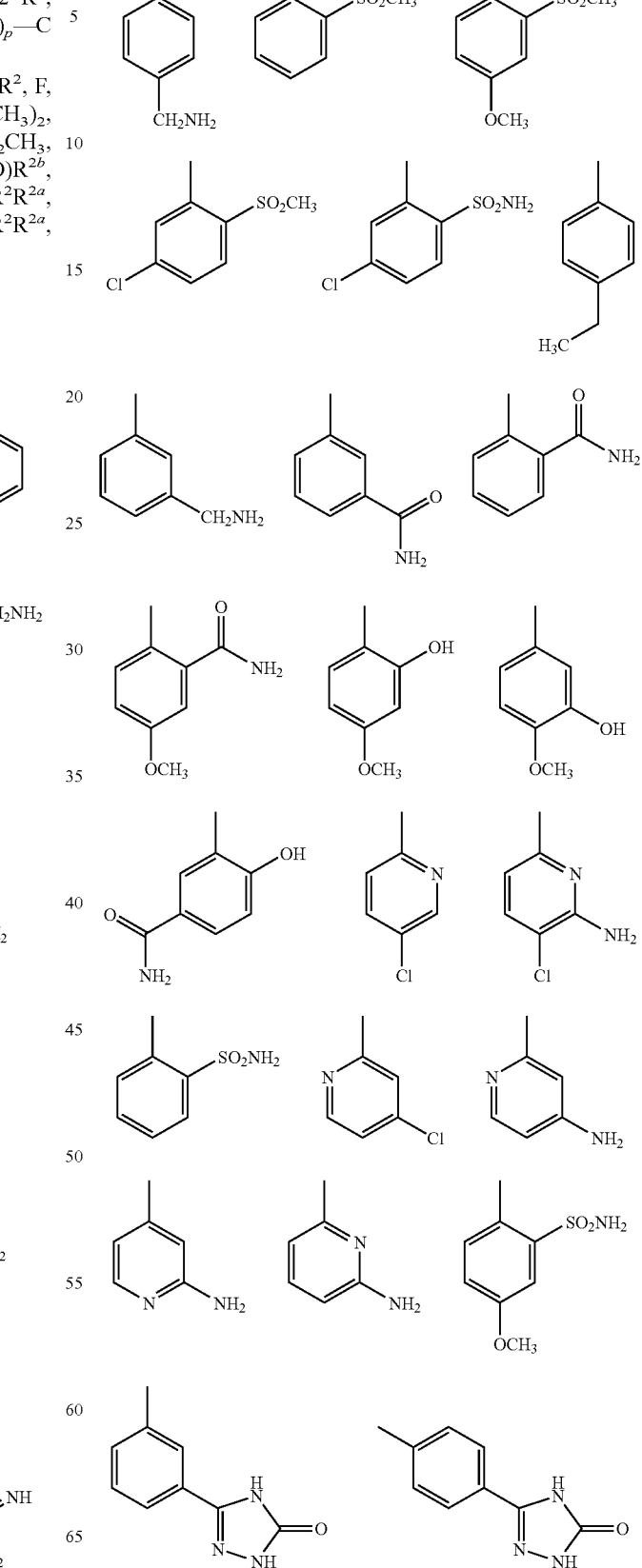

-continued
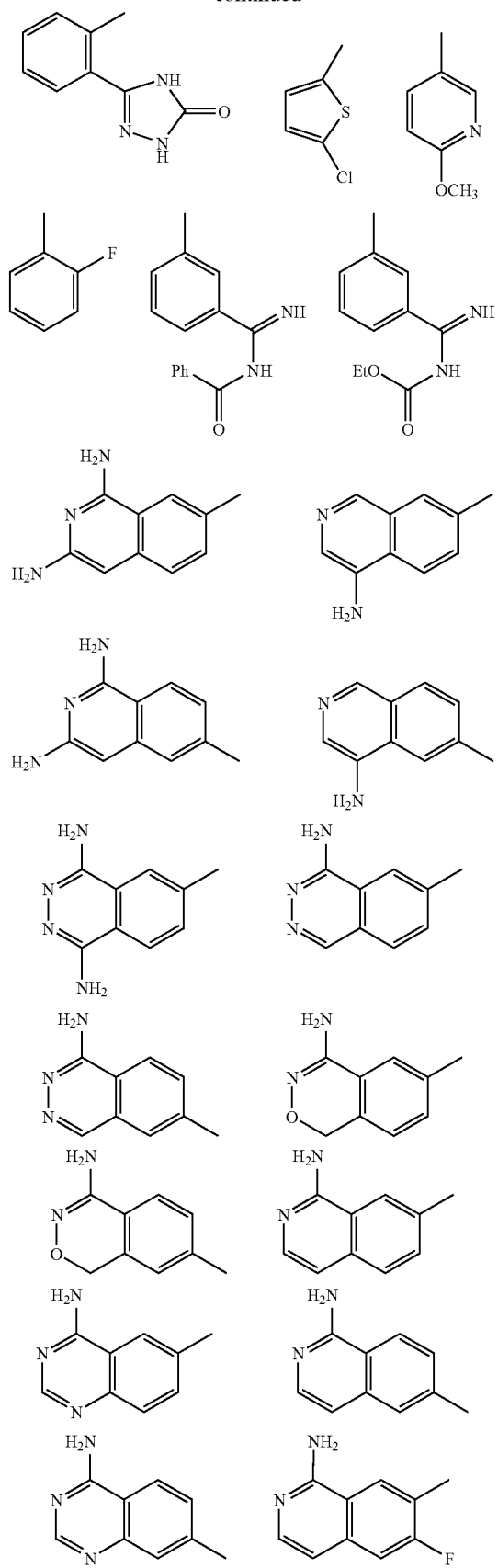
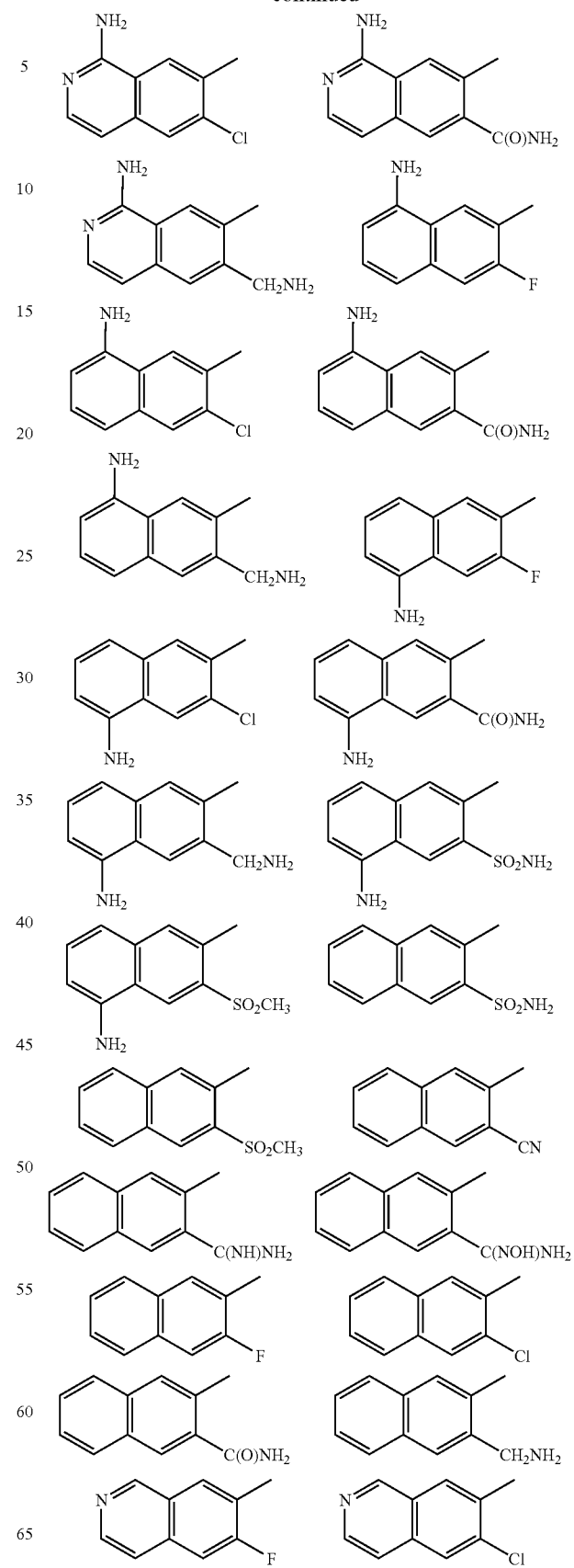

-continued
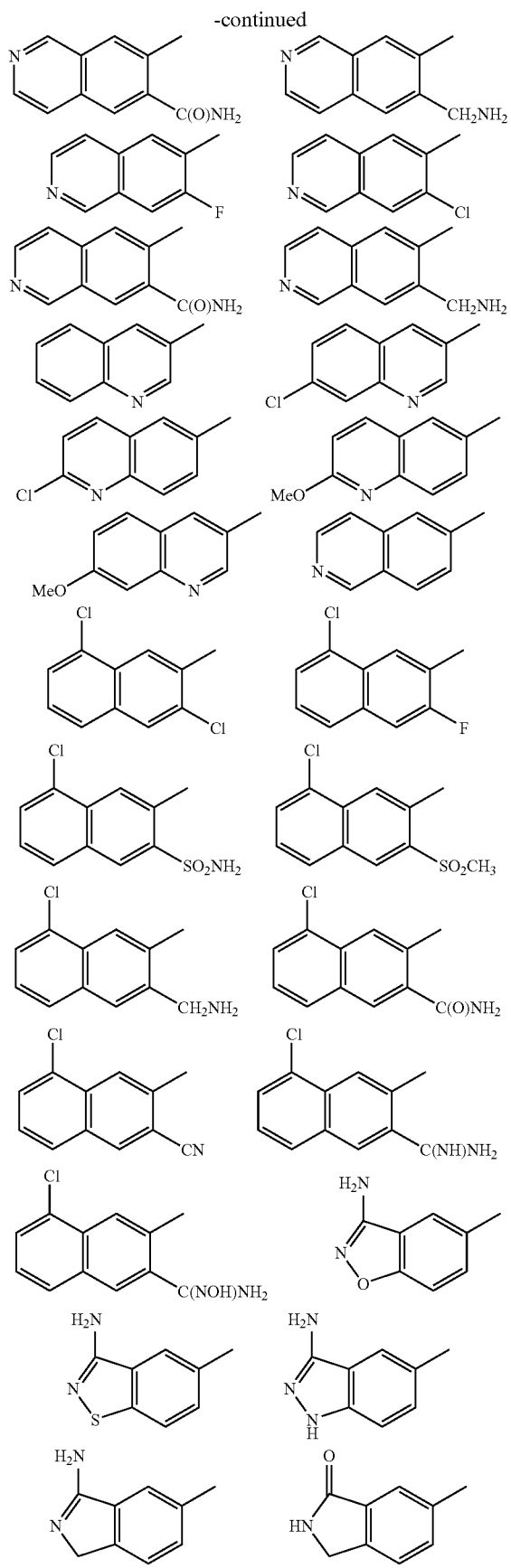
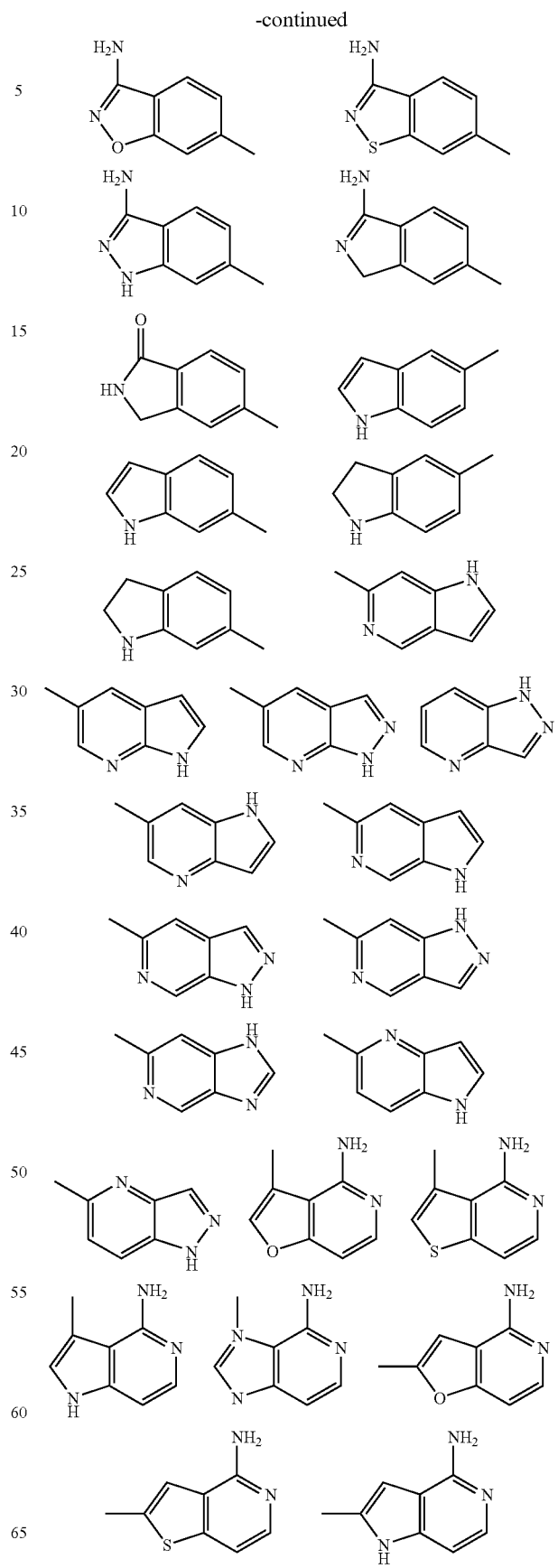

-continued
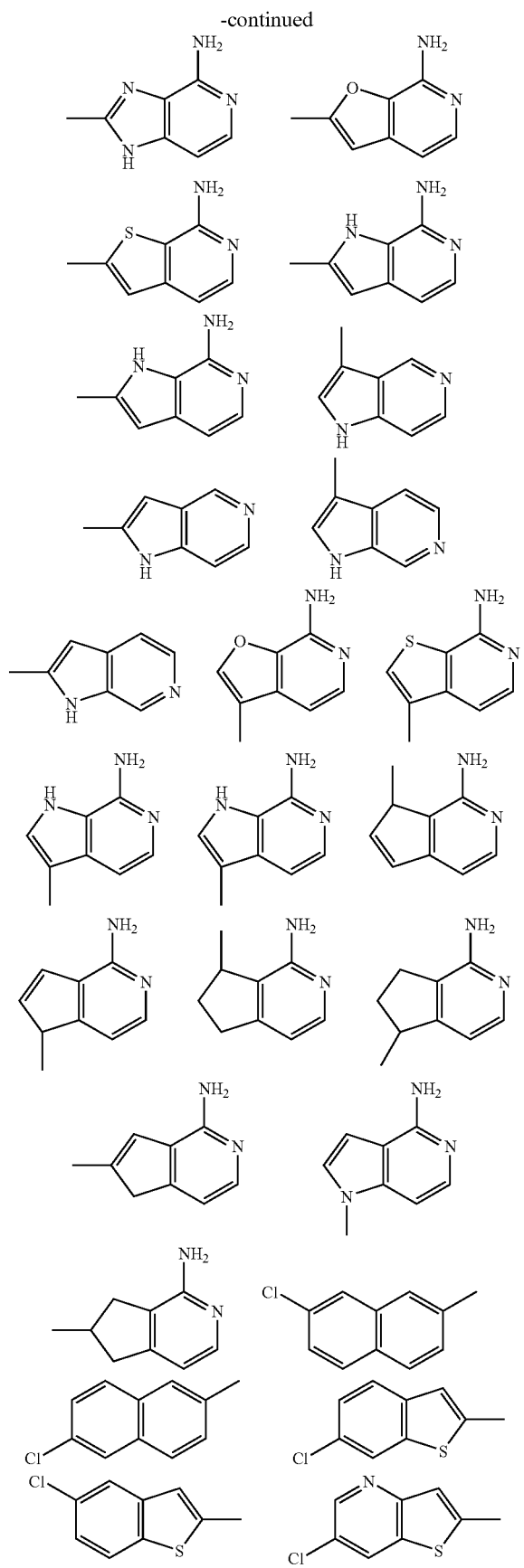
-continued
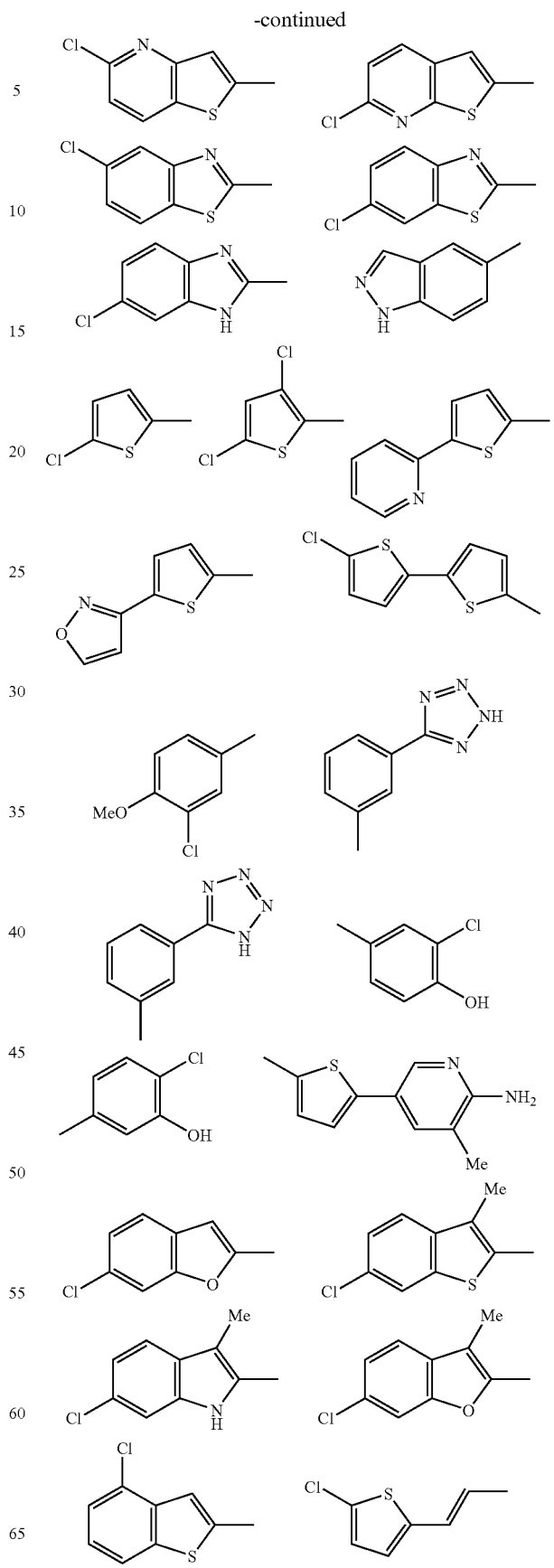

-continued
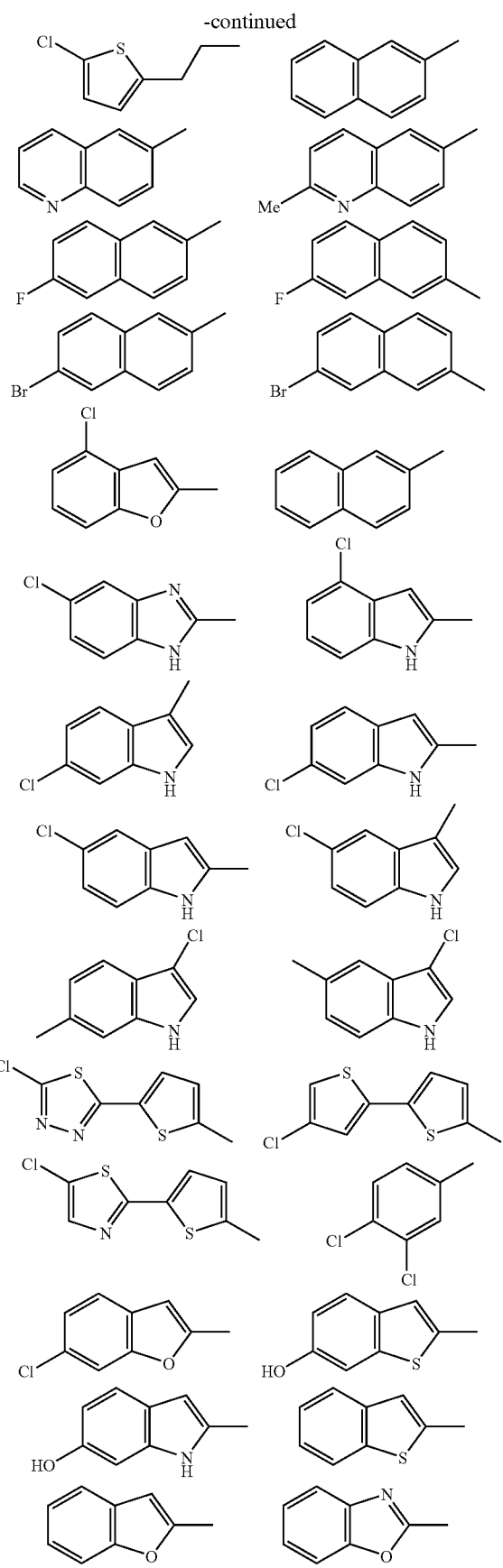
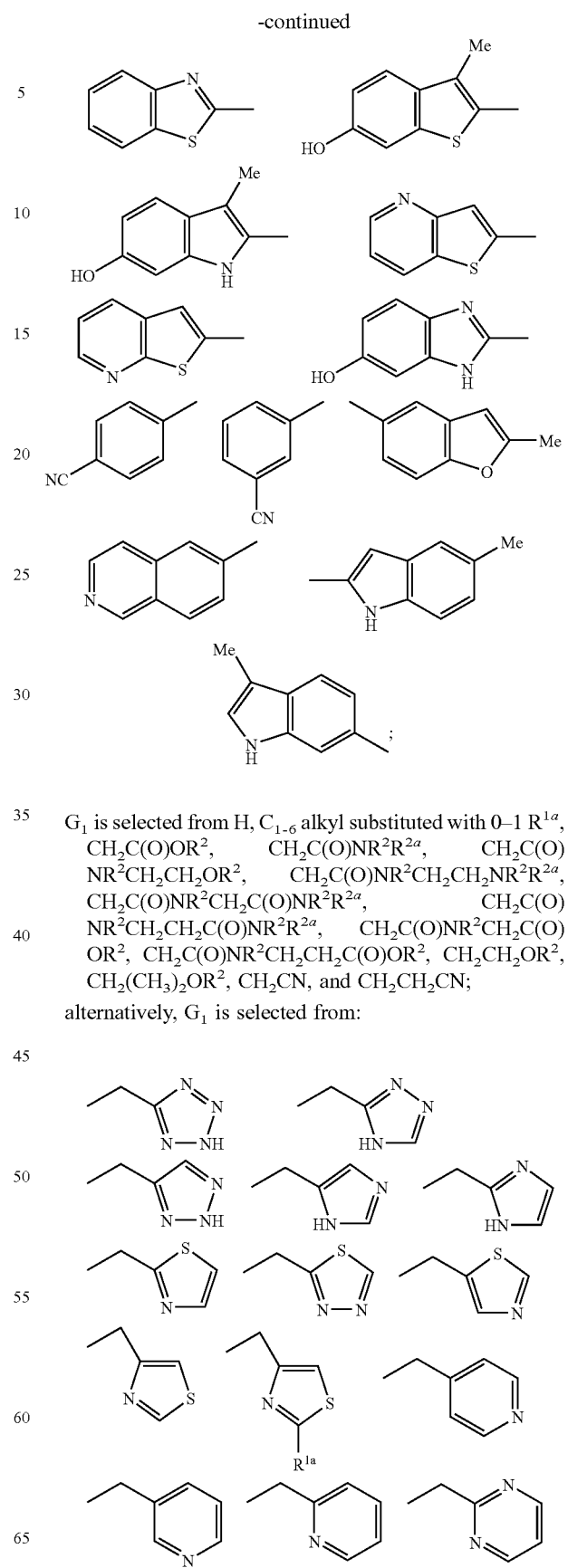
$G_1$ is selected from H, $C_{1-6}$ alkyl substituted with 0–1 $R^{1a}$, $CH_2C(O)OR^2$, $CH_2C(O)NR^2R^{2a}$, $CH_2C(O)NR^2CH_2CH_2OR^2$, $CH_2C(O)NR^2CH_2CH_2NR^2R^{2a}$, $CH_2C(O)NR^2CH_2C(O)NR^2R^{2a}$, $CH_2C(O)NR^2CH_2CH_2C(O)NR^2R^{2a}$, $CH_2C(O)NR^2CH_2C(O)OR^2$, $CH_2C(O)NR^2CH_2CH_2C(O)OR^2$, $CH_2CH_2OR^2$, $CH_2(CH_3)_2OR^2$, $CH_2CN$, and $CH_2CH_2CN$;
alternatively, $G_1$ is selected from:

-continued

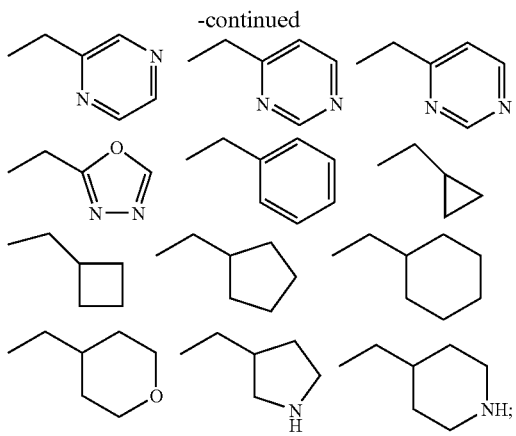

B is selected methyl, ethyl, 2-propyl, 1-butyl, 2-methyl-1-propyl, 1,1-dimethyl-1-ethyl, 1-pentyl, 2-pentyl, 3-pentyl, 3-hexyl, cyclopropyl, cyclobutyl, cyclopentyl, cyclohexyl, $CH(CF_3)_2$, $CH(CHF_2)CH_3$, $CH_2CF_3$, $CH(CF_2CF_3)_2$, $CH(Cl)CF_3$, $C(O)CH_2CH_3$, $C(O)CH(CH_3)_2$, $C(O)CH_2CH_2CH_3$, $C(O)NHCH_2CH_3$, $C(O)N(CH_3)_2$, $C(O)N(CH_3)(CH_2CH_3)$, $C(O)OCH_2CH_3$, $C(O)C(CH_3)_3$, $SO_2CH_3$, $SO_2CH_2CH_3$, $SO_2CH_2CH_2CH_3$, $SO_2CH(CH_3)_2$, $SO_2CH(CH_3)CH_2CH_3$, $SO_2N(CH_3)_2$, $SO_2N(CH_3)CH_2CH_3$, $OCH_3$, $OCH_2CH_3$, $OCH(CH_3)_2$, $OCH(CH_3)CH_2CH_3$, $SCH_3$, $SCH_2CH_3$, $SCH(CH_3)_2$, $SCH(CH_3)CH_2CH_3$, $SCH(CH_2CH_3)_2$, $N(CH_3)_2$, $N(CH_2CH_3)_2$, $N(CH_3)CH_2CH_3$, $N(CH_2CH_3)CH_2CH_2CH_3$, $NHC(O)CH_3$, $NHC(O)CH_2CH_3$, $NHC(O)CH(CH_3)_2$, and $NHC(O)CH(CH_3)CH_2CH_3$;

$R^{1a}$, at each occurrence, is selected from H, $-(CH_2)_r-R^{1b}$, $-(CH_2)_r-O-(CH_2)_r-R^{1b}$, $-(CH_2)_r-C(=NR^{1b})NR^3R^{1b}$, $NR^3(CR^3R^{3a})_rR^{1c}$, $O(CR^3R^{3a})_rR^{1c}$, $(CH_2)_rNR^3(CH_2)_rR^{1b}$, $(CH_2)_rC(O)NR^2(CH_2)_rR^{1b}$, $CO_2(CH_2)_rR^{1b}$, $O(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—S, O—O, or N—CN bond;

$R^{1b}$ is selected from H, $CH_3$, $CH_2CH_3$, F, Cl, Br, —CN, —CHO, $CF_3$, $(CH_2)_rOR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NR^2R^{2a}$, $C(O)NR^2R^{2a}$, $SO_2NR^2R^{2a}$, $NR^2SO_2NR^2R^{2a}$, $NR^2SO_2R^2$, $C(O)NR^2SO_2R^2$, $SO_2NR^2C(O)R^2$, $C_{3-10}$ carbocycle substituted with 0–2 $R^4$, and 4–10 membered heterocycle consisting of carbon atoms and from 1–4 heteroatoms selected from the group consisting of N, O, and $S(O)_p$ and substituted with 0–2 $R^4$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, phenyl substituted with 0–2 $R^{4b}$, a benzyl substituted with 0–2 $R^{4b}$, a 5–6 membered heterocycle-$CH_2$ group wherein said heterocycle consists of: carbon atoms and 1–4 heteroatoms selected from the group consisting of N, O, and $S(O)_p$ and substituted with 0–2 $R^{4b}$, and a 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, benzyl, phenyl substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle containing from 1–4 heteroatoms selected from the group consisting of N, O, and $S(O)_p$ and substituted with 0–2 $R^{4b}$;

$R^4$, at each occurrence, is selected from H, =O, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $CF_3$, and $CF_2CF_3$;

$R^{4a}$ is selected from H, =O, $CH_3$, $NR^{2d}R^{2d}$, $OR^{2d}$, $-NR^{2d}C(O)R^{2d}$, $-C(O)R^{2d}$, $-OC(O)R^{2d}$, $-C(O)NR^{2d}R^{2d}$, and $-C(O)OR^{2d}$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR_3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

4. A compound according to claim 3, wherein:

$G$-$G_2$- is selected from the group:

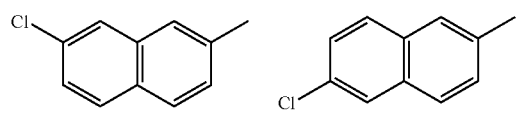

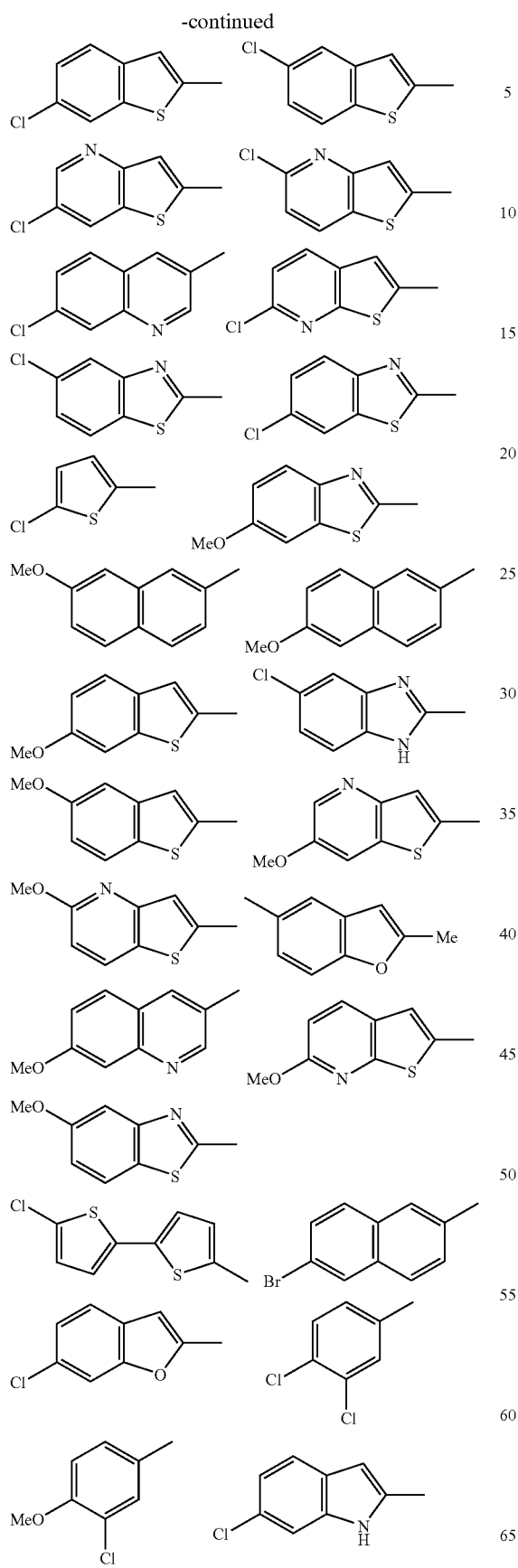
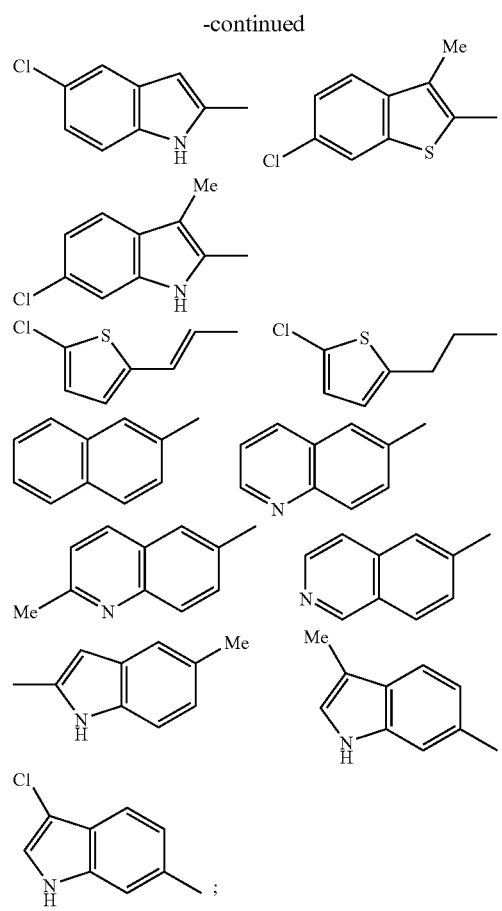
$G_1$ is selected from H, $C_{1-4}$ alkyl substituted with 0–1 $R^{1a}$, $CH_2C(O)OR^2$, $CH_2C(O)NR^2R^{2a}$, $CH_2C(O)NHCH_2CH_2OR^2$, $CH_2C(O)NHCH_2CH_2NR^2R^{2a}$, $CH_2C(O)N(CH_3)CH_2CH_2OR^2$, $CH_2C(O)N(CH_3)CH_2CH_2NR^2R^{2a}$, $CH_2C(O)NHCH_2C(O)NR^2R^{2a}$, $CH_2C(O)NHCH_2CH_2C(O)NR^2R^{2a}$, $CH_2C(O)NHCH_2C(O)OR^2$, $CH_2C(O)NHCH_2CH_2C(O)OR^2$, $CH_2CH_2OR^2$, $CH_2(CH_3)_2OR^2$, $CH_2CN$, and $CH_2CH_2CN$;
alternatively, $G_1$ is selected from:
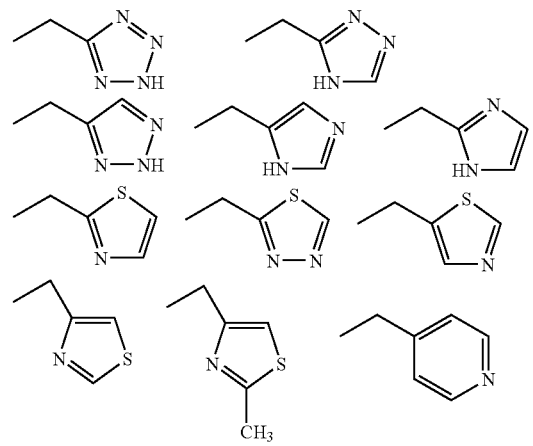

-continued

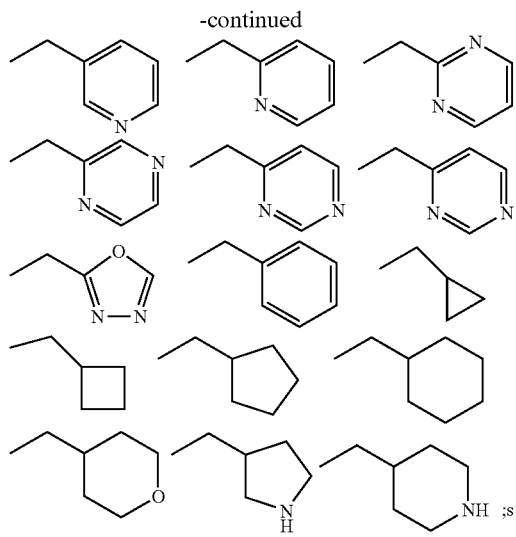

R$^{1a}$ is selected from H, R$^{1b}$, C(CH$_3$)$_2$R$^{1b}$, CH(CH$_3$)R$^{1b}$, CH$_2$R$^{1b}$, CH$_2$CH$_2$R$^{1b}$, CH$_2$OCH$_2$CH$_2$R$^{1b}$, OCH$_2$CH$_2$R$^{1b}$, (CH$_2$)$_r$NR$^3$CH$_2$CH$_2$R$^{1b}$, NR$^3$(CR$^3$R$^{3a}$)$_r$R$^{1c}$, O(CR$^3$R$^{3a}$)$_r$R$^{1c}$, (CH$_2$)$_r$C(O)NR$^2$(CH$_2$)$_r$R$^{1b}$, S(O)$_p$(CH$_2$)$_r$R$^{1d}$, O(CH$_2$)$_r$R$^{1d}$, NR$^3$(CH$_2$)$_r$R$^{1d}$, OC(O)NR$^3$(CH$_2$)$_r$R$^{1d}$, NR$^3$C(O)NR$^3$(CH$_2$)$_r$R$^{1d}$, NR$^3$C(O)O(CH$_2$)$_r$R$^{1d}$, and NR$^3$C(O)(CH$_2$)$_r$R$^{1d}$, provided that R$^{1a}$ forms other than an N-halo, N—S, O—O, or N—CN bond;

R$^{1b}$ is selected from H, CH$_3$, CH$_2$CH$_3$, F, Cl, Br, —CN, —CHO, CF$_3$, (CH$_2$)$_r$OR$^2$, NR$^2$R$^{2a}$, C(O)R$^{2b}$, CO$_2$R$^{2b}$, OC(O)R$^2$, CO$_2$R$^{2a}$, S(O)$_p$R$^2$, NR$^2$(CH$_2$)$_r$OR$^2$, NR$^2$C(O)R$^{2b}$, NR$^2$C(O)NR$^2$R$^{2a}$, C(O)NR$^2$R$^{2a}$, SO$_2$NR$^2$R$^{2a}$, NR$^2$SO$_2$NR$^2$R$^{2a}$, NR$^2$SO$_2$R$^2$, C(O)NR$^2$SO$_2$R$^2$, SO$_2$NR$^2$C(O)R$^2$, C$_{3-6}$ carbocycle substituted with 0–2 R$^4$, and 4–10 membered heterocycle consisting of carbon atoms and from 1–4 heteroatoms selected from the group consisting of N, O, and S(O)$_p$ and substituted with 0–2 R$^4$, provided that R$^{1b}$ forms other than an O—O, N-halo, N—S, or N—CN bond;

R$^{2a}$, at each occurrence, is selected from H, CH$_3$, CH$_2$CH$_3$, CH$_2$CH$_2$CH$_3$, CH(CH$_3$)$_2$, CH$_2$CH$_2$OH, CH$_2$CH$_2$CH$_2$OH, CH$_2$CH$_2$NMe$_2$, CH$_2$CH$_2$CH$_2$NMe$_2$, and benzyl;

alternatively, NR$^2$R$^{2a}$ forms a 5 or 6 membered saturated, partially saturated or unsaturated ring substituted with 0–1 R$^{4b}$ and consisting of: 0–1 additional heteroatoms selected from the group consisting of N, O, and S(O)$_p$;

R$^{2b}$, at each occurrence, is selected from OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl, phenyl substituted with 0–1 R$^{4b}$, and 5–6 membered aromatic heterocycle consisting of: carbon atoms and 1–4 heteroatoms selected from the group consisting of N, O, and S(O)$_p$ and substituted with 0–1 R$^{4b}$;

R$^{2c}$, at each occurrence, is selected from OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl, phenyl substituted with 0–1 R$^{4b}$, and 5–6 membered aromatic heterocycle containing from 1–4 heteroatoms selected from the group consisting of N, O, and S(O)$_p$ and substituted with 0–1 R$^{4b}$;

R$^4$, at each occurrence, is selected from H, =O, OH, OR$^2$, CH$_2$OR$^2$, (CH$_2$)$_2$OR$^2$, F, Br, Cl, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, CF$_3$, and CF$_2$CF$_3$;

R$^{4a}$ is selected from H, =O, CH$_3$, NR$^{2d}$R$^{2d}$, and OR$^{2d}$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, and CF$_3$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, and SO$_2$NR$^2$R$^{2a}$.

5. A compound according to claim 4, wherein:

G-G$_2$- is selected from:

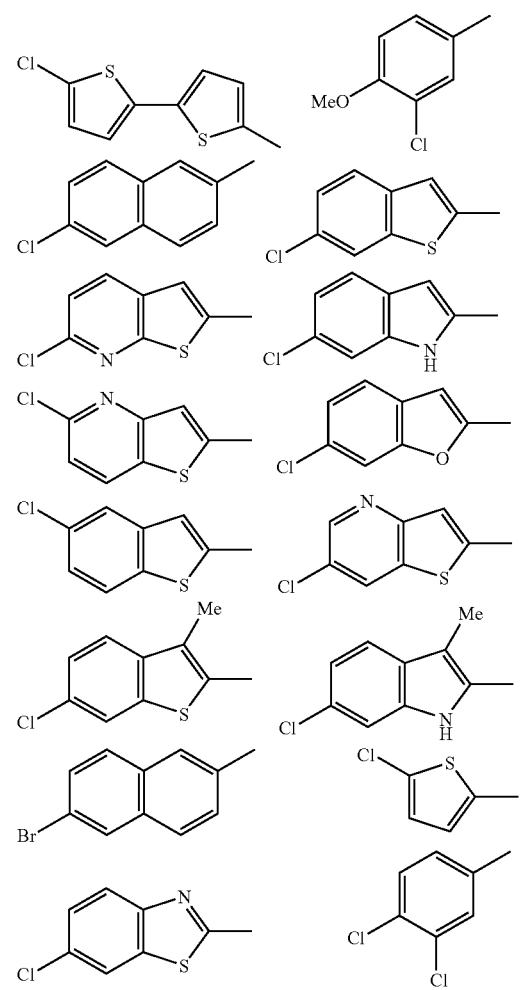

-continued

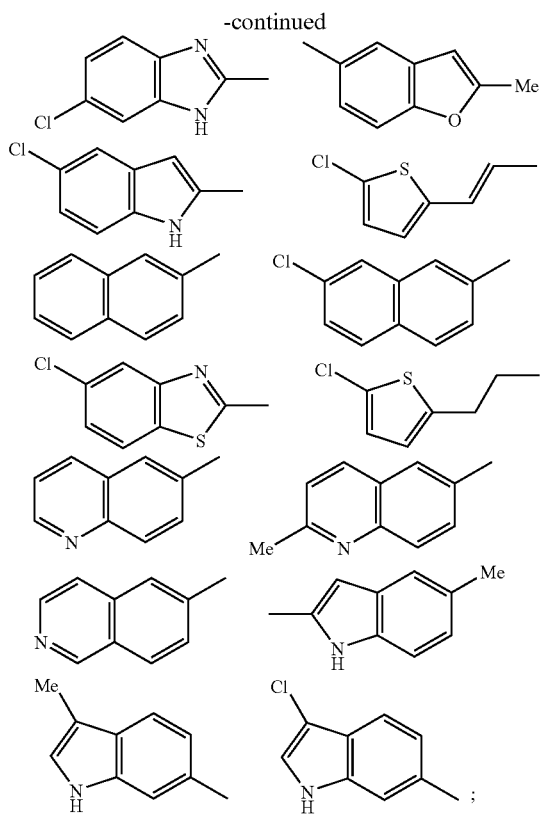

B is selected from methyl, ethyl, 2-propyl, 1-butyl, 2-methyl-1-propyl, 1-pentyl, cyclopropyl, cyclobutyl, cyclopentyl, cyclohexyl, $CH(CF_3)_2$, $CH(CHF_2)CH_3$, $CH_2CF_3$, $CH(CF_2CF_3)_2$, $C(O)NHCH_2CH_3$, $C(O)N(CH_3)_2$, $C(O)CH_2CH_2CH_3$, $C(O)C(CH_3)_3$, $N(CH_3)_2$, $N(CH_2CH_3)_2$, $NHC(O)CH_2CH_3$, $NHC(O)CH(CH_3)_2$, and $SO_2CH_3$;

$R^{1a}$ is selected from H, $CH_3$, $CH_2CH_3$, $CH_2CH_2CH_3$, $CH_2(CH_3)_2$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $NHCOCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, $NHSO_2NHCH_3$, $NHSO_2N(CH_3)_2$, $NHCO_2R^{2a}$, $NHC(O)NHR^{2a}$, $CH_2OCH_2CH_2NR^2R^{2a}$, $C(O)NR^2R^{2a}$, $CH_2CH_2OR^2$, $CH_2C(O)NR^2CH_2CH_2OR^2$, $C(O)NHCH_2CH_2NR^2R^{2a}$, $CH_2C(O)NHCH_2CH_2NR^2R^{2a}$, $C(O)NCH_3CH_2CH_2NR^2R^{2a}$, $CH_2C(O)NCH_3CH_2CH_2NR^2R^{2a}$, $CH_2NHCH_2CH_2NR^2R^{2a}$, $CH_2N(CH_3)CH_2CH_2NR^2R^{2a}$, phenyl substituted with 0–2 $R^{4b}$, —$CH_2$-phenyl substituted with 0–2 $R^{4b}$, 5–10 membered aromatic heterocycle consisting of carbon atoms and from 1–4 heteroatoms selected from the group consisting of N, O, and $S(O)_p$ and substituted with 0–2 $R^{4b}$, and —$CH_2$-5–10 membered aromatic heterocycle consisting of carbon atoms and from 1–4 heteroatoms selected from the group consisting of N, O, and $S(O)_p$ and substituted with 0–2 $R^{4b}$, provided that $R^{1a}$ forms other than an N-halo, N—S, O—O, or N—CN bond;

$R^2$, at each occurrence, is selected from H, $CH_3$, $CH_2CH_3$, $CH_2CH_2CH_3$, $CH(CH_3)_2$, $CH_2CH_2OH$, $CH_2CH_2CH_2OH$, $CH_2CH_2NMe_2$, $CH_2CH_2CH_2NMe_2$, phenyl substituted with 0–1 $R^{4b}$, benzyl substituted with 0–1 $R^{4b}$, 5 membered aromatic heterocycle-$CH_2$ group wherein the heterocycle consists of: carbon atoms and 1–4 heteroatoms selected from the group consisting of N, O, and $S(O)_p$ and substituted with 0–1 $R^{4b}$ and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$, $CH_2CH_2OH$, $CH_2CH_2CH_2OH$, $CH_2CH_2NMe_2$, and $CH_2CH_2CH_2NMe_2$, alternatively, $NR^2R^{2a}$ forms a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{4a}$ is selected from H, =O, $CH_3$, $N(CH_3)_2$, OH, and O-t-butyl; and $R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$.

6. A compound according to claim 5, wherein the compound is selected from:

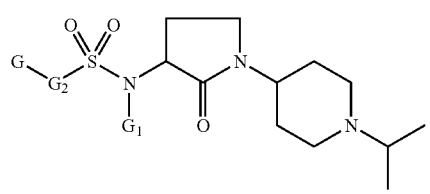

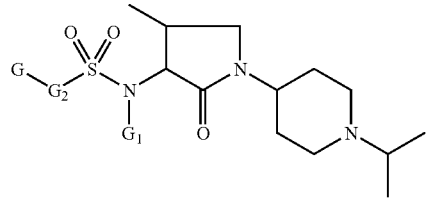

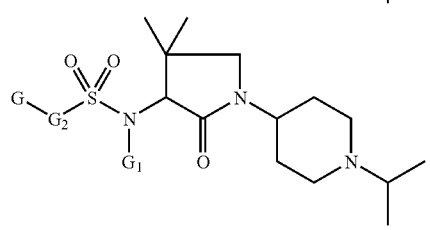

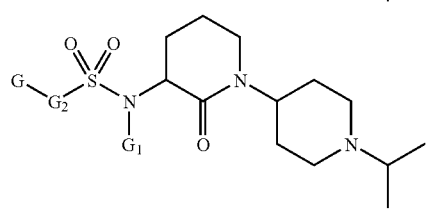

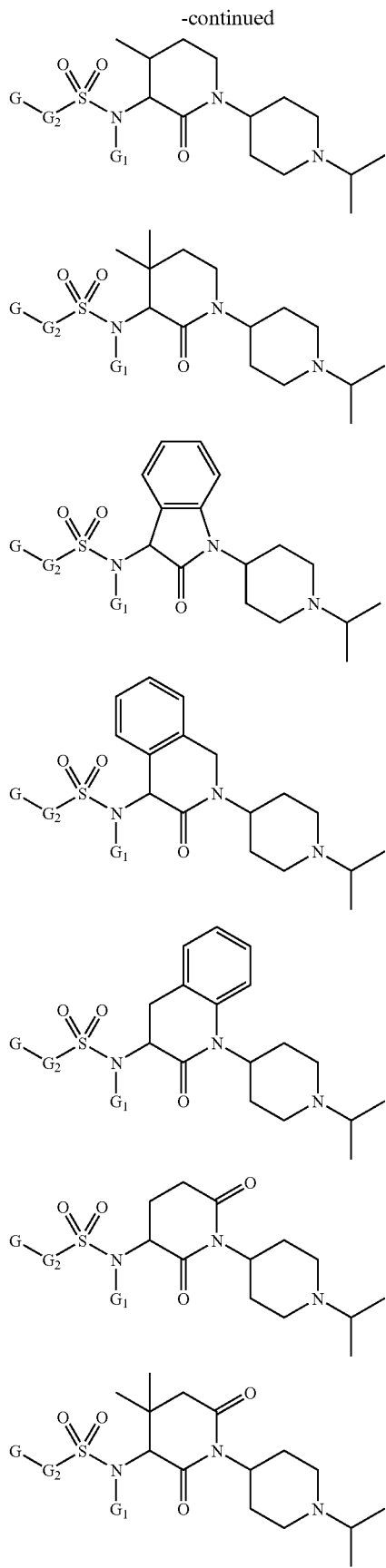

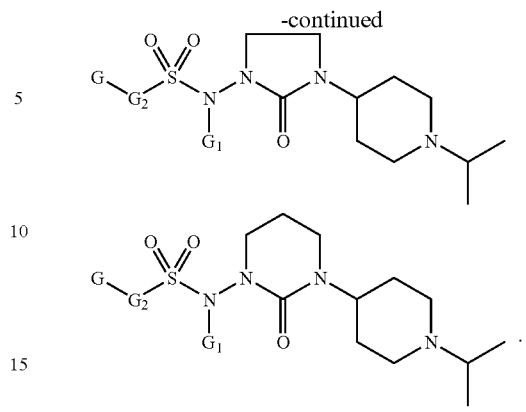

7. A compound according to claim 1, wherein the compound is selected from the group:

(S)-6-chloro-naphthalene-2-sulfonic acid (1'-cyclopentyl-2-oxo-[1,4']bipiperidinyl-3-yl)-amide;
(S)-6-chloro-naphthalene-2-sulfonic acid (1'-isopropyl-2-oxo-[1,4']bipiperidinyl-3-yl)-amide;
(S)-6-chloro-naphthalene-2-sulfonic acid (1'-cyclohexyl-2-oxo-[1,4']bipiperidinyl-3-yl)-amide;
(S)-6-chloro-naphthalene-2-sulfonic acid (1'-acetyl-2-oxo-[1,4']bipiperidinyl-3-yl)-amide;
(S)-6-chloro-naphthalene-2-sulfonic acid [1'-(2-dimethylamino-acetyl)-2-oxo-[1,4']bipiperidinyl-3-yl]-amide;
(S)-[(6-chloro-naphthalene-2-sulfonyl)-(1'-isopropyl-2-oxo-[1,4']bipiperidinyl-3-yl)-amino]-acetic acid methyl ester;
(S)-2-[(6-chloro-naphthalene-2-sulfonyl)-(1'-isopropyl-2-oxo-[1,4']bipiperidinyl-3-yl)-amino]-acetamide;
(S)-6-chloro-naphthalene-2-sulfonic acid (1'-cyclobutyl-2-oxo-[1,4']bipiperidinyl-3-yl)-amide;
(S)-6-chloro-naphthalene-2-sulfonic acid [1'-(4-hydroxy-butyl)-2-oxo-[1,4']bipiperidinyl-3-yl]-amide;
(S)-6-chloro-naphthalene-2-sulfonic acid (1'-sec-butyl-2-oxo-[1,4']bipiperidinyl-3-yl)-amide;
(S)-6-chloro-naphthalene-2-sulfonic acid [2-oxo-1'-(tetrahydro-pyran-4-yl)-[1,4']bipiperidinyl-3-yl]-amide;
(S)-6-chloro-naphthalene-2-sulfonic acid (1'-methyl-2-oxo-[1,4']bipiperidinyl-3-yl)-amide;
(R)-6-chloro-naphthalene-2-sulfonic acid (1'-isopropyl-2-oxo-[1,4']bipiperidinyl-3-yl)-amide;
(S)-6-chloro-naphthalene-2-sulfonic acid [1'-(1-ethyl-propyl)-2-oxo-[1,4']bipiperidinyl-3-yl]-amide;
(S)-6-chloro-naphthalene-2-sulfonic acid (1'-ethyl-2-oxo-[1,4']bipiperidinyl-3-yl)-amide;
(S)-naphthalene-2-sulfonic acid (1'-isopropyl-2-oxo-[1,4']bipiperidinyl-3-yl)-amide;
(S)-6-chloro-benzo[b]thiophene-2-sulfonic acid (1'-isopropyl-2-oxo-[1,4']bipiperidinyl-3-yl)-amide;
(S)-5-chloro-benzo[b]thiophene-2-sulfonic acid (1'-isopropyl-2-oxo-[1,4']bipiperidinyl-3-yl)-amide;
(S)-5-chloro-thiophene-2-sulfonic acid (1'-isopropyl-2-oxo-[1,4']bipiperidinyl-3-yl)-amide;
(S)-7-chloro-naphthalene-2-sulfonic acid (1'-isopropyl-2-oxo-[1,4']bipiperidinyl-3-yl)-amide;
(S)-6-bromo-naphthalene-2-sulfonic acid (1'-isopropyl-2-oxo-[1,4']bipiperidinyl-3-yl)-amide;
(S)-5-chloro-1H-indole-2-sulfonic acid (1'-isopropyl-2-oxo-[1,4']bipiperidinyl-3-yl)-amide;
(S)-benzo[b]thiophene-2-sulfonic acid (1'-isopropyl-2-oxo-[1,4']bipiperidinyl-3-yl)-amide;

(S)-2-(5-chloro-thiophen-2-yl)-ethenesulfonic acid (1'-isopropyl-2-oxo-[1,4']bipiperidinyl-3-yl)-amide;
(S)-2-methyl-quinoline-6-sulfonic acid (1'-isopropyl-2-oxo-[1,4']bipiperidinyl-3-yl)-amide;
(S)-5-chloro-thieno[3,2-b]pyridine-2-sulfonic acid (1'-isopropyl-2-oxo-[1,4']bipiperidinyl-3-yl)-amide;
(S)-2-(4-chloro-phenyl)-ethenesulfonic acid (1'-isopropyl-2-oxo-[1,4']bipiperidinyl-3-yl)-amide;
(S)-2-thiophen-2-yl-ethanesulfonic acid (1'-isopropyl-2-oxo-[1,4']bipiperidinyl-3-yl)-amide;
(S)-[(6-chloro-naphthalene-2-sulfonyl)-(1'-isopropyl-2-oxo-[1,4']bipiperidinyl-3-yl)-amino]-acetic acid;
(S)-6-chloro-N-(1-(1-isopropylpiperidin-4-yl)-2-oxopiperidin-3-yl)-N-methylnaphthalene-2-sulfonamide;
(S)-6-chloro-N-(cyanomethyl)-N-(1-(1-isopropylpiperidin-4-yl)-2-oxopiperidin-3-yl)naphthalene-2-sulfonamide;
(S)-6-chloro-N-ethyl-N-(1-(1-isopropylpiperidin-4-yl)-2-oxopiperidin-3-yl)naphthalene-2-sulfonamide;
(S)-5-bromo-N-(1-(1-isopropylpiperidin-4-yl)-2-oxopiperidin-3-yl)-3-methylbenzo[b]thiophene-2-sulfonamide;
(S)-5-chloro-N-(1-(1-isopropylpiperidin-4-yl)-2-oxopiperidin-3-yl)-3-methylbenzo[b]thiophene-2-sulfonamide;
(S)-6-chloro-N-(1-(1-isopropylpiperidin-4-yl)-2-oxopiperidin-3-yl)-N-((2-methylthiazol-4-yl)methyl)naphthalene-2-sulfonamide;
(S)-6-chloro-N-(1-(1-isopropylpiperidin-4-yl)-2-oxopiperidin-3-yl)-N-(thiazol-4-ylmethyl)naphthalene-2-sulfonamide;
(S)-6-chloro-N-(1-(1-isopropylpiperidin-4-yl)-2-oxopiperidin-3-yl)-N-((5-methylisoxazol-3-yl)methyl)naphthalene-2-sulfonamide;
(S)-6-chloro-N-((3,5-dimethylisoxazol-4-yl)methyl)-N-(1-(1-isopropylpiperidin-4-yl)-2-oxopiperidin-3-yl)naphthalene-2-sulfonamide;
(S)-6-chloro-N-(1-(1-isopropylpiperidin-4-yl)-2-oxopiperidin-3-yl)-N-methylbenzo[b]thiophene-2-sulfonamide;
(S)-6-chloro-N-(cyanomethyl)-N-(1-(1-isopropylpiperidin-4-yl)-2-oxopiperidin-3-yl)benzo[b]thiophene-2-sulfonamide;
(S)-methyl 2-(6-chloro-N-(1-(1-isopropylpiperidin-4-yl)-2-oxopiperidin-3-yl)benzo[b]thiophene-2-sulfonamido)acetate;
(S)-2-(6-chloro-N-(1-(1-isopropylpiperidin-4-yl)-2-oxopiperidin-3-yl)benzo[b]thiophene-2-sulfonamido)acetic acid;
(S)-2-(6-chloro-N-(1-(1-isopropylpiperidin-4-yl)-2-oxopiperidin-3-yl)benzo[b]thiophene-2-sulfonamido)acetamide;
(S)-tert-butyl 2-(2-chloro-N-(1-(1-isopropylpiperidin-4-yl)-2-oxopiperidin-3-yl)naphthalene-6-sulfonamido)acetate;
(S)-6-chloro-N-(1-(1-cyanopiperidin-4-yl)-2-oxopyrrolidin-3-yl)naphthalene-2-sulfonamide;
(S)-6-chloro-N-cyano-N-(1-(1-cyanopiperidin-4-yl)-2-oxopyrrolidin-3-yl)naphthalene-2-sulfonamide;
(S)-5-chloro-N-(1-(1-isopropylpiperidin-4-yl)-2-oxopiperidin-3-yl)-N-methylbenzo[b]thiophene-2-sulfonamide;
(S)-5-chloro-N-(cyanomethyl)-N-(1-(1-isopropylpiperidin-4-yl)-2-oxopiperidin-3-yl)benzo[b]thiophene-2-sulfonamide;
(S)-2-(5-chloro-N-(1-(1-isopropylpiperidin-4-yl)-2-oxopiperidin-3-yl)benzo[b]thiophene-2-sulfonamido)acetic acid;
(S)-6-chloro-N-(1-(1-isopropylpiperidin-4-yl)-2-oxopiperidin-3-yl)thieno[2,3-b]pyridine-2-sulfonamide;
(S)-4,6-dichloro-N-(1-(1-isopropylpiperidin-4-yl)-2-oxopiperidin-3-yl)benzo[b]thiophene-2-sulfonamide;
6-chloro-N-((3S,4R)-1-(1-isopropylpiperidin-4-yl)-4-methyl-2-oxopyrrolidin-3-yl)naphthalene-2-sulfonamide;
6-chloro-N-((3S)-1-(1-isopropylpiperidin-4-yl)-4-methyl-2-oxopyrrolidin-3-yl)benzo[b]thiophene-2-sulfonamide;
6-chloro-N-((3S,4R)-1-(1-isopropylpiperidin-4-yl)-4-methyl-2-oxopiperidin-3-yl)naphthalene-2-sulfonamide;
6-chloro-N-((3S,4R)-1-(1-isopropylpiperidin-4-yl)-4-methyl-2-oxopiperidin-3-yl)benzo[b]thiophene-2-sulfonamide; and
(S)-N-(4-(3-(2-chloronaphthalene-6-sulfonamido)-2-oxopyrrolidin-1-yl)phenyl)-2-(dimethylamino)-N-methylacetamide;
or a pharmaceutically acceptable salt form thereof.

8. A pharmaceutical composition, comprising: a pharmaceutically acceptable carrier and a therapeutically effective amount of a compound of claim 1 or a pharmaceutically acceptable salt form thereof.

9. A method for treating a thromboembolic disorder, comprising:
administering to a patient in need thereof a therapeutically effective amount of a compound of claim 1 or a pharmaceutically acceptable salt form thereof.

10. A method according to claim 9, wherein the thromboembolic disorder is selected from the group consisting of arterial cardiovascular thromboembolic disorders, venous cardiovascular thromboembolic disorders, and thromboembolic disorders in the chambers of the heart.

11. A method according to claim 9, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

12. A pharmaceutical composition, comprising: a pharmaceutically acceptable carrier and a therapeutically effective amount of a compound of claim 2 or a pharmaceutically acceptable salt form thereof.

13. A pharmaceutical composition, comprising: a pharmaceutically acceptable carrier and a therapeutically effective amount of a compound of claim 3 or a pharmaceutically acceptable salt form thereof.

14. A pharmaceutical composition, comprising: a pharmaceutically acceptable carrier and a therapeutically effective amount of a compound of claim 4 or a pharmaceutically acceptable salt form thereof.

15. A pharmaceutical composition, comprising: a pharmaceutically acceptable carrier and a therapeutically effective amount of a compound of claim 5 or a pharmaceutically acceptable salt form thereof.

16. A pharmaceutical composition, comprising: a pharmaceutically acceptable carrier and a therapeutically effective amount of a compound of claim 6 or a pharmaceutically acceptable salt form thereof.

17. A pharmaceutical composition, comprising: a pharmaceutically acceptable carrier and a therapeutically effective amount of a compound of claim 7 or a pharmaceutically acceptable salt form thereof.

18. A method for treating a thromboembolic disorder, comprising:
   administering to a patient in need thereof a therapeutically effective amount of a compound of claim 2 or a pharmaceutically acceptable salt form thereof.

19. A method for treating a thromboembolic disorder, comprising:
   administering to a patient in need thereof a therapeutically effective amount of a compound of claim 3 or a pharmaceutically acceptable salt form thereof.

20. A method for treating a thromboembolic disorder, comprising:
   administering to a patient in need thereof a therapeutically effective amount of a compound of claim 4 or a pharmaceutically acceptable salt form thereof.

21. A method for treating a thromboembolic disorder, comprising:
   administering to a patient in need thereof a therapeutically effective amount of a compound of claim 5 or a pharmaceutically acceptable salt form thereof.

22. A method for treating a thromboembolic disorder, comprising:
   administering to a patient in need thereof a therapeutically effective amount of a compound of claim 6 or a pharmaceutically acceptable salt form thereof.

23. A method for treating a thromboembolic disorder, comprising:
   administering to a patient in need thereof a therapeutically effective amount of a compound of claim 7 or a pharmaceutically acceptable salt form thereof.

* * * * *